(12) United States Patent
Bou Arévalo et al.

(10) Patent No.: US 10,517,939 B2
(45) Date of Patent: Dec. 31, 2019

(54) LIVE ATTENUATED VACCINES

(71) Applicants: SERVICIO GALEGO DE SAÚDE (SERGAS), Santiago de Compostela (ES); FUNDACIÓN PROFESOR NOVOA SANTOS, A Coruña (ES)

(72) Inventors: Germán Bou Arévalo, A Coruña (ES); María Clara Póvoa Cabral, A Coruña (ES); Astrid Pérez Gómez, A Coruña (ES); María Merino Carballeira, A Coruña (ES); Alejandro Beceiro Casas, A Coruña (ES); Patricia García Fernández, A Coruña (ES)

(73) Assignees: SERVICIO GALEGO DE SAÚDE (SERGAS), Santiago de Compostela (ES); FUNDACIÓN PROFESOR NOVOA SANTOS, A Coruña (ES)

( * ) Notice: Subject to any disclaimer, the term of this patent is extended or adjusted under 35 U.S.C. 154(b) by 0 days.

(21) Appl. No.: 15/028,176

(22) PCT Filed: Oct. 13, 2014

(86) PCT No.: PCT/EP2014/071926
§ 371 (c)(1),
(2) Date: Apr. 8, 2016

(87) PCT Pub. No.: WO2015/052350
PCT Pub. Date: Apr. 16, 2015

(65) Prior Publication Data
US 2016/0235834 A1 Aug. 18, 2016

(30) Foreign Application Priority Data

Oct. 11, 2013 (ES) .................................. 201331504
Apr. 25, 2014 (EP) .................................... 14382153

(51) Int. Cl.
*A61K 39/104* (2006.01)
*A61K 39/085* (2006.01)
*C12R 1/385* (2006.01)
*C12N 1/36* (2006.01)
*C07K 16/12* (2006.01)
*A61K 39/00* (2006.01)
*C12R 1/01* (2006.01)
*C12R 1/445* (2006.01)
(Continued)

(52) U.S. Cl.
CPC .......... *A61K 39/104* (2013.01); *A61K 39/085* (2013.01); *A61K 39/1045* (2013.01); *C07K 16/1214* (2013.01); *C07K 16/1217* (2013.01); *C07K 16/1271* (2013.01); *C12N 1/36* (2013.01); *C12N 9/1096* (2013.01); *C12N 9/90* (2013.01); *C12R 1/01* (2013.01); *C12R 1/385* (2013.01); *C12R 1/445* (2013.01); *G01N 33/56911* (2013.01); *A61K 2039/522* (2013.01); *A61K 2039/54* (2013.01); *A61K 2039/575* (2013.01); *C07K 2317/33* (2013.01)

(58) Field of Classification Search
CPC .. A61K 2039/523; A61K 39/04; A61K 39/00; A61K 39/12; A61K 2300/00; A61K 47/6803; A61K 47/6855; A61K 31/337; A61K 31/427; A61K 38/07; A61K 39/39558; A61K 47/6817; A61K 47/6849; A61K 47/6861; A61K 2039/505; A61K 2039/53; A61K 2039/543; A61K 2039/57; C12N 15/74; C12N 15/86; C12N 15/88; C12N 2770/24211; C12N 2770/36143; C12N 2840/203; C12N 1/20; C07D 401/12; C07D 417/12; C07D 207/08; C07D 207/325; C07K 5/0205; C07K 5/06043; C07K 5/101; C07K 14/25; C07K 16/2896; C07K 2317/24; C07K 2317/76; C07K 5/02; C07K 5/06
See application file for complete search history.

(56) References Cited

U.S. PATENT DOCUMENTS

| 5,811,105 A * | 9/1998 | Dougan ............. A61K 39/0275 424/184.1 |
| 2008/0107683 A1* | 5/2008 | Hone ..................... C12N 15/86 424/201.1 |

(Continued)

FOREIGN PATENT DOCUMENTS

WO    WO-99/25376 A1    5/1999

OTHER PUBLICATIONS

New Riverside University Dictionary. The Riverside Publishing Company, p. 933, 1984.*

(Continued)

*Primary Examiner* — Sarvamangala Devi
(74) *Attorney, Agent, or Firm* — McCarter & English, LLP; Jill Ann Mello

(57) ABSTRACT

The present invention refers to a method for the production of live attenuated bacterial strains, suitable as vaccine candidates, comprising the steps of: A. providing a bacterial strain capable of expressing glutamate racemase and possibly D-amino acid transaminase and comprising a peptidoglycan cell wail, and B. inactivating the gene or genes encoding for the glutamate racemase enzyme and, if needed, the gene or genes encoding for the enzyme D-amino acid transaminase in such way that the bacterial strain is no longer capable of expressing a functional glutamate racemase and/or a functional D-amino acid transaminase; wherein the inactivation of said genes causes said bacterial strain to be auxotrophic for D-glutamate.

13 Claims, 53 Drawing Sheets
Specification includes a Sequence Listing.

(51) Int. Cl.
  *C12N 9/10* (2006.01)
  *C12N 9/90* (2006.01)
  *G01N 33/569* (2006.01)

(56) References Cited

U.S. PATENT DOCUMENTS

2014/0206016 A1* 7/2014 Lozano Sanchez ..... C12Q 1/04
                                                    435/7.1
2018/0079803 A1* 3/2018 McBride ............ C07K 16/1246

OTHER PUBLICATIONS

Illustrated Stedman's Medical Dictionary (24th Edition, Williams and Wilkins, London, p. 707, 1982.*
Aranda, J. et al., "A rapid and simple method for constructing stable mutants of *Acinetobacter baumannii*," *Microbiology*, vol. 10, Issue 279, 12 pages.
Cabral, M. P. et al., "Blockade of glutamate racemisation during cell-wall formation prevents biofilms and proliferation of Acinetobacter baumannii in vivo", Meeting Abstract, 27th ESCMID Congress, Berlin, Apr. 2013, retrieved from the Internet: URL:http//registration.akm.ch/einsicht.php?XNABSTRACT_ID=163512&XNSPRACHE_ID=2&XNKONGRESS_ID=180&XNMASKEN_ID=900, last retrieved on Jan. 16, 2015.
Fisher, S. L., "Glutamate racemase as a target for drug discovery", *Microbial Biotechnology*, vol. 1, No. 5, pp. 345-360, 2008.
International Search Report and Written Opinion for PCT/EP2014/071926, dated May 29, 2015.

* cited by examiner

```
  1  -MTAIQPLFTELEPMPKALADAPIGIFDSGIGGMSVAAEIAKYLPNERIVYYADTAYVPY   59  A3M1P5   A3M1P5_ACIBT
  1  ----------------MNNNNNPIGMIDSGLGGLSLFKYIRQALPNEDIIYFADSKYVPY   44  A3MA43   A3MA43_ACIBT
  1  MATKLQDGNTPCLAATPSEPRPTVLVFDSGVGGLSVYDEIRHLLPDLHYIYAFDNVAFPY   60  P22634   MURI_ECOLI
  1  ----------------MAVESAAVGVFDSGVGGLSVLREIRARLPSESLLYVADNAHVPY   44  Q9HVD0   MURI_PSEAE
                     : ::***:**:*:    *   **.  :*  *.  .**

60  GPRSDEEIRELTARAVD-WLYRQGCKIAVVACNTASAFSLDHLREHYGEHFPIVGLVPAL  118  A3M1P5   A3M1P5_ACIBT
 45  GDRESDWIVSRITHLISNLVIHGKCKAIVIACNTMTAVAVETIRAQI--NVPLIAIEPAV  102  A3MA43   A3MA43_ACIBT
 61  GEKSEAFIVERVVAIVTAVQERYPLALAVVACNTASTVSLPALREKF--DFPVVGVVPAI  118  P22634   MURI_ECOLI
 45  GEKSAEYIRERCERIGD-FLLEQGAKALVLACNTATAAAAAELRERYP-QVPLVAMEPAV  102  Q9HVD0   MURI_PSEAE
       *  :.    *  .       .     *:****  ::  :  :*  :   .*::.: **:

119  KPAVLQTRSKVVAVLATPATFRGQLIKDVVEKFAVPAGVKVMTLTSLELVPCVEAGQQMS  178  A3M1P5   A3M1P5_ACIBT
103  KPAVAMTLSKHIAVLATATTVKGKNLKSLIETYAQD--IKVSLVPCIGLAEKIETGKAHT  160  A3MA43   A3MA43_ACIBT
119  KPAARLTANGIVGLLATRGTVKRSYTHELIARFANE--CQIEMLGSAEMVELAEAKLHGE  176  P22634   MURI_ECOLI
103  KPAAAATRNGRVGVLATTGTLKSARFAALLDRFASD--VQVFTQPCPGLVERIEAGDLYG  160  Q9HVD0   MURI_PSEAE
     ***.  *    ::.:***  *.:         ::  :*    ::        . :.   *:

179  PVCLNALREVLQPAVE--QGADYLVLGCTHYPFLNEAIHHLFDNQFTLVDSGLAVARQTA  236  A3M1P5   A3M1P5_ACIBT
161  AEVKDYLKNILAPLVE--QKVDTIILGCTHYPFVSDTIQEIVGRDIQIIEPSEAVTAQLI  218  A3MA43   A3MA43_ACIBT
177  DVSLDALKRILRPWLRMKEPPDTVVLGCTHFPLLQEELLQVLPEGTRLVDSGAAIARRIA  236  P22634   MURI_ECOLI
161  PQTRALLERLLAPILE--QGCDTLILGCTHYPFVKPLLAELIPAEMAVIDTGAAVARQLE  218  Q9HVD0   MURI_PSEAE
           *..:* *  :.   :    *  ::*****:*:: .  .:.      ::: . *:: :

237  RILIKNELLCDQIRQNVARIECYVSGNNADALQP----VLQNMIPQELTWTLHNLS-----  288  A3M1P5   A3M1P5_ACIBT
219  RQLNQYHLSSES--PNEGNHIIWTSSDPLEVADVTFSLLGTRLPVETT----LDN----F--  266  A3MA43   A3MA43_ACIBT
237  WLLEHEAPDAKSADANIAFCMAMTP--G----------AEQLLPVLQRYGFETLEKLAVL  284  P22634   MURI_ECOLI
219  RVLSARALLASGQAATPR---FWTS------ALPE---EMERILP--ILWGSPESVGKLVV  265  Q9HVD0   MURI_PSEAE
      *            ..   .       .                    :*

289  -  288  A3M1P5   A3M1P5_ACIBT
267  -  266  A3MA43   A3MA43_ACIBT
285  G  285  P22634   MURI_ECOLI
266  -  265  Q9HVD0   MURI_PSEAE
```

Figure 4

LB + 10 mM D-Glu          LB

A
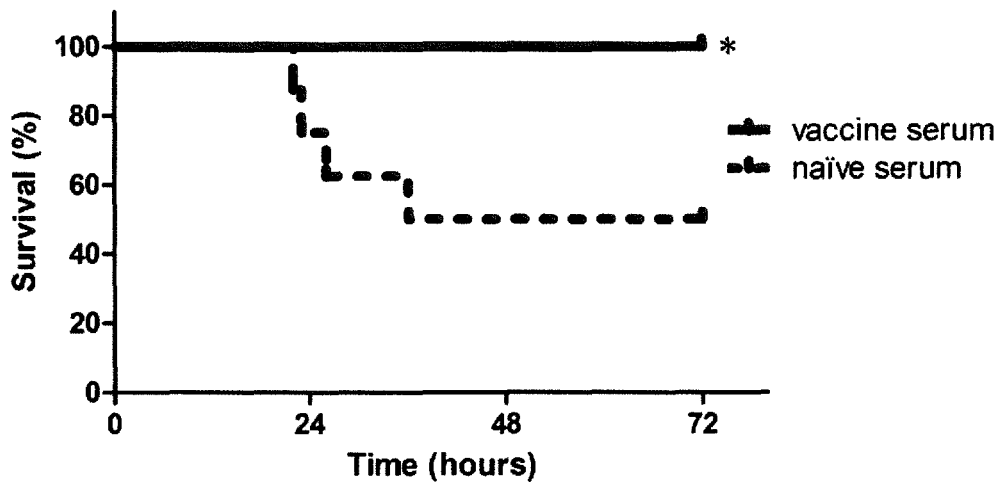
B
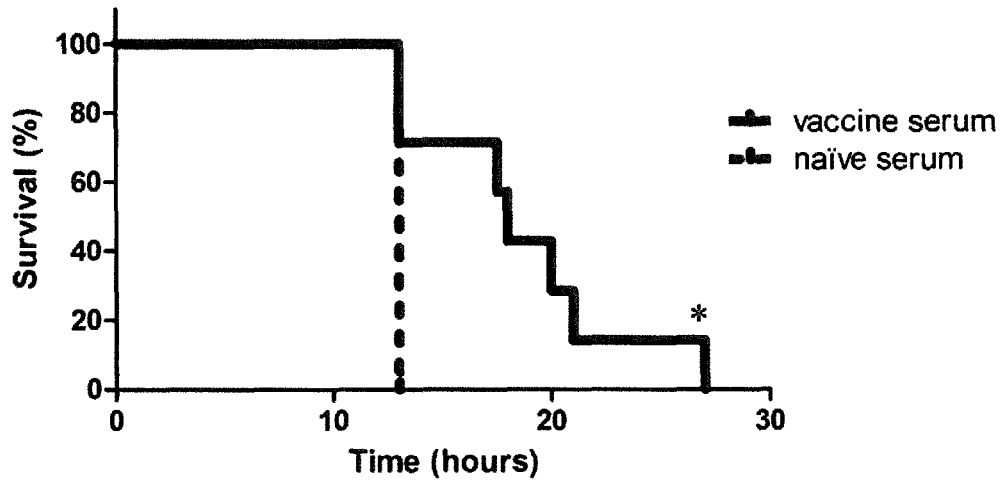
Figure 27

Cross-reactivity of IgGs
A CA-MRSA USA300LAC (Human origin)
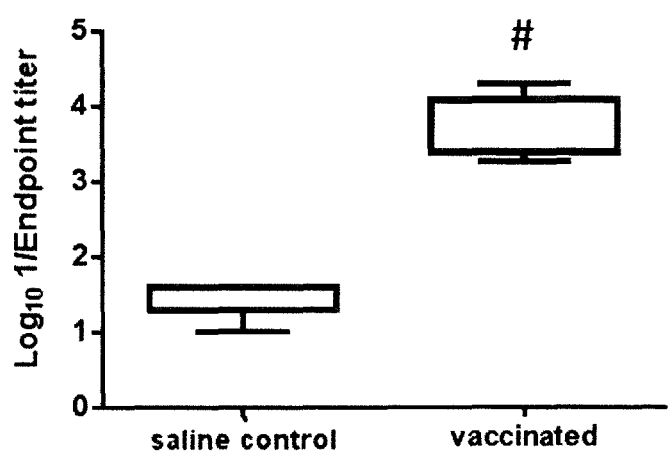
B RF122 (Bovine origin)
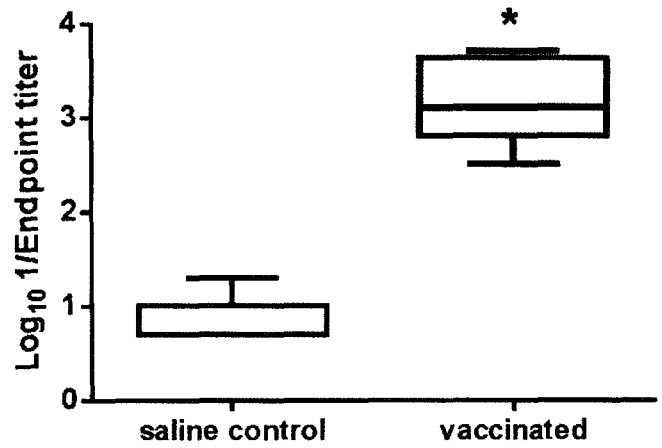
Figure 40

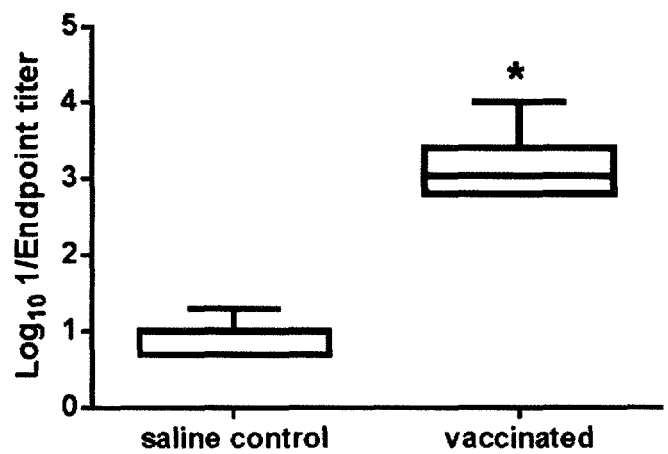
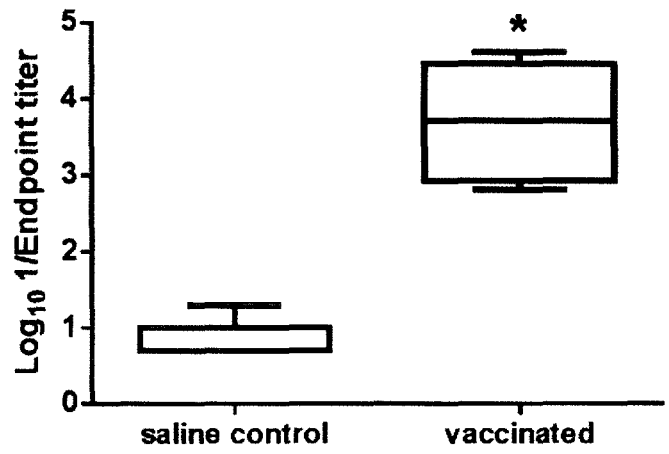
Figure 40

```
                        SEQUENCE LISTING

<160> NUMBER OF SEQ ID NOS: 50

<210> SEQ ID NO 1
<211> LENGTH: 288
<212> TYPE: PRT
<213> ORGANISM: Acinetobacter baumannii

<400> SEQUENCE: 1

Met Thr Ala Ile Gln Pro Leu Phe Thr Glu Leu Glu Pro Met Pro Lys
1               5                   10                  15

Ala Leu Ala Asp Ala Pro Ile Gly Ile Phe Asp Ser Gly Ile Gly Gly
            20                  25                  30

Met Ser Val Ala Ala Glu Ile Ala Lys Tyr Leu Pro Asn Glu Arg Ile
        35                  40                  45

Val Tyr Tyr Ala Asp Thr Ala Tyr Val Pro Tyr Gly Pro Arg Ser Asp
    50                  55                  60

Glu Glu Ile Arg Glu Leu Thr Ala Arg Ala Val Asp Trp Leu Tyr Arg
65                  70                  75                  80

Gln Gly Cys Lys Ile Ala Val Val Ala Cys Asn Thr Ala Ser Ala Phe
                85                  90                  95

Ser Leu Asp His Leu Arg Glu His Tyr Gly Glu His Phe Pro Ile Val
            100                 105                 110

Gly Leu Val Pro Ala Leu Lys Pro Ala Val Leu Gln Thr Arg Ser Lys
        115                 120                 125

Val Val Ala Val Leu Ala Thr Pro Ala Thr Phe Arg Gly Gln Leu Ile
    130                 135                 140

Lys Asp Val Val Glu Lys Phe Ala Val Pro Ala Gly Val Lys Val Met
145                 150                 155                 160
```

```
Thr Leu Thr Ser Leu Glu Leu Val Pro Cys Val Glu Ala Gly Gln Gln
                165                 170                 175

Met Ser Pro Val Cys Leu Asn Ala Leu Arg Glu Val Leu Gln Pro Ala
            180                 185                 190

Val Glu Gln Gly Ala Asp Tyr Leu Val Leu Gly Cys Thr His Tyr Pro
        195                 200                 205

Phe Leu Asn Glu Ala Ile His His Leu Phe Asp Asn Gln Phe Thr Leu
    210                 215                 220

Val Asp Ser Gly Leu Ala Val Ala Arg Gln Thr Ala Arg Ile Leu Ile
225                 230                 235                 240

Lys Asn Glu Leu Leu Cys Asp Gln Ile Arg Gln Asn Val Ala Arg Ile
                245                 250                 255

Glu Cys Tyr Val Ser Gly Asn Asn Ala Asp Ala Leu Gln Pro Val Leu
            260                 265                 270

Gln Asn Met Ile Pro Gln Glu Leu Thr Trp Thr Leu His Asn Leu Ser
        275                 280                 285

<210> SEQ ID NO 2
<211> LENGTH: 266
<212> TYPE: PRT
<213> ORGANISM: Acinetobacter baumannii

<400> SEQUENCE: 2

Met Asn Asn Asn Asn Pro Ile Gly Met Ile Asp Ser Gly Leu Gly
1               5                   10                  15

Gly Leu Ser Leu Phe Lys Tyr Ile Arg Gln Ala Leu Pro Asn Glu Asp
            20                  25                  30

Ile Ile Tyr Phe Ala Asp Ser Lys Tyr Val Pro Tyr Gly Asp Arg Glu
        35                  40                  45

Ser Asp Trp Ile Val Ser Arg Thr Thr His Leu Ile Ser Asn Leu Val
    50                  55                  60

Thr His Gly Lys Cys Lys Ala Ile Val Ile Ala Cys Asn Thr Met Thr
65                  70                  75                  80

Ala Val Ala Val Glu Thr Ile Arg Ala Gln Ile Asn Val Pro Leu Ile
                85                  90                  95

Ala Ile Glu Pro Ala Val Lys Pro Ala Val Ala Met Thr Leu Ser Lys
            100                 105                 110

His Ile Ala Val Leu Ala Thr Ala Thr Thr Val Lys Gly Lys Asn Leu
        115                 120                 125

Lys Ser Leu Ile Glu Thr Tyr Ala Gln Asp Ile Lys Val Ser Leu Val
130                 135                 140

Pro Cys Ile Gly Leu Ala Glu Lys Ile Glu Thr Gly Lys Ala His Thr
145                 150                 155                 160

Ala Glu Val Lys Asp Tyr Leu Lys Asn Ile Leu Ala Pro Leu Val Glu
                165                 170                 175

Gln Lys Val Asp Thr Ile Ile Leu Gly Cys Thr His Tyr Pro Phe Val
            180                 185                 190

Ser Asp Thr Ile Gln Glu Ile Val Gly Arg Asp Ile Gln Ile Ile Glu
        195                 200                 205

Pro Ser Glu Ala Val Thr Ala Gln Leu Ile Arg Gln Leu Asn Gln Tyr
    210                 215                 220

His Leu Ser Ser Glu Ser Pro Asn Glu Gly Asn His Ile Ile Trp Thr
225                 230                 235                 240

Ser Ser Asp Pro Leu Glu Val Ala Asp Val Thr Phe Ser Leu Leu Gly
                245                 250                 255
```

```
Thr Arg Leu Pro Val Glu Thr Thr Asp Phe
            260                 265
```

<210> SEQ ID NO 3
<211> LENGTH: 285
<212> TYPE: PRT
<213> ORGANISM: Escherichia coli

<400> SEQUENCE: 3

```
Met Ala Thr Lys Leu Gln Asp Gly Asn Thr Pro Cys Leu Ala Ala Thr
1               5                   10                  15

Pro Ser Glu Pro Arg Pro Thr Val Leu Val Phe Asp Ser Gly Val Gly
            20                  25                  30

Gly Leu Ser Val Tyr Asp Glu Ile Arg His Leu Leu Pro Asp Leu His
        35                  40                  45

Tyr Ile Tyr Ala Phe Asp Asn Val Ala Phe Pro Tyr Gly Glu Lys Ser
    50                  55                  60

Glu Ala Phe Ile Val Glu Arg Val Val Ala Ile Val Thr Ala Val Gln
65                  70                  75                  80

Glu Arg Tyr Pro Leu Ala Leu Ala Val Val Ala Cys Asn Thr Ala Ser
                85                  90                  95

Thr Val Ser Leu Pro Ala Leu Arg Glu Lys Phe Asp Phe Pro Val Val
            100                 105                 110

Gly Val Val Pro Ala Ile Lys Pro Ala Ala Arg Leu Thr Ala Asn Gly
        115                 120                 125

Ile Val Gly Leu Leu Ala Thr Arg Gly Thr Val Lys Arg Ser Tyr Thr
    130                 135                 140

His Glu Leu Ile Ala Arg Phe Ala Asn Glu Cys Gln Ile Glu Met Leu
145                 150                 155                 160

Gly Ser Ala Glu Met Val Glu Leu Ala Glu Ala Lys Leu His Gly Glu
                165                 170                 175

Asp Val Ser Leu Asp Ala Leu Lys Arg Ile Leu Arg Pro Trp Leu Arg
            180                 185                 190

Met Lys Glu Pro Pro Asp Thr Val Val Leu Gly Cys Thr His Phe Pro
        195                 200                 205

Leu Leu Gln Glu Glu Leu Leu Gln Val Leu Pro Glu Gly Thr Arg Leu
    210                 215                 220

Val Asp Ser Gly Ala Ala Ile Ala Arg Arg Thr Ala Trp Leu Leu Glu
225                 230                 235                 240

His Glu Ala Pro Asp Ala Lys Ser Ala Asp Ala Asn Ile Ala Phe Cys
                245                 250                 255

Met Ala Met Thr Pro Gly Ala Glu Gln Leu Leu Pro Val Leu Gln Arg
            260                 265                 270

Tyr Gly Phe Glu Thr Leu Glu Lys Leu Ala Val Leu Gly
        275                 280                 285
```

<210> SEQ ID NO 4
<211> LENGTH: 265
<212> TYPE: PRT
<213> ORGANISM: Pseudomonas aeruginosa

<400> SEQUENCE: 4

```
Met Ala Val Glu Ser Ala Ala Val Gly Val Phe Asp Ser Gly Val Gly
1               5                   10                  15

Gly Leu Ser Val Leu Arg Glu Ile Arg Ala Arg Leu Pro Ser Glu Ser
            20                  25                  30
```

Leu Leu Tyr Val Ala Asp Asn Ala His Val Pro Tyr Gly Glu Lys Ser
             35                  40                  45

Ala Glu Tyr Ile Arg Glu Arg Cys Glu Arg Ile Gly Asp Phe Leu Leu
 50                  55                  60

Glu Gln Gly Ala Lys Ala Leu Val Leu Ala Cys Asn Thr Ala Thr Ala
 65                  70                  75                  80

Ala Ala Ala Ala Glu Leu Arg Glu Arg Tyr Pro Gln Val Pro Leu Val
                 85                  90                  95

Ala Met Glu Pro Ala Val Lys Pro Ala Ala Ala Thr Arg Asn Gly
                100                 105                 110

Arg Val Gly Val Leu Ala Thr Thr Gly Thr Leu Lys Ser Ala Arg Phe
             115                 120                 125

Ala Ala Leu Leu Asp Arg Phe Ala Ser Asp Val Gln Val Phe Thr Gln
130                 135                 140

Pro Cys Pro Gly Leu Val Glu Arg Ile Glu Ala Gly Asp Leu Tyr Gly
145                 150                 155                 160

Pro Gln Thr Arg Ala Leu Leu Glu Arg Leu Leu Ala Pro Ile Leu Glu
                165                 170                 175

Gln Gly Cys Asp Thr Leu Ile Leu Gly Cys Thr His Tyr Pro Phe Val
            180                 185                 190

Lys Pro Leu Leu Ala Glu Leu Ile Pro Ala Glu Met Ala Val Ile Asp
            195                 200                 205

Thr Gly Ala Ala Val Ala Arg Gln Leu Glu Arg Val Leu Ser Ala Arg
210                 215                 220

Ala Leu Leu Ala Ser Gly Gln Ala Ala Thr Pro Arg Phe Trp Thr Ser
225                 230                 235                 240

Ala Leu Pro Glu Glu Met Glu Arg Ile Leu Pro Ile Leu Trp Gly Ser
                245                 250                 255

Pro Glu Ser Val Gly Lys Leu Val Val
            260                 265

<210> SEQ ID NO 5
<211> LENGTH: 266
<212> TYPE: PRT
<213> ORGANISM: Staphylococcus aureus

<400> SEQUENCE: 5

Met Asn Lys Pro Ile Gly Val Ile Asp Ser Gly Val Gly Gly Leu Thr
 1               5                  10                  15

Val Ala Lys Glu Ile Met Arg Gln Leu Pro Asn Glu Thr Ile Tyr Tyr
             20                  25                  30

Leu Gly Asp Ile Gly Arg Cys Pro Tyr Gly Pro Arg Pro Gly Glu Gln
             35                  40                  45

Val Lys Gln Tyr Thr Val Glu Ile Ala Arg Lys Leu Met Glu Phe Asp
 50                  55                  60

Ile Lys Met Leu Val Ile Ala Cys Asn Thr Ala Thr Ala Val Ala Leu
65                  70                  75                  80

Glu Tyr Leu Gln Lys Thr Leu Ser Ile Pro Val Ile Gly Val Ile Glu
                 85                  90                  95

Pro Gly Ala Arg Thr Ala Ile Met Thr Thr Arg Asn Gln Asn Val Leu
                100                 105                 110

Val Leu Gly Thr Glu Gly Thr Ile Lys Ser Glu Ala Tyr Arg Thr His
            115                 120                 125

Ile Lys Arg Ile Asn Pro His Val Glu Val His Gly Val Ala Cys Pro

```
                130             135                 140
Gly Phe Val Pro Leu Val Glu Gln Met Arg Tyr Ser Asp Pro Thr Ile
145                 150                 155                 160

Thr Ser Ile Val Ile His Gln Thr Leu Lys Arg Trp Arg Asn Ser Glu
                165                 170                 175

Ser Asp Thr Val Ile Leu Gly Cys Thr His Tyr Pro Leu Leu Tyr Lys
                180                 185                 190

Pro Ile Tyr Asp Tyr Phe Gly Gly Lys Lys Thr Val Ile Ser Ser Gly
            195                 200                 205

Leu Glu Thr Ala Arg Glu Val Ser Ala Leu Leu Thr Phe Ser Asn Glu
        210                 215                 220

His Ala Ser Tyr Thr Glu His Pro Asp His Arg Phe Phe Ala Thr Gly
225                 230                 235                 240

Asp Pro Thr His Ile Thr Asn Ile Ile Lys Glu Trp Leu Asn Leu Ser
                245                 250                 255

Val Asn Val Glu Arg Ile Ser Val Asn Asp
            260                 265

<210> SEQ ID NO 6
<211> LENGTH: 282
<212> TYPE: PRT
<213> ORGANISM: Staphylococcus aureus

<400> SEQUENCE: 6

Met Glu Lys Ile Phe Leu Asn Gly Glu Phe Val Ser Pro Ser Glu Ala
1               5                   10                  15

Lys Val Ser Tyr Asn Asp Arg Gly Tyr Val Phe Gly Asp Gly Ile Tyr
            20                  25                  30

Glu Tyr Ile Arg Val Tyr Asn Gly Lys Leu Phe Thr Val Thr Glu His
        35                  40                  45

Tyr Glu Arg Phe Leu Arg Ser Ala Asn Glu Ile Gly Leu Asp Leu Asn
    50                  55                  60

Tyr Ser Val Glu Glu Leu Ile Glu Leu Ser Arg Lys Leu Val Asp Met
65                  70                  75                  80

Asn Gln Ile Glu Thr Gly Ala Ile Tyr Ile Gln Ala Thr Arg Gly Val
                85                  90                  95

Ala Glu Arg Asn His Ser Phe Pro Thr Pro Glu Val Glu Pro Ala Ile
            100                 105                 110

Val Ala Tyr Thr Lys Ser Tyr Asp Arg Pro Tyr Asp His Leu Glu Asn
        115                 120                 125

Gly Val Asn Gly Val Thr Val Glu Asp Ile Arg Trp Leu Arg Cys Asp
    130                 135                 140

Ile Lys Ser Leu Asn Leu Leu Gly Asn Val Leu Ala Lys Glu Tyr Ala
145                 150                 155                 160

Val Lys Tyr Asn Ala Val Glu Ala Ile Gln His Arg Gly Glu Thr Val
                165                 170                 175

Thr Glu Gly Ser Ser Ser Asn Ala Tyr Ala Ile Lys Asp Gly Val Ile
            180                 185                 190

Tyr Thr His Pro Ile Asn Asn Tyr Ile Leu Asn Gly Ile Thr Arg Ile
        195                 200                 205

Val Ile Lys Lys Ile Ala Glu Asp Tyr Asn Ile Pro Phe Lys Glu Glu
    210                 215                 220

Thr Phe Thr Val Asp Phe Leu Lys Asn Ala Asp Glu Val Ile Val Ser
225                 230                 235                 240
```

```
Ser Thr Ser Ala Glu Val Thr Pro Val Ile Lys Leu Asp Gly Glu Pro
            245                 250                 255

Val Asn Asp Gly Lys Val Gly Pro Ile Thr Arg Gln Leu Gln Glu Gly
        260                 265                 270

Phe Glu Lys Tyr Ile Glu Ser His Ser Ile
        275                 280

<210> SEQ ID NO 7
<211> LENGTH: 32
<212> TYPE: DNA
<213> ORGANISM: Artificial Sequence
<220> FEATURE:
<223> OTHER INFORMATION: UP0380(NotI)F

<400> SEQUENCE: 7
cccgcggccg cggggtcctg cacctacgat ga                          32

<210> SEQ ID NO 8
<211> LENGTH: 30
<212> TYPE: DNA
<213> ORGANISM: Artificial Sequence
<220> FEATURE:
<223> OTHER INFORMATION: UP0380(BamHI)R

<400> SEQUENCE: 8
cccggatccg ggacctccaa tacctgaatc                             30

<210> SEQ ID NO 9
<211> LENGTH: 30
<212> TYPE: DNA
<213> ORGANISM: Artificial Sequence
<220> FEATURE:
<223> OTHER INFORMATION: DOWN0380(BamHI)F

<400> SEQUENCE: 9
cccggatccg gggctctgtt gtaggcattc                             30

<210> SEQ ID NO 10
<211> LENGTH: 30
<212> TYPE: DNA
<213> ORGANISM: Artificial Sequence
<220> FEATURE:
<223> OTHER INFORMATION: DOWN0380(SphI)R

<400> SEQUENCE: 10
cccgcatgcg ggcatccttg tgattgcatt                             30

<210> SEQ ID NO 11
<211> LENGTH: 32
<212> TYPE: DNA
<213> ORGANISM: Artificial Sequence
<220> FEATURE:
<223> OTHER INFORMATION: UP3398(NotI)F_II

<400> SEQUENCE: 11
cccgcggccg cgggttggtc aggtccttgt tg                          32

<210> SEQ ID NO 12
<211> LENGTH: 30
<212> TYPE: DNA
<213> ORGANISM: Artificial Sequence
<220> FEATURE:
<223> OTHER INFORMATION: UP3398(BamHI)R_II

<400> SEQUENCE: 12
```
cccggatccg ggtacagccg tcatggtgtt                              30

<210> SEQ ID NO 13
<211> LENGTH: 30
<212> TYPE: DNA
<213> ORGANISM: Artificial Sequence
<220> FEATURE:
<223> OTHER INFORMATION: DOWN3398(BamHI)F

<400> SEQUENCE: 13
cccggatccg ggacgcgttt acctgtagaa                              30

<210> SEQ ID NO 14
<211> LENGTH: 30
<212> TYPE: DNA
<213> ORGANISM: Artificial Sequence
<220> FEATURE:
<223> OTHER INFORMATION: DOWN3398(SphI)R

<400> SEQUENCE: 14
cccgcatgcg ggagcggtac aactaattgg                              30

<210> SEQ ID NO 15
<211> LENGTH: 18
<212> TYPE: DNA
<213> ORGANISM: Artificial Sequence
<220> FEATURE:
<223> OTHER INFORMATION: EXTFW0380

<400> SEQUENCE: 15
gcaattaggc acttgagg                                           18

<210> SEQ ID NO 16
<211> LENGTH: 18
<212> TYPE: DNA
<213> ORGANISM: Artificial Sequence
<220> FEATURE:
<223> OTHER INFORMATION: EXTRV0380

<400> SEQUENCE: 16
atacgctcag gttgcatc                                           18

<210> SEQ ID NO 17
<211> LENGTH: 18
<212> TYPE: DNA
<213> ORGANISM: Artificial Sequence
<220> FEATURE:
<223> OTHER INFORMATION: INTFW0380

<400> SEQUENCE: 17
agcctatgtt ccgtatgg                                           18

<210> SEQ ID NO 18
<211> LENGTH: 18
<212> TYPE: DNA
<213> ORGANISM: Artificial Sequence
<220> FEATURE:
<223> OTHER INFORMATION: INTRV0380

<400> SEQUENCE: 18
tcaaccagtg tgaattgg                                           18

<210> SEQ ID NO 19
<211> LENGTH: 18
<212> TYPE: DNA
<213> ORGANISM: Artificial Sequence

<220> FEATURE:
<223> OTHER INFORMATION: EXTFW3398

<400> SEQUENCE: 19
ccgattggaa tgattgac								18

<210> SEQ ID NO 20
<211> LENGTH: 18
<212> TYPE: DNA
<213> ORGANISM: Artificial Sequence
<220> FEATURE:
<223> OTHER INFORMATION: EXTRV3398

<400> SEQUENCE: 20
agagcattct ggtcgaag								18

<210> SEQ ID NO 21
<211> LENGTH: 18
<212> TYPE: DNA
<213> ORGANISM: Artificial Sequence
<220> FEATURE:
<223> OTHER INFORMATION: INTFW3398

<400> SEQUENCE: 21
tagcaataga accagcgg								18

<210> SEQ ID NO 22
<211> LENGTH: 18
<212> TYPE: DNA
<213> ORGANISM: Artificial Sequence
<220> FEATURE:
<223> OTHER INFORMATION: INTRV3398

<400> SEQUENCE: 22
ttgtgccgtt acagcttc								18

<210> SEQ ID NO 23
<211> LENGTH: 30
<212> TYPE: DNA
<213> ORGANISM: Artificial Sequence
<220> FEATURE:
<223> OTHER INFORMATION: UPPA4662(HindIII)F_II

<400> SEQUENCE: 23
cccaagcttg ggggcaatcc gccgtatatc						30

<210> SEQ ID NO 24
<211> LENGTH: 32
<212> TYPE: DNA
<213> ORGANISM: Artificial Sequence
<220> FEATURE:
<223> OTHER INFORMATION: UPPA4662(NotI)R

<400> SEQUENCE: 24
cccgcggccg cggggggcgtt gcccgcagac gg						32

<210> SEQ ID NO 25
<211> LENGTH: 32
<212> TYPE: DNA
<213> ORGANISM: Artificial Sequence
<220> FEATURE:
<223> OTHER INFORMATION: DOWNPA4662(NotI)F

<400> SEQUENCE: 25
cccgcggccg cgggtcgttc ctggcagacg tg						32

```
<210> SEQ ID NO 26
<211> LENGTH: 30
<212> TYPE: DNA
<213> ORGANISM: Artificial Sequence
<220> FEATURE:
<223> OTHER INFORMATION: DOWNPA4662(XbaI)R

<400> SEQUENCE: 26
ccctctagag ggtccgctct cgcagtccga                                30

<210> SEQ ID NO 27
<211> LENGTH: 18
<212> TYPE: DNA
<213> ORGANISM: Artificial Sequence
<220> FEATURE:
<223> OTHER INFORMATION: EXTFWPA4662

<400> SEQUENCE: 27
gtatcggcaa ggtggagt                                             18

<210> SEQ ID NO 28
<211> LENGTH: 18
<212> TYPE: DNA
<213> ORGANISM: Artificial Sequence
<220> FEATURE:
<223> OTHER INFORMATION: EXTRVPA4662

<400> SEQUENCE: 28
gaatggcttg atcgagtc                                             18

<210> SEQ ID NO 29
<211> LENGTH: 18
<212> TYPE: DNA
<213> ORGANISM: Artificial Sequence
<220> FEATURE:
<223> OTHER INFORMATION: INTFWPA4662

<400> SEQUENCE: 29
atccgaatcg ttgctcta                                             18

<210> SEQ ID NO 30
<211> LENGTH: 18
<212> TYPE: DNA
<213> ORGANISM: Artificial Sequence
<220> FEATURE:
<223> OTHER INFORMATION: INTRVPA4662

<400> SEQUENCE: 30
acaatacgcg ctccagct                                             18

<210> SEQ ID NO 31
<211> LENGTH: 30
<212> TYPE: DNA
<213> ORGANISM: Artificial Sequence
<220> FEATURE:
<223> OTHER INFORMATION: murIUP(MluI)F

<400> SEQUENCE: 31
cccacgcgtg ggccgaaaca aaaaacagta                                30

<210> SEQ ID NO 32
<211> LENGTH: 32
<212> TYPE: DNA
<213> ORGANISM: Artificial Sequence
<220> FEATURE:
<223> OTHER INFORMATION: murIUP(NotI)R
```

```
<400> SEQUENCE: 32
cccgcggccg cgggattcgg tcatccttac tt                              32

<210> SEQ ID NO 33
<211> LENGTH: 32
<212> TYPE: DNA
<213> ORGANISM: Artificial Sequence
<220> FEATURE:
<223> OTHER INFORMATION: murIDOWN(NotI)F

<400> SEQUENCE: 33
cccgcggccg cggggaggat ttttaatgaa ag                              32

<210> SEQ ID NO 34
<211> LENGTH: 30
<212> TYPE: DNA
<213> ORGANISM: Artificial Sequence
<220> FEATURE:
<223> OTHER INFORMATION: murIDOWN(BglII)R

<400> SEQUENCE: 34
cccagatctg ggtttcttcc attgaacttc                                 30

<210> SEQ ID NO 35
<211> LENGTH: 20
<212> TYPE: DNA
<213> ORGANISM: Artificial Sequence
<220> FEATURE:
<223> OTHER INFORMATION: murIF

<400> SEQUENCE: 35
tgtcggaggt ttgacagtag                                            20

<210> SEQ ID NO 36
<211> LENGTH: 20
<212> TYPE: DNA
<213> ORGANISM: Artificial Sequence
<220> FEATURE:
<223> OTHER INFORMATION: murIR

<400> SEQUENCE: 36
ctaacttcac gagccgtttc                                            20

<210> SEQ ID NO 37
<211> LENGTH: 20
<212> TYPE: DNA
<213> ORGANISM: Artificial Sequence
<220> FEATURE:
<223> OTHER INFORMATION: murIExtF

<400> SEQUENCE: 37
gcttgcccta aaggtattcc                                            20

<210> SEQ ID NO 38
<211> LENGTH: 20
<212> TYPE: DNA
<213> ORGANISM: Artificial Sequence
<220> FEATURE:
<223> OTHER INFORMATION: murIExtR

<400> SEQUENCE: 38
gggccactca tacttatgac                                            20

<210> SEQ ID NO 39
```

```
<211> LENGTH: 20
<212> TYPE: DNA
<213> ORGANISM: Artificial Sequence
<220> FEATURE:
<223> OTHER INFORMATION: murIseqF

<400> SEQUENCE: 39
atgactgaac aatcagtgaa                                              20

<210> SEQ ID NO 40
<211> LENGTH: 20
<212> TYPE: DNA
<213> ORGANISM: Artificial Sequence
<220> FEATURE:
<223> OTHER INFORMATION: murIseqR

<400> SEQUENCE: 40
tgatggtgcc atgtaaagtt                                              20

<210> SEQ ID NO 41
<211> LENGTH: 27
<212> TYPE: DNA
<213> ORGANISM: Artificial Sequence
<220> FEATURE:
<223> OTHER INFORMATION: datUP(MluI)F

<400> SEQUENCE: 41
cccacgcgtg aaacgtattc atatgat                                      27

<210> SEQ ID NO 42
<211> LENGTH: 29
<212> TYPE: DNA
<213> ORGANISM: Artificial Sequence
<220> FEATURE:
<223> OTHER INFORMATION: datUP(NotI)R

<400> SEQUENCE: 42
cccgcggccg catattattc ctccacgca                                    29

<210> SEQ ID NO 43
<211> LENGTH: 29
<212> TYPE: DNA
<213> ORGANISM: Artificial Sequence
<220> FEATURE:
<223> OTHER INFORMATION: datDOWN(NotI)F

<400> SEQUENCE: 43
cccgcggccg caattctttc atcatattt                                    29

<210> SEQ ID NO 44
<211> LENGTH: 27
<212> TYPE: DNA
<213> ORGANISM: Artificial Sequence
<220> FEATURE:
<223> OTHER INFORMATION: datDOWN(BglII)R

<400> SEQUENCE: 44
cccagatctg cgaatctaaa ctcggta                                      27

<210> SEQ ID NO 45
<211> LENGTH: 20
<212> TYPE: DNA
<213> ORGANISM: Artificial Sequence
<220> FEATURE:
<223> OTHER INFORMATION: datF

<400> SEQUENCE: 45
```

```
tattcaagca acgcgtggtg                                                    20

<210> SEQ ID NO 46
<211> LENGTH: 20
<212> TYPE: DNA
<213> ORGANISM: Artificial Sequence
<220> FEATURE:
<223> OTHER INFORMATION: datR

<400> SEQUENCE: 46
agttgacgtg taattgggcc                                                    20

<210> SEQ ID NO 47
<211> LENGTH: 20
<212> TYPE: DNA
<213> ORGANISM: Artificial Sequence
<220> FEATURE:
<223> OTHER INFORMATION: datExtF

<400> SEQUENCE: 47
gtcatgggtg acgtgacaac                                                    20

<210> SEQ ID NO 48
<211> LENGTH: 20
<212> TYPE: DNA
<213> ORGANISM: Artificial Sequence
<220> FEATURE:
<223> OTHER INFORMATION: datExtR

<400> SEQUENCE: 48
gcaccacctg ctgaatcaag                                                    20

<210> SEQ ID NO 49
<211> LENGTH: 20
<212> TYPE: DNA
<213> ORGANISM: Artificial Sequence
<220> FEATURE:
<223> OTHER INFORMATION: datseqF

<400> SEQUENCE: 49
gccggttgta acagaagatg                                                    20

<210> SEQ ID NO 50
<211> LENGTH: 20
<212> TYPE: DNA
<213> ORGANISM: Artificial Sequence
<220> FEATURE:
<223> OTHER INFORMATION: datseqR

<400> SEQUENCE: 50
caattgccgg gtctgcaatc                                                    20
```

LIVE ATTENUATED VACCINES

RELATED APPLICATIONS

This application is a 35 U.S.C. § 371 national stage filing of International Application No. PCT/EP2014/071926, filed on Oct. 13, 2014, which claims priority to European Patent Application No. 14382153.6, filed on Apr. 25, 2014, and Spanish Patent Application No. P201331504, filed on Oct. 11, 2013. The entire contents of each of the foregoing applications are incorporated herein by reference.

FIELD OF THE INVENTION

Live attenuated bacteria vaccines are provided. Also provided are methods by which such vaccines can be obtained.

BACKGROUND OF THE INVENTION

The means by which a warm blooded animal, including a human, overcomes microbial pathogenesis is a complex process. Immunity to microbial pathogenesis is one means by which a warm blooded animal avoids pathogenesis, or suffers a less intense pathogenic state. Incomplete immunity to a given pathogen results in morbidity and mortality in a population exposed to a pathogen. It is generally agreed that vaccines based on live but attenuated micro-organisms (live attenuated vaccines) induce a highly effective type of immune response. Such vaccines have the advantage that, once the animal host has been vaccinated, entry of the microbial pathogen into the host induces an accelerated recall of earlier, cell-mediated or humoral immunity which is able to control the further growth of the organism before the infection can assume clinically significant proportions. Vaccines based on a killed pathogen (killed vaccine) are generally conceded to be unable to achieve this type of response. However, vaccines that contain a live pathogen present, depending on the level of attenuation, the danger that the vaccinated host upon vaccination may contract the disease against which protection is being sought. Therefore, it would be desirable to have a vaccine that possesses the immunising attributes of a live micro-organism but that is not capable of causing undesirable side effects upon vaccination.

However, it is important to note that the effective use of an attenuated bacterial strain as a vaccine candidate cannot be predicted merely by such level of attenuation. In this regard, the general approach for attenuating bacteria is the removal of one or more virulence factors (genetic modified organisms—GMOs), in most cases, however, virulence factors also play a role in inducing immunity as protective epitopes. In those cases, deletion of virulence factors unavoidably impairs the immunogenic capacities of the bacterium. This is of course an unwanted situation. Therefore, a live vaccine should preferably retain the antigenic complement of the wild type strain.

Moreover, once attenuation level is established, the immune response to a particular type of vaccine candidate and the success of a vaccine composition including such micro-organisms may still be influenced by many factors as detailed below:

a. The live attenuated vaccine strain should preferably have substantially no probability for reverting to its original state (usually a virulent wild type strain) and none of the genes manipulated should be complemented by other genes causing the bacteria to be capable of causing disease (stable mutations are preferred).

b. The presence of endotoxins in a live vaccine can be a disadvantage if not considered as these molecules can cause serious systemic reactions. Also, the administration of whole-cell vaccines is a classical risk factor for local reactogenicity (severe pain, local swelling and edema, panniculitis or ulcer, etc).

c. The viability and fitness of the attenuated GMO should not be drastically affected, as some replication is expected to occur in the body to create enough of the micro-organism and its antigens to stimulate the immune system. In fact, any mutation in a gene may interfere with replication or may damage the live micro-organism in the vial, causing the vaccine to be ineffective. Therefore, each type of genetic modification must be carefully evaluated for unexpected effects on the cell.

d. Moreover, gene sharing or protein moonlighting—a phenomenon by which a protein can perform more than one function—should be considered when selecting a gene target for genetic manipulation. Many proteins that moonlight are enzymes. One example is Glutamate racemase (MurI) which is a critical enzyme in cell wall biosynthesis but also plays a role in gyrase inhibition. Owing to its multifunctional character, the usefulness of MurI-targeted strategies cannot be predicted unless mutations in these genes are obtained and evaluated for the impact on the bacterial cell physiology.

e. In addition, the type of immune response elicited by a vaccine may not be appropriate to provide an adequate protection against infection (vaccine failure). The specific requirements for an effective vaccine will vary according to the nature of the pathogen. In the case of extracellular pathogens, the major antibodies provide adaptative mechanisms for the defense of the organism, while the presence of T cells is essential in controlling intracellular organisms. In consequence, live attenuated vaccines serve as better immunogens that killed bacteria or subunit compositions by means of simple multiplication, as well as by the modifications of bacterial antigens that occur during in vivo infection. Thereby, a live attenuated strain could engender a broader and adequate immune response, especially in the intracellular phase. In this sense, gene-targeted strategies of attenuation should be carefully tested in vaccine candidates, as the ability of the manipulated bacteria to exploit the natural pathways of infection could be potentially impaired and not trigger a broadly protective immune response.

f. In addition, irrespectively of the attenuation level or the type of immune response elicited, the number of doses administrated to achieve an acceptable level of protection with a specific GMO (effective and lasting) can be unsustainable for a vaccine schedule.

g. Furthermore, the route of administration of a vaccine can determine the type of immune response mounted and to be crucial for its success. Depending on the route of administration, the vaccine may enter the organism in different ways: skin (in this case the antigen is taken up by Langerhans cells that act as antigen-presenting cells in the T-zone of regional lymph nodes); mucosa (here the capture of antigen is carried out mainly by M cells and the immune response is developed in the Peyer's patches) or blood (the antigen would target the spleen where it would be processed by splenic macrophages). Consequently, once attenuation level is established for a GMO, the site of vaccine administration could determine the failure or success of vaccination. In this regard, it has been demonstrated that intramammary but not intraperitoneally administration of a live attenuated *S. aureus* strain significantly decreases the bacterial load in mammary glands after challenge with the wild type strain. The proposed vaccine candidate, *S. aureus* 8325-4 A523, is a temperature-sensitive mutant isolated after mutagenesis with nitrosoguanidine, which replicates well at low temperatures (below 32° C.) but undergoes a limited number of divisions when transferred to the mammalian body temperature. The authors performed challenge experiments with the *S. aureus* 8325-4 wild type strain to compare bacterial loads in mammary glands between vaccinated and non-vaccinated animals as measure of vaccine protection efficacy. These authors concluded the following: "The number of *S. aureus* CFU recovered from the mammary glands of mice immunized by the intramammary route was significantly lower ($7 \times 10^2$ CFU) than that found in control mice ($1.5 \times 10^5$ CFU). Conversely, the number of CFU recovered from mammary glands of mice immunized by any of the intraperitoneal protocols was as high as that recovered form control mice glands (P>0.5)". Therefore, even with a potentially good candidate, the route of administration can determine the efficacy of the live attenuated mutant as a vaccine.

h. Lastly, a vaccine can be unable to induce cross-reactive antibodies against multiple strains of the same bacterial species. Although live attenuated strains can elicit antibodies that are protective in animal models, this protection is generally seen only when the parental strain used to create the vaccine strain is also used in the challenge studies. Broad-based protection against other strains usually is not reliable generated or tested. Moreover, antibodies produced, although adequately elicited and cross-reactive, may not last long nor be protective in a model of challenge with the wild type pathogen.

In summary, a live vaccine should be sufficiently attenuated (or a-virulent) to avoid unacceptable pathological effects, but on the other hand it must elicit an adequate immune response capable of conferring a lasting protection in the host against the disease (protective immunity) independently of the bacterial strain.

Demonstrating that a live vaccine is sufficiently attenuated (or a-virulent) to avoid unacceptable pathological effects and elicits an adequate immune response capable of conferring a lasting protection in the host against the disease (protective immunity) independently of the bacterial strain, is not an easy task. In this sense, WO99/25376 describes a method of eliciting a T cell immune response against an antigen in a mammal which comprises administering to said mammal an auxotrophic attenuated strain of *Listeria* which expresses the antigen. Said auxotrophic attenuated strain is described therein as having a mutation in at least one gene whose protein product is essential for growth of the *Listeria*. In particular, the invention describes an auxotrophic attenuated strain for the synthesis of D-alanine which further comprises DNA encoding a heterologous antigen, wherein the heterologous antigen is preferably an HIV-1 antigen.

In WO99/25376, the results are presented as showing that the auxotrophic strain of *Listeria* provides protection against challenge by *L. monocytogenes* in BALB/c mice making this strain alledgely suitable for use in a vaccine composition for protection against an infection caused by this organism. However, the experimental examples provided therein merely establish that attenuated auxotrophic D-alanine mutants of *L. monocytogenes* elicit a CTL (host cytotoxic T cell) response. An antibody-mediated immune response (humoral immunity) is not considered therein nor are results provided in this sense. Moreover, the protection effect of this mutant is therein determined by measuring the bacterial counts in the spleen of infected mice after challenge with the wild type *Listeria*. In this sense, the effectiveness of a vaccine against acute and lethal bacterial infections (especially those causing sepsis) can only be asessed if survival assays are conducted. In addition, mutant *Listeria* injected without D-alanine are described therein as providing little protection. In contrast, when D-alanine was supplemented in the initial inoculum of the mutant organism to achieve the same protection as the wild type strain (at the time of initial immunization), this had the effect of reducing the lethal dose of the mutant about 10 fold, a serious limitation for the safety of this mutant if the lost of attenuation is considered. Therefore, the results provided in WO99/25376 for the D-alanine mutants therein described, fail to demonstrate the usefulness of these mutant strains as vaccine candidates against extracellular bacterial pathogens and acute systemic infections. Moreover, the lack of cross-protection data with these mutants does not assure the effectiveness of a vaccine composed of D-alanine auxotrophs to generate a broadly protective immune response against other *L. monocytogenes* strains, much less its usefulness for generating vaccine candidates in other bacterial species.

In addition, in the detailed description of WO99/25376, the inventors make the following suggestion: "Additional potential useful targets for the generation of additional include the genes involved in the synthesis of the cell wall component D-glutamic acid. To generate D-glutamic acid auxotrophic mutants, it is necessary to inactivate the dat gene, which is involved in the conversion of D-glu+pyr to alpha-ketoglutarate+D-ala and the reverse reaction. It is also necessary to inactivate the glutamate racemase gene, dga". However, one of ordinary skill in the art will know that there is no reasonable expectation of success in light of the information presented therein that D-glutamic acid auxotrophic strains of *Listeria* can presumably confer a satisfactory level of attenuation to avoid unacceptable pathological effects and elicit an adequate immune response capable of conferring a lasting protection in the host against the disease (protective immunity). As discussed above, each gene-targeted strategy should be evaluated case by case. Moreover, the glutamate racemase enzyme has moonlinghtening functions that can affect celular viability if its coding genes are manipulated. In this sense, the use of glutamate racemase as a target to generate D-glutamate auxotrophic vaccine strains to confer protection against bacterial infections cannot be extrapolated from the previous invention, because there is no sustained evidence presented, and it is not obvious that such a strain can be immunogenic.

The latter statement, namely that it is not obvious that such D-glutamate auxotrophic vaccine strain can be immunogenic, is further sustained by the fact that there are no studies nor inventions demonstrating the ability of D-glutamate auxotrophic micro-organisms to be useful as live vaccines for conferring protection against bacterial-caused diseases in the current state of vaccine development. In this sense, and despite the considerable level of attenuation of a D-glutamic acid auxotrophic mutant demonstrated in M. P. Cabral et al, "*Blockade of glutamate racemisation during cell-wall formation prevents biofilm and proliferation of*

*Acinetobacter baumannii in vivo*", Abstract of the 23$^{rd}$ ESCMID congress (European Society of Clinical Microbiology and Infectious Diseases) held in Berlin from the 27$^{th}$ to the 30$^{th}$ of April, 2013 (the only reference showing a relation between D-glutamate auxotrophy and in vivo loss of virulence), it is noted that one of the main obstacles to the development of vaccines is the difficulty in achieving a satisfactory level of attenuation without severely compromising immunogenicity (protection). So, correlation between attenuation and protection need to be invariably tested for each gene-targeted modification strategy in order to develop an effective vaccine against bacterial infections. In this sense, the above mentioned document (M. P. Cabral et al, "*Blockade of glutamate racemisation during cell-wall formation prevents biofilm and proliferation of Acinetobacter baumannii in vivo*", Abstract of the 23$^{rd}$ ESCMID congress (European Society of Clinical Microbiology and Infectious Diseases) held in Berlin from the 27$^{th}$ to the 30$^{th}$ of April, 2013), even thought it describes the attenuation of an *Acinetobacter baumannii* strain characterized by the in-frame deletions of glutamate racemase genes, fails to provide any data showing the protective efficacy of such a strain against *A. baumannii* infections. Providing data showing the protective efficacy of an attenuated strain is crucial to determine the usefulness of such a strain as a vaccine as demonstrated in the following prior art documents.

In M. K. Hondalus et al, "*Attenuation of and protection induced by a leucine auxotroph of Mycobacterium tuberculosis*", Infection and Immunity 68 (2000) 2888-2898, a leucine auxotroph of *M. tuberculosis* was created by allelic exchange so that the mutant was unable to replicate in macrophages (proving that the bacteria was attenuated). In fact, FIG. 5 of this document shows how mice infected with the leucine auxotroph of *M. tuberculosis* had a 100% survival rate 22 weeks post-infection (establishing that leucine auxotroph was indeed attenuated). However, the leucine auxotrophic mutant was shown to be less effective than the live BCG vaccine in reducing organ burdens and tissue pathology of BALB/c mice challenged intravenously. This document illustrates that it is not enough to have an attenuated strain to have a vaccine and that immunogenicity is a key issue.

Furthermore, in M. S. Jr Pavelka et al, "*Vaccine efficacy of a lysisne auxotroph of Mycobacterium tuberculosis*", Infection and Immunity 71 (2003) 4190-4192, it was demonstrated that a single intravenous immunization of mice with the *M. tuberculosis* mutant (a lysine auxotroph of *M. tuberculosis*) did not generate a significant protective response to the subsequent aerosol and that a single immunization with the auxotroph was insufficient for reducing the bacterial burden in the lungs and spleens relative to a single immunization with BCG. Only the triple immunized mice survived as long as the control mice immunized with a single dose of BCG. Consequently, again it can be concluded that immunogenicity is a key and separate issue from attenuation.

Moreover, prior art reference Ann-Mari Svennerholm et al, "*Vaccines against enterotoxigenic Escherichia coli*", Expert review of vaccines 7 (2008) 795-804, describes genetically attenuated ETEC (enterotoxigenic *Escherichia coli*) strains as live oral vectors and characterized as safe. However when evaluating these same strains for protection, neither the attack rate for diarrhea nor the total stool volume was significantly diminished in vaccines versus placebo recipients.

Lastly, H. K. Kim et al, "*Identifying protective antigens of Staphylococcus aureus, a pathogen that suppresses host immune responses*", FASEB J. 25 (2011) 3605-3612, describes whether three attenuated mutants derived from the Newman strain by transposon insertional mutagenesis can elicit protective immunity in mice. These mutants were constructed in order to block the expression of exoproteins, surface proteins as well as the processing of surface proteins, namely saeR (*S. aureus* exoprotein), mgrA (multiple gene regulator A) and srtA (sortase A). However, mutants lacking saeR or mgrA, despite being attenuated in mice, did not to confer protective immunity to subsequent *S. aureus* infection.

Consequently, even if a reduced virulence (good level of attenuation) for a particular derivative strain is achieved, its protective capacity in the host must be experimentally assessed to be able to conclude its usefulness as a live vaccine.

BRIEF DESCRIPTION OF THE INVENTION

A first aspect of the invention refers to a method for the production of a pharmaceutical composition, preferably a vaccine, comprising mutant live auxotrophic bacterial strains for D-glutamate, wherein the pharmaceutical composition is suitable for the prophylactic treatment (before infection) and/or therapeutic treatment (after infection or after the clinical manifestation of the disease caused by the infection) of animals and/or humans against infection with the wild type form of the mutant auxotrophic bacteria of the composition, and wherein said pharmaceutical composition is produced by a method comprising the steps of:

a. obtaining mutant live auxotrophic bacterial strains for D-glutamate;
b. introducing said mutant live auxotrophic bacerial strains in a pharmaceutically acceptable carrier or diluent and optionally adding an adjuvant; and
c. Optionally freeze-drying the pharmaceutical composition.

In preferred embodiment of the first aspect of the invention, the production method comprises the steps of:

a. providing a bacterial strain capable of expressing glutamate racemase and possibly D-amino acid transaminase and comprising a peptidoglycan cell wall;
b. inactivating the gene or genes encoding for the glutamate racemase enzyme and, if needed, the gene or genes encoding for the enzyme D-amino acid transaminase in such way that the bacterial strain is no longer capable of expressing a functional glutamate racemase and/or a functional D-amino acid transaminase, wherein the inactivation of said genes thus causes said bacterial strain to be auxotrophic for D-glutamate; and
c. introducing said mutant live auxotrophic bacterial strains in a pharmaceutically acceptable carrier or diluent and optionally adding an adjuvant; and
d. Optionally freeze-drying the pharmaceutical composition.

In another preferred embodiment of the first aspect of the invention or of any of its preferred embodiments, the pharmaceutical composition is a vaccine and the production method comprises adding an adjuvant.

In another preferred embodiment of the first aspect of the invention or of any of its preferred embodiments, the bacterial strain of step a) is a gram positive or gram negative bacteria. Preferably, the bacterial strain of step a) is selected from the list of bacterial species consisting of: *Acinetobacter baumannii, Acinetobacter baylyi, Acinetobacter calcoaceticus, Acinetobacter haemolyticus, Acinetobacter junii, Acinetobacter lwoffii, Acinetobacter nosocomialis, Acinetobacter*

*pittii, Acinetobacter radioresistens, Actinobacillus lignieresii, Actinobacillus suis, Aeromonas caviae, Aeromonas hydrophila, Aeromonas veronii* subsp. *sobria, Aggregatibacter actinomycetemcomitans, Arcobacter butzleri, Arcobacter nitrofigilis, Bacillus amyloliquefaciens, Bacillus anthracis, Bacillus bataviensis, Bacillus cellulosilyticus, Bacillus cereus, Bacillus clausii, Bacillus licheniformis, Bacillus megaterium, Bacillus pumilus, Bacillus subtilis, Bacillus thuringiensis, Bacteroides fragilis, Bordetella avium, Bordetella bronchiseptica, Bordetella pertusis, Bordetella petrii, Brucella abortus, Brucella melitensis, Brucella suis, Burkholderia cenocepacia, Burkholderia mallei, Burkholderia multivorans, Burkholderia pseudomallei, Burkholderia thailandensis, Campylobacter concisus, Campylobacter fetus* subsp. *fetus, Campylobacter fetus* subsp. *venerealis, Campylobacter gracilis, Campylobacter hominis, Campylobacter jejuni, Campylobacter rectus, Campylobacter showae, Campylobacter upsaliensis, Citrobacter freundii, Citrobacter koseri, Clostridium asparagiforme, Clostridium botulinum, Clostridium butyricum, Clostridium difficile, Clostridium perfringens, Clostridium saccharobutylicum, Clostridium tetani, Corynebacterium diphtheriae, Corynebacterium pseudotuberculosis, Enterobacter aerogenes, Enterobacter cloacae, Enterococcus faecalis, Enterococcus faecium, Erysipelothrix rhusiopathiae, Escherichia coli, Fusobacterium necrophorum, Fusobacterium nucleatum, Granulicatella adiacens, Granulicatella elegans, Haemophilus equigenitalis, Haemophilus influenzae, Haemophilus parainfluenzae, Haemophilus paragallinarum, Haemophilus parasuis, Haemophilus pleuropneumoniae, Haemophilus somnus, Helicobacter pylori, Klebsiella oxytoca, Klebsiella pneumoniae, Legionella oakridgensis, Legionella pneumophila, Leptospira biflexa, Leptospira illini, Leptospira interrogans, Listeria monocytogenes, Lysinibacillus fusiformis, Lysinibacillus sphaericus, Moraxella bovis, Morganella morganii, Mycobacterium abscessus, Mycobacterium africanum, Mycobacterium avium, Mycobacterium bovis, Mycobacterium leprae, Mycobacterium tuberculosis, Neisseria gonorrhoeae, Neisseria meningitidis, Pasteurella multocida, Plesiomonas shigelloides, Propionibacterium acnes, Proteus hanseri, Proteus mirabilis, Pseudomonas aeruginosa, Salmonella cholerasuis, Salmonella enterica* subsp. *enterica, Salmonella enteritidis, Salmonella paratyphi, Salmonella typhi, Serratia plymuthica, Shigella boydii, Shigella dysenteriae, Shigella flexneri, Staphylococcus arlettae, Staphylococcus aureus, Staphylococcus capitis, Staphylococcus caprae, Staphylococcus carnosus, Staphylococcus epidermidis, Staphylococcus equorum, Staphylococcus haemolyticus, Staphylococcus hominis, Staphylococcus lugdunensis, Staphylococcus pasteuri, Staphylococcus pettenkoferi, Staphylococcus pseudointermedius, Staphylococcus saprophyticus, Staphylococcus simiae, Staphylococcus simulans, Staphylococcus warneri, Stenotrophomonas maltophilia, Streptococcus agalactiae, Streptococcus dysgalactiae, Streptococcus dysgalactiae* subsp. *equisimilis, Streptococcus equi, Streptococcus pneumoniae, Streptococcus pyogenes, Streptococcus uberis, Streptococcus zooepidermicus, Taylorella asinigenitalis, Taylorella equigenitalis, Treponema carateum, Treponema cuniculi, Treponema hyodisenteriae, Treponema pallidum, Treponema suis, Veillonella atypica, Veillonella dispar, Veillonella parvula, Veillonella ratti, Vibrio cholerae, Vibrio parahaemolyticus, Vibrio vulnificans, Yersinia enterocolitica, Yersinia pestis* and *Yersinia pseudotuberculosis.*

More preferably, said bacterial strain of step a) is selected from the list consisting of the following species: *Acinetobacter baumannii, Pseudomonas aeruginosa* and *Staphylococcus aureus.* Still more preferably, the bacterial strain is the bacterial strain of *A. baumannii* designated *Acinetobacter baumannii* Delta0380/Delta3398 and deposited under the Budapest treaty before the Spanish Type Culture Collection on Apr. 14, 2014 with strain number 8588 by Fundación Profesor Novoa Santos. Still more preferably, the bacterial strain is the bacterial strain of *P. aeruginosa* designated *Pseudomonas aeruginosa* DeltaPA4662 and deposited under the Budapest treaty before the Spanish Type Culture Collection on Apr. 14, 2014 with strain number 8589 by Fundación Profesor Novoa Santos. Still more preferably, the bacterial strain is the bacterial strain of *S. aureus* designated 132deltamurI/deltadat and deposited under the Budapest treaty before the Spanish Type Culture Collection on Jun. 11, 2014 with strain number 8587 by Fundación Profesor Novoa Santos.

A second aspect of the invention refers to a pharmaceutical composition, preferably a vaccine, comprising mutant live auxotrophic bacerial strains for D-glutamate and a pharmaceutically acceptable carrier or diluent and optionally an adjuvant, wherein said pharmaceutical composition is suitable for the prophylactic (before infection) and/or therapeutic treatment (after infection or after the clinical manifestation of the disease caused by the infection) of animals and/or humans against infection with the wild type form of the mutant auxotrophic bacteria of the composition.

In a preferred embodiment of the second aspect of the invention, said pharmaceutical composition is a vaccine and said vaccine optionally comprises an adjuvant.

In another preferred embodiment of the second aspect of the invention or of any of its preferred embodiments, said pharmaceutically acceptable carrier or diluent is selected from the list consisting of water, culture fluid, a solution of physiological salt concentration and/or stabilisers such as SPGA, carbohydrates (e.g. sorbitol, mannitol, starch, sucrose, glucose, dextran), proteins such as albumin or casein, protein containing agents such as bovine serum or skimmed milk and buffers (e.g. phosphate buffer).

In another preferred embodiment of the second aspect of the invention or of any of its preferred embodiments, said adjuvant is selected from the list consisting of Freunds Complete and Incomplete adjuvant, vitamin E, non-ionic block polymers, muramyldipeptides, ISCOMs (immune stimulating complexes), Saponins, mineral oil, vegetable oil, CARBOPOL®, the *E. coli* heat-labile toxin (LT) or Cholera toxin (CT), aluminium hydroxide, aluminium phosphate or aluminium oxide, oil-emulsions (e.g. of Bayol F® or Marcol 52®), saponins and vitamin-E solubilisate.

In another preferred embodiment of the second aspect of the invention or of any of its preferred embodiments, said pharmaceutical composition comprises a dose of mutant live auxotrophic bacterial strains for D-glutamate ranging between $10^3$ and $10^{10}$ bacteria.

In another preferred embodiment of the second aspect of the invention or of any of its preferred embodiments, said pharmaceutical composition is in a freeze-dried form.

In another preferred embodiment of the second aspect of the invention or of any of its preferred embodiments, the bacterial strain is selected from the list of bacterial species consisting of: *Acinetobacter baumannii, Acinetobacter baylyi, Acinetobacter calcoaceticus, Acinetobacter haemolyticus, Acinetobacter junii, Acinetobacter lwoffii, Acinetobacter nosocomialis, Acinetobacter pittii, Acinetobacter radioresistens, Actinobacillus lignieresii, Actinobacillus suis, Aeromonas caviae, Aeromonas hydrophila, Aeromonas veronii* subsp. *sobria, Aggregatibacter actinomycetemcomitans, Arcobacter butzleri, Arcobacter nitrofigilis, Bacillus* amyloliquefaciens, Bacillus anthracis, Bacillus bataviensis, Bacillus cellulosilyticus, Bacillus cereus, Bacillus clausii, Bacillus licheniformis, Bacillus megaterium, Bacillus pumilus, Bacillus subtilis, Bacillus thuringiensis, Bacteroides fragilis, Bordetella avium, Bordetella bronchiseptica, Bordetella pertusis, Bordetella petrii, Brucella abortus, Brucella melitensis, Brucella suis, Burkholderia cenocepacia, Burkholderia mallei, Burkholderia multivorans, Burkholderia pseudomallei, Burkholderia thailandensis, Campylobacter concisus, Campylobacter fetus subsp. fetus, Campylobacter fetus subsp. venerealis, Campylobacter gracilis, Campylobacter hominis, Campylobacter jejuni, Campylobacter rectus, Campylobacter showae, Campylobacter upsaliensis, Citrobacter freundii, Citrobacter koseri, Clostridium asparagiforme, Clostridium botulinum, Clostridium butyricum, Clostridium difficile, Clostridium perfringens, Clostridium saccharobutylicum, Clostridium tetani, Corynebacterium diphtheriae, Corynebacterium pseudotuberculosis, Enterobacter aerogenes, Enterobacter cloacae, Enterococcus faecalis, Enterococcus faecium, Erysipelothrix rhusiopathiae, Escherichia coli, Fusobacterium necrophorum, Fusobacterium nucleatum, Granulicatella adiacens, Granulicatella elegans, Haemophilus equigenitalis, Haemophilus influenzae, Haemophilus parainfluenzae, Haemophilus paragallinarum, Haemophilus parasuis, Haemophilus pleuropneumoniae, Haemophilus somnus, Helicobacter pylori, Klebsiella oxytoca, Klebsiella pneumoniae, Legionella oakridgensis, Legionella pneumophila, Leptospira biflexa, Leptospira illini, Leptospira interrogans, Listeria monocytogenes, Lysinibacillus fusiformis, Lysinibacillus sphaericus, Moraxella bovis, Morganella morganii, Mycobacterium abscessus, Mycobacterium africanum, Mycobacterium avium, Mycobacterium bovis, Mycobacterium leprae, Mycobacterium tuberculosis, Neisseria gonorrhoeae, Neisseria meningitidis, Pasteurella multocida, Plesiomonas shigelloides, Propionibacterium acnes, Proteus hanseri, Proteus mirabilis, Pseudomonas aeruginosa, Salmonella cholerasuis, Salmonella enterica subsp. enterica, Salmonella enteritidis, Salmonella paratyphi, Salmonella typhi, Serratia plymuthica, Shigella boydii, Shigella dysenteriae, Shigella flexneri, Staphylococcus arlettae, Staphylococcus aureus, Staphylococcus capitis, Staphylococcus caprae, Staphylococcus carnosus, Staphylococcus epidermidis, Staphylococcus equorum, Staphylococcus haemolyticus, Staphylococcus hominis, Staphylococcus lugdunensis, Staphylococcus pasteuri, Staphylococcus pettenkoferi, Staphylococcus pseudointermedius, Staphylococcus saprophyticus, Staphylococcus simiae, Staphylococcus simulans, Staphylococcus warneri, Stenotrophomonas maltophilia, Streptococcus agalactiae, Streptococcus dysgalactiae, Streptococcus dysgalactiae subsp. equisimilis, Streptococcus equi, Streptococcus pneumoniae, Streptococcus pyogenes, Streptococcus uberis, Streptococcus zooepidermicus, Taylorella asinigenitalis, Taylorella equigenitalis, Treponema carateum, Treponema cuniculi, Treponema hyodisenteriae, Treponema pallidum, Treponema suis, Veillonella atypica, Veillonella dispar, Veillonella parvula, Veillonella ratti, Vibrio cholerae, Vibrio parahaemolyticus, Vibrio vulnificans, Yersinia enterocolitica, Yersinia pestis and Yersinia pseudotuberculosis.

More preferably, said bacterial strain of step a) is selected from the list consisting of the following species: Acinetobacter baumannii, Pseudomonas aeruginosa and Staphylococcus aureus. Still more preferably, the bacterial strain is the bacterial strain of A. baumannii designated Acinetobacter baumannii Delta0380/Delta3398 and deposited under the Budapest treaty before the Spanish Type Culture Collection on Apr. 14, 2014 with strain number 8588 by Fundación Profesor Novoa Santos. Still more preferably, the bacterial strain is the bacterial strain of P. aeruginosa designated Pseudomonas aeruginosa DeltaPA4662 and deposited under the Budapest treaty before the Spanish Type Culture Collection on Apr. 14, 2014 with strain number 8589 by Fundación Profesor Novoa Santos. Still more preferably, the bacterial strain is the bacterial strain of S. aureus designated 132deltamurI/deltadat and deposited under the Budapest treaty before the Spanish Type Culture Collection on Jun. 11, 2014 with strain number 8587 by Fundación Profesor Novoa Santos.

A third aspect of the invention refers to a mutant live auxotrophic bacterial strain for D-glutamate, wherein said bacterial strain is the bacterial strain of P. aeruginosa designated Pseudomonas aeruginosa DeltaPA4662 and deposited under the Budapest treaty before the Spanish Type Culture Collection on Apr. 14, 2014 with strain number 8589 by Fundación Profesor Novoa Santos.

A third aspect of the invention also refers to a mutant live auxotrophic bacterial strain for D-glutamate, wherein said bacterial strain is the bacterial strain of S. aureus designated 132deltamurI/deltadat and deposited under the Budapest treaty before the Spanish Type Culture Collection on Jun. 11, 2014 with strain number 8587 by Fundación Profesor Novoa Santos.

A fourth aspect of the invention refers to the bacterial strain as defined in the third aspect of the invention, for use as a medicament, in particular for use as a vaccine.

A fifth aspect of the invention refers to the pharmaceutical composition of the second aspect of the invention or the mutant live auxotrophic bacterial strain for D-glutamate of the third or fourth aspects of the invention, for use in a method of prophylactic treatment (before infection) and/or therapeutic treatment (after infection or after the clinical manifestation of the disease caused by the infection) of animals and/or humans against infection with the wild type form of the mutant auxotrophic bacteria of the composition.

A sixth aspect of the invention refers to an antibody or fragment thereof selected from the group consisting of Fab, F(ab')2, Fv, scFv, di-scFv and sdAB, capable of recognizing a mutant live auxotrophic bacterial strain for D-glutamate, wherein said antibody or fragment thereof is suitable for the prophylactic treatment (before infection) and/or therapeutic treatment (after infection or after the clinical manifestation of the disease caused by the infection) of animals and/or humans against infection with the wild type form of the mutant auxotrophic bacteria of the composition.

A seventh aspect of the invention refers to an antibody or fragment thereof selected from the group consisting of Fab, F(ab')2, Fv, scFv, di-scFv and sdAB, obtained or obtainable after immunization of a mammal with a mutant live auxotrophic bacterial strain for D-glutamate, wherein said antibody or fragment thereof is suitable for the prophylactic treatment (before infection) and/or therapeutic treatment (after infection or after the clinical manifestation of the disease caused by the infection) of animals and/or humans against infection with the wild type form of the mutant auxotrophic bacteria of the composition An eighth aspect of the invention refers to a pharmaceutical composition, preferably a vaccine, comprising the antibodies or fragments thereof of any of the sixth or seventh aspects of the invention and a pharmaceutically acceptable carrier or diluent and optionally an adjuvant, wherein said pharmaceutical composition is suitable for the prophylactic (before infection) and/or therapeutic treatment (after infection or after the clinical manifestation of the disease caused by the infection) of animals and/or humans against infection with the wild type form of the mutant auxotrophic bacteria of the composition. In a preferred embodiment of the eighth aspect of the invention, said pharmaceutical composition is a vaccine wherein said vaccine optionally comprises an adjuvant.

A ninth aspect of the invention refers to the antibodies or fragments thereof of the sixth or seventh aspects of the invention, for use in therapy, in particular for use in passive immunization.

A tenth aspect of the invention refers to the pharmaceutical composition of the eighth aspect of the invention or the antibodies or fragments thereof of any of the sixth or seventh aspects of the invention, for use in a method of prophylactic treatment (before infection) and/or therapeutic treatment (after infection or after the clinical manifestation of the disease caused by the infection) of animals and/or humans against infection with the wild type form of the mutant auxotrophic bacteria of the composition.

An eleventh aspect of the invention refers to the pharmaceutical composition of the second or eighth aspects of the invention or the mutant live auxotrophic bacterial strain for D-glutamate of the third aspect of the invention or the antibodies or fragments thereof of any of the sixth or seventh aspects of the invention, for use in a method of prophylactic treatment (before infection) and/or therapeutic treatment (after infection or after after the clinical manifestation of the disease caused by the infection) of animals and/or humans against infection with the wild type form of the mutant auxotrophic bacteria of the composition and wherein said composition, bacterial strain or antibody or fragment thereof is administered intranasally, intradermally, subcutaneously, orally, by aerosol, intramuscularly, wing web and eye-drop administration.

In addition, the authors of the present invention have surprisingly found that by using a kit or device comprising an antibody or fragment thereof of the invention, the kit permits a reliable qualitative and/or quantitative analysis of bacterial species in a biological of sample of a subject and, in particular, in the plasma of subjects suspected of suffering from a disease of bacterial origin.

Therefore, a twelfth aspect of the invention refers to a kit or device comprising the antibody or fragment thereof of any of the seventh or eighth aspect of the invention.

A preferred embodiment of the twelfth aspect of the invention refers to a kit or device for detecting an infection of bacterial origin through an immunoassay comprising:
(i) a first antibody called "capture antibody" as defined in any of the sixth or seventh aspects of the invention, wherein said first antibody is preferably attached to a solid support;
(ii) a second labeled antibody called "detection antibody" which recognizes a region other than the region recognized by the first antibody, wherein said second antibody comprises a marker which may be fluorescent, luminescent or an enzyme;
(iii) a reagent showing affinity for the second antibody, said reagent being coupled to a first member of a binding pair; and
(iv) a second member of a binding pair coupled to a fluorescent, luminescent or an enzyme, wherein the binding pair is selected from the group consisting of: hapten and antibody; antigen and antibody; biotin and avidin; biotin and streptavidin; a biotin analogue and avidin; a biotin analogue and streptavidin; sugar and lectin; an enzyme and a cofactor; a nucleic acid or a nucleic acid analogue and the complementary nucleic acid or nucleic acid analogue.

A thirteenth aspect of the invention refers to the use of the kit or device of the twelfth aspect of the invention, for the qualitative and/or quantitative determination of bacterial species or bacterial strains in a biological sample from a mammal, in particular, in the plasma of a mammal suspected of suffering from a bacterial disease.

A fourteenth aspect of the invention refers to a method of cultivation of bacterial strains auxotrophic for D-glutamate comprising the utilization of a concentration of D-glutamate between 0.00001 and 120 mM. Preferably, the concentration range of D-glutamate is between 0.01-50 mM. More preferably, the concentration range of D-glutamate is between 10-20 mM.

BRIEF DESCRIPTION OF THE FIGURES

FIG. 4 shows the alignment of the amino acid sequences of the two MurI glutamate racemases of *A. baumannii* ATCC 17978 (A3MIP5_ACIBT, SEQ ID NO: 1 and A3MA43_ACIBT, SEQ ID NO: 2), *Escherichia coli* (MURI_ECOLI, SEQ ID NO: 3) and *P. aeruginosa* (MURI_PSEAE, SEQ ID NO: 4) using the Clustal Omega program. Identical residues in all the glutamate racemases are depicted with a dark gray background.

FIG. 27 is the percent survival of BALB/c mice (n=8) following intraperitoneal injection of a 0.4× dose of P. aeruginosa PAO1 wild type strain. In (A), mice were passively immunized with vaccine serum (generated with the ΔPA4662 vaccine) or administrated naïve serum prior to infection. In (By, mice were administered two dosis of vaccine serum (generated with the ΔPA4662 strain) or naïve serum after the development of an acute sepsis symptoms. *P<0.05 survival of mice passively immunized with vaccine serum compared to mice receiving naïve serum. P-value, according to the Mantel-Cox test (log-rank test).

FIG. 40 shows the cross-reactivity ($Log_{10}$ 1/Endpoint titer) of IgG antibodies produced by BALB/c mice (n=6-9) pre-immunized with a 10× dose of ΔmurI/Δdat strain, and in non-immunized mice (saline control) against *S. aureus* strains of different origin: (A) USA300LAC (human); (B) RF122 (bovine); (C) ED133 (ovine); (D) ED98 (poultry). The antibody titers were determined by indirect ELISA. #P<0.0001 and *P<0.0006 compared with the group of non-immunized mice. P-value according to the Mann-Whitney U test. The boxes represent the first and third quartiles; the horizontal line represents the median; the whiskers represent the range.

DESCRIPTION OF THE INVENTION

Definitions

Figure 1:
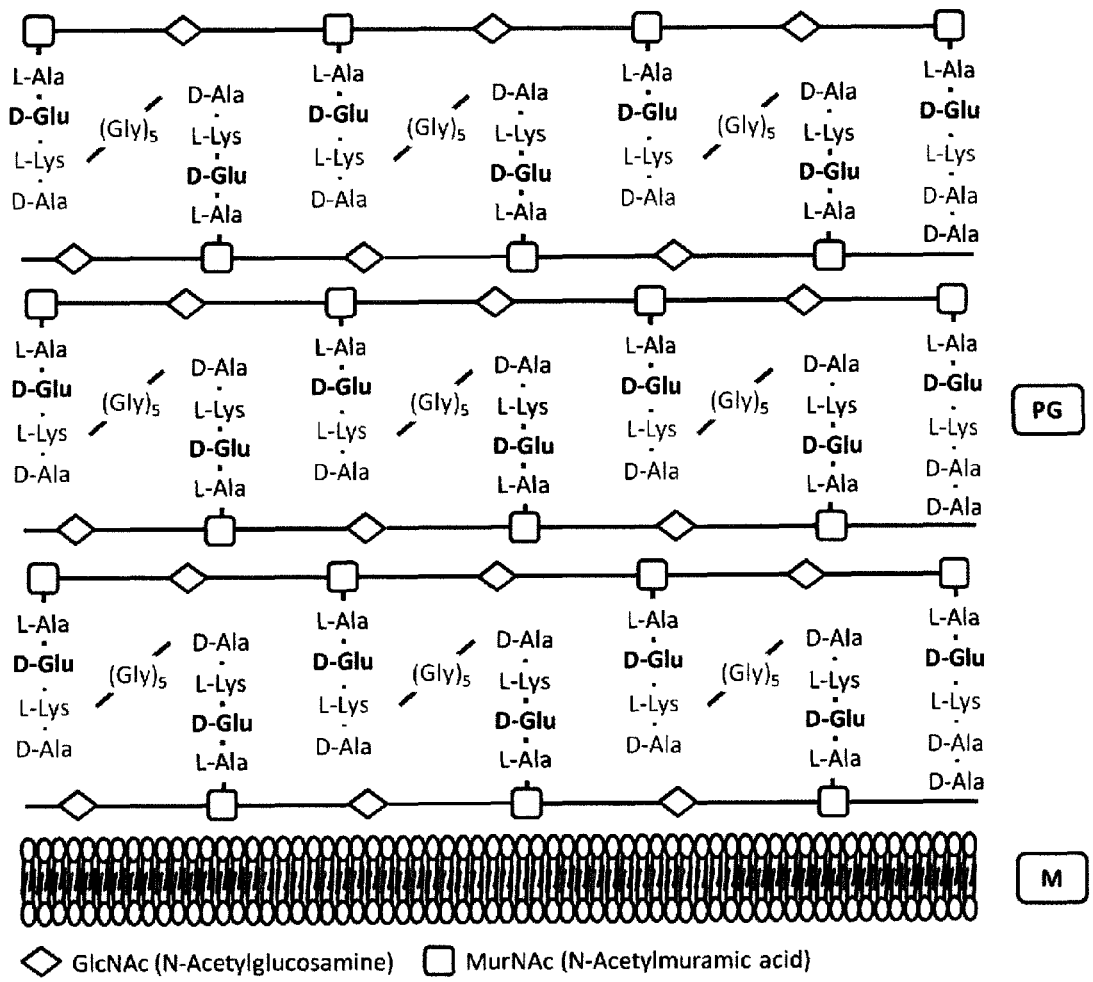
FIG. 1 schematically shows the general structure of the bacterial wall of a gram positive bacterium (non-depicted teichoic acids and proteins). PG: peptidoglycan (murein). M: cytoplasmic membrane.

In the context of the present invention, the term "D-glutamate" is understood as the compound or molecule with molecular formula $C_5H_9NO_4$, molecular weight 147.129 (g/mol) and having the D-enantiomer form of glutamate. Its systematic name is "D-glutamic acid", but it can also be designated as (without being limited to) "D-Glu", "D-2-amino pentanoic acid", "glutamic acid D-form", "(R)-2-amino pentanoic acid" and H-D-Glu-OH. Its nomenclature in the IUPAC (International Union of Pure and Applied Chemistry) system is (2R)-2-amino pentanoic acid and its identifier in the "PubChem Compound" database is 6893-26-1.

In the context of the present invention, the term "glutamate racemase" is understood as the protein catalyzing the interconversion reaction of L-glutamate to D-glutamate, which is necessary for bacterial wall synthesis. Its EC identifier (Enzyme Commission number) is 5.1.1.3. This protein is easily and invariably identified in nucleotide or amino acid sequence databases by its EC code, which refers to an enzyme of which the catalytic activity is L-glutamate=D-glutamate, because the designation thereof can be variable. Therefore, in some *Acinetobacter baumannii* strains, the glutamate racemase enzymatic function can be attributed to proteins the designation of which is L-alanine-LD-glutamate racemase/epimerase, Asp/Glu/hydantoin racemase, bacitracin synthetase 1 (BA1), aspartate/glutamate racemase, among others.

In the context of the present invention, the term "D-amino acid transaminase" is understood as the protein catalyzing the interconversion reaction of D-alanine and 2-oxoglutarate to pyruvate and D-glutamate. Its EC identifier is 2.6.1.21. This protein is easily and invariably identified in nucleotide or amino acid sequence databases by its EC code, which refers to an enzyme of which the catalytic activity is D-alanine+2-oxoglutarate=pyruvate+D-glutamate, because the designation thereof can be variable.

In the context of the present invention, the term "auxotrophic for D-glutamate" is understood as the lack of a functional metabolic pathway generating the D-glutamate substance, on which the thus designated bacterium depends for growth, due to the inability to synthesize this compound.

In the context of the present invention, the term "MurI" is understood as being synonymous with the term "glutamate racemase".

In the context of the present invention, the term "Dat" is understood as being synonymous with the term "D-amino acid transaminase".

In the context of the present invention, the term "murI" is understood as a gene or nucleotide sequence encoding a glutamate racemase protein. Depending on the *Acinetobacter baumannii*, *Pseudomonas aeruginosa* and *Staphylococcus aureus* strain, the chromosomal genes encoding the glutamate racemase protein can be called (without being limited to) murI, murI_1 or murI_2, or they can be uniquely identified by their chromosomal locus.

In the context of the present invention, the term "dat" is understood as a gene or nucleotide sequence encoding a D-amino acid transaminase protein. Depending on the *Staphylococcus aureus* strain, the chromosomal genes encoding the D-amino acid transaminase protein can be called (without being limited to) dat, or it can be uniquely identified by their chromosomal locus.

In the context of the present invention, the term "inactivation" is understood as the blocking of the expression of a specific gene or of a protein either through molecular modification or negative regulation of one or both. Molecular modification includes the use of conventional recombinant DNA techniques which in turn include: the substitution of one or several nucleotides, the insertion of one or several nucleotides, the partial or complete deletion of a gene, chemically-induced or radiation-induced disruption by mutagenesis. Negative regulation of the expression of a gene or protein includes transcriptional and post-transcriptional gene silencing.

In the context of the present invention, the term "*Acinetobacter baumannii*" is defined as any microorganism belonging to the "Bacteria" domain, "Proteobacteria" phylum, "Gammaproteobacteria" class, "Pseudomonadales" order, "Moraxellaceae" family, "*Acinetobacter*" genus, "*calcoaceticus/baumannii*" complex and "*A. baumannii*" species.

The microorganisms thus defined are characterized by being gram negative, strictly aerobic, non-fermenting and oxidase-negative.

In the context of the present invention, the term "ATCC 17978" refers to any bacterial strain with the identifier 17978 in the American Type Culture Collection and belonging to the "Bacteria" domain, "Proteobacteria" phylum, "Gammaproteobacteria" class, "Pseudomonadales" order, "Moraxellaceae" family, "*Acinetobacter*" genus, "*calcoaceticus/baumannii*" complex and "*A. baumannii*" species.

In the context of the present invention, the term "locus A2S_0380" is defined as physical position "0380" in the chromosome of *A. baumannii* strain ATCC 17978 the gene of which is referred to as A1S_0380 or murI and the product of which is glutamate racemase protein.

In the context of the present invention, the term "locus A1S_3398" is defined as physical position "3398" in the chromosome of *A. baumannii* strain ATCC 17978 the gene of which is referred to as A1S_3398 or murI and the product of which is glutamate racemase protein.

In the context of the present invention, the term "Δ0380" is defined as the absence of locus A1S_0380 in the chromosome of *Acinetobacter baumannii* strain ATCC 17978.

In the context of the present invention, the term "Δ3398" is defined as the absence of locus A1S_3398 in the chromosome of *Acinetobacter baumannii* strain ATCC 17978.

In the context of the present invention, the term "double mutation Δ0380/Δ3398" is defined as the simultaneous absence of loci A1S_0380 and A1S_3398 in the chromosome of *Acinetobacter baumannii* strain ATCC 17978.

In the context of the present invention, the term "ATCC 19606" refers to any bacterial strain with the identifier 19606 in the American Type Culture Collection and belonging to the "Bacteria" domain, "Proteobacteria" phylum, "Gammaproteobacteria" class, "Pseudomonadales" order, "Moraxellaceae" family, "*Acinetobacter*" genus, "*calcoaceticus/baumannii*" complex and "*A. baumannii*" species.

In the context of the present invention, the term "AbH12O-A2" as used herein, refers to the bacterial strain thus designated and belonging to the "Bacteria" domain, "Proteobacteria" phylum, "Gammaproteobacteria" class, "Pseudomonadales" order, "Moraxellaceae" family, "*Acinetobacter*" genus, "calcoaceticus/baumannii" complex and "*A. baumannii*" species. It is a highly invasive strain which was isolated in a hospital outbreak that caused several patients to die, and is characterized by its resistance pattern with respect to multiple antibiotics (described in Merino et al., *Antimicrob Agents Chemother,* 54(6):2724-7 (2010)).

In the context of the present invention, the term "Ab307-0294", as used herein, refers to the bacterial strain thus designated and belonging to the "Bacteria" domain, "Proteobacteria" phylum, "Gammaproteobacteria" class, "Pseudomonadales" order, "Moraxellaceae" family, "*Acinetobacter*" genus, "*calcoaceticus/baumannii*" complex and "*A. baumannii"* species. This is a highly virulent capsulated strain of *A. baumannii* that has been studied as a model pathogen (as described in Russo et al, Infection and Immunity, 78 (9): 3993-4000 (2010)).

In the context of the present invention, the term "*Pseudomonas aeruginosa*" is defined as any organism belonging to the "Bacteria" domain, "Proteobacteria" phylum, "Gammaproteobacteria" class, "Pseudomonadales" order, "Pseudomonadaceae" family, "*Pseudomonas*" genus and "*P. aeruginosa*" species. *P. aeruginosa* is a Gram negative, aerobic, coccobacillus bacterium with unipolar motility.

In the context of the present invention, the term "PAO1" refers to any bacterial strain with the universal identifier PAO1 and belonging to the "Bacteria" domain, "Proteobacteria" phylum, "Gammaproteobacteria" class, "Pseudomonadales" order, "Pseudomonadaceae" family, "*Pseudomonas*" genus and "*P. aeruginosa*" species.

In the context of the present invention, the term "PA4662" is defined as physical position "4662" in the chromosome of *P. aeruginosa* strain PAO1 the gene of which is referred to as PA4662 or murI and the product of which is glutamate racemase protein.

In the context of the present invention, the term "ΔPA4662" is defined as the absence of locus PA4662 in the chromosome of *Pseudomonas aeruginosa* strain PAO1.

In the context of the present invention, the terms "PA28562", "PA51430664", "PA26132" and "PA29475", as used herein, refer to the bacterial strains thus designated and belonging to the "Bacteria" domain, "Proteobacteria" phylum, "Gammaproteobacteria" class, "Pseudomonadales" order, "Pseudomonadaceae" family, "*Pseudomonas*" genus and "*P. aeruginosa*" species.

In the context of the present invention, the term "PAST175", as used herein, refers to the bacterial strain with the MLST sequence type 175 (ST175) and belonging to "Bacteria" domain, "Proteobacteria" phylum, "Gammaproteobacteria" class, "Pseudomonadales" order, "Pseudomonadaceae" family, "*Pseudomonas*" genus and "*P. aeruginosa*" species. This strain was previously identified as an internationally spred high-risk clone, as described in M. Garcia-Castillo et al, Journal of Clinical Microbiology 49 (2011) 2905-2910.

In the context of the present invention, the term "PA12142", as used herein, refers to the bacterial strain 12142 (epidemic Liverpool strain) as described in M. Tomás et al, Antimicrobial Agents and Chemotherapy 54 (2010) 2219-2224. This strain belongs to "Bacteria" domain, "Proteobacteria" phylum, "Gammaproteobacteria" class, "Pseudomonadales" order, "Pseudomonadaceae" family, "*Pseudomonas*" genus and "*P. aeruginosa"*.

In the context of the present invention, the term "*Staphylococcus aureus*" is defined as any microorganism belonging to the "Bacteria" domain, "Firmicutes" phylum, "Bacilli" class, "Bacillales" order, "Staphylococcaceae" family, "*Staphylococcus*" genus and "*S. aureus*" species. The microorganisms thus defined are characterized by being Gram positive, facultative anaerobic, coccal bacterium.

In the context of the present invention, the term "132" refers to any bacterial strain with the same designation and belonging to the "Bacteria" domain, "Firmicutes" phylum, "Bacilli" class, "Bacillales" order, "Staphylococcaceae" family, "*Staphylococcus*" genus and "*S. aureus*" species. This is a clinical methicillin resistant strain (Vergara-Irigaray et al, Infection and Immunity, 77 (9):3978-3991 (2009)), and was used in this invention as a model to generate an auxotrophic mutant of "*Staphylococcus aureus"*.

In the context of the present invention, the term "ΔmurI" is defined as the absence of locus murI in the chromosome of *Staphylococcus aureus* strain 132.

In the context of the present invention, the term "Δdat" is defined as the absence of locus dat in the chromosome of *Staphylococcus aureus* strain 132.

In the context of the present invention, the term "double mutation ΔmurI/Δdat" is defined as the simultaneous absence of murI and dat genes in the chromosome of *Staphylococcus aureus* strain 132.

In the context of the present invention, the term "132 Δspa", as used herein, is meant a microorganism with the same designation and belonging to the "Bacteria" domain, "Firmicutes" phylum, "Bacilli" class, "Bacillales" order, "Staphylococcaceae" family, "*Staphylococcus*" genus and "*S. aureus*" species. The microorganism thus defined is a *S. aureus* 132 strain with deletion in the spa gene (Vergara-Irigaray et al, Infection and Immunity, 77 (9): 3978-3991 (2009)).

In the context of the present invention, the term "RN4220", as used herein, is meant a microorganism with the same designation and belonging to the "Bacteria" domain, "Firmicutes" phylum, "Bacilli" class, "Bacillales" order, "Staphylococcaceae" family, "*Staphylococcus*" genus and "*S. aureus*" species. The microorganism thus defined is a *S. aureus* cloning intermediate strain (Nair et al, Journal Bacteriology, 193(9): 2332-2335 (2011)).

In the context of the present invention, the term "USA300LAC", as used herein, is meant a microorganism with the same designation and belonging to the "Bacteria" domain, "Firmicutes" phylum, "Bacilli" class, "Bacillales" order, "Staphylococcaceae" family, "*Staphylococcus*" genus and "*S. aureus*" species. The microorganism thus defined is an epidemic methicillin-resistant *S. aureus* strain responsible for community acquired infections in healthy individuals (Diep et al, Lancet 4; 397(9512):731-739 (2006)).

In the context of the present invention, the term "RF122", as used herein, refers to the bacterial strain with the MLST sequence type 151 (ST175) and clonal complex 151

(CC151) and belonging to the "Bacteria" domain, "Firmicutes" phylum, "Bacilli" class, "Bacillales" order, "Staphylococcaceae" family, "*Staphylococcus*" genus and "*S. aureus*" species. The microorganism thus defined is a bovine mastitis-causing strain isolated from a cow presenting clinical mastitis (Herron-Olson L et al, PloS ONE 2:e1120 (2007)).

In the context of the present invention, the term "ED133", as used herein, refers to the bacterial strain with the MLST sequence type 133 (ST175) and clonal complex 133 (CC133) and belonging to the "Bacteria" domain, "Firmicutes" phylum, "Bacilli" class, "Bacillales" order, "Staphylococcaceae" family, "*Staphylococcus*" genus and "*S. aureus*" species. The microorganism thus defined is an ovine mastitis-causing strain isolated in France (Guinane et al, Genome Biol Evol 2:454-466 (2010)).

In the context of the present invention, the term "ED98", as used herein, refers to the bacterial strain with the MLST sequence type 5 (ST5) and clonal complex 5 (CC5) and belonging to the "Bacteria" domain, "Firmicutes" phylum, "Bacilli" class, "Bacillales" order, "Staphylococcaceae" family, "*Staphylococcus*" genus and "*S. aureus*" species. The microorganism thus defined is an avian-adapted strain isolated from a diseased broiler chicken (Lowder et al, PNAS 106(46):19545-50 (2009)).

In the context of the present invention, the term "glutamate racemase-deficient bacterial strains" is understood as any bacterial strain unable to produce a functional and/or active form of glutamate racemase enzyme. This deficiency can be due to: blocking of the expression of the coding genes thereof, post-transcriptional modifications and post-translational modifications affecting enzymatic activity, allosteric regulation or the cellular location of this enzyme.

In the context of the present invention, the term "passive immunization" is used to refer to the administration of antibodies or fragments thereof to an individual with the intent of conferring immunity to that individual.

In the context of the present invention, the expression "therapeutically effective amount" refers to the amount of antibodies of the invention or of attenuated bacterial strains of the invention that allow producing the desired effect. The pharmaceutically acceptable adjuvants and carriers that can be used in said compositions are carriers known by persons skilled in the art. The compositions provided by this invention can be facilitated through any administration route, for which purpose said composition will be formulated in the suitable dosage form and with the excipients that are pharmacologically acceptable for the chosen administration route.

In the context of the present invention, the term "vaccine" refers to an antigenic preparation used to establish an immune system response to a disease.

DETAILED DESCRIPTION OF THE INVENTION

As already stated, a bacterial strain is auxotrophic for D-glutamate if it has completely lost the ability to produce D-glutamate. Throughout the present invention we shall show that bacterial strains auxotrophic for D-glutamate have characteristics that make them especially suitable for use as vaccines. This is the case, since these specific types of bacterial strains (auxotrophic for D-glutamate) are sufficiently a-virulent (attenuated) to avoid unacceptable pathological effects, induce a sufficient level of immunity in the host and have substantially no probability for reverting to a virulent wild type strain.

All of these characteristics provide for a novel technological platform for the design and production of vaccines having potential application in a wide variety of bacterial strains (universality). This fact (the versatility or universality of the invention) is clearly demonstrated throughout the present invention since the authors have put the invention into practice in three completely unrelated bacterial species (*Acinetobacter baumannii* (*A. baumannii*), *Pseudomonas aeruginosa* (*P. aeruginosa*) and *Staphylococcus aureus* (*S. aureus*)). For each of these completely unrelated bacterial species D-glutamate auxotrophic strains were produced and as demonstrated in the examples below, all of these mutant strains were sufficiently a-virulent (attenuated) to avoid unacceptable pathological effects but capable of inducing a sufficient level of immunity in the host. Consequently all of these strains are excellent vaccine candidates.

In order to demonstrate the above, the authors of the present invention first needed to prove that all auxotrophic D-glutamate strains gave rise to attenuated strains incapable of producing unacceptable pathological effects in the host. For this purpose the authors used nosocomial pathogen *A. baumannii* (see example 5).

For this purpose and as shown in example 5, the authors of the present invention induced a systemic infection in BALB/c mice through, on the one hand, the intraperitoneal administration of an inoculum of *A. baumannii* wild type strain ATCC 17978 and through, on the other hand, the intraperitoneal administration of an inoculum of the double mutant strain Δ0380/Δ3398 (an *A. baumannii* strain deficient in the enzyme glutamate racemase and thus a D-glutamate auxotrophic strain).

Figure 10:
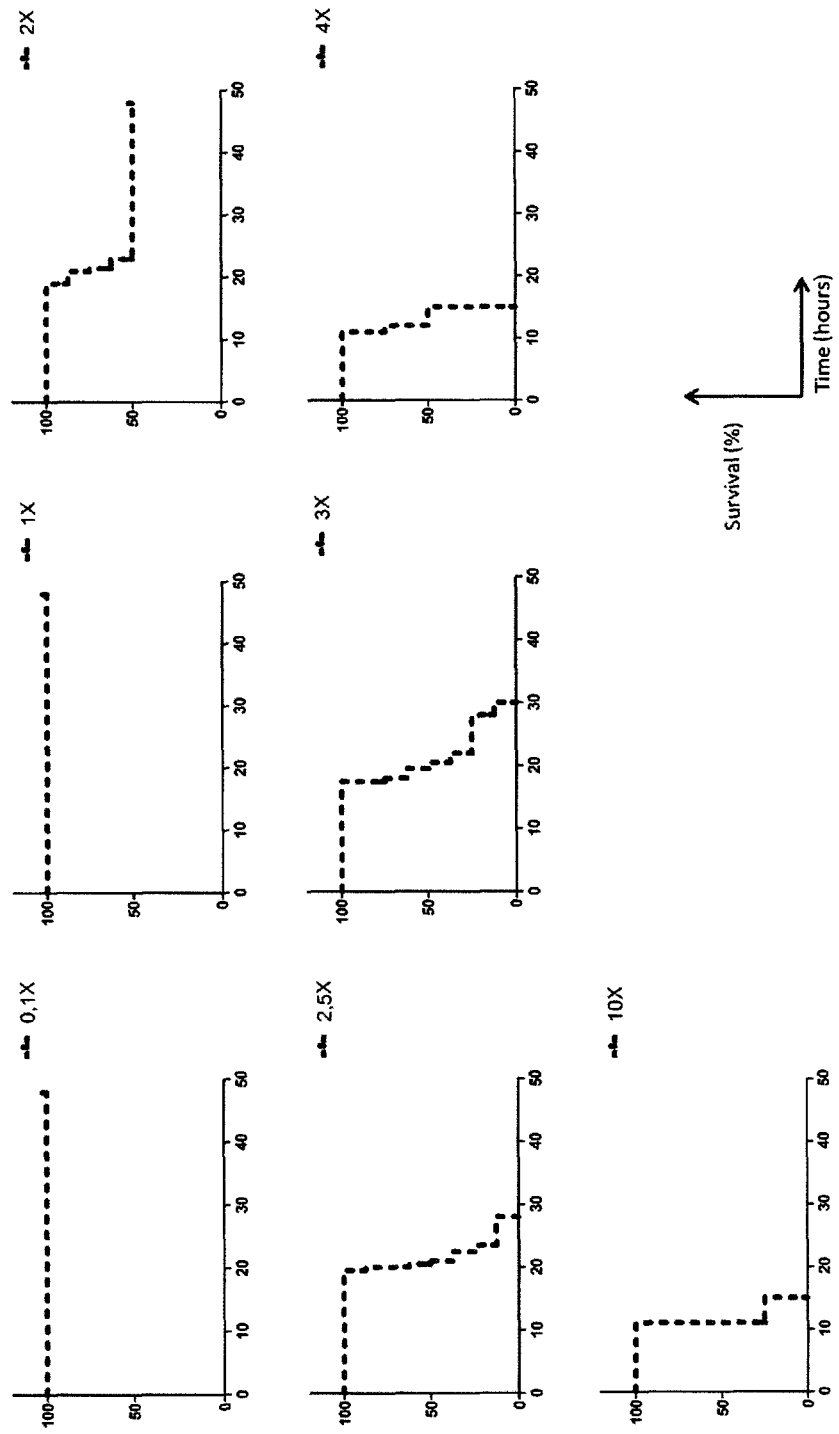
FIG. 10 shows the percentage of survival of BALB/c mice after intraperitoneal injection with different doses of *A. baumannii* wild type strain ATCC 17978 (A) and Δ0380/Δ3398 mutant strain (B) (n=6) to determine the lethal dose (LD) for which 100% of susceptible mice will die ($LD_{100}$) (A) $LD_{100}$=2.5×; (B) $LD_{100}$=6×. Mice survival was monitored during 7 days.
Figure 10:
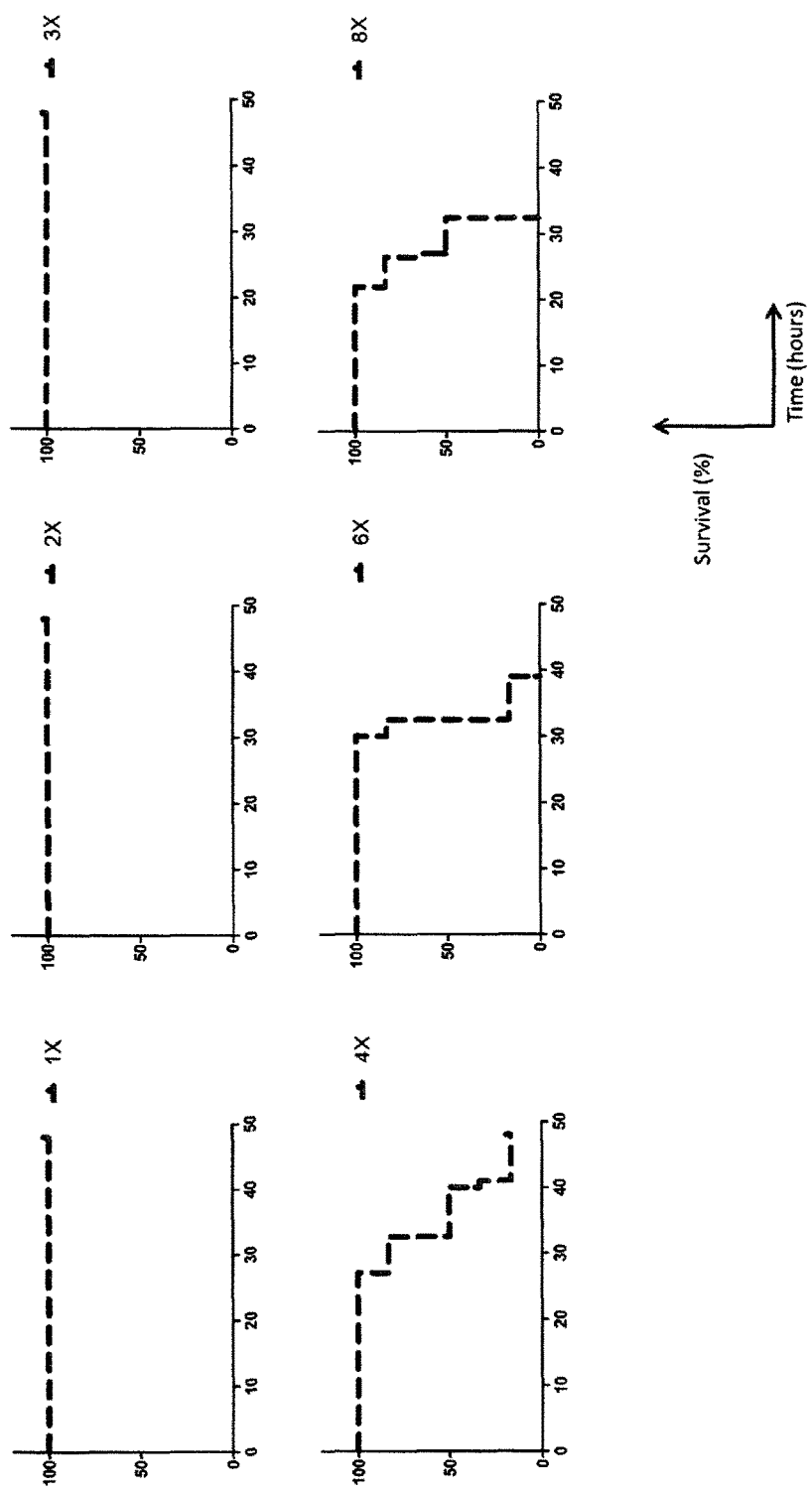

FIG. 10A illustrates part of the results from this experiment; in particular the different percentages of survival of mice when infected with increasing doses of the wild type strain. From this data it can be concluded that doses from 2× onwards provide for a gradual decrease in the survival of the mice. In fact, it can be observed that the lethal dose 100 ($LD_{100}$), understood as the minimum dose necessary to reduce survival of mice to 0%, for wild type strain ATCC 17978 is 2.5×. Moreover, this figure also shown that when the dose is above 3×, a much rapid reduction in the survival percentage is observed.

On the other hand, FIG. 10B shows different levels of survival rates of mice infected with increasing doses of the double mutant strain Δ0380/Δ3398. In this case and in clear contrast with FIG. 10A, the $LD_{100}$ (lethal dose 100) is 6×. This dose is certainly much higher than the lethal dose corresponding to the wild type strain. In fact, a 6× dose is so high that the authors of the invention firmly believe that the death of the mice was not due to the replication of the bacteria but to a septic shock, which clearly indicates that this (the double mutant strain) is an a-virulent or attenuated bacterial strain.

Additionally and in order to confirm the above results, the authors of the present invention induced, as can be observed in example 6, a systemic infection in BALB/c mice through the intraperitoneal administration of the following inoculums of *A. baumannii*: wild type strain ATCC 17978 and mutant strains Δ0380, Δ3398 and Δ0380/Δ3398.

In this sense, it is important to note that as illustrated in the examples of the present invention, of all of the strains used and mentioned in the precedent paragraph, only the double mutant strain Δ0380/Δ3398 is considered to be auxotrophic for D-glutamate thus requiring the addition of exogenous D-glutamate in the culture medium for growth and survival. In addition, it is also noted that in the model of acute infection illustrated in example 6, the infection occurs with a rapid spread through the blood of the bacteria thus resulting in the death of the mice between 11 and 30 hours post-infection (see FIG. 10A). Lastly, it is also important to note that from the counts of bacteria in the liver, the authors of the present invention can obtain a measurement of the invasive and replicative capacity of the different strains.

Figure 11:
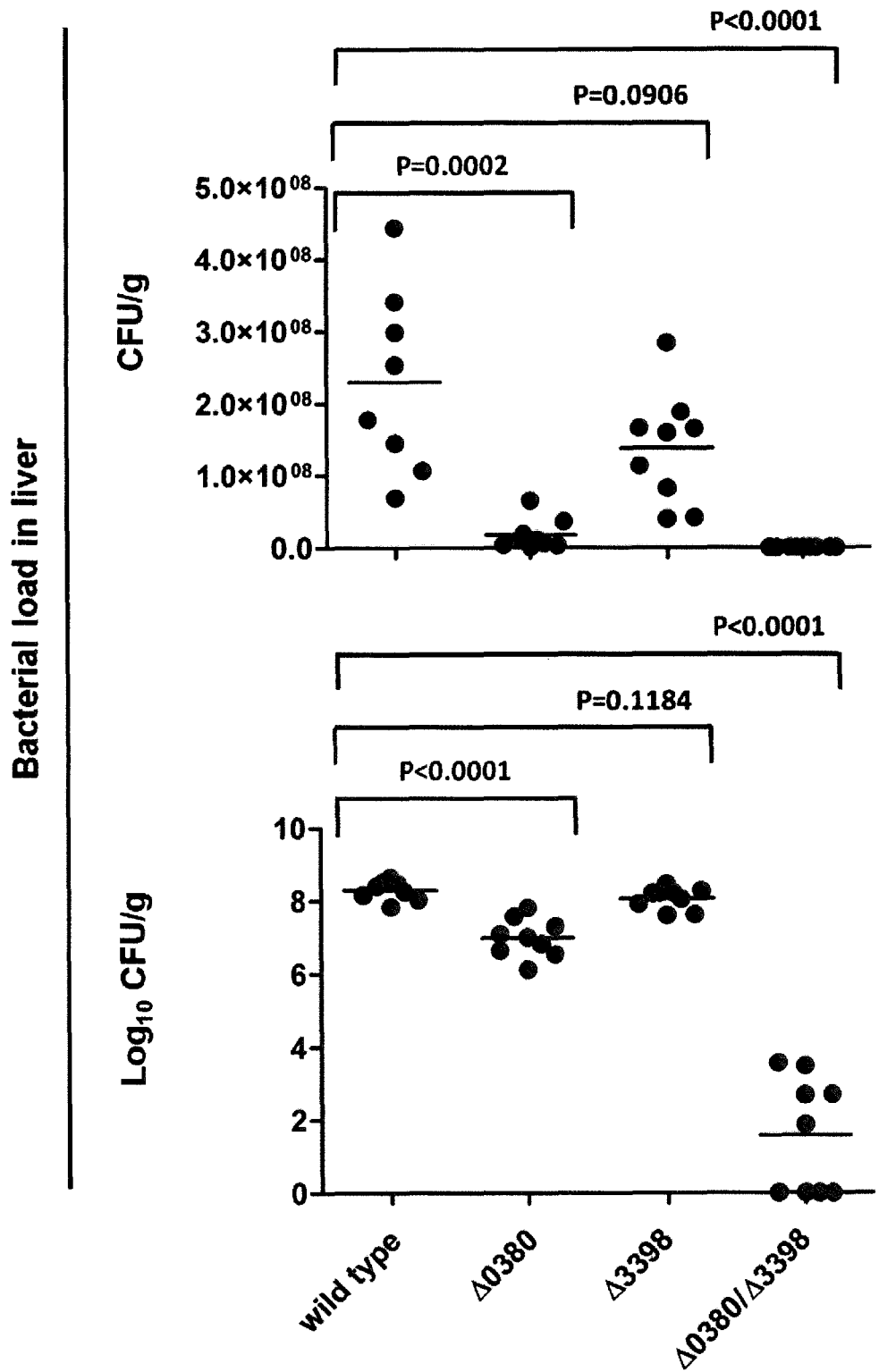
FIG. 11 shows the bacterial load in the liver of BALB/c mice (n=8-9 mice) 12 hours post-infection with a 2× dose of the *A. baumannii* wild type strain ATCC 17978, strain Δ0380, strain Δ3398 and strain Δ0380/Δ3398. P-value according to the Mann-Whitney U test. Each dot represents the individual bacterial load of the liver of a mouse and each horizontal line represents the respective average for each group.

That said and as shown in FIG. 11, the following average values were obtained from the experiment illustrated in example 6: 8.29 $Log_{10}$ CFU (colony forming units)/g in the liver of those mice infected with the wild type strain; 6.88 $Log_{10}$ CFU/g in the liver of those mice infected with the Δ0380 strain; 8.06 $Log_{10}$ CFU/g in the liver of those mice infected with the mutant strain Δ3398 and 1.59 $Log_{10}$ CFU/g in the liver of those mice infected with the double mutant strain Δ0380/Δ3398.

Based on these results, it can be concluded that the counts of the double mutant strain Δ0380/Δ3398 and of mutant strain Δ0380 were considerably inferior from those observed for the wild type strain. The most dramatic and obvious reduction being the one observed when analyzing the colony counts of the double mutant strain Δ0380/Δ3398, in which a decrease of nearly 7 $Log_{10}$ values in the average bacterial load was obtained. Moreover, surprisingly in 44.4% of mice infected with the double mutant strain no bacteria were recovered.

Consequently, again this clearly indicates that this (the double mutant strain) is an a-virulent or attenuated bacterial strain.

Nevertheless, the authors of the present invention in order to confirm the universality of the platform, conducted further experiments with auxotrophic D-glutamate strains pertaining to two additional and completely unrelated bacterial species, namely with P. aeruginosa and S. aureus. As we shall see below, auxotrophic strains of these two species also produced attenuated strains incapable of producing unacceptable pathological effects in the host.

In this sense, as illustrated in example 16, BALB/c mice were administered different doses of P. aeruginosa PAO1 wild type strain and of mutant strain ΔPA4662 with the purpose of determining the lethal doses of these strains during an acute sepsis infection. Mice were monitored for 7 days after infection and survival rates were determined for different doses of injected bacteria.

Figure 24:
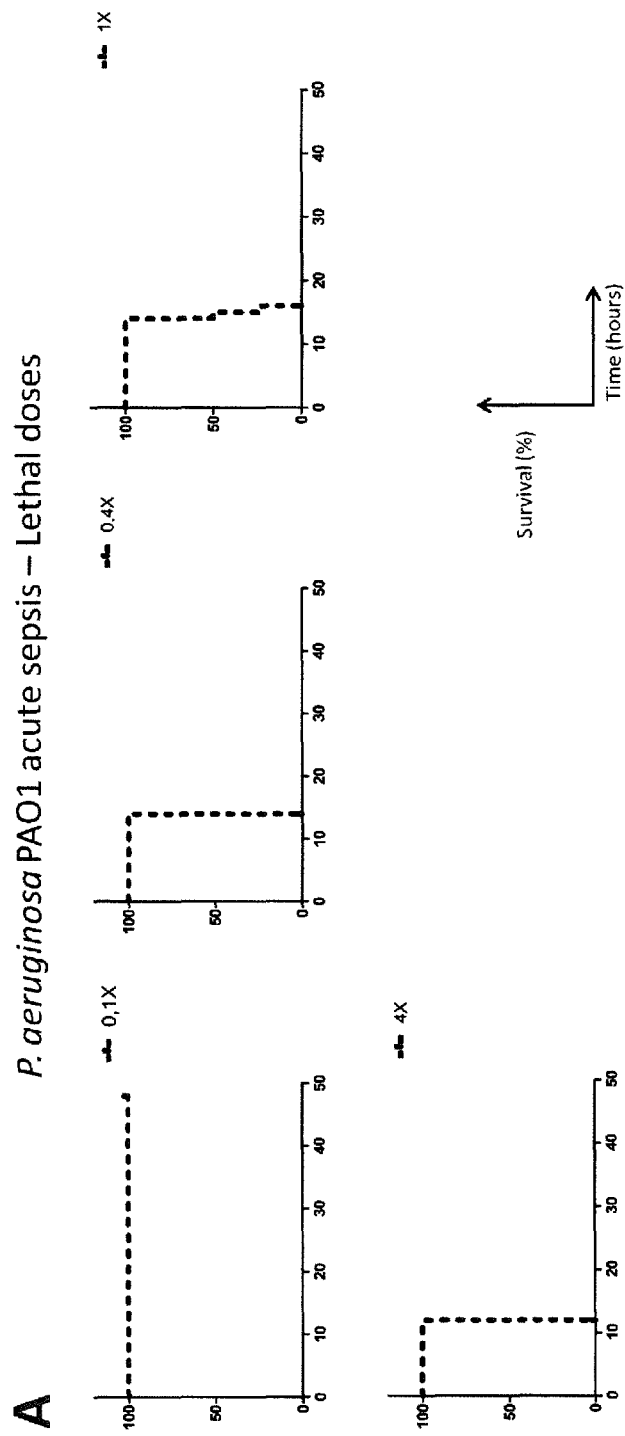
FIG. 24 shows the percentage of survival of BALB/c mice after intraperitoneal injection with different doses of P. aeruginosa wild type strain PAO1 (A) and ΔPA4662 mutant strain (B) (n=4) to determine the lethal dose (LD) for which 100% of susceptible mice will die ($LD_{100}$) (A) $LD_{100}$=0.4×; (B) $LD_{100}$>40×. Mice survival was monitored during 7 days.
Figure 24:
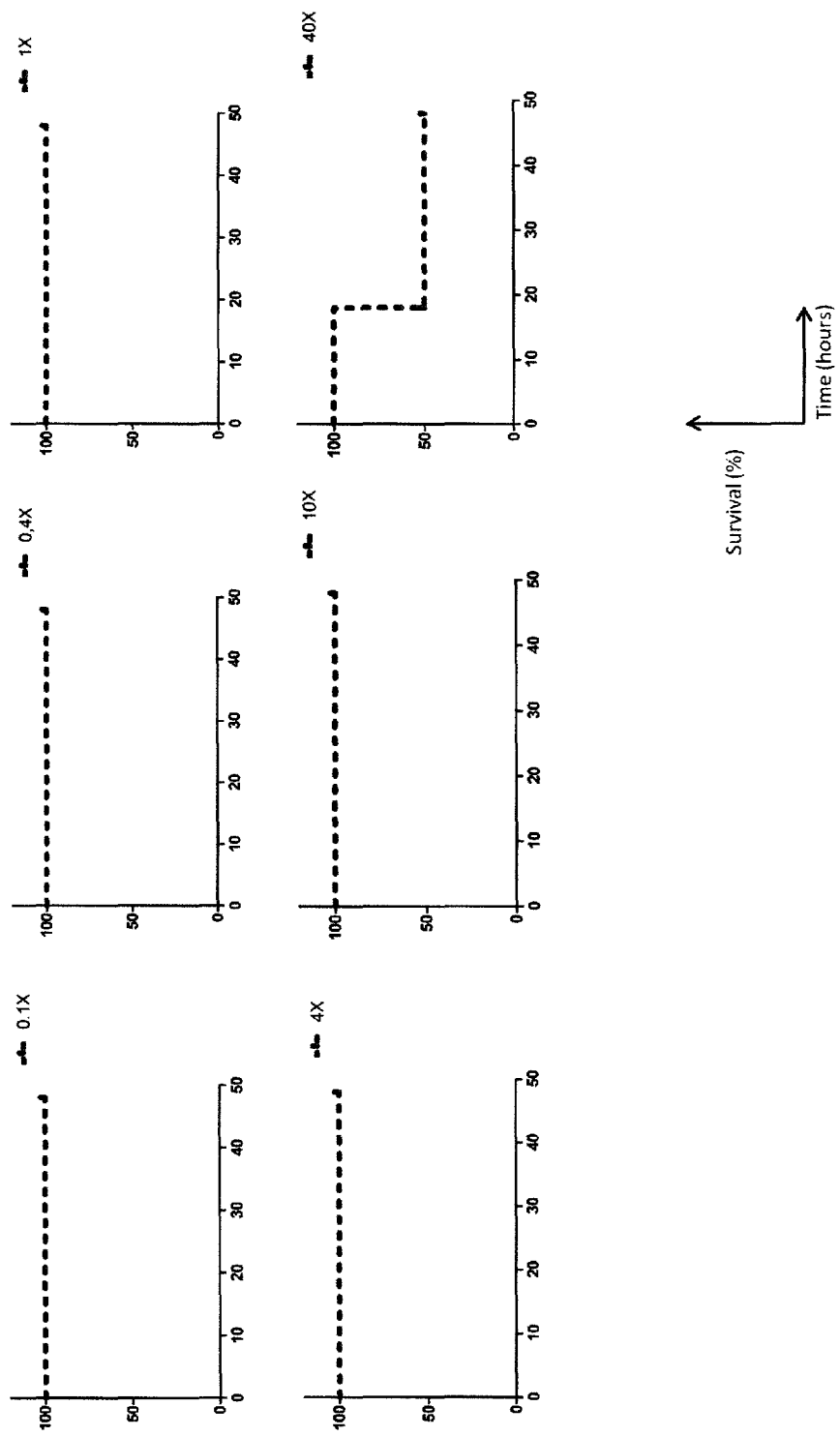

In FIG. 24A we can observe different degrees of survival in animals infected with increasing doses of P. aeruginosa PAO1 wild type strain. For this strain, the $LD_{100}$ is =0.4×. In FIG. 24B we can observe different degrees of survival in animals infected with increasing doses of the ΔPA4662 mutant strain. For this strain, the $LD_{100}$ is >40×, a very high dose of bacterial inoculum which can lead to the death of the mice from septic shock (and not due to replication of the bacteria). This indicates that this strain (ΔPA4662) has a much reduced virulence in comparison with the wild type strain (a dose 100 times higher than the wild type strain $LD_{100}$ only decreases by 50% the survival rate of the mice).

Lastly the authors of the present invention further confirmed the concept of universality of the platform technology of the invention by using a still further bacterial species, namely by proving that auxotrophic D-glutamate strains pertaining to the species S. aureus also produced attenuated strains incapable of producing unacceptable pathological effects in the host.

In this sense and as illustrated in example 25, systemic infection was produced in BALB/c mice with S. aureus 132 wild type and double mutant strains by intraperitoneal injection with 3% of hog mucin.

Figure 35:
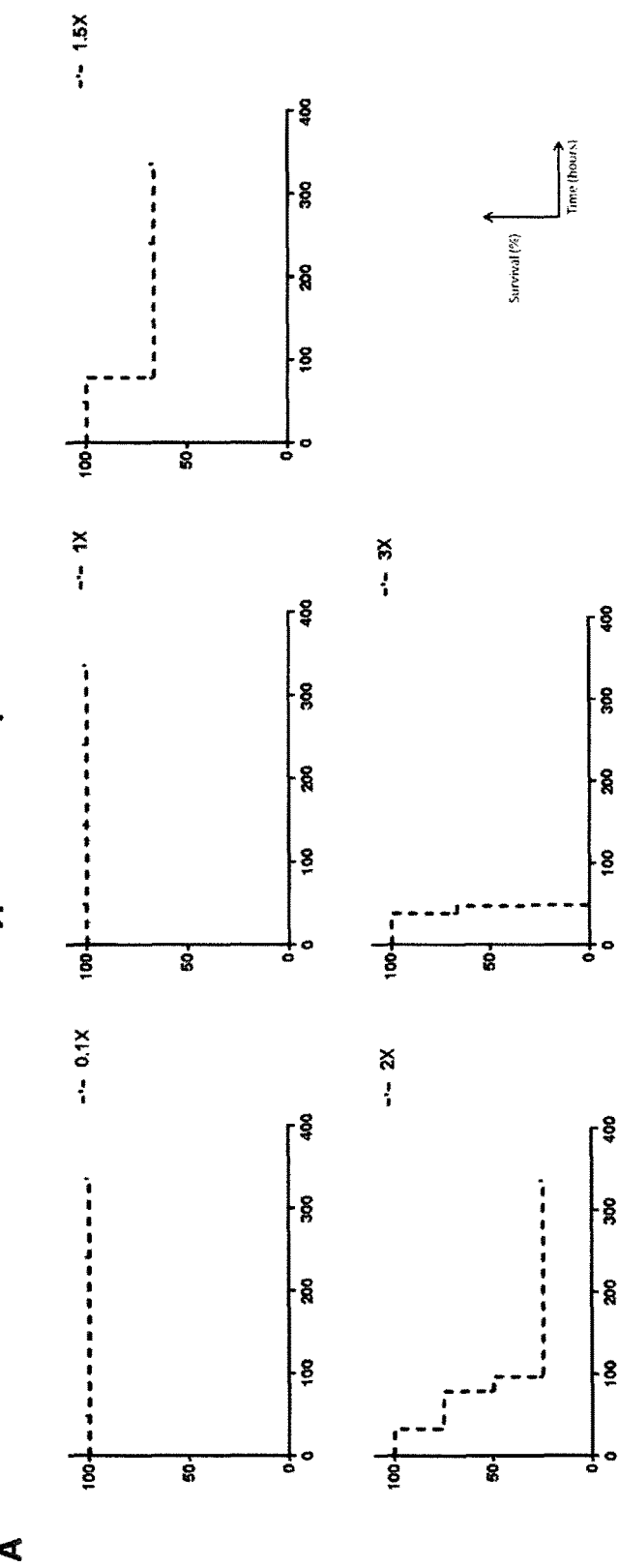
FIG. 35 shows the percentage of survival of BALB/c mice after intraperitoneal injection with different doses of S. aureus 132 wild type (A) and ΔmurI/Δdat mutant (B) (n=3-4) to determine the lethal dose (LD) for which 100% of susceptible mice will die ($LD_{100}$) (A) $LD_{100}$=3×; (B) $LD_{100}$>30×. Mice survival was monitored during 14 days.
Figure 35:
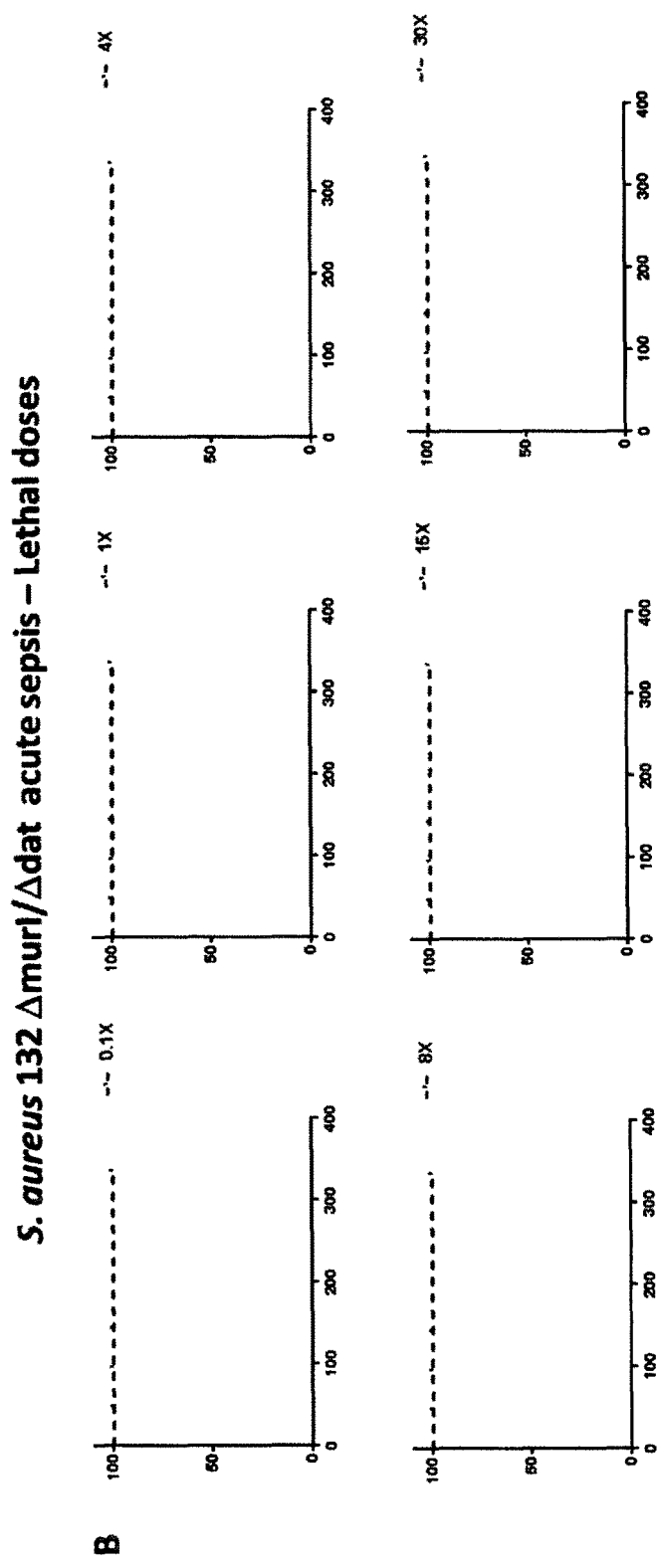

As shown in FIG. 35A, the minimum dose of the wild type strain that reduces survival of these mice to 0% was determined to be $LD_{100}$=3×. In clear contrast with FIG. 35A, FIG. 35B illustrates that inoculating a dose of the double mutant 10-fold higher than the $LD_{100}$ of the wild type strain results in a 100% survival rate. Therefore, the lethal dose for the double mutant is greater than 30× $LD_{100}$>30×. This clearly demonstrates that the double mutant of S. aureus is an attenuated strain showing lower virulence potential than the wild type counterpart.

In summary these data demonstrate that all bacterial strains auxotrophic for D-glutamate are attenuated. However, it is widely known that it is not enough that a bacterial strain is attenuated to be useful as a vaccine candidate since it must also be able to generate an immune response and induce protection. Furthermore, these mutant strains should preferentially contain all antigens immunologically necessary to confer cross-protection.

Thus, in order to assess the immune response mediated by antibodies to different vaccination regimens, the authors conducted the experiment illustrated in example 8 wherein BALB/c mice were immunized by intraperitoneal injection with the double mutant strain Δ0380/Δ3398 by using a 1× dose on days 0 and 14. Additionally, a further group of control mice were administered of saline serum identically at days 0 and 14. On the seventh day post-immunization, sera from the mice immunized with a single dose of the vaccine (administered on day 0) was retrieved, similarly, 21 days after the first administration, sera from the mice also immunized with the remaining dose was also retrieved along with the sera from the control mice, from those injected with saline serum.

These sera were used to determine the titer of antibodies (IgG) by using the ELISA technique against different strains of A. baumannii, including ATCC 17978, ATCC 19606 and AbH12O-A2 and thus measuring the ability of the vaccine to generate broad immune response (example 9). It is noteworthy that A. baumannii strain AbH12O-A2 is a highly invasive strain, isolated in a hospital outbreak that killed several patients and is characterized by a pattern of resistance to multiple antibiotics.

Figure 13:
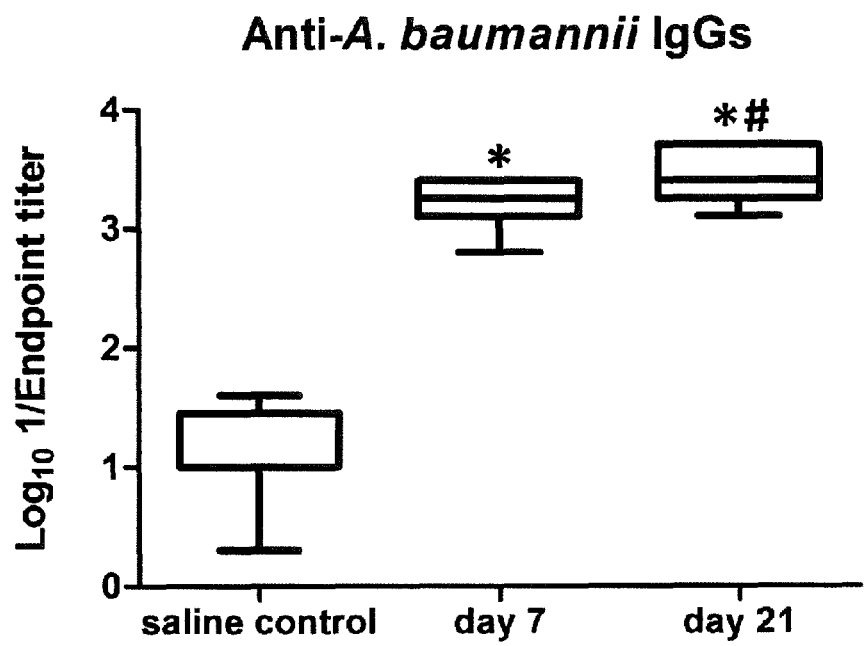
FIG. 13 shows the $Log_{10}$ 1/Endpoint titer of IgG antibodies produced against the *A. baumannii* strain ATCC 17978 in BALB/c mice (n=12) on post-vaccination days 7 and 21, and in non-vaccinated control mice (saline control). The antibody titers were determined by indirect ELISA. *P<0.0001 compared with the group of non-vaccinated mice; #P<0.0240 compared with the production of IgGs on post-vaccination day 7; P-value according to the Mann-Whitney U test. The boxes represent the first and third quartiles; the horizontal line represents the median; the whiskers represent the range.
Figure 15:
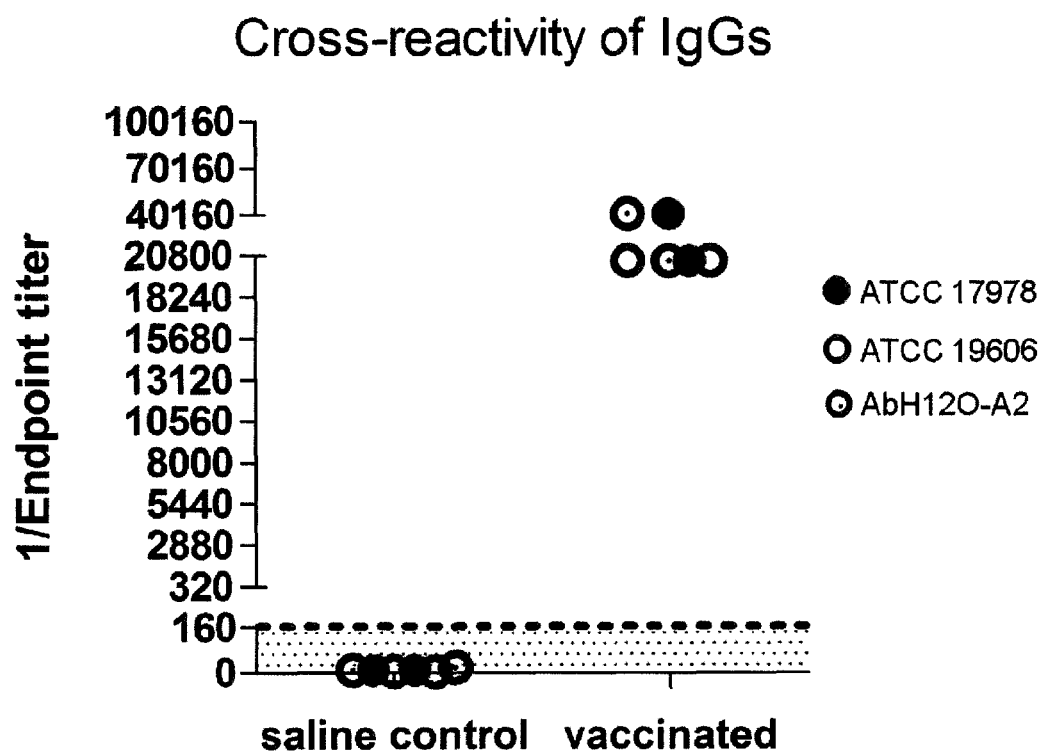
FIG. 15 shows the cross-reactivity (titer) of IgG antibodies produced by BALB/c mice on post-vaccination day 21 and in non-vaccinated control mice (saline control) against three different *A. baumannii* strains: ATCC 17978, ATCC 19606 and AbH12O-A2.

In all immunized mice significant levels of antibodies were detected against the wild type strain as compared to non-vaccinated mice (FIG. 13). Antibody production was significantly elevated at days 7 and 21, namely after injection of the first dose and of the second dose of the double mutant bacterial strain Δ0380/Δ3398, respectively as compared to non-vaccinated mice. Moreover, the production of antibodies at day 21 (after 2 successive injections of the double mutant strain Δ0380/Δ3398) was significantly higher than the production of antibodies at day 7. The production of antibodies obtained at day 21 against A. baumannii wild type strain ATCC 17978 were similar to those obtained against A. baumannii strains ATCC 19606 and A. baumannii AbH12O-A2 (FIG. 15). This result demonstrates that immunization with strain Δ0380/Δ3398 not only generates antibodies against the wild type strain but also generates IgG antibodies that react against other bacterial strains with different resistance and virulence patterns such as the ATCC 19606 strain and strain AbH12O-A2.

In addition, to further confirm that these bacteria (bacterial strains auxotrophic for D-glutamate) were capable of generating a strong immune response, further experiments were conducted in bacterial species P. aeruginosa and S. aureus.

Figure 44:
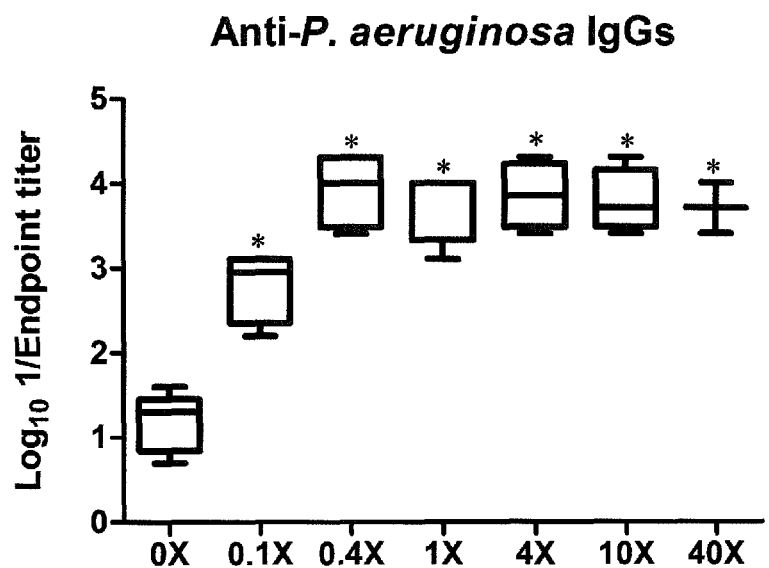
FIG. 44 shows the endpoint titer $Log_{10}$ of IgG antibodies produced against *P. aeruginosa* strain PAO1 in BALB/c mice on post-vaccination day 40 with different dosis of *P. aeruginosa* strain PAO1 (0.1×; 0.4×; 1×; 4×, 10× and 40×) and in the non-vaccinated control mice (0×). The antibody titers were determined by indirect ELISA. *P<0.001 compared with the group of non-immunized mice; P-value according to unpaired t test. The boxes represent the first and third quartiles; the horizontal line represents the median; the whiskers represent the range.
Figure 45:
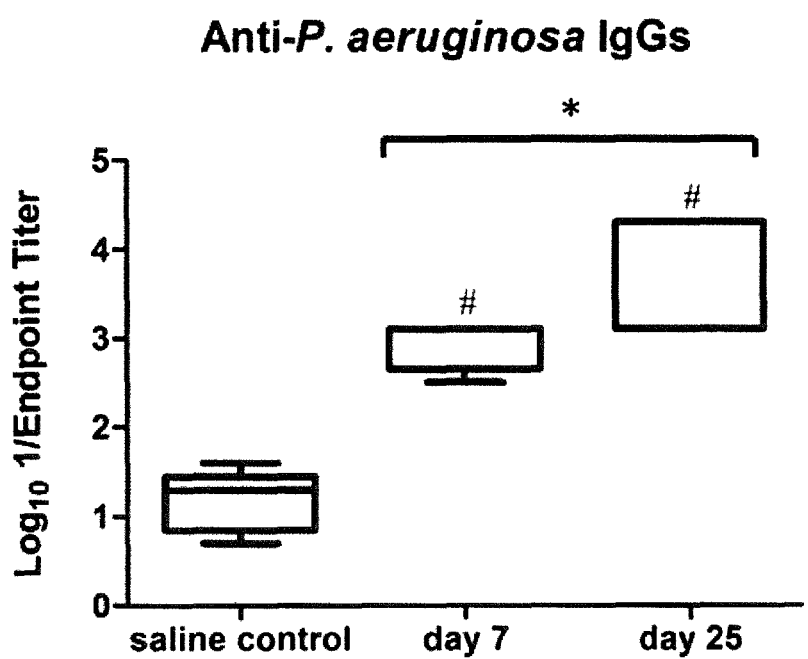
FIG. 45 shows the endpoint titer $Log_{10}$ of IgG antibodies produced against the *P. aeruginosa* strain PAO1 in BALB/c mice (n=5) on post-vaccination days 7 and 25, and in non-vaccinated control mice. The antibody titers were determined by indirect ELISA. #P<0.0001 compared with the group of non-immunized mice; *P<0.05 comparison between post-vaccination days 7 and 25; P-value according to unpaired t test. The boxes represent the first and third quartiles; the horizontal line represents the median; the whiskers represent the range.

As illustrated in example 16, one vaccine dose of 0.1× of P. aeruginosa ΔPA4662 mutant strain is sufficient to trigger IgG production significantly, even when detected at day 40$^{th}$ after the administration (FIG. 44). Nonetheless, vaccine doses equal or greater than 0.4× elicit higher levels of IgG production. Moreover, IgG production is significantly higher when the 2$^{nd}$ vaccine dose is administered (FIG. 45).

Figure 46:
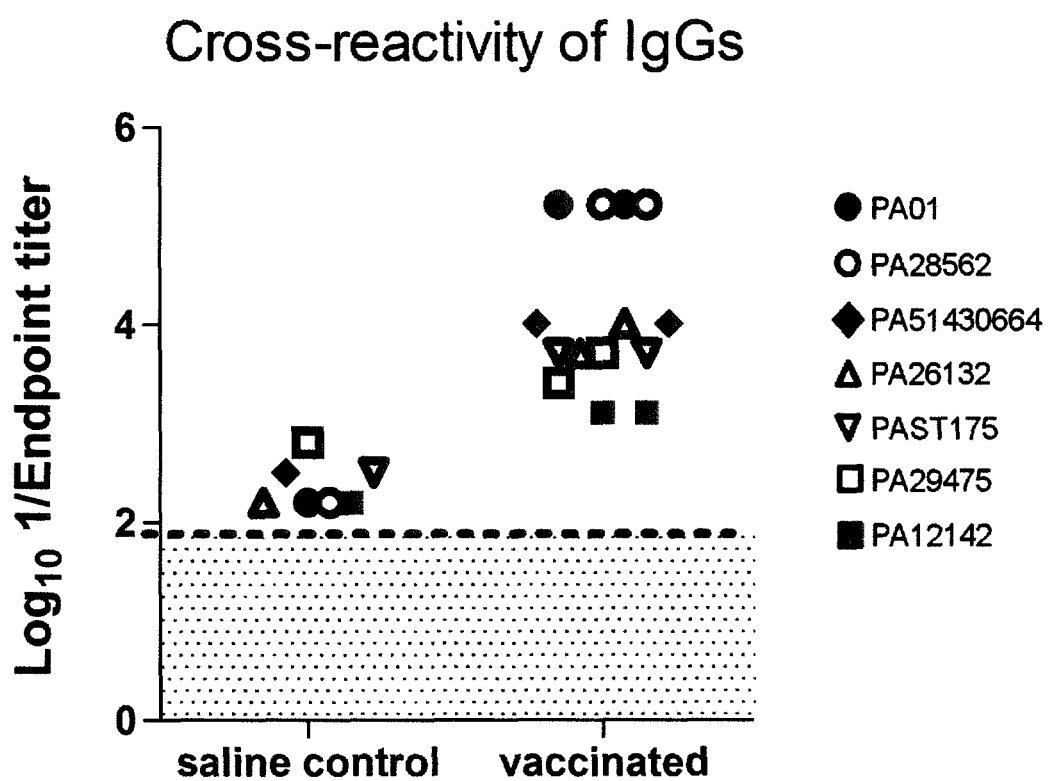
FIG. 46 shows the cross-reactivity (titer) of IgG antibodies produced by BALB/c mice on post-vaccination day 34 and in non-vaccinated control mice (saline control) against multiple *P. aeruginosa* strains: PAO1, PA28562, PA51430664, PA26132, PAST175, PA29475 and PA12142.

Additionally, ELISA was performed with respect to different strains of *P. aeruginosa* with sera obtained from mice vaccinated with the ΔPA4662 and mice administrated saline to measure the capacity of ΔPA4662 vaccine to generate a broad immune response. Results similar to those observed with respect to *P. aeruginosa* strain PAO1 were obtained with strain PA28562 whereas high levels of cross-reactivity were also seen with respect to rest of *P. aeruginosa* strains tested (FIG. 46). This demonstrates that immunization with strain ΔPA4662 not only generates antibodies against the isogenic wild type strain, but also generates IgG antibodies that react against multiple *P. aeruginosa* strains.

Figure 39:
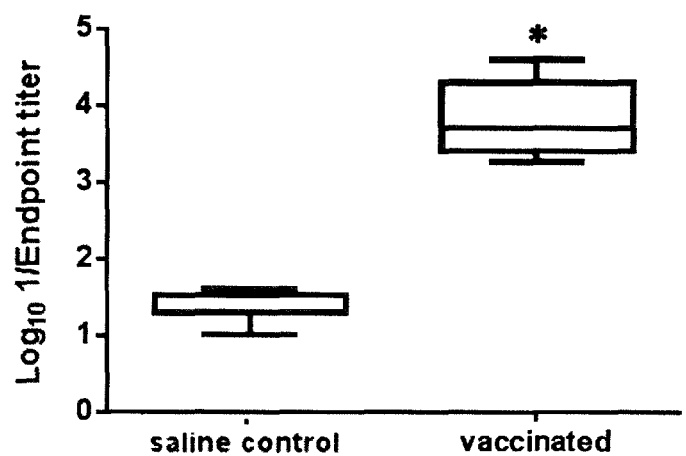
FIG. 39 shows the $Log_{10}$ 1/Endpoint titer of IgG antibodies produced against the isogenic *S. aureus* 132 Δspa strain in BALB/c mice (n=8-10) pre-immunized with a 10× dose of ΔmurI/Δdat strain, and in non-immunized mice (saline control). The antibody titers were determined by indirect ELISA. *P<0.0001 compared with the group of non-immunized mice. P-value according to the Mann-Whitney U test. The boxes represent the first and third quartiles; the horizontal line represents the median; the whiskers represent the range.

Lastly, as illustrated in examples 28 and 29 the authors of the present invention evaluated the immune response mediated by antibodies against a strain of *S. aureus* (called *S. aureus* 132 Δspa, Protein-A-deficient) and the cross-reactivity against four unrelated *S. aureus* strains of human and animal origin. For this purpose, BALB/c mice were immunized by intraperitoneal injection of the double mutant ΔmurI/Δdat on days 0 and 14. The sera samples from each mouse collected on day 21 were used to determine the titer of antibodies (IgG) against the isogenic *S. aureus* 132 Δspa strain (FIG. 39), as well as against an epidemic MRSA community-acquired USA300LAC strain and three strains of animal origin (FIG. 40). As shown in FIGS. 39 and 40, all mice immunized with the double mutant ΔmurI/Δdat strain produced significant levels of specific antibodies against each bacteria as compared with the non-vaccinated mice, demonstrating the ability of the *S. aureus* ΔmurI/Δdat mutant to elicit IgGs antibodies that recognize not only the isogenic Δspa counterpart but also a clinical epidemic strain and other strains isolated from different hosts such as bovine, ovine and poultry.

Therefore, the data presented so far not only demonstrates that all bacterial strains auxotrophic for D-glutamate are attenuated but also that these strains contain all antigens immunologically necessary to generate an immune response and to confer cross-protection.

Finally, to verify whether the bacterial strains auxotrophic for D-glutamate confer an acceptable level of protection, the authors of the present invention conducted a series of experiments with nosocomial pathogen *A. baumannii* in order to assessed the effectiveness as a vaccine of the double mutant strain Δ0380/Δ3398. As illustrated in example 10, mutant strain Δ0380/Δ3398 was administered to BALB/c mice on days 0 and 14. Control mice were administered only saline identically at days 0 and 14. Twenty one days after the first injection, mice were challenged with *A. baumannii* strains ATCC 17978, AbH12O-A2 and Ab307-0294, independently, in order to establish a lethal systemic infection. After the challenge, mice were monitored for 7 days to determine the survival rate of vaccinated mice compared to control mice (non-vaccinated).

Figure 16:
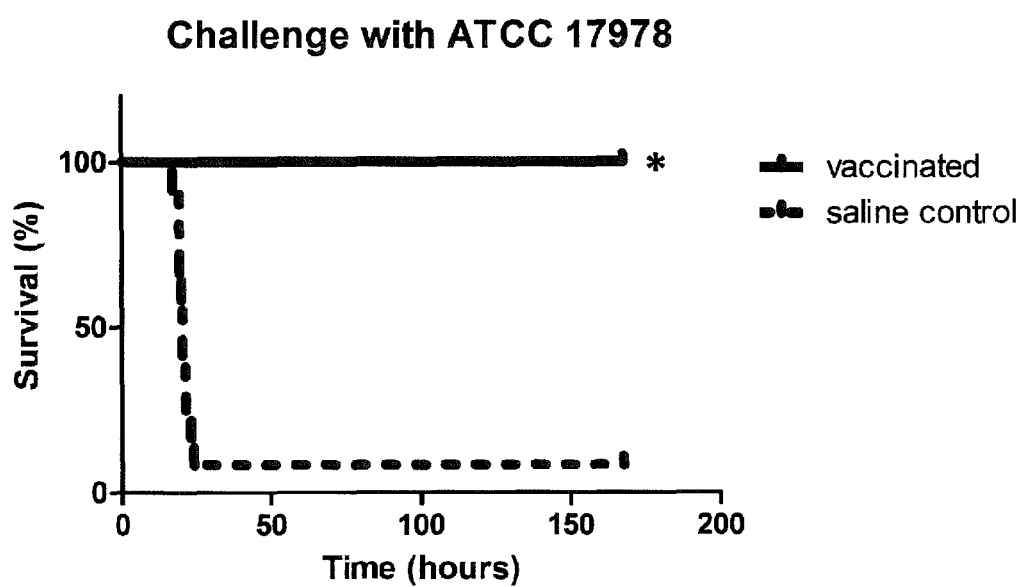
FIG. 16 is the percent survival of BALB/c mice (n=12) following intraperitoneal infection with a 4× dose of *A. baumannii* ATCC 17978 wild type strain. Vaccinated mice were immunized on days 0 and 14 with *A. baumannii* Δ0380/Δ3398 strain and infected with the wild type strain at day 21. Non-vaccinated mice were administered saline on days 0 and 14 and infected with the wild type strain at the same day. *P<0.0001 survival of vaccinated group compared to control group. P-value, according to the Mantel-Cox test (log-rank test).

When infected with *A. baumannii* ATCC 17978 strain, 11 deaths were observed in the group of unvaccinated mice during the first 24 hours, which means a mortality rate of 92% in this group. In contrast, all vaccinated mice survived to the challenge, overcoming the infection, which means a 100% survival (see FIG. 16) rate in this group.

Figure 17:
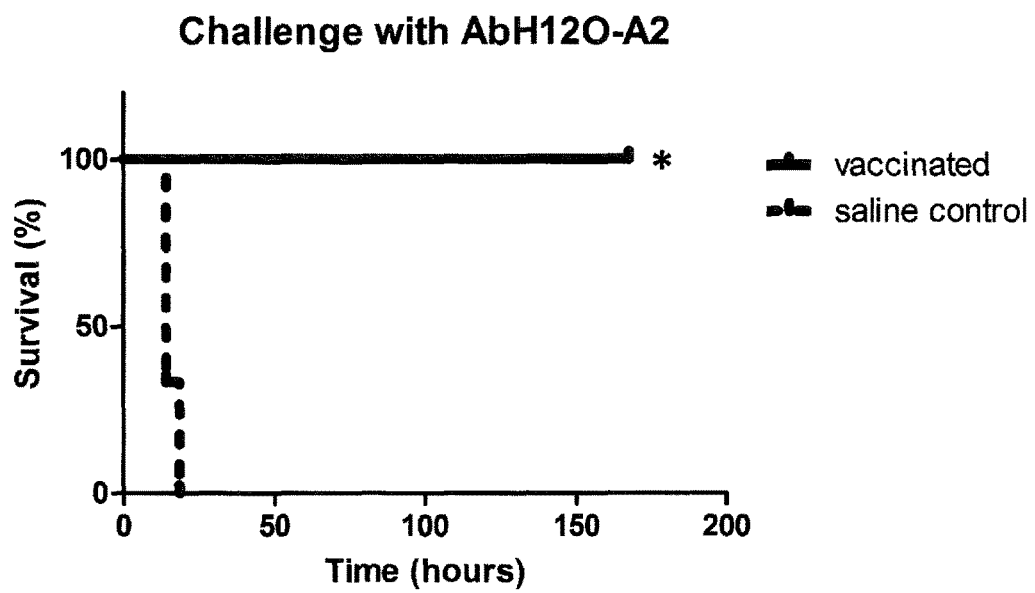
FIG. 17 is the percent survival of BALB/c mice (n=9) following intraperitoneal infection with a 4× dose of *A. baumannii* AbH12O-A2 strain. Vaccinated mice were immunized on days 0 and 14 with *A. baumannii* Δ0380/Δ3398 strain and infected with the clinical strain at day 21. Non-vaccinated mice were administered saline on days 0 and 14 and infected with the clinical strain at the same day. *P<0.0001 survival of vaccinated group compared to control group. P-value, according to the Mantel-Cox test (log-rank test).

In addition, it was determined whether the response produced by immunization with the Δ0380/Δ3398 strain was sufficient to provide protection from lethal infection with other *A. baumannii* strains, including highly virulent and pathogenic strains. In the case of challenge with the AbH12O-A2 strain, 9 deaths were observed in the group of non-vaccinated mice during the first 19 hours, which means a mortality rate of 100%. In contrast, all vaccinated mice survived (100% survival rate) (see FIG. 17).

Figure 18:
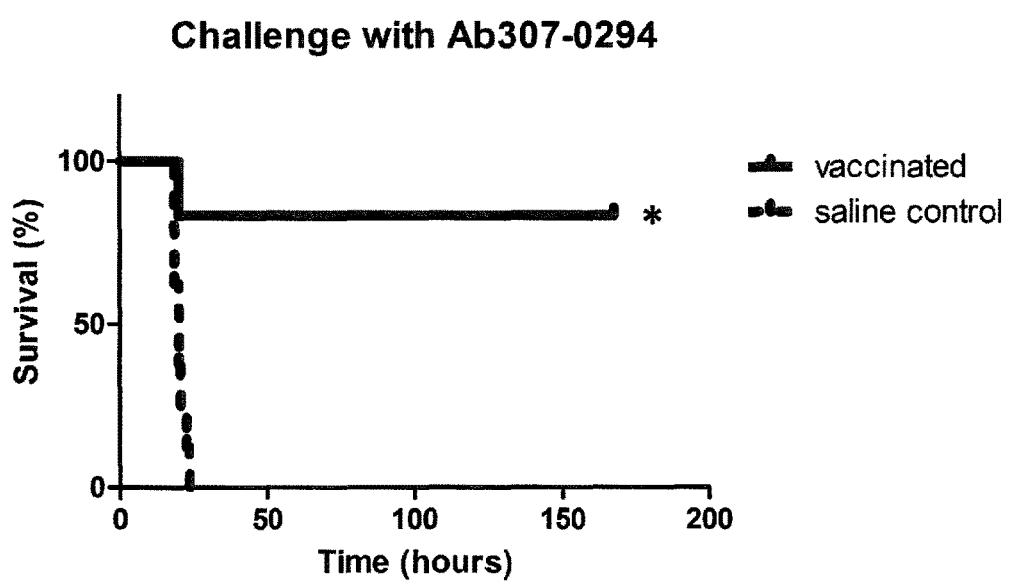
FIG. 18 is the percent survival of BALB/c mice (n=6-8) following intraperitoneal infection with a 0.75× dose of the capsulated *A. baumannii* Ab307-0294 strain. Vaccinated mice were immunized on days 0 and 14 with *A. baumannii* Δ0380/Δ3398 strain and infected with the highly virulent strain at day 21. Non-vaccinated mice were administered saline on days 0 and 14 and infected with Ab307-0294 strain at the same day. *P=0.0022 survival of vaccinated group compared to control group. P-value, according to the Mantel-Cox test (log-rank test).

In the case of challenge with the Ab307-0294 capsulated strain, we recorded a 100% mortality rate in the group of non-vaccinated mice within the first 24 hours and a 83% survival rate in the group of mice previously immunized with the Δ0380/Δ3398 strain (see FIG. 18). This confirms that vaccination with the mutant strain confers protection against a systemic infection caused by an *A. baumannii* strain with marked virulence.

All these results suggest that vaccination with the Δ0380/Δ3398 strain can provide protective immunity against infection with a diverse group of *A. baumannii* strains.

Furthermore, in order to verify whether other bacterial strains also auxotrophic for D-glutamate confer an acceptable level of protection, the authors of the present invention conducted additional experiments with pathogens *P. aeruginosa* (as illustrated in example 18) and *S. aureus* (as illustrated in examples 26 and 27).

As illustrated in example 18, mutant strain PA4662 was administered to BALB/c mice on days 0 and 14. Control mice were administered only saline identically days. Twenty five days after the first injection, mice were challenged with *P. aeruginosa* strain PAO1, in order to establish a lethal systemic infection. After the challenge, mice were monitored for 7 days to determine the survival rate of vaccinated mice compared to control mice.

Figure 26:
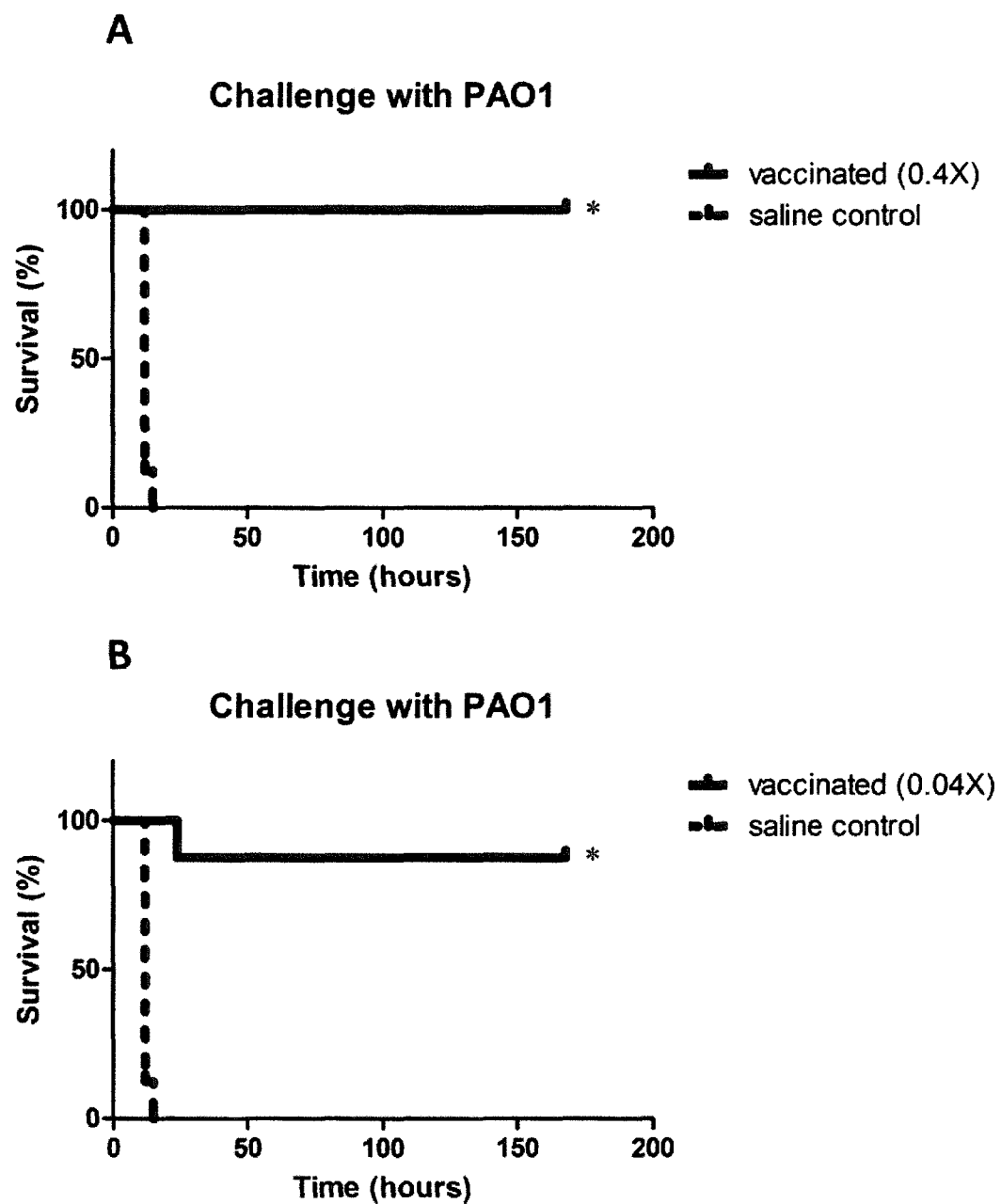
FIG. 26 is the percent survival of BALB/c mice (n=8) following intraperitoneal infection with a 0.4× dose of P. aeruginosa PAO1 wild type strain. Vaccinated mice were immunized on days 0 and 14 with P. aeruginosa ΔPA4662 strain (0.4× dose—A; 0.04× dose—B) and infected with the wild type strain at day 25. Non-vaccinated mice were administered saline on days 0 and 14 and infected with the wild type strain at the same day. *P<0.0001 survival of vaccinated group compared to control group. P-value, according to the Mantel-Cox test (log-rank test).

When infected with *P. aeruginosa* PAO1 wild type strain, 8 deaths were observed in the group of non-vaccinated mice during the first 15 hours, which means a mortality rate of 100% in this group. In contrast, all vaccinated mice survived to the challenge, overcoming the infection, which means a 100% survival (see FIG. 26) rate in this group.

Figure 36:
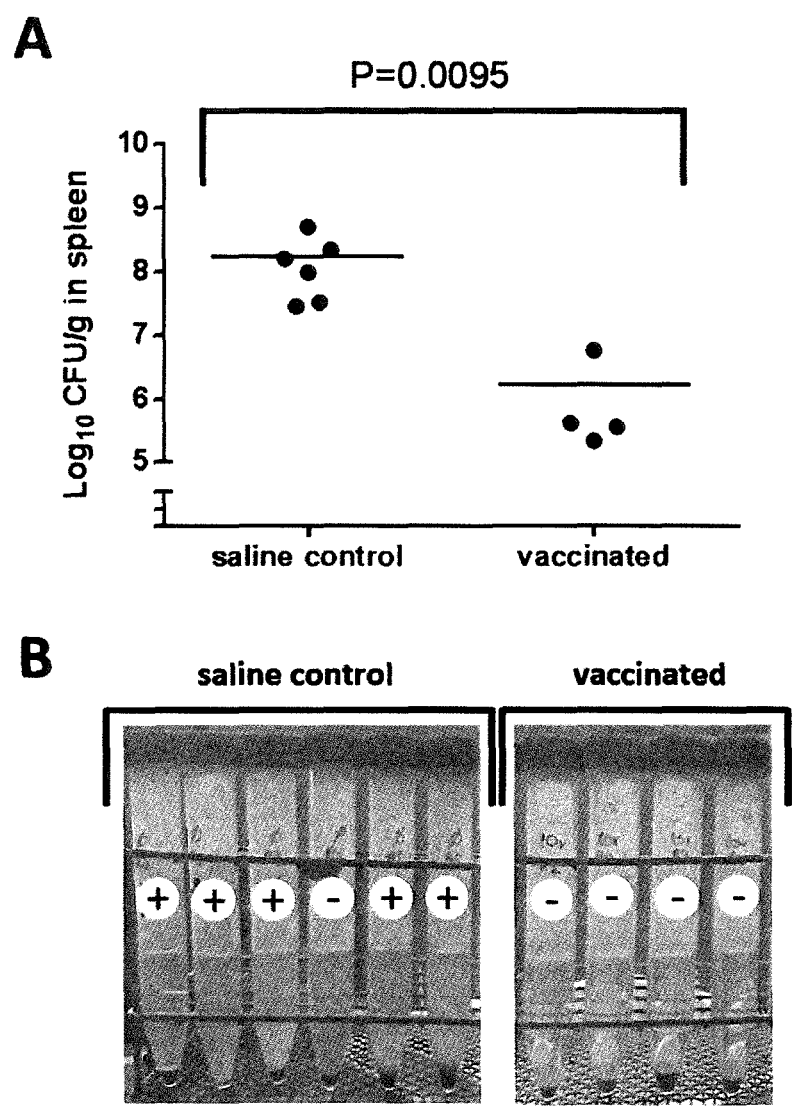
FIG. 36 shows the bacterial load in the spleen (A) and blood cultures (B) of BALB/c mice (n=4-6) 20 hours post-infection with a 5× dose of the S. aureus 132 wild type strain after mice were pre-immunized on days 0 and 14 with a 10× dose of strain ΔmurI/Δdat, or non-immunized (saline control). Each dot represents the individual bacterial load of spleen of a mouse. The average value of each group is represented by a horizontal line. P=0.0095 compared with the group of non-vaccinated mice. P-value according to the Mann-Whitney U test. Blood cultures from each mouse were incubated 18 hours at 37° C. without shaking: (+), positive; (−), negative.

As illustrated in example 26, to evaluate the effectiveness (protection level) of the *S. aureus* double mutant ΔmurI/Δdat strain as a vaccine, BALB/c mice were immunized intraperitoneally with the double mutant ΔmurI/Δdat on days 0 and 14. One group of mice were administered saline at identically days. At day 21, mice were infected with a lethal inoculum of *S. aureus* wild type strain. At 20 or 22 hours post-infection (FIGS. 36 and 37, respectively) bacterial counts in spleens and blood of mice were determined. So, the protective effect of vaccination with the double mutant ΔmurI/Δdat of *S. aureus* was confirmed as pre-immunization with this strain caused a significant decrease in bacterial loads.

Figure 38:
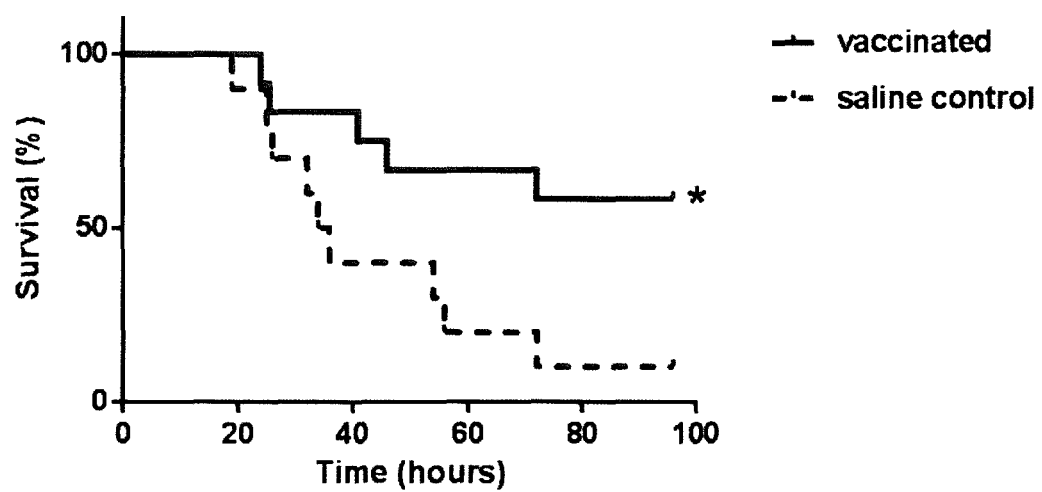
FIG. 38 is the percent survival of BALB/c mice (n=10-13) following intraperitoneal infection with a 5× dose of *S. aureus* 132 wild type strain. Vaccinated mice were immunized on days 0 and 14 with a 10× dose of ΔmurI/Δdat strain while non-immunized mice were administered saline at the same days. *P=0.031 compared with the group of non-vaccinated mice. P-value according to Mann-Whitney U test. Mice survival was monitored until 96 hours.

Moreover, as indicated in example 27, when pre-immunized BALB/c mice with ΔmurI/Δdat strain were challenged with a lethal dose of *S. aureus* 132 wild type strain significant differences in survival were observed when compared to non-immunized mice. In this case, 8 mice of vaccinated group survived to the challenge, overcoming the infection, which means a 61.5% survival rate in this group (FIG. 38) whereas a mortality rate of 90% were observed in non-vaccinated group.

All together, these results demonstrate that vaccination with ΔPA4662 and ΔmurI/Δdat strains provides protective immunity against infection with *P. aeruginosa* and *S. aureus*, respectively.

The experimental examples described herein provide procedures and results which establish that bacterial strains auxotrophic for D-glutamate are sufficiently a-virulent (attenuated) to avoid unacceptable pathological effects, induce a sufficient level of immunity in the host independently of the administration route and have a substantially level of security (both environmental and for the host) for their use in active or passive immunization.

Therefore, one embodiment of the invention relates to live attenuated bacteria suitable as vaccine candidates that are no longer capable of producing D-glutamate.

Live attenuated bacteria for use according to the invention as vaccine candidates can be obtained in several ways as explained below. In this sense, it is important to understand that both gram positive and gram negative bacteria have a peptidoglycan cell wall that gives them their characteristic shape and provides them with mechanical protection. Peptidoglycan, also known as murein, is a polymer consisting of sugars and amino acids that form a mesh-like layer outside the plasma membrane of bacteria (but not Archaea), forming the cell wall. The sugar component consists of alternating residues of β-(1,4) linked N-acetylglucosamine and N-acetylmuramic acid.

The peptidoglycan layer is substantially thicker in gram positive bacteria (20 to 80 nanometers) than in gram negative bacteria (7 to 8 nanometers), with the attachment of the S-layer. Peptidoglycan forms around 90% of the dry weight of gram positive bacteria but only 10% of gram negative strains. Thus, presence of high levels of peptidoglycan is the primary determinant of the characterization of bacteria as gram positive. In gram positive strains, it is important in attachment roles and serotyping purposes. For both gram positive and gram negative bacteria, particles of approximately 2 nm can pass through the peptidoglycan cell wall.

Figure 2:
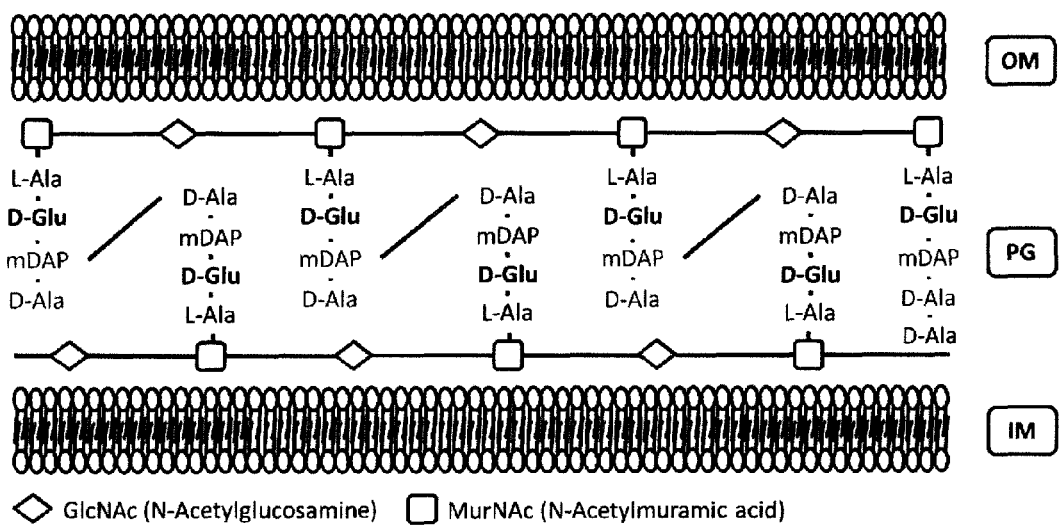
FIG. 2 schematically shows the structure and constitution of the bacterial wall of a gram negative bacterium (non-depicted lipopolysaccharides and proteins). PG: peptidoglycan (murein). OM: outer membrane. IM: inner membrane.
Figure 3:
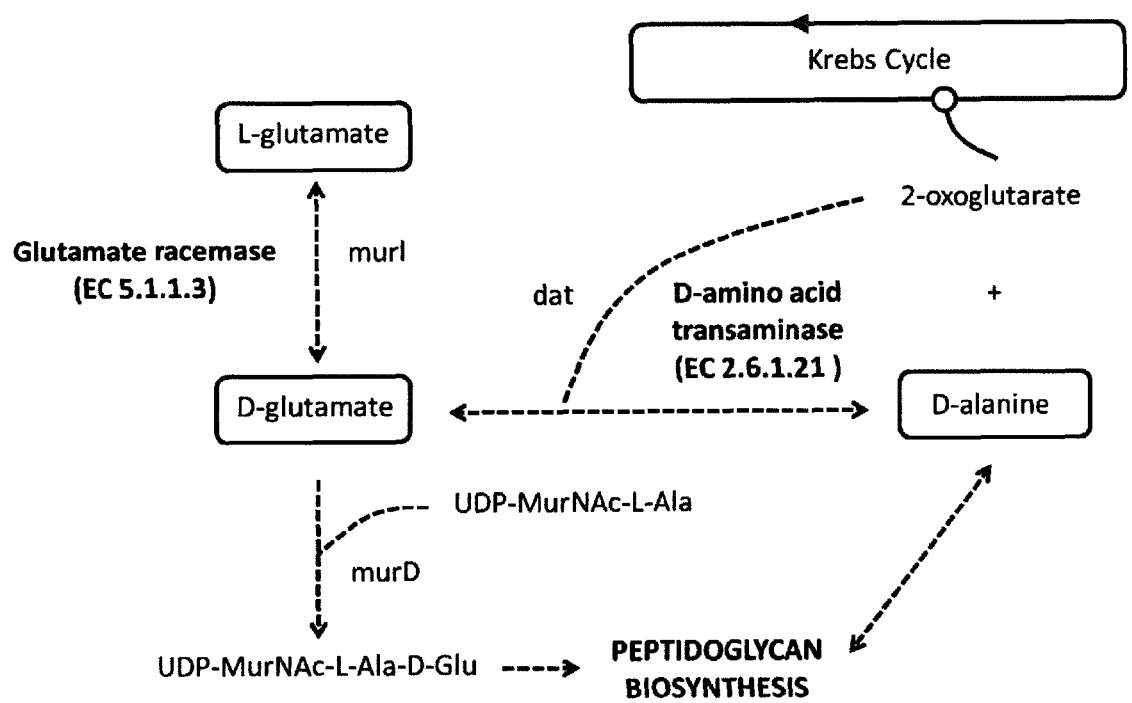
FIG. 3 schematically shows the sequence of metabolic processes culminating in the formation of D-glutamate and the incorporation thereof in the bacterial cell wall peptidoglycan. The dat, murI and murD genes depicted in the figure encode the Dat, MurI and MurD proteins, respectively.

As clearly illustrated in FIGS. 1 and 2, D-glutamate is one of the main components of the peptidoglycan cell wall and thus D-glutamate is necessary for cell wall peptidoglycan synthesis. Two enzymes catalyze the formation of D-glutamate (see FIG. 3):
1. the glutamate racemase (EC 5.1.1.3), MurI, an enzyme that catalyzes the chemical reaction
   L-glutamate ⇌ D-glutamate
   Thus, this enzyme has one substrate, L-glutamate, and one product, D-glutamate; and
2. D-amino acid transaminase, Dat (EC 2.6.1.21), an enzyme that catalyzes the following chemical reaction:
   D-alanine+2-oxoglutarate ⇌ pyruvate+D-glutamate
   Hence, the two substrates of this enzyme are D-alanine and 2-oxoglutarate, whereas its two products are pyruvate and D-glutamate.

D-glutamate, once synthesized, is added as a monomer unit to the peptidoglycan cell wall by an specific enzyme, namely by enzyme UDP-N-acetylmuramoyl-L-alanine: 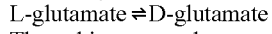 D-glutamate ligase (EC 6.3.2.9).

Therefore, the two enzymes that are capable of catalyzing the formation of D-glutamate are glutamate racemase and D-amino acid transaminase. However, the enzyme D-amino acid transaminase is not present in all bacterial strains. In contrast, the glutamate racemase gene is conserved in all species that produce peptidoglycan as *Acinetobacter baumannii, Bacillus anthracis, Bacillus cereus, Bacillus subtilis, Enterococcus faecalis, Enterococcus faecium, Escherichia coli, Helicobacter pylori, Klebsiella pneumoniae, Staphylococcus aureus, Pseudomonas aeruginosa, Streptococcus pyogenes*, etc.

In many of these bacteria, including *E. coli*, there is thus a sole protein capable of catalyzing the synthesis of D-glutamate, namely glutamate racemase. In these cases, this enzyme is essential for bacterial growth, since it is the sole source of D-glutamate in the cell. However, in other bacteria such as *Staphylococcus haemolyticus, Bacillus sphaericus,* *Bacillus* sp. YM-1 and *S. aureus* both Dat and MurI proteins are present and can thus functionally complement each other.

*A. baumannii* ATCC 17978 as *E. coli*, fails to have the Dat protein, but comprises two different genes encoding for MurI, in particular MurI 1 (locus A1S_0380) and MurI 2 (A1S_3398 locus). Both genes show a 29.8% identity between each other at the amino acid level, and 33.2 and 23.2% identity with *E. coli* K12 MurI protein respectively.

Therefore, an auxotrophic strain for D-glutamate can be easily obtained through the inactivation of the gene or of the different genes encoding glutamate racemase MurI and also, for those bacteria further comprising both Dat and MurI proteins, the additional inactivation of the gene or genes encoding D-amino acid transaminase. This means that for those bacteria not comprising the Dat enzyme, in some cases, in order to produce an auxotrophic strain for D-glutamate, the inactivation of a single gene of glutamate racemase is needed, such as in the case of *E. coli* strain K12 and *P. aeruginosa* strain PAO1, in other cases the inactivation of two different genes encoding for glutamate racemase is needed, as in the case of the strain of *A. baumannii* ATCC 17978, or in some other cases the inactivation of three different genes for glutamate racemase is needed, such as in the case of *A. baumannii* strain ABNIH10, that is, by inactivating the totality of the genes encoding glutamate racemase. In other cases, both the inactivation of the genes encoding the protein MurI as well as those genes encoding the enzyme D-amino acid transaminase, Dat, is required, as is the case of some gram positive bacteria like *Staphylococcus aureus, Staphylococcus haemolyticus, Bacillus sphaericus* and *Bacillus* sp. YM-1.

Consequently, a first aspect of the invention refers to a novel platform technology for the design and production of vaccines based on live attenuated bacterial strains auxotrophic for D-glutamate. This novel platform technology has potential in a wide variety of bacterial strains (universality). This fact (the versatility or universality of the invention) has been clearly demonstrated throughout the present invention since the authors have putted the invention into practice in three completely unrelated bacterial species (*Acinetobacter baumannii* (*A. baumannii*), *Pseudomonas aeruginosa* (*P. aeruginosa*) and *Staphylococcus aureus* (*S. aureus*)) as shown in the examples.

Thus, a preferred embodiment of the first aspect of the invention refers to a method for the production of a pharmaceutical composition, preferably a vaccine, comprising mutant live auxotrophic bacterial strains for D-glutamate, wherein the pharmaceutical composition is suitable for the prophylactic treatment (before infection) and/or therapeutic treatment (after infection or after the clinical manifestation of the disease caused by the infection) of animals and/or humans against infection with the wild type form of the mutant auxotrophic bacterial strain of the composition, and wherein said pharmaceutical composition is produced by a method comprising the steps of:
a. obtaining mutant live auxotrophic bacterial strains for D-glutamate;
b. introducing said mutant live auxotrophic bacerial strains in a pharmaceutically acceptable carrier or diluent and optionally adding an adjuvant; and
c. Optionally freeze-drying the pharmaceutical composition.

In another preferred embodiment of the first aspect of the invention, the production method comprises the steps of:

a. providing a bacterial strain capable of expressing glutamate racemase and possibly D-amino acid transaminase and comprising a peptidoglycan cell wall;
b. inactivating the gene or genes encoding for the glutamate racemase enzyme and, if needed, the gene or genes encoding for the enzyme D-amino acid transaminase in such way that the bacterial strain is no longer capable of expressing a functional glutamate racemase and/or a functional D-amino acid transaminase, wherein the inactivation of said genes thus causes said bacterial strain to be auxotrophic for D-glutamate; and
c. introducing said mutant live auxotrophic bacterial strains in a pharmaceutically acceptable carrier or diluent and optionally adding an adjuvant; and
d. Optionally freeze-drying the pharmaceutical composition.

The inactivation mentioned in step b) above can be an insertion, a deletion, a substitution or a combination thereof, provided that the inactivation leads to the failure to express a functional glutamate racemase and/or a functional D-amino acid transaminase protein. A functional glutamate racemase and/or a functional D-amino acid transaminase protein is understood to be a protein having the regulating characteristics of the wild-type protein. Therefore, a glutamate racemase and/or a functional D-amino acid transaminase protein that is defective and thus incapable of participating in the synthesis of D-glutamate is considered to be a non-functional protein.

In another preferred embodiment of the first aspect of the invention or of any of its preferred embodiments, the pharmaceutical composition is a vaccine and the production method comprises adding an adjuvant.

In another preferred embodiment of the first aspect of the invention or of any of its preferred embodiments, the bacterial strain of step a) is a gram positive or gram negative bacteria. Preferably, the bacterial strain of step a) is selected from the list of bacterial species consisting of: *Acinetobacter baumannii, Acinetobacter baylyi, Acinetobacter calcoaceticus, Acinetobacter haemolyticus, Acinetobacter junii, Acinetobacter lwoffii, Acinetobacter nosocomialis, Acinetobacter pittii, Acinetobacter radioresistens, Actinobacillus lignieresii, Actinobacillus suis, Aeromonas caviae, Aeromonas hydrophila, Aeromonas veronii subsp. sobria, Aggregatibacter actinomycetemcomitans, Arcobacter butzleri, Arcobacter nitrofigilis, Bacillus amyloliquefaciens, Bacillus anthracis, Bacillus bataviensis, Bacillus cellulosilyticus, Bacillus cereus, Bacillus clausii, Bacillus licheniformis, Bacillus megaterium, Bacillus pumilus, Bacillus subtilis, Bacillus thuringiensis, Bacteroides fragilis, Bordetella avium, Bordetella bronchiseptica, Bordetella pertusis, Bordetella petrii, Brucella abortus, Brucella melitensis, Brucella suis, Burkholderia cenocepacia, Burkholderia mallei, Burkholderia multivorans, Burkholderia pseudomallei, Burkholderia thailandensis, Campylobacter concisus, Campylobacter fetus subsp. fetus, Campylobacter fetus subsp. venerealis, Campylobacter gracilis, Campylobacter hominis, Campylobacter jejuni, Campylobacter rectus, Campylobacter showae, Campylobacter upsaliensis, Citrobacter freundii, Citrobacter koseri, Clostridium asparagiforme, Clostridium botulinum, Clostridium butyricum, Clostridium difficile, Clostridium perfringens, Clostridium saccharobutylicum, Clostridium tetani, Corynebacterium diphtheriae, Corynebacterium pseudotuberculosis, Enterobacter aerogenes, Enterobacter cloacae, Enterococcus faecalis, Enterococcus faecium, Erysipelothrix rhusiopathiae, Escherichia coli, Fusobacterium necrophorum, Fusobacterium nucleatum, Granulicatella adiacens, Granulicatella elegans, Haemophilus equigenitalis, Haemophilus influenzae, Haemophilus parainfluenzae, Haemophilus paragallinarum, Haemophilus parasuis, Haemophilus pleuropneumoniae, Haemophilus somnus, Helicobacter pylori, Klebsiella oxytoca, Klebsiella pneumoniae, Legionella oakridgensis, Legionella pneumophila, Leptospira biflexa, Leptospira illini, Leptospira interrogans, Listeria monocytogenes, Lysinibacillus fusiformis, Lysinibacillus sphaericus, Moraxella bovis, Morganella morganii, Mycobacterium abscessus, Mycobacterium africanum, Mycobacterium avium, Mycobacterium bovis, Mycobacterium leprae, Mycobacterium tuberculosis, Neisseria gonorrhoeae, Neisseria meningitidis, Pasteurella multocida, Plesiomonas shigelloides, Propionibacterium acnes, Proteus hanseri, Proteus mirabilis, Pseudomonas aeruginosa, Salmonella cholerasuis, Salmonella enterica subsp. enterica, Salmonella enteritidis, Salmonella paratyphi, Salmonella typhi, Serratia plymuthica, Shigella boydii, Shigella dysenteriae, Shigella flexneri, Staphylococcus arlettae, Staphylococcus aureus, Staphylococcus capitis, Staphylococcus caprae, Staphylococcus carnosus, Staphylococcus epidermidis, Staphylococcus equorum, Staphylococcus haemolyticus, Staphylococcus hominis, Staphylococcus lugdunensis, Staphylococcus pasteuri, Staphylococcus pettenkoferi, Staphylococcus pseudointermedius, Staphylococcus saprophyticus, Staphylococcus simiae, Staphylococcus simulans, Staphylococcus warneri, Stenotrophomonas maltophilia, Streptococcus agalactiae, Streptococcus dysgalactiae, Streptococcus dysgalactiae subsp. equisimilis, Streptococcus equi, Streptococcus pneumoniae, Streptococcus pyogenes, Streptococcus uberis, Streptococcus zooepidermicus, Taylorella asinigenitalis, Taylorella equigenitalis, Treponema carateum, Treponema cuniculi, Treponema hyodisenteriae, Treponema pallidum, Treponema suis, Veillonella atypica, Veillonella dispar, Veillonella parvula, Veillonella ratti, Vibrio cholerae, Vibrio parahaemolyticus, Vibrio vulnificans, Yersinia enterocolitica, Yersinia pestis* and *Yersinia pseudotuberculosis*. More preferably, said bacterial strain of step a) is selected from the list consisting of the following species: *Acinetobacter baumannii, Pseudomonas aeruginosa* and *Staphylococcus aureus*. Still more preferably, the bacterial strain is the bacterial strain of *A. baumannii* designated *Acinetobacter baumannii* Delta0380/Delta3398 and deposited under the Budapest treaty before the Spanish Type Culture Collection on Apr. 14, 2014 with strain number 8588 by Fundación Profesor Novoa Santos. Still more preferably, the bacterial strain is the bacterial strain of *P. aeruginosa* designated *Pseudomonas aeruginosa* DeltaPA4662 and deposited under the Budapest treaty before the Spanish Type Culture Collection on Apr. 14, 2014 with strain number 8589 by Fundación Profesor Novoa Santos. Still more preferably, the bacterial strain is the bacterial strain of *S. aureus* designated 132deltamurI/deltadat and deposited under the Budapest treaty before the Spanish Type Culture Collection on Jun. 11, 2014 with strain number 8587 by Fundación Profesor Novoa Santos.

In addition, one further embodiment of the first aspect of the present inventions refers to a method for the production of live attenuated bacterial strains (from hereinafter "method for the production of live attenuated bacterial strains of the invention") suitable as vaccine candidates comprising the steps of:
a. providing a bacterial strain capable of expressing glutamate racemase and possibly D-amino acid transaminase and comprising a peptidoglycan cell wall; and b. inactivating the gene or genes encoding for the glutamate racemase enzyme and, if needed, the gene or genes encoding for the enzyme D-amino acid transaminase in such way that the bacterial strain is no longer capable of expressing a functional glutamate racemase and/or a functional D-amino acid transaminase wherein the inactivation of said genes thus causes said bacterial strain to be auxotrophic for D-glutamate.

In a preferred embodiment of the "method for the production of live attenuated bacterial strains of the invention", the bacterial strain of step a) is a gram positive or gram negative bacteria.

In another preferred embodiment of the "method for the production of live attenuated bacterial strains of the invention", the bacterial strain of step a) has as the only way of synthesis of D-glutamate the glutamate racemase enzyme the method thus comprising the inactivation of the genes encoding for this enzyme, namely for glutamate racemase.

In a more preferred embodiment of the "method for the production of live attenuated bacterial strains of the invention", the bacterial strain of step a) is selected from the list of bacterial species consisting of: *Acinetobacter baumannii, Acinetobacter baylyi, Acinetobacter calcoaceticus, Acinetobacter haemolyticus, Acinetobacter junk Acinetobacter lwoffii, Acinetobacter nosocomialis, Acinetobacter pittii, Acinetobacter radioresistens, Actinobacillus lignieresii, Actinobacillus suis, Aeromonas caviae, Aeromonas hydrophila, Aeromonas veronii* subsp. *sobria, Aggregatibacter actinomycetemcomitans, Arcobacter butzleri, Arcobacter nitrofigilis, Bacillus amyloliquefaciens, Bacillus anthracis, Bacillus bataviensis, Bacillus cellulosilyticus, Bacillus cereus, Bacillus clausii, Bacillus licheniformis, Bacillus megaterium, Bacillus pumilus, Bacillus subtilis, Bacillus thuringiensis, Bacteroides fragilis, Bordetella avium, Bordetella bronchiseptica, Bordetella pertusis, Bordetella petrii, Brucella abortus, Brucella melitensis, Brucella suis, Burkholderia cenocepacia, Burkholderia mallei, Burkholderia multivorans, Burkholderia pseudomallei, Burkholderia thailandensis, Campylobacter concisus, Campylobacter fetus* subsp. *fetus, Campylobacter fetus* subsp. *venerealis, Campylobacter gracilis, Campylobacter hominis, Campylobacter jejuni, Campylobacter rectus, Campylobacter showae, Campylobacter upsaliensis, Citrobacter freundii, Citrobacter koseri, Clostridium asparagiforme, Clostridium botulinum, Clostridium butyricum, Clostridium difficile, Clostridium perfringens, Clostridium saccharobutylicum, Clostridium tetani, Corynebacterium diphtheriae, Corynebacterium pseudotuberculosis, Enterobacter aerogenes, Enterobacter cloacae, Enterococcus faecalis, Enterococcus faecium, Erysipelothrix rhusiopathiae, Escherichia coli, Fusobacterium necrophorum, Fusobacterium nucleatum, Granulicatella adiacens, Granulicatella elegans, Haemophilus equigenitalis, Haemophilus influenzae, Haemophilus parainfluenzae, Haemophilus paragallinarum, Haemophilus parasuis, Haemophilus pleuropneumoniae, Haemophilus somnus, Helicobacter pylori, Klebsiella oxytoca, Klebsiella pneumoniae, Legionella oakridgensis, Legionella pneumophila, Leptospira biflexa, Leptospira illini, Leptospira interrogans, Listeria monocytogenes, Lysinibacillus fusiformis, Lysinibacillus sphaericus, Moraxella bovis, Morganella morganii, Mycobacterium abscessus, Mycobacterium africanum, Mycobacterium avium, Mycobacterium bovis, Mycobacterium leprae, Mycobacterium tuberculosis, Neisseria gonorrhoeae, Neisseria meningitidis, Pasteurella multocida, Plesiomonas shigelloides, Propionibacterium acnes, Proteus hanseri, Proteus mirabilis, Pseudomonas aeruginosa, Salmonella cholerasuis, Salmonella enterica* subsp. *enterica, Salmonella enteritidis, Salmonella paratyphi, Salmonella typhi, Serratia plymuthica, Shigella boydii, Shigella dysenteriae, Shigella flexneri, Staphylococcus arlettae, Staphylococcus aureus, Staphylococcus capitis, Staphylococcus caprae, Staphylococcus carnosus, Staphylococcus epidermidis, Staphylococcus equorum, Staphylococcus haemolyticus, Staphylococcus hominis, Staphylococcus lugdunensis, Staphylococcus pasteuri, Staphylococcus pettenkoferi, Staphylococcus pseudointermedius, Staphylococcus saprophyticus, Staphylococcus simiae, Staphylococcus simulans, Staphylococcus warneri, Stenotrophomonas maltophilia, Streptococcus agalactiae, Streptococcus dysgalactiae, Streptococcus dysgalactiae* subsp. *equisimilis, Streptococcus equi, Streptococcus pneumoniae, Streptococcus pyogenes, Streptococcus uberis, Streptococcus zooepidermicus, Taylorella asinigenitalis, Taylorella equigenitalis, Treponema carateum, Treponema cuniculi, Treponema hyodisenteriae, Treponema pallidum, Treponema suis, Veillonella atypica, Veillonella dispar, Veillonella parvula, Veillonella ratti, Vibrio cholerae, Vibrio parahaemolyticus, Vibrio vulnificans, Yersinia enterocolitica, Yersinia pestis* and *Yersinia pseudotuberculosis*.

In an even more preferred embodiment of the "method for the production of live attenuated bacterial strains of the invention" said bacterial strain of step a) is selected from the list consisting of the following species: *Acinetobacter baumannii, Pseudomonas aeruginosa* and *Staphylococcus aureus*.

In a still more preferred embodiment of the "method for the production of live attenuated bacterial strains of the invention", said bacterial strain of step a) is the bacterial strain of *A. baumannii* designated ATCC 17978 and the method comprises the inactivation of the locus A1S_0380 and A1S_3398 (see example 2).

In a still more preferred embodiment of the "method for the production of live attenuated bacterial strains of the invention", said bacterial strain of step a) is the bacterial strain of *P. aeruginosa* designated PAO1 and the method comprises inactivating the PA4662 gene (see example 15).

In a still more preferred embodiment of the "method for the production of live attenuated bacterial strains of the invention", said bacterial strain of step a) is the bacterial strain of *S. aureus* designated 132 and the method comprises inactivating the murI and dat genes (see example 22).

In addition and as already stated throughout the text, because of their unexpected attenuated but immunogenic character in vivo, the bacterial strains as defined in the present invention are very suitable as a basis for live attenuated vaccines.

In relation to the use as a vaccine of the bacterial strains of the invention mentioned in the precedent paragraph, the present invention further relates, namely as a second aspect of the invention, to live attenuated pharmaceutical compositions, in particular to live attenuated vaccine compositions, comprising the mutant auxotrophic bacterial strains as defined herein.

These compositions are especially suitable for the protection of animals and humans against infection with the wild type form of the mutant auxotrophic bacteria. Such animals can be selected from the group consisting of placental (including humans), marsupial and monotremes. Such pharmaceutical compositions, in particular vaccine compositions, comprise an immunogenically effective amount of the live attenuated bacterium as defined herein. In addition to an immunogenically effective amount of the live attenuated bacterium described above, a pharmaceutical composition, in particular a vaccine, according to the present invention also contains a pharmaceutically acceptable carrier. Such a carrier may be as simple as water, but it may e.g. also comprise culture fluid in which the bacteria were cultured. Another suitable carrier is e.g. a solution of physiological salt concentration.

The useful dosage to be administered will vary depending on the age, weight and animal vaccinated the mode of administration and the type of pathogen against which vaccination is sought.

The pharmaceutical composition, in particular the vaccine, may comprise any dose of bacteria, sufficient to evoke an immune response. Doses ranging between $10^3$ and $10^{10}$ bacteria are e.g. very suitable doses.

Optionally, one or more compounds having adjuvant activity may be added to the pharmaceutical composition, in particular to the vaccine. Adjuvants are non-specific stimulators of the immune system. They enhance the immune response of the host to the vaccine. Examples of adjuvants known in the art are Freunds Complete and Incomplete adjuvant, vitamin E, non-ionic block polymers, muramyldipeptides, ISCOMs (immune stimulating complexes, cf. for instance European Patent EP 109942), Saponins, mineral oil, vegetable oil, and CARBOPOL®. Adjuvants, especially suitable for mucosal application are e.g. the E. coli heat-labile toxin (LT) or Cholera toxin (CT). Other suitable adjuvants are for example aluminium hydroxide, aluminium phosphate or aluminium oxide, oil-emulsions (e.g. of Bayol F® or Marcol 52®, saponins or vitamin-E solubilisate.

Other examples of pharmaceutically acceptable carriers or diluents useful in the present invention include stabilisers such as SPGA, carbohydrates (e.g. sorbitol, mannitol, starch, sucrose, glucose, dextran), proteins such as albumin or casein, protein containing agents such as bovine serum or skimmed milk and buffers (e.g. phosphate buffer). Especially when such stabilisers are added to the vaccine, the vaccine is very suitable for freeze-drying. Therefore, in a more preferred form, the vaccine is in a freeze-dried form.

For administration to animals or humans, the pharmaceutical composition, in particular the vaccine, according to the present invention can be given inter alia intranasally, intradermally, subcutaneously, orally, by aerosol or intramuscularly. For application to poultry, wing web and eye-drop administration are very suitable. The medicament, pharmaceutical composition or vaccine of the invention can be used both in asymptomatic patients as well as in those who have already shown symptoms of the disease.

Therefore, a second aspect of the invention refers to a pharmaceutical composition, preferably a vaccine, comprising mutant live auxotrophic bacerial strains for D-glutamate and a pharmaceutically acceptable carrier or diluent and optionally an adjuvant, wherein said pharmaceutical composition is suitable for the prophylactic (before infection) and/or therapeutic treatment (after infection or after the clinical manifestation of the disease caused by the infection) of animals and/or humans against infection with the wild type form of the mutant auxotrophic bacteria of the composition.

In a preferred embodiment of the second aspect of the invention, said pharmaceutical composition is a vaccine and said vaccine optionally comprises an adjuvant.

In another preferred embodiment of the second aspect of the invention or of any of its preferred embodiments, said pharmaceutically acceptable carrier or diluent is selected from the list consisting of water, culture fluid, a solution of physiological salt concentration and/or stabilisers such as SPGA, carbohydrates (e.g. sorbitol, mannitol, starch, sucrose, glucose, dextran), proteins such as albumin or casein, protein containing agents such as bovine serum or skimmed milk and buffers (e.g. phosphate buffer).

In another preferred embodiment of the second aspect of the invention or of any of its preferred embodiments, said adjuvant is selected from the list consisting of Freunds Complete and Incomplete adjuvant, vitamin E, non-ionic block polymers, muramyldipeptides, ISCOMs (immune stimulating complexes), Saponins, mineral oil, vegetable oil, CARBOPOL®, the E. coli heat-labile toxin (LT) or Cholera toxin (CT), aluminium hydroxide, aluminium phosphate or aluminium oxide, oil-emulsions (e.g. of Bayol F® or Marcol 52®, saponins and vitamin-E solubilisate.

In another preferred embodiment of the second aspect of the invention or of any of its preferred embodiments, said pharmaceutical composition comprises a dose of mutant live auxotrophic bacterial strains for D-glutamate ranging between $10^3$ and $10^{10}$ bacteria.

In another preferred embodiment of the second aspect of the invention or of any of its preferred embodiments, said pharmaceutical composition is in a freeze-dried form.

In another preferred embodiment of the second aspect of the invention or of any of its preferred embodiments, the bacterial strain is selected from the list of bacterial species consisting of: Acinetobacter baumannii, Acinetobacter baylyi, Acinetobacter calcoaceticus, Acinetobacter haemolyticus, Acinetobacter junk Acinetobacter lwoffii, Acinetobacter nosocomialis, Acinetobacter pittii, Acinetobacter radioresistens, Actinobacillus lignieresii, Actinobacillus suis, Aeromonas caviae, Aeromonas hydrophila, Aeromonas veronii subsp. sobria, Aggregatibacter actinomycetemcomitans, Arcobacter butzleri, Arcobacter nitrofigilis, Bacillus amyloliquefaciens, Bacillus anthracis, Bacillus bataviensis, Bacillus cellulosilyticus, Bacillus cereus, Bacillus clausii, Bacillus licheniformis, Bacillus megaterium, Bacillus pumilus, Bacillus subtilis, Bacillus thuringiensis, Bacteroides fragilis, Bordetella avium, Bordetella bronchiseptica, Bordetella pertusis, Bordetella petrii, Brucella abortus, Brucella melitensis, Brucella suis, Burkholderia cenocepacia, Burkholderia mallei, Burkholderia multivorans, Burkholderia pseudomallei, Burkholderia thailandensis, Campylobacter concisus, Campylobacter fetus subsp. fetus, Campylobacter fetus subsp. venerealis, Campylobacter gracilis, Campylobacter hominis, Campylobacter jejuni, Campylobacter rectus, Campylobacter showae, Campylobacter upsaliensis, Citrobacter freundii, Citrobacter koseri, Clostridium asparagiforme, Clostridium botulinum, Clostridium butyricum, Clostridium difficile, Clostridium perfringens, Clostridium saccharobutylicum, Clostridium tetani, Corynebacterium diphtheriae, Corynebacterium pseudotuberculosis, Enterobacter aerogenes, Enterobacter cloacae, Enterococcus faecalis, Enterococcus faecium, Erysipelothrix rhusiopathiae, Escherichia coli, Fusobacterium necrophorum, Fusobacterium nucleatum, Granulicatella adiacens, Granulicatella elegans, Haemophilus equigenitalis, Haemophilus influenzae, Haemophilus parainfluenzae, Haemophilus paragallinarum, Haemophilus parasuis, Haemophilus pleuropneumoniae, Haemophilus somnus, Helicobacter pylori, Klebsiella oxytoca, Klebsiella pneumoniae, Legionella oakridgensis, Legionella pneumophila, Leptospira biflexa, Leptospira illini, Leptospira interrogans, Listeria monocytogenes, Lysinibacillus fusiformis, Lysinibacillus sphaericus, Moraxella bovis, Morganella morganii, Mycobacterium abscessus, Mycobacterium africanum, Mycobacterium avium, Mycobacterium bovis, Mycobacterium leprae, Mycobacterium tuberculosis, Neisseria gonorrhoeae, Neisseria meningitidis, Pasteurella multocida, Plesiomonas shigelloides, Propionibacterium acnes, Proteus hanseri, Proteus mirabilis, Pseudomonas aeruginosa, Salmonella cholerasuis, Salmonella enterica subsp. enterica, Salmonella enteritidis, Salmonella paratyphi, Salmonella typhi, Serratia plymuthica, Shigella boydii, Shigella dysenteriae, Shigella flexneri, Staphylococcus arlettae, Staphylococcus aureus, Staphylococcus capitis, Staphylococcus caprae, Staphylococcus carnosus, Staphylococcus epidermidis, Staphylococcus equorum, Staphylococcus haemolyticus, Staphylococcus hominis, Staphylococcus lugdunensis, Staphylococcus pasteuri, Staphylococcus pettenkoferi, Staphylococcus pseudointermedius, Staphylococcus saprophyticus, Staphylococcus simiae, Staphylococcus simulans, Staphylococcus warneri, Stenotrophomonas maltophilia, Streptococcus agalactiae, Streptococcus dysgalactiae, Streptococcus dysgalactiae subsp. equisimilis, Streptococcus equi, Streptococcus pneumoniae, Streptococcus pyogenes, Streptococcus uberis, Streptococcus zooepidermicus, Taylorella asinigenitalis, Taylorella equigenitalis, Treponema carateum, Treponema cuniculi, Treponema hyodisenteriae, Treponema pallidum, Treponema suis, Veillonella atypica, Veillonella dispar, Veillonella parvula, Veillonella ratti, Vibrio cholerae, Vibrio parahaemolyticus, Vibrio vulnificans, Yersinia enterocolitica, Yersinia pestis and Yersinia pseudotuberculosis.

More preferably, said bacterial strain of step a) is selected from the list consisting of the following species: Acinetobacter baumannii, Pseudomonas aeruginosa and Staphylococcus aureus. Still more preferably, the bacterial strain is the bacterial strain of A. baumannii designated Acinetobacter baumannii Delta0380/Delta3398 and deposited under the Budapest treaty before the Spanish Type Culture Collection on Apr. 14, 2014 with strain number 8588 by Fundación Profesor Novoa Santos. Still more preferably, the bacterial strain is the bacterial strain of P. aeruginosa designated Pseudomonas aeruginosa DeltaPA4662 and deposited under the Budapest treaty before the Spanish Type Culture Collection on Apr. 14, 2014 with strain number 8589 by Fundación Profesor Novoa Santos. Still more preferably, the bacterial strain is the bacterial strain of S. aureus designated 132deltamurI/deltadat and deposited under the Budapest treaty before the Spanish Type Culture Collection on Jun. 11, 2014 with strain number 8587 by Fundación Profesor Novoa Santos.

A third aspect of the invention refers to a live attenuated bacterial strain, obtain or obtainable by means of the method of the first aspect of the invention or by means of any of the preferred embodiments of the first aspect of the invention.

A different embodiment of the third aspect of the present invention relates to a live attenuated D-glutamate auxotrophic bacterial strain, suitable as a vaccine, characterized in that in said strain the genes encoding for the glutamate racemase enzyme and, if existent, the genes encoding for the enzyme D-amino acid transaminase, are inactivated.

Such inactivation can be an insertion, a deletion, a substitution or a combination thereof, provided that the inactivation leads to the failure to express a functional glutamate racemase and a functional D-amino acid transaminase protein. A functional glutamate racemase and/or a functional D-amino acid transaminase protein is understood to be a protein having the regulating characteristics of the wild-type protein. Therefore, a glutamate racemase and/or a functional D-amino acid transaminase protein that is defective and thus incapable of participating in the synthesis of D-glutamate is considered to be a non-functional protein.

In a preferred embodiment of the third aspect of the invention, the bacterial strain is a gram positive or gram negative bacteria.

In another preferred embodiment of the third aspect of the invention, the bacterial strain has as the only way of synthesis of D-glutamate the glutamate racemase enzyme the bacteria thus being characterized by the inactivation of the genes encoding for this enzyme, namely for glutamate racemase.

In a more preferred embodiment of the third aspect of the invention, the bacterial strain is selected from the list of bacterial species consisting of: Acinetobacter baumannii, Acinetobacter baylyi, Acinetobacter calcoaceticus, Acinetobacter haemolyticus, Acinetobacter junii, Acinetobacter lwoffii, Acinetobacter nosocomialis, Acinetobacter pittii, Acinetobacter radioresistens, Actinobacillus lignieresii, Actinobacillus suis, Aeromonas caviae, Aeromonas hydrophile, Aeromonas veronii subsp. sobria, Aggregatibacter actinomycetemcomitans, Arcobacter butzleri, Arcobacter nitrofigilis, Bacillus amyloliquefaciens, Bacillus anthracis, Bacillus bataviensis, Bacillus cellulosilyticus, Bacillus cereus, Bacillus clausii, Bacillus licheniformis, Bacillus megaterium, Bacillus pumilus, Bacillus subtilis, Bacillus thuringiensis, Bacteroides fragilis, Bordetella avium, Bordetella bronchiseptica, Bordetella pertusis, Bordetella petrii, Brucella abortus, Brucella melitensis, Brucella suis, Burkholderia cenocepacia, Burkholderia mallei, Burkholderia multivorans, Burkholderia pseudomallei, Burkholderia thailandensis, Campylobacter concisus, Campylobacter fetus subsp. fetus, Campylobacter fetus subsp. venerealis, Campylobacter gracilis, Campylobacter hominis, Campylobacter jejuni, Campylobacter rectus, Campylobacter showae, Campylobacter upsaliensis, Citrobacter freundii, Citrobacter koseri, Clostridium asparagiforme, Clostridium botulinum, Clostridium butyricum, Clostridium difficile, Clostridium perfringens, Clostridium saccharobutylicum, Clostridium tetani, Corynebacterium diphtheriae, Corynebacterium pseudotuberculosis, Enterobacter aerogenes, Enterobacter cloacae, Enterococcus faecalis, Enterococcus faecium, Erysipelothrix rhusiopathiae, Escherichia coli, Fusobacterium necrophorum, Fusobacterium nucleatum, Granulicatella adiacens, Granulicatella elegans, Haemophilus equigenitalis, Haemophilus influenzae, Haemophilus parainfluenzae, Haemophilus paragallinarum, Haemophilus parasuis, Haemophilus pleuropneumoniae, Haemophilus somnus, Helicobacter pylori, Klebsiella oxytoca, Klebsiella pneumoniae, Legionella oakridgensis, Legionella pneumophila, Leptospira biflexa, Leptospira illini, Leptospira interrogans, Listeria monocytogenes, Lysinibacillus fusiformis, Lysinibacillus sphaericus, Moraxella bovis, Morganella morganii, Mycobacterium abscessus, Mycobacterium africanum, Mycobacterium avium, Mycobacterium bovis, Mycobacterium leprae, Mycobacterium tuberculosis, Neisseria gonorrhoeae, Neisseria meningitidis, Pasteurella multocida, Plesiomonas shigelloides, Propionibacterium acnes, Proteus hanseri, Proteus mirabilis, Pseudomonas aeruginosa, Salmonella cholerasuis, Salmonella enterica subsp. enterica, Salmonella enteritidis, Salmonella paratyphi, Salmonella typhi, Serratia plymuthica, Shigella boydii, Shigella dysenteriae, Shigella flexneri, Staphylococcus arlettae, Staphylococcus aureus, Staphylococcus capitis, Staphylococcus caprae, Staphylococcus carnosus, Staphylococcus epidermidis, Staphylococcus equorum, Staphylococcus haemolyticus, Staphylococcus hominis, Staphylococcus lugdunensis, Staphylococcus pasteuri, Staphylococcus pettenkoferi, Staphylococcus pseudointermedius, Staphylococcus saprophyticus, Staphylococcus simiae, Staphylococcus simulans, Staphylococcus warneri, Stenotrophomonas maltophilia, Streptococcus agalactiae, Streptococcus dysgalactiae, Streptococcus dysgalactiae subsp. equisimilis,

*Streptococcus equi, Streptococcus pneumoniae, Streptococcus pyogenes, Streptococcus uberis, Streptococcus zooepidermicus, Taylorella asinigenitalis, Taylorella equigenitalis, Treponema carateum, Treponema cuniculi, Treponema hyodisenteriae, Treponema pallidum, Treponema suis, Veillonella atypica, Veillonella dispar, Veillonella parvula, Veillonella ratti, Vibrio cholerae, Vibrio parahaemolyticus, Vibrio vulnificans, Yersinia enterocolitica, Yersinia pestis* and *Yersinia pseudotuberculosis*.

In an even more preferred embodiment of the third aspect of the invention said bacterial strain is selected from the list consisting of the following species: *Acinetobacter baumannii, Pseudomonas aeruginosa* and *Staphylococcus aureus*.

In a still more preferred embodiment of the third aspect of the invention, said bacterial strain is the bacterial strain of *A. baumannii* designated ATCC 17978 characterized by the inactivation of the locus A1S_0380 and A1S_3398 (see example 2).

In a still more preferred embodiment of the third aspect of the invention, said bacterial strain is the bacterial strain of *P. aeruginosa* designated PAO1 characterized by the inactivation of the PA4662 gene (see example 15).

In a still more preferred embodiment of the third aspect of the invention, said bacterial strain is a bacterial strain of *S. aureus* designated 132 characterized by the inactivation of the murI and dat genes (see example 22).

In a still more preferred embodiment of the third aspect of the invention, said bacterial strain is the bacterial strain of *A. baumannii* designated *Acinetobacter baumannii* Delta0380/Delta3398 and deposited under the Budapest treaty before the Spanish Type Culture Collection on Apr. 14, 2014 with strain number 8588 by Fundación Profesor Novoa Santos.

In a still more preferred embodiment of the third aspect of the invention, said bacterial strain is the bacterial strain of *P. aeruginosa* designated *Pseudomonas aeruginosa* DeltaPA4662 and deposited under the Budapest treaty before the Spanish Type Culture Collection on Apr. 14, 2014 with strain number 8589 by Fundación Profesor Novoa Santos.

In a still more preferred embodiment of the third aspect of the invention, said bacterial strain is the bacterial strain of *S. aureus* designated 132deltamurI/deltadat and deposited under the Budapest treaty before the Spanish Type Culture Collection on Jun. 11, 2014 with strain number 8587 by Fundación Profesor Novoa Santos. A fourth aspect of the invention refers to the bacterial strain as defined in the third aspect of the invention, for use as a medicament, in particular for use as a vaccine.

A fifth aspect of the invention refers to the pharmaceutical composition of the second aspect of the invention or the mutant live auxotrophic bacterial strain for D-glutamate of the third aspect of the invention, for use in a method of prophylactic treatment (before infection) and/or therapeutic treatment (after infection or after the clinical manifestation of the disease caused by the infection) of animals and/or humans against infection with the wild type form of the mutant auxotrophic bacteria of the composition.

A sixth aspect of the invention refers to an antibody or fragment thereof selected from the group consisting of Fab, F(ab')2, Fv, scFv, di-scFv and sdAB, capable of recognizing a mutant live auxotrophic bacterial strain for D-glutamate, wherein said antibody or fragment thereof is suitable for the prophylactic treatment (before infection) and/or therapeutic treatment (after infection or after the clinical manifestation of the disease caused by the infection) of animals and/or humans against infection with the wild type form of the mutant auxotrophic bacteria of the composition.

An seventh aspect of the invention refers to an antibody or fragment thereof selected from the group consisting of Fab, F(ab')2, Fv, scFv, di-scFv and sdAB, obtained or obtainable after immunization of a mammal with a mutant live auxotrophic bacterial strain for D-glutamate, wherein said antibody or fragment thereof is suitable for the prophylactic treatment (before infection) and/or therapeutic treatment (after infection or after the clinical manifestation of the disease caused by the infection) of animals and/or humans against infection with the wild type form of the mutant auxotrophic bacteria of the composition In a preferred embodiment of the seventh aspect of the invention, the mammal used for the immunization is selected from the group consisting of placental (including humans), marsupial and monotremes.

An eighth aspect of the invention refers to a pharmaceutical composition, preferably a vaccine, comprising the antibodies or fragments thereof of any of the sixth or seventh aspects of the invention and a pharmaceutically acceptable carrier or diluent and optionally an adjuvant, wherein said pharmaceutical composition is suitable for the prophylactic (before infection) and/or therapeutic treatment (after infection or after the clinical manifestation of the disease caused by the infection) of animals and/or humans against infection with the wild type form of the mutant auxotrophic bacteria of the composition. In a preferred embodiment of the ninth aspect of the invention, said pharmaceutical composition is a vaccine wherein said vaccine optionally comprises an adjuvant.

A ninth aspect of the invention refers to the antibodies or fragments thereof of the sixth or seventh aspects of the invention, for use in therapy, in particular for use in passive immunization.

A tenth aspect of the invention refers to the pharmaceutical composition of the ninth aspect of the invention or the antibodies or fragments thereof of any of the sixth or seventh aspects of the invention, for use in a method of prophylactic treatment (before infection) and/or therapeutic treatment (after infection or after the clinical manifestation of the disease caused by the infection) of animals and/or humans against infection with the wild type form of the mutant auxotrophic bacteria of the composition.

An eleventh aspect of the invention refers to the pharmaceutical composition of the second or eighth aspects of the invention or the mutant live auxotrophic bacterial strain for D-glutamate of the third aspect of the invention or the antibodies or fragments thereof of any of the sixth or seventh aspects of the invention, for use in a method of prophylactic treatment (before infection) and/or therapeutic treatment (after infection or after after the clinical manifestation of the disease caused by the infection) of animals and/or humans against infection with the wild type form of the mutant auxotrophic bacteria of the composition and wherein said composition, bacterial strain or antibody or fragment thereof is administered intranasally, intradermally, subcutaneously, orally, by aerosol, intramuscularly, wing web and eye-drop administration.

Figure 50:
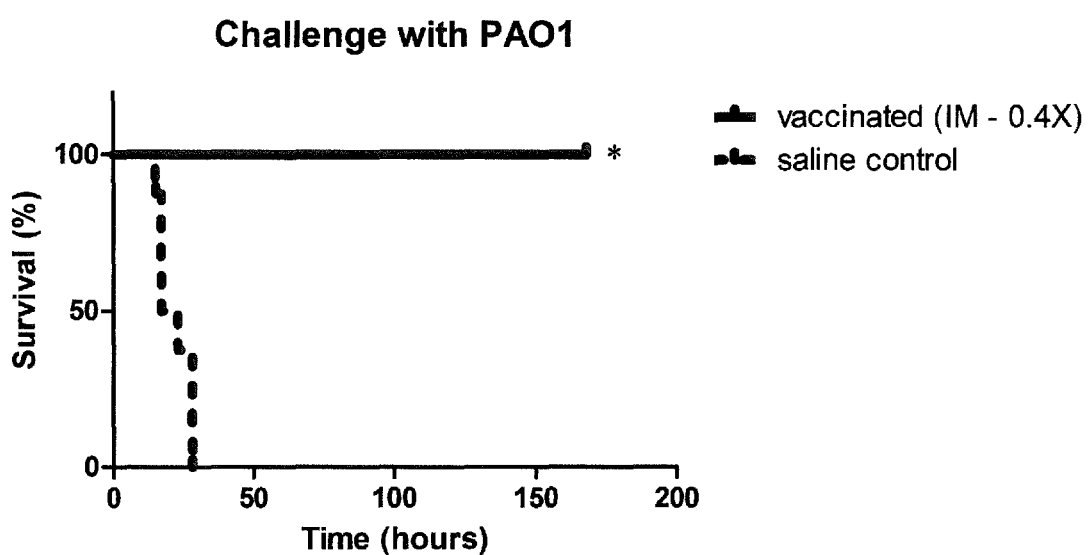
FIG. 50 is the percent survival of BALB/c mice (n=8) following intraperitoneal infection with a 0.4× dose of *P. aeruginosa* PAO1 wild type strain. Vaccinated mice were immunized on days 0, 14 and 28 with *P. aeruginosa* ΔPA4662 strain by intramuscular route and infected with the wild type strain at day 35. Non-vaccinated mice were administered saline on days 0, 14 and 28 and infected with the wild type strain at the same day. *P<0.0001 survival of vaccinated group compared to non-vaccinated group. P-value, according to the Mantel-Cox test (log-rank test).

In this sense, variation in IgG sera levels were observed for the three D-glutamate auxotrophic strains of *A. baumanii, P. aeuginosa* and *S. aureus* species, these levels being dependent on whether the vaccine is administered by intraperitoneal, intramuscular, subcutanous or intranasar route. Likewise, the vaccine schedule of administration (doses composition and frequency of administration) can affect the final levels of antibodies produced (see example 34). Therefore, determining the most appropriate schedule and route of vaccination for optimal antibody titers may need to be determined for each pathogen. For this purpose, to correlate the humoral response obtained by administration routes other than intraperitoneal (not routinely used) with protective efficacy, the authors evaluated the use of ΔPA4662 vaccine strain administrated via intramuscular (preferred route for administration in humans) because this one elicited similar high level of IgGs as the intraperitoneal route (see example 18). In this regard, mice were challenged with *P. aeruginosa* PAO1 wild type as before. After the challenge, the authors observed 100% mortality in the group of non-vaccinated mice whereas all vaccinated mice showed 100% survival (see FIG. 50). This result suggests that vaccination using the intramuscular route of administration is at least as effective as the intraperitoneal route.

In addition, it is noted that the medicament, pharmaceutical composition or vaccine composition of the present invention can be used both in asymptomatic patients as well as in those who have already shown symptoms of the disease.

Furthermore, the authors of the present invention have surprisingly found that by using a kit or device comprising an antibody or fragment thereof of the invention, the kit or device permits a reliable qualitative and/or quantitative analysis of bacterial species in a biological of sample of a subject and, in particular, in the plasma of subjects suspected of suffering from a disease of bacterial origin.

Therefore a further aspect of the invention, namely a twelfth aspect of the invention, relates to a kit or device comprising an antibody or fragment thereof of the invention for use in the qualitative and/or quantitative determination of bacterial species in a biological sample from a mammal, in particular, in the plasma of a mammal suspected of suffering from a bacterial disease.

A preferred embodiment of the twelfth aspect of the invention relates to a kit for detecting an infection of bacterial origin through an immunoassay comprising:
  (i) a first antibody called "capture antibody" obtain or obtainable according to the sixth or seventh aspect of the invention capable of recognizing the bacterial species causing the infection, wherein said first antibody is preferably attached to a solid support;
  (ii) a second labeled antibody called "detection antibody" which recognizes a region other than the region recognized by the first antibody, wherein said second antibody comprises a marker which may be fluorescent, luminescent or an enzyme;
  (iii) a reagent showing affinity for the second antibody, said reagent being coupled to a first member of a binding pair; and
  (iv) a second member of a binding pair coupled to a fluorescent, luminescent or an enzyme, wherein the binding pair is selected from the group consisting of: hapten and antibody; antigen and antibody; biotin and avidin; biotin and streptavidin; a biotin analogue and avidin; a biotin analogue and streptavidin; sugar and lectin; an enzyme and a cofactor; a nucleic acid or a nucleic acid analogue and the complementary nucleic acid or nucleic acid analogue.

In the context of the present invention, the first antibody is called "capture antibody", which means that this antibody is used to retrieve from a sample all bacterial species to which the antibody specifically binds. There is practically no limitation on the type of antibody that can be used as a capture antibody provided that it has been obtained according to the seventh aspect of the invention. Antibodies suitable for use as capture antibodies include but are not limited to the following: "intact antibodies", "Fab" fragments, "F(ab')2 fragments, "Fv" fragments, single chain Fv fragments or "scFv", "Diabodies" and "bispecific antibodies" (Bab)

All these antibody fragments can be further modified using conventional techniques known in the art, for example, by using deletion(s), insertion(s), substitution(s), or addition(s) of amino acid and/or recombination(s) and/or any other modification(s) (e.g. posttranslational and chemical modifications, such as glycosylation and phosphorylation changes) known in the art either.

Antibodies suitable as capture antibodies include both polyclonal and monoclonal antibodies. For production of polyclonal antibodies various hosts can be immunized including goats, rabbits, rats, mice, camels, dromedaries, llamas, humans, birds and others. Depending on the host species, various adjuvants may be used to increase the immunological response.

For production of monoclonal antibodies, conventional techniques can be used. For example, monoclonal antibodies can be obtained using the hybridoma method first described by Kohler et al, Nature, 256:495 (1975) using the procedure described in detail in units 11.4 to 11.11 of Ausubel, F M et al. (Current Protocols in Molecular Biology, John Wiley & Sons Inc.; rings edition, 2003). Alternatively, monoclonal antibodies may be isolated by recombinant DNA from phage antibody libraries generated using the techniques described in McCafferty et al, Nature 348:552-554 (1990). Clacksoii at al, Nature, 352: 624-628 (1991) and Marks at al, J. Mol. Biol, 222:581-597 (1991) describe the isolation of murine and human antibodies, respectively, using phage libraries. Subsequent publications describe the production of high affinity human antibodies (in the nM range) by chain shuffling (Marks et al, Biol Technology, 10:779-783 (1992)), as well as combinatorial infection and in vivo recombination as a strategy for constructing very large phage libraries (Waterhouse at al, Nucl Acids Res, 21: 2265-2266 (1993)). Thus, these techniques are viable alternatives to traditional hybridoma techniques of monoclonal antibodies for the isolation of monoclonal antibodies.

A thirteenth aspect of the invention refers to the use of the kit or device of the twelfth aspect of the invention, for the qualitative and/or quantitative determination of bacterial species or bacterial strains in a biological sample from a mammal, in particular, in the plasma of a mammal suspected of suffering from a bacterial disease.

Lastly, a fourteenth aspect of the present invention refers to a method of cultivation of bacterial strains auxotrophic for D-glutamate comprising the utilization of different concentrations of D-glutamate.

In a preferred embodiment of the fourteenth aspect of the invention, the range of concentration of D-glutamate is 0.00001-120 mM.

In a still more preferred embodiment of this aspect of the invention, said range of concentration of D-glutamate is 0.01-50 mM.

Even more preferably, said range of concentration of D-glutamate is 10-20 mM.

Lastly, a further aspect of the invention refers to killed mutant auxotrophic bacterial strain for D-glutamate or to immunological fragments of the killed bacteria thereof as well as to the use of these bacteria or to its immunological fragments thereof for the uses described in the present invention.

The purpose of the following examples is merely to illustrate the invention and not to limit the same.

EXAMPLES

Example 1: Analysis and Identification of the Nucleotides and of the Amino Acid Sequences of the Genes Encoding the *A. baumannii* ATCC 17978 Glutamate Racemase Enzyme The authors of the present invention conducted a search for genes encoding glutamate racemase enzyme in the *A. baumannii* ATCC 17978 genome annotation using the Protein Knowledgebase (UniProtKB) database search tool. Two amino acid sequences corresponding to proteins MurI (locus A1S_0380 and locus A1S_3398) were identified. These sequences were compared to one another, and to other glutamate racemase protein sequences present in other bacterial species the genomes of which were sequenced, by means of the Clustal Omega alignment tool.

As a result of the previous analysis the genes encoding glutamate racemase protein in the *A. baumannii* ATCC 17978 genome were identified. Two candidate genes for possible glutamate racemases were thus found: the gene annotated as A1S_0380 encoding a 288 amino acid protein called murI and gene A1S_3398 encoding a 266 amino acid protein also called murI.

FIG. 4 shows the alignment of the amino acid sequences of different glutamate racemase proteins, including both MurI (locus A1S_0380) and MurI (locus A1S_3398) proteins of *A. baumannii* ATCC 17978 and the glutamate racemase genes of *E. coli*, strain K12, and *P. aeruginosa*, strain PAO1. MurI protein encoded in locus A1S_0380 and MurI protein encoded in locus A1S_3398 of *A. baumannii* ATCC 17978 share a 29.8% similarity with one another on the amino acid sequence level, and they have a 33.2% and 23.2% similarity with MurI protein of *E. coli* (strain K12), respectively, and 35.8% and 37.5% similarity with MurI protein of *P. aeruginosa* (strain PAO1), respectively.

Example 2: Construction and Characterization of Different *A. baumannii* Mutant Strains without Glutamate Racemase Genes Homologous double recombination was carried out using suicide vector pMo130 to construct the different mutant strains. First, the A1S_0380 murI and A1S_3398 murI genes were deleted independently, both mutant strains called Δ0380 and Δ3398, respectively, being obtained. Fragments of about 1.000 bps corresponding to the upstream and downstream regions of each of the genes were amplified by means of PCR to construct these mutants. Both fragments were cloned into vector pMo130 using the resulting recombinant plasmid to remove the A1S_0380 murI and A1S_3398 murI genes by means of homologous double recombination.

The A1S_0380 murI gene upstream fragment was obtained by means of PCR amplification with oligonucleotides UP0380(NotI)F and UP0380(BamHI)R, the resulting PCR product being digested by NotI and BamHI restriction enzymes. The A1S_0380 murI gene downstream fragment was obtained by means of PCR amplification with oligonucleotides DOWN0380(BamHI)F and DOWN0380(SphI)R, the resulting PCR product being digested with BamHI and SphI restriction enzymes. Digested locus A1S_0380 murI gene upstream and downstream fragments were ligated into vector pMo130, which is previously linearized with NotI and SphI enzymes, recombinant plasmid called pMo130UP/DOWN0380 being obtained.

Recombinant plasmid pMo130UP/DOWN3398 was obtained in the same way as in the preceding case. The oligonucleotides used in this case were UP3398(NotI)F_II and UP3398(BamHI)R_II for upstream fragment amplification and oligonucleotides DOWN3398(BamHI)F and DOWN3398(SphI)R for downstream fragment amplification of locus A1S_3398 murI gene.

Plasmids pMo130UP/DOWN0380 and pMo130UP/DOWN3398 were introduced in *E. coli* TG1 by electroporation, The different TG1 strains transformed with each of the preceding plasmids were cultured in LB with kanamycin (50 μg/mL) for 18 h at 37° C. The obtained colonies were sprayed with pyrocatechol (0.45 M) and only the yellow colonies, expressing xylE reporter gene of plasmid pMo130, were selected. Oligonucleotides UP0380(NotI)F and DOWN0380(SphI)R were used for simultaneous upstream and downstream fragment amplification of plasmid pMo130UP/DOWN0380 introduced by electroporation in yellow kanamycin-resistant TG1 colonies. In turn, oligonucleotides UP3398(NotI)F_II and DOWN3398(SphI)R were used for simultaneous upstream and downstream fragment amplification of plasmid pMo130UP/DOWN3398.

Plasmids pMo130UP/DOWN0380 and pMo130UP/DOWN3398 obtained from the transformed TG1 strains were individually introduced in *A. baumannii* ATCC 17978 by electroporation, as described above. The co-integrant colonies were selected in LB medium agar with kanamycin (50 μg/mL) and sprayed with pyrocatechol (0.45 M) for selecting the yellow colonies (XylE+). For the subsequent individual resolution of the co-integrant colonies, these were inoculated in 1 mL of LB medium and grown for at least 4 hours at 37° C. under stirring. The cultures were serially diluted and seeded in LB agar containing 15% sucrose (the sacB gene contained in plasmid pMo130 confers sensitivity to sucrose). The resulting colonies were sprayed with pyrocatechol, and white colonies (resolved co-integrants) were analyzed by PCR to confirm Δ0380 and Δ3398 deletions, produced by the allelic exchange of plasmids pMo130UP/DOWN0380 and pMo130UP/DOWN3398 with alleles A1S_0380 and A1S_3398, respectively. Oligonucleotides EXTFW0380 with EXTRV0380 and INTFW0380 with INTRV0380 were used to confirm the Δ0380 mutation. Oligonucleotides EXTFW3398 with EXTRV3398 and INTFW3398 with INTRV3398 were used to confirm the Δ3398 mutation.

The double mutant (Δ0380/Δ3398) was constructed following the previously described protocol for constructing single mutants. Plasmid pMo130UP/DOWN3398 was introduced in mutant Δ0380 by electroporation, and the co-integrant colonies were resolved as was previously done, except the colonies were grown in LB agar with and without 10 mM D-glutamate to identify the possible *A. baumannii* ATCC 17978 double mutants Δ0380/Δ3398 since the colonies with the double mutation require this compound to grow.

The presence of locus Δ0380 in mutant Δ0380, locus Δ3398 in mutant Δ3398 and both loci Δ0380 and Δ3398 in the double mutant, as well as the absence of the corresponding wild type loci, was confirmed by means of PCR with the following oligonucleotide pairs: EXTFW0380/EXTRV0380, INTFW0380/INTRV0380, EXTFW3398/EXTRV3398, INTFW3398/INTRV3398, UP0380(NotI)F/DOWN0380(SphI)R, UP3398(NotI)F_II/DOWN3398(SphI)R, as appropriate in each case.

Figure 5:
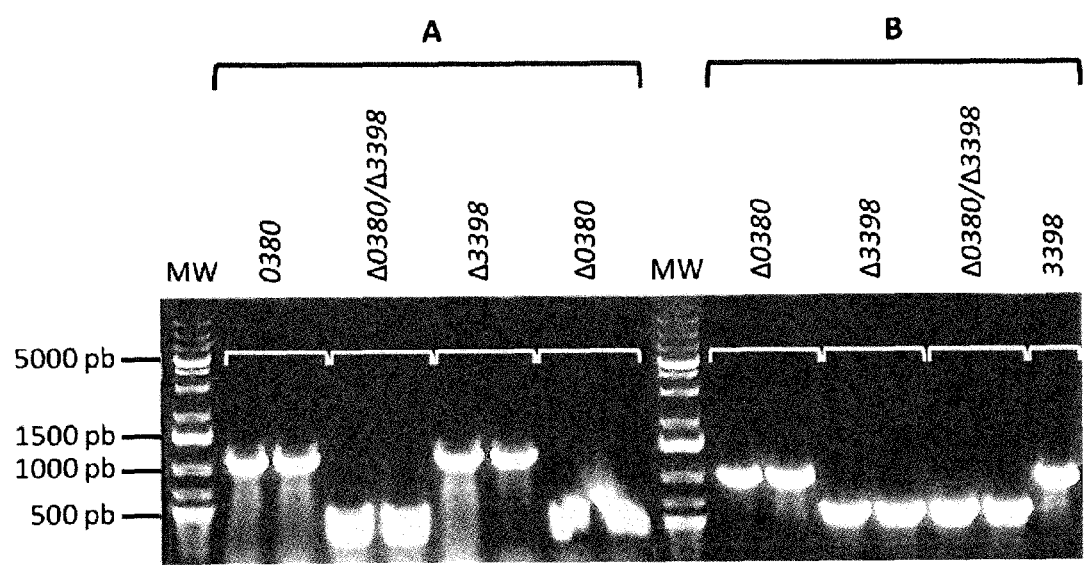
FIG. 5 shows PCR confirmation of the deletions in *Acinetobacter baumannii* ATCC 17978 mutants Δ0380, Δ3398 and Δ0380/Δ3398. A: Oligonucleotides EXTFW0380 and EXTRV0380 were used to generate fragments with 1116 bps from strains carrying wild type locus A1S_0380 or a 345 by fragment from strains carrying mutant locus Δ0380. B: Oligonucleotides EXTFW3398 and EXTRV3398 were used to generate fragments with 1056 bps from strains carrying wild type locus A1S_3398 or a 516 bp fragment from strains carrying mutant locus Δ3398. The DNA fragments in each lane have the following matchups: MW, molecular weight pattern; 0380, amplicon generated from the strain carrying wild type locus A2S_0380; 3398, amplicon generated from the strain carrying wild type locus A1S_3398; Δ0380/Δ3398, amplicon generated from the defective strain in the two loci A1S_0380 and A1S_3398; Δ3398 and Δ0380, amplicons generated from the defective strains in loci A1S_3398 and A1S_0380, respectively.

FIG. 5 shows the results of the PCR performed to confirm the different mutations present in the three constructed *A. baumannii* ATCC 17978 mutant strains. The presence of the wild type loci A1S_0380 murI or A1S_3398 murI or the respective mutant variants, Δ0380 and Δ3398, in each of the new mutant strains constructed (Δ0380, Δ3398 and Δ0380/Δ3398), was confirmed by PCR with the oligonucleotides mentioned above.

Figure 6:
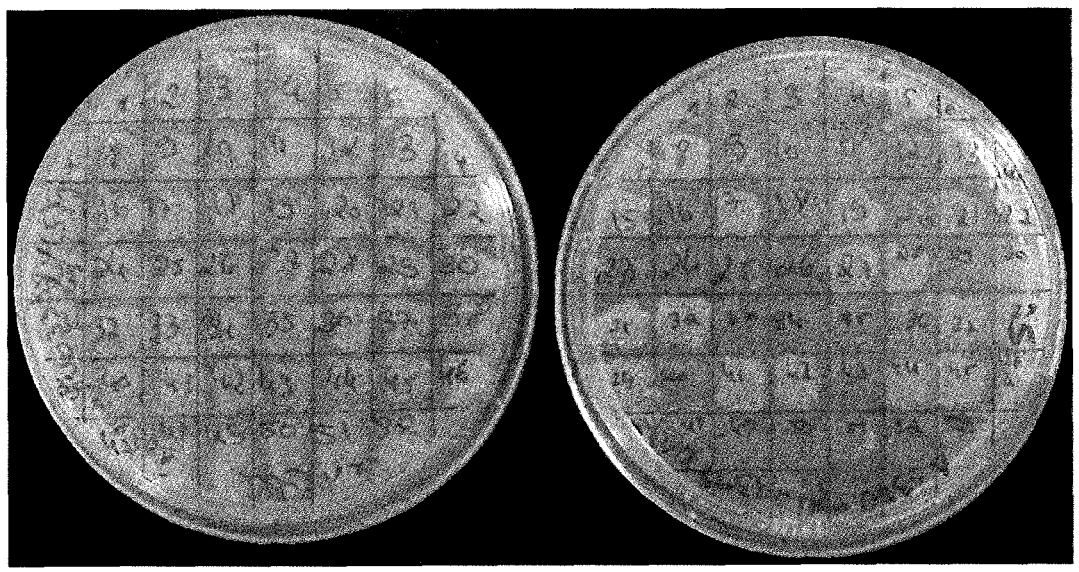
FIG. 6 shows the screening of the colonies resulting from the co-integrants during construction of the *A. baumannii* ATCC 17978 double mutant Δ0380/Δ3398. The individual colonies were selected from LB agar with 15% sucrose and 10 mM D-glutamate and inoculated in the same position in LB agar plates with and without 10 mM D-glutamate. Colonies with the Δ0380/Δ3398 genotype grow exclusively in plates with D-glutamate; colonies with the Δ0380 genotype grow with and without D-glutamate.

The culture of the different mutant strains in the presence and absence of D-glutamate showed that the loss of a single gene encoding glutamate racemase protein in *A. baumannii* ATCC 17978 does not affect growth of this bacterium. However, double mutant Δ0380/Δ3398 is auxotrophic, requiring the exogenous addition of D-glutamate in the culture medium to allow growth. FIG. 6 shows the method of selecting colonies with the double mutant Δ0380/Δ3398 genotype. This strain only grows in LB agar supplemented with D-glutamate. This characteristic is used to select co-integrant colonies with individual Δ0380 mutation, which does not require D-glutamate to grow.

In summary, the obtained results demonstrate that the presence of any of the two wild type loci studied, i.e., both A1S_0380 murI and A1S_3398 murI, is sufficient for normal growth in LB agar without added 0-glutamate, and that the simultaneous deletion of both genes make this strain unable to grow in LB agar. It is in turn demonstrated that the A1S_0380 murI and A1S_3398 mud genes of *A. baumannii* ATCC 17978 are the only genes responsible for the production of D-glutamate in this strain.

Example 3: Effect of D-glutamate on Double Mutant (Δ0380/Δ3398) Growth and Viability in Liquid Culture Medium To determine the growth and viability curve, *A. baumannii* wild type strain ATCC 17978 and the double mutant strain were cultured for 18 h at 37° C. in LB supplemented with 10 mM D-glutamate. The bacterial cultures were centrifuged and the pellets washed twice with LB and adjusted to $OD_{600\ nm}$=0.1. 100 μL were subsequently inoculated in 100 mL liquid LB with and without 10 mM D-glutamate, and these cultures were incubated at 37° C. under stirring, taking samples every 60 minutes for 7 hours, and finally, after 24 hours, to determine optical density of the medium. In parallel, samples were taken every 2 hours up to 6 hours, and finally, another sample was taken after 24 hours to determine the CFU (Colony Forming Units) in LB agar with 10 mM D-glutamate. All cultures were made in triplicate.

Figure 7:
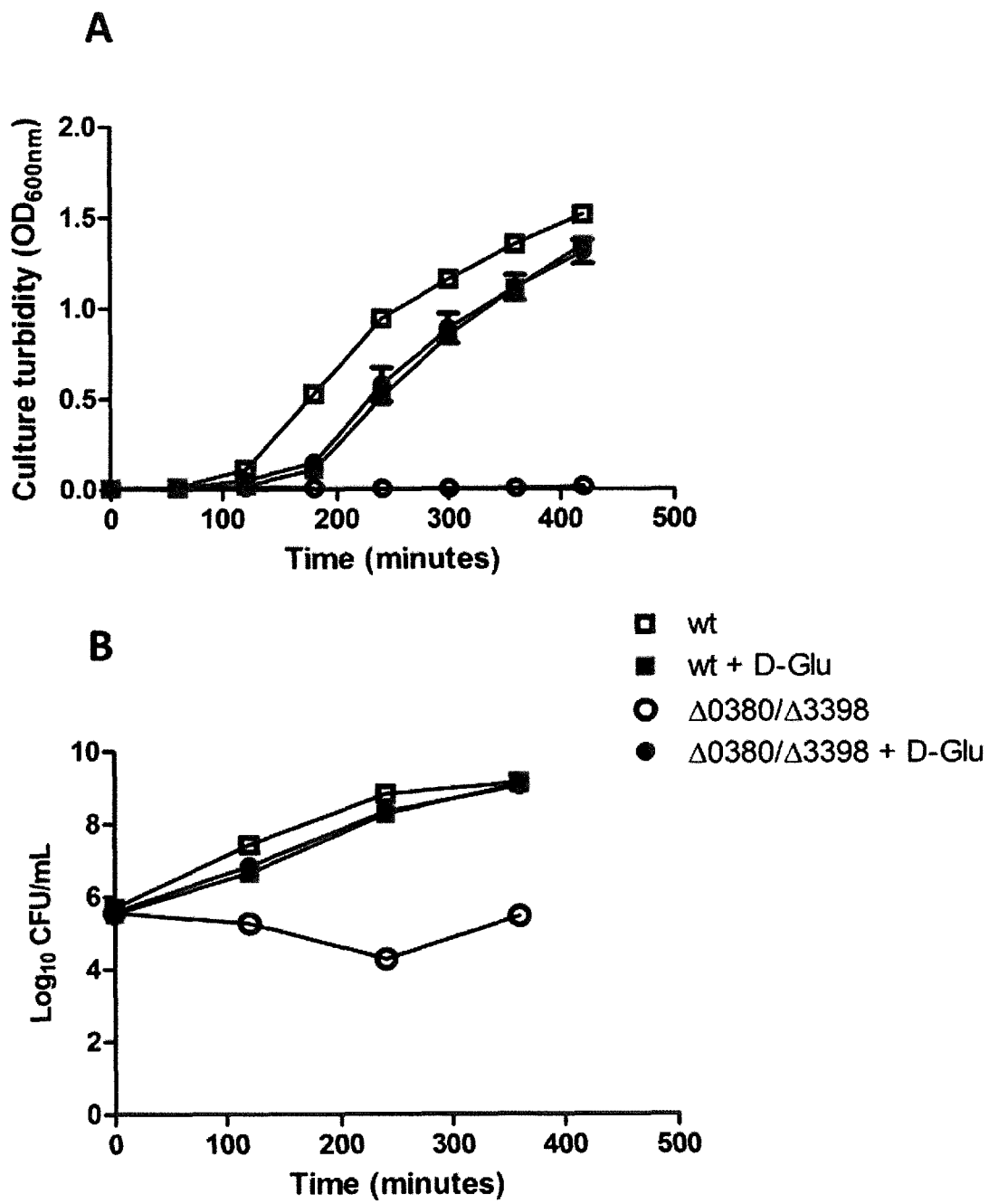
FIG. 7 shows the growth and viability assays of *A. baumannii* wild type strain ATCC 17978 and of double mutant strain Δ0380/Δ3398. Strain Δ0380/Δ3398 shows normal growth in culture medium supplemented with 10 mM of D-glutamate but is unable to grow without the exogenous supply of this compound. In contrast, the wild type strain grows as per normal in LB medium with and without the addition of D-glutamate. In each panel, the solid squares (■) represent wild type strain in medium with D-glutamate; empty squares (□) represent the wild type strain without D-glutamate; solid circles (●) represent the double mutant in medium with D-glutamate and empty circles (○) represent the double mutant in medium without D-glutamate. A: Double mutant and wild type strain culture optical density. B: Double mutant and wild type strain culture viability ($Log_{10}$ CFU/mL).

Growth curves for wild type strain ATCC 17978 as well as for mutant strain Δ0380/Δ3398 were made to evaluate the effect of the absence of D-glutamate as a function of time and the viability of these strains in the presence and absence of this compound. Complete absence of bacterial growth of double mutant Δ0380/Δ3398 in culture medium without D-glutamate (FIG. 7A) was observed. However, the growth of this strain in the presence of D-glutamate was similar to the growth of the wild-type strain in the same conditions. When analyzing cell viability for 6 hours of double mutant Δ0380/Δ3398 in the absence of D-glutamate it was observed that unlike the wild-type strain, double mutant viability drops significantly (1 log 10) in the first 4 hours of culture due to the limitation of this compound (FIG. 7B).

Example 4: Morphological Analysis of *A. baumannii* Wild Type Strain ATCC 17978 and Double Mutant Strain (Δ0380/Δ3398) by Means of Electron Microscopy To take microphotographs by scanning electron microscopy (SEM), the *A. baumannii* wild type strain ATCC 17978 and double mutant strain were cultured for 18 h at 37° C. in LB supplemented with 10 mM D-glutamate. The bacterial cultures were centrifuged, the pellets washed twice with 0.1% NaCl and suspended in LB. 50 μL of the last cultures were inoculated in 5 mL of LB with D-glutamate at concentrations of 0; 0.1; 1.25 and 10 mM. The cultures were incubated at 37° C. under stirring for 2 hours and were subsequently centrifuged and washed twice with PBS. The pellets were then fixed with 4% paraformaldehyde in 0.1 M PBS pH 7.4 for 30 min. After fixing, the samples were washed again twice with PBS, and each sample was dehydrated in increasing series of ethanol (50%, 70%, 90% and 100%) for 10 minutes each. The samples were then dried to the critical point with $CO_2$ (Bal-Tec CPD 030), fixed in aluminum supports, and coated with a layer of gold (Bal-Tec SCD 004 sputter coater). Observation was conducted and photographs were taken using a Jeol JSM-6400 transmission electron microscope.

To take microphotographs by transmission electron microscopy (TEM), double mutant Δ0380/Δ3398 was cultured in LB agar supplemented with 10 mM D-glutamate for 18 h at 37° C. Subsequent passage to MH agar was performed and it was incubated at 37° C. for 18 h. After incubation, 2-3 colonies were dissolved in PBS buffer, the suspension was centrifuged and the resulting pellet was washed first with cacodylate buffer, and immediately after that the cells were fixed in cold 2.5% glutaraldehyde prepared in 0.2 M sodium cacodylate buffer pH 7.4 for 4 hours at room temperature. The pellets were then washed with cacodylate buffer, dehydrated in acetone and embedded in SPURR (Spurr's Epoxy Embedding Medium). Ultrathin sections (70 nm) of these samples were obtained and they were stained with uranyl acetate and lead citrate for observation under a JEOL JEM 1010 (80 kV) electron transmission microscope.

Figure 8:
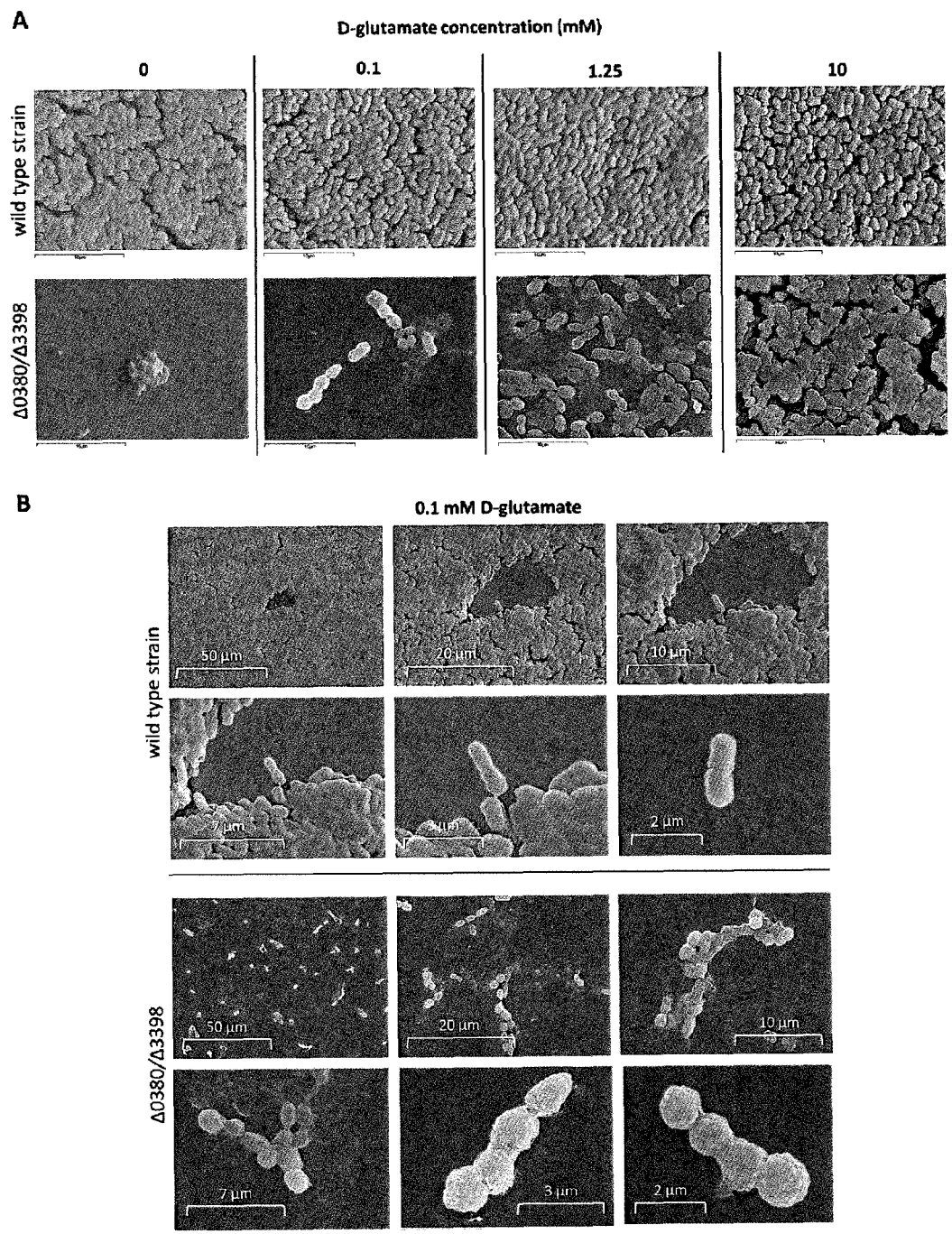
FIG. 8 shows the differences at the cell division and morphology level in the *A. baumannii* ATCC 17978 Δ0380/Δ3398 double mutant with respect to the wild type homologue thereof in the presence of different concentrations of D-glutamate. Microphotographs were taken with a scanning electron microscope. A: Both strains were cultured at increasing concentrations of D-glutamate and the microphotographs were taken on the same scale (the bar indicates a scale of 10 μm); B: Both strains were cultured in the presence of 0.1 mM D-glutamate, and the microphotographs were taken progressively on scales of a decreasing order.

At the microscopic level, significant morphological and structural changes were observed in strain Δ0380/Δ3398 as the exogenous supply of D-glutamate decreases. FIG. 8 shows the microphotographs taken with a scanning microscope of both strains cultured in the presence of different concentrations of D-glutamate. Therefore, in FIG. 8A, it can be seen how double mutant Δ0380/Δ3398 is unable to divide in the absence of D-glutamate. The bacterial cells seen in the figure with 0 mM D-glutamate are reminiscent of the inoculum previously grown with this compound. In the presence of 0.1 mM D-glutamate, the bacterial cells show some growth, though it is very slow and very peculiar with an irregular division pattern, in which they form filamentous aggregates of cells with atypical binary fission. A mass of protoplasts is also observed (the absence of cell wall leaves the bacteria protoplasm surrounded by only the cell membrane, the protoplast). In the presence of 1.25 mM D-glutamate greater cell density is seen with respect to the preceding condition (reflection of a higher growth rate) but with many protoplasts. Some cell aggregates with atypical binary fission continue to be visible, and, though lower in number, part of the cells now has an appearance similar to their wild-type morphology. Finally, in medium supplemented with 10 mM D-glutamate, all the cells have an appearance similar to their wild-type homologue, both at the density level and at the cell morphology level. No atypical division is observed.

Furthermore, as can be seen in FIG. 8B, the authors of the present invention took several microphotographs in the bacterial preparations with 0.1 mM D-glutamate, on different scales, both of double mutant Δ0380/Δ3398 and of the wild-type strain. This latter strain has typical Gram-negative coccobacillus morphology and a regular cell division pattern, with typical binary fission, a high cell density being observed. In the case of the double mutant, the preceding morphologies and atypical cell divisions are observed, with a subsequent low cell density. The presence of protoplasts is evident, as they are always visible in the vicinity of the structurally intact cell forms, arising as derivations or "ghosts" of the previous ones. Within these complexes, the appearance of the cell wall is different in comparison with the wild-type strain because the cell surface is rough and irregular. The profound alteration at the division level is also evident because a large amount of cell filaments consisting of 3 or more units is observed.

Figure 9:
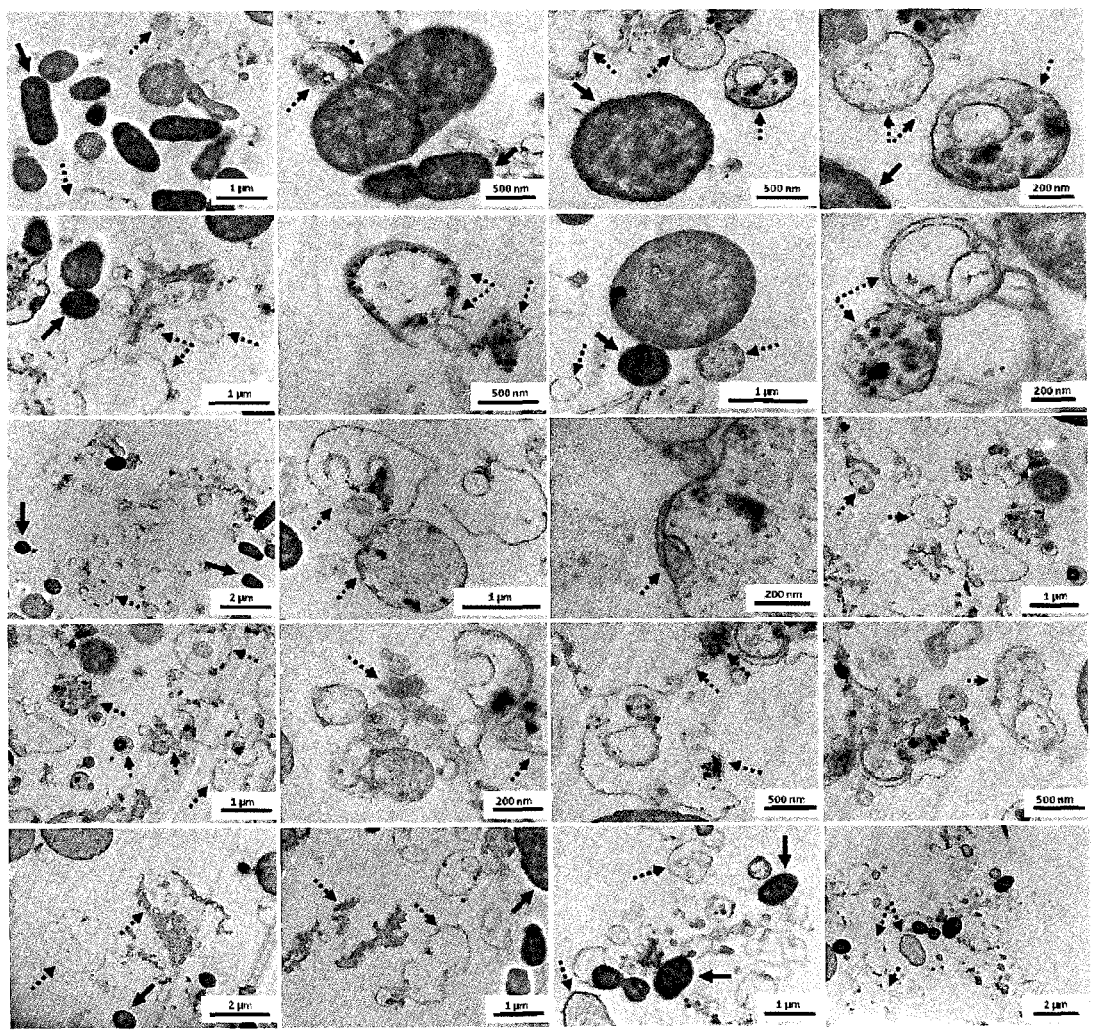
FIG. 9 shows different atypical morphologies, progressive degeneration of the cell wall and lysis of the *A. baumannii* ATCC 17978 mutant strain Δ0380/Δ3398 when kept in the absence of D-glutamate. Microphotographs were taken with a transmission electron microscope on different scales. Black arrows indicate intact bacterial cells with normal morphology or atypical cell division; dashed arrows indicate fragmented cells without bacterial cell wall, lysed cells or disorganized internal content, dispersed genetic material, aggregation of membranes and/or liposomes.

As with the electron scanning microscopy, transmission electron microscopy studies were performed and they show that the cell wall of double mutant Δ0380/Δ3398, when kept in the absence of D-glutamate, experiences progressive destruction as a result of the inactivation of the glutamate racemase protein function, cell lysis and subsequent bacterial death taking place. FIG. 9 shows different stages of cell wall degeneration, ranging from cells with an altered conformation that lose their semi-rigid structure to cells showing several ruptures and displacement of the outer membrane, lysis and extrusion of the intracellular content (especially genetic material). Cells still maintaining the inner membrane (remnants of the inoculum grown with D-glutamate) and having the genetic material dispersed therein are also seen because glutamate racemase is an enzyme that can act in the modulation of DNA gyrase. Finally, the mechanism of bacterial destruction is as follows: the absence of cell wall leaves the bacteria protoplasm surrounded by only the cell membrane (protoplast), which makes this strain an organism that is extraordinarily sensitive to variations in tonicity of the medium. Then the phenomenon of clearing occurs, which takes place when the protoplasts explode and leave cytoplasmic membrane residues called "ghosts", membrane and liposome aggregates also being generated.

Example 5: Determining the Lethal Dose (LD) of *A. baumannii* Wild Type ATCC 17978 and Double Mutant Strain Δ0380/Δ3398 in BALB/c Mice in an Acute Infection Model The authors of the present invention produced systemic infection in BALB/c mice through the intraperitoneal administration of an inoculum in saline of *A. baumannii* wild type strain ATCC 17978 and double mutant strain Δ0380/Δ3398. To prepare the inocula, the bacteria were cultured in LB (wild type strain) and LB+10 mM D-glutamate (double mutant) at 37° C. under shaking until reaching $OD_{600\ nm}=0.7$ (this inoculum is called 1×). The cultures were centrifuged, and the bacterial pellets were washed twice with LB. Once washed, the bacterial suspensions were adjusted according to the previous $OD_{600\ nm}$ to different doses (0.1×; 1×; 2×; 2.5×; 3×; 4×; 6×; 8× and 10×) with 0.9% NaCl and inoculated (100 µL) in female BALB/c mice intraperitoneally (1× being understood as the bacterial inoculum with $OD_{600\ nm}=0.7$; 0.1× being understood as the bacterial inoculum 1× diluted 10-fold; 2× being understood as the bacterial inoculum 1× concentrated two-fold; and so on and so forth). The mice were monitored for 7 days post-infection to determine survival with the different doses. The lethal doses (LD) were determined according to survival observed in both cases, $LD_{100}$ being understood as the minimum lethal dose for 100% of the mice.

FIG. 10A shows different degrees of survival in mice when they are infected with increasing doses of the wild type strain. A gradual decrease in survival of the mice is observed with respect to the 2× dose, the $LD_{100}$ (2.5×) being able to be determined, and $LD_{100}$ being understood as the minimum dose necessary to reduce survival of mice to 0%. When the administered dose is greater than 3×, a more rapid reduction in survival is observed.

FIG. 10B shows different degrees of survival in mice infected with increasing doses of double mutant Δ0380/Δ3398. In the case of this strain, $LD_{100}$ is 6×, a very high dose of bacterial inoculum, indicating that this strain is less virulent. Like in the case of the wild type strain, when the bacterial dose administered is greater than $LD_{100}$, a more rapid reduction in survival of the mice is observed.

Example 6: Determining the Bacterial Load in the Liver in a Systemic Infection Model with the *A. baumannii* Wild Type Strain ATCC 17978 and Mutant Strains Δ0380, Δ3398 and Δ0380/Δ3398 in BALB/c Mice As described above, a systemic infection was established in BALB/c mice through the intraperitoneal administration of an inoculum in saline of *A. baumannii* wild type strain ATCC 17978 and mutant strains Δ0380, Δ3398 and Δ0380/Δ3398. The wild type strain and single mutants Δ0380 and Δ3398 were cultured in LB, and double mutant Δ0380/Δ3398 in LB+10 mM D-glutamate at 37° C. under shaking until reaching $OD_{600\ nm}=0.7$ (1×). The cultures were centrifuged, and the bacterial pellets were washed twice with LB. Once washed, the bacterial suspensions were adjusted according to the previous $OD_{600\ nm}$ to the 2× dose with 0.9% NaCl and inoculated (100 µL) in male BALB/c mice (n=8-9) intraperitoneally. The mice were sacrificed with sodium thiopental at 12 hours post-infection. Livers were extracted and weighed aseptically, and after being homogenized in 0.9% NaCl, the CFU per gram of liver were determined in LB agar (wild type strain, Δ0380 and Δ3398) and LB agar with 10 mM D-glutamate (double mutant Δ0380/Δ3398).

It is observed in this acute infection model that the infection takes place with a rapid spread through the blood, causing the mice to die between 11 and 30 hours post-infection (FIG. 10A). Based on the bacteria count in the organs, the authors of the present invention can obtain a measurement of the invasive and replicative capacity of the different strains. The following average values were thus obtained: 8.29 $Log_{10}$ CFU/g (mice infected with the wild type strain); 6.88 $Log_{10}$ CFU/g (mice infected with strain Δ0380); 8.06 $Log_{10}$ CFU/g (mice infected with strain Δ3398) and 1.59 $Log_{10}$ CFU/g (mice infected with strain Δ0380/Δ3398) (FIG. 11).

Based on these values, significant differences were observed (P<0.0001, Mann-Whitney U test) in the counts of the strains Δ0380 and Δ0380/Δ3398 compared to the wild type strain. The most drastic and evident reduction was observed when analyzing the colony count of double mutant strain Δ0380/Δ3398, in which a reduction of almost 7 log values were obtained in the average bacterial load and 44.4% of animals from the organs of which bacteria was not recovered.

Example 7: Determining the Bacterial Load in the Liver, Spleen, and Lung in a Systemic Infection Model with *A. baumannii* Wild Type Strain ATCC 17978 in BALB/c Mice Pre-Immunized with Double Mutant Δ0380/Δ3398

To evaluate the efficacy (level of protection) of strain Δ0380/Δ3398 as a vaccine, male BALB/c mice (n=10) were immunized intraperitoneally (100 μL) with strain Δ0380/Δ3398 in saline at 1× dose on days 0 and 14. A group of control mice (n=10) was administered 100 uL of saline in an identical manner on days 0 and 14. On day 21, the mice were infected with a 4× inoculum of *A. baumannii* wild type strain ATCC 17978 by intraperitoneal injection. The mice were sacrificed with sodium thiopental 12 hours post-infection. The liver, spleen and lung of each of the mice were processed aseptically, and the CFU were determined, as described above. The bacterial inocula were prepared and adjusted as described above.

Figure 12:
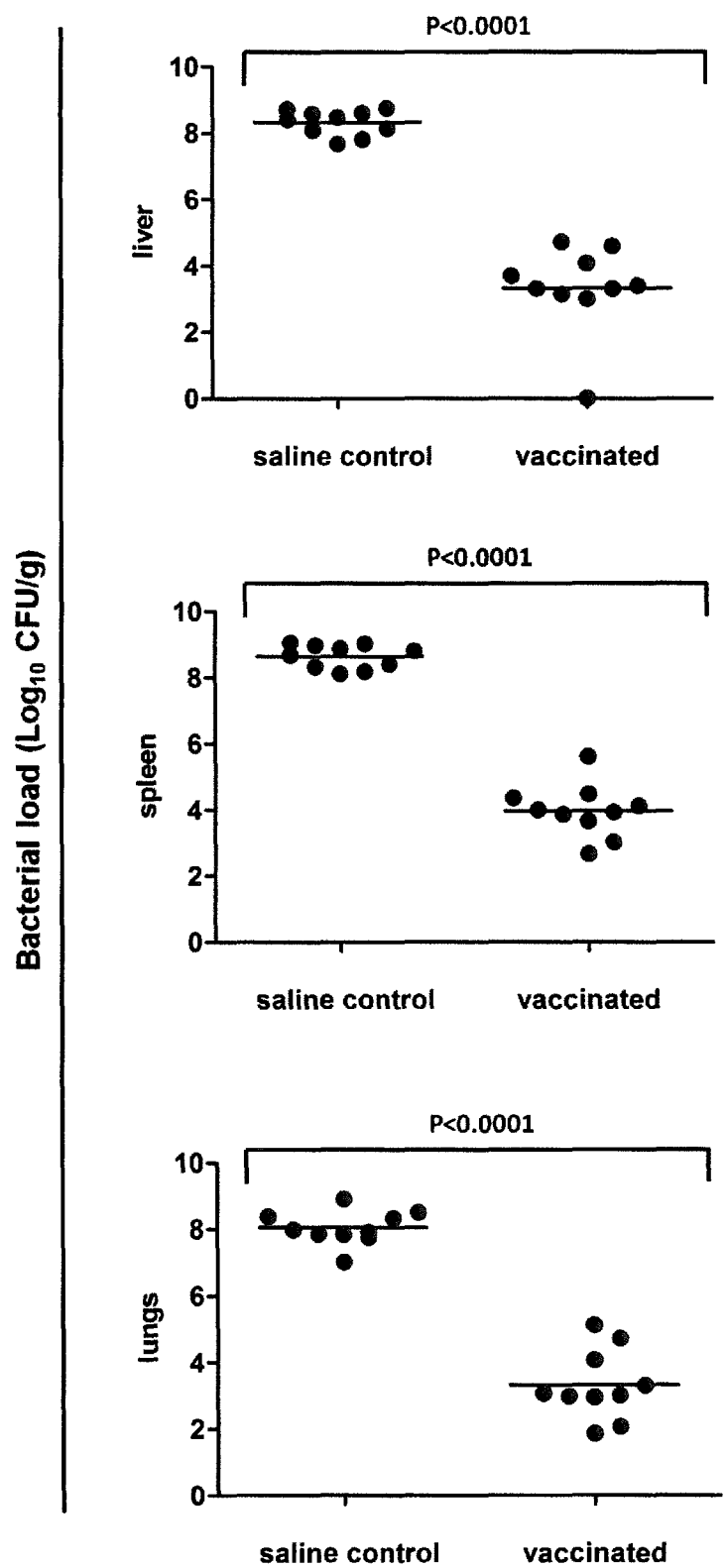
FIG. 12 shows the bacterial load in the liver, spleen and lungs of BALB/c mice (n=10) 12 hours post-infection with a 4× dose of the *A. baumannii* wild type strain ATCC 17978 administered on day 21, after the mice were pre-immunized on days 0 and 14 with strain Δ0380/Δ3398, or non-immunized (saline control). P-value according to the Mann-Whitney U test. Each dot represents the individual bacterial load of the organ of a mouse. The average value of each group is represented by a horizontal line.

The protective effect of the vaccination with the double mutant Δ0380/Δ3398 was thus confirmed when it was observed that pre-immunization with this strain causes a very significant reduction in the bacterial load of different organs of mice infected with a lethal dose of *A. baumannii* ATCC 17978. In fact, a severe reduction in the bacterial load of each of the organs of immunized mice was observed in comparison with the bacterial load of non-immunized mice ($P<0.0001$, Mann-Whitney U test) (FIG. 12).

Example 8: Quantification of IgG Antibodies Against *A. baumannii* ATCC 17978 Through Indirect ELISA in BALB/c Mice Subjected to Different Vaccination Regimens with Strain Δ0380/Δ3398

To evaluate the antibody-mediated immune response at different vaccination regimens, male BALB/c mice (n=12) were immunized through intraperitoneal injection (100 μL) of strain Δ0380/Δ3398 in saline at 1× dose on days 0 and 14. A group of control mice (n=12) was administered 100 μL of saline in an identical manner on days 0 and 14. On day 7 post-immunization, sera were obtained from 12 of the mice immunized with a single dose of the vaccine (administered on day 0), and on day 21, sera were obtained from the remaining mice immunized with two doses of the vaccine (administered on days 0 and 14) (n=12) together with the sera of the control mice (n=12), injected with saline. To obtain the sera, the mice were anesthetized with sodium thiopental and blood was drawn through puncture of the retro-orbital plexus. The sera were separated from the blood cells by centrifugation and stored at −80° C. until subsequent analysis thereof. 1×, 0.5×, 0.1×, 0.05× and 0.01× doses of vaccine were prepared in an identical manner, and the mice (n=6/dose) were immunized on days 0 and 14, as was previously done. On day 21, sera were obtained from the immunized mice and from the control mice (0×), injected with saline.

IgG quantification was performed by means of an indirect Enzyme-linked Immunosorbent Assay (ELISA). 96-well ELISA plates were "coated" with *A. baumannii* wild type strain ATCC 17978 which was fixed to the bottom of the wells after 18 h of incubation at 4° C. in 100 mM carbonate-bicarbonate buffer, pH 9.6. Five (5) washings were performed with phosphate buffered saline (PBS) to remove the unfixed bacteria. The residual sites were blocked by means of incubating at 25° C. for 1 h with 200 μL per well of blocking solution (5% skim milk in PBS). The content of the plates was aspirated and washed 5 times with washing buffer (0.005% TWEEN® 20 in PBS). The plates were incubated for 1 h at 25° C. with 100 μL of the sera serially diluted in dilution buffer (DMEM culture medium with 5-10% FCS). Five (5) washings were performed with washing buffer to remove the antibodies that have not reacted. 100 μL per well of secondary antibody (peroxidase-labeled mouse IgG) diluted 1/5000 in dilution buffer were added. It was incubated for 1 h at 25° C. in the dark. The plates were washed 5 times with washing buffer to remove the labeled anti-antibodies that did not react. Development was performed by means of incubation for 3 min with 100 μL of TMB substrate (peroxidase substrate). The reaction was stopped with 50 μL of 1 M HCl per well. The colorimetric reading was taken at 450 nm. To determine the IgG titers in each case, the endpoint titer, the maximum serum dilution having a value that exceeds the blank absorbance reading (absorbance of the dilution buffer) by 0.1 values, is sought.

As discussed above, the blood samples collected from each mouse were used to determine the antibody (IgG) titer by means of the ELISA technique with respect to *A. baumannii* ATCC 17978 and thus measure the capacity of the vaccine to generate an immune response. Significant levels of antibodies against the wild type strain were detected in all the immunized mice with respect to non-vaccinated mice (FIG. 13). Antibody production was significantly higher both on day 7 and on day 21 (after one injection and after two injections of strain Δ0380/Δ3398, respectively) compared to non-vaccinated mice. Furthermore, antibody production on day 21 (after 2 successive injections in time with strain Δ0380/Δ3398) was significantly greater than antibody production on day 7 (a single injection of strain Δ0380/Δ3398).

Figure 14:
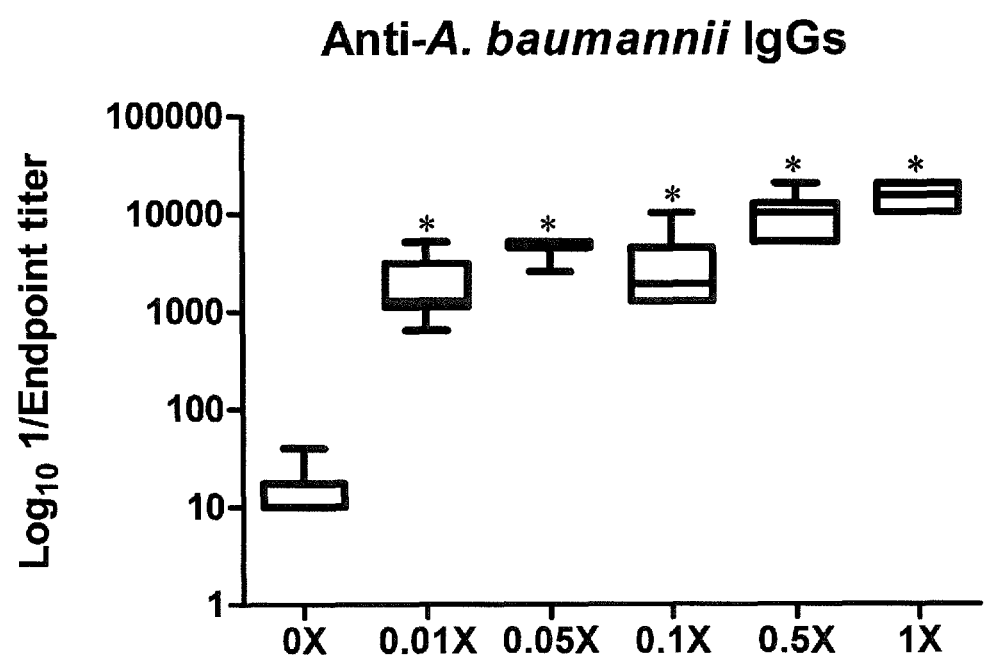
FIG. 14 shows the $Log_{10}$ 1/Endpoint titer of IgG antibodies produced against *A. baumannii* strain ATCC 17978 in BALB/c mice (n=6) on post-vaccination day 21 with different doses of *A. baumannii* strain ATCC 17978 (0.01×; 0.05×; 0.1×; 0.5× and 1×) and in the non-vaccinated control mice (0×). The antibody titers were determined by indirect ELISA. *P<0.05 compared with the group of non-vaccinated mice; P-value according to the Mann-Whitney U test. The boxes represent the first and third quartiles; the horizontal line represents the median; the whiskers represent the range.

On the other hand, the efficacy of different doses of strain Δ0380/Δ3398 was determined in order to determine the minimum dose necessary to stimulate the mouse immune system. To that end, groups of 6 mice were immunized on days 0 and 14 with is each of the following doses: 0.5×, 0.1×, 0.05× and 0.01× (2, 10, 20 and 100-fold lower, respectively). Significant differences between IgG antibody production on day 21 were observed between the group of mice immunized with the 0.01× dose compared to mice in the control group ($P<0.01$, Mann-Whitney U test) (FIG. 14), although to a lesser extent than the higher vaccine dose. This demonstrates that a dose 100-fold lower than the 1× dose is enough to trigger IgG production in mice, demonstrating the efficacy of this strain as a vaccine.

Example 9: Cross-Reactivity Assay with IgG Antibodies of BALB/c Mice Immunized with Strain Δ0380/Δ3398 with Respect to *A. baumannii* ATCC 17978, *A. baumannii* ATCC 19606 and *A. baumannii* AbH12O-A2

ELISA was performed with respect to *A. baumannii* ATCC 19606 and *A. baumannii* AbH12O-A2 with the previously obtained sera to evaluate the antibody-mediated immune response in BALB/c mice immunized with strain Δ0380/Δ3398 and thus measure the capacity of the vaccine to generate a broad immune response. It must be pointed out that *Acinetobacter baumannii* strain AbH12O-A2 is a highly invasive strain which was isolated in a hospital outbreak that caused several patients to die, and is characterized by its resistance pattern with respect to multiple antibiotics. To that end, plates with *A. baumannii* strain ATCC 17978, *A. baumannii* strain ATCC 19606 and *A. baumannii* strain AbH12O-A2 were "coated" as described above. Five (5) washings were performed with PBS and subsequent blocking was performed with 5% skim milk in PBS. The content of the plates was aspirated and washed 5 times with washing buffer. The plates were incubated for 1 hour at 25° C. with 100 μL of the test sera diluted 1/5 in dilution buffer. Five (5) washings were performed with washing buffer and 100 μL per well of peroxidase-labeled mouse IgG diluted 1/5000 were added. It was incubated for 1 h at 25° C. in the dark.

The plates were washed 5 times and development was performed by means of incubating for 3 minutes with 100 μL of TMB substrate. The reaction was stopped with 50 μL of 1 M HCl per well and the color developed at 450 nm was read. The endpoint titer was determined in each case as described above.

Results similar to those observed with respect to *A. baumannii* strain ATCC 17978 were obtained with respect to *A. baumannii* strain ATCC 19606 and *A. baumannii* strain AbH12O-A2 (FIG. 15), similar antibody titers being observed and demonstrating that immunization with strain Δ0380/Δ3398 not only generates antibodies against the isogenic wild type strain, but also generates IgG antibodies against other strains with different resistance and virulence patterns such as strain ATCC 19606 and strain AbH12O-A2.

Example 10: Protection of BALB/c Mice Against Challenge with Different *A. baumannii* Strains by Immunization with the Δ0380/Δ3398 Mutant To evaluate the efficacy of the mutant strain Δ0380/Δ3398 as a vaccine, BALB/c mice (n=6-12) were administered 100 μL of Δ0380/Δ3398 strain (1×* dose in saline) on days 0 and 14. Control mice were administered only saline identically at days 0 and 14. Twenty one days after the second injection, mice were challenged with *A. baumannii* strains ATCC 17978 (4× dose in saline), AbH12O-A2 (4× dose in saline) and Ab307-0294 (0.75×), independently, in order to establish a lethal systemic infection in both cases (100 μL of intraperitoneal injection). After the challenge, mice were monitored for 7 days to determine the survival rate of vaccinated mice compared to control mice (unvaccinated).
*in the case of the challenge with Ab307-0294 strain, vaccinated mice were administered 0.1× and 1× doses of the Δ0380/Δ3398 strain, respectively, on days 0 and 14.

When infected with a 4× dose of the *A. baumannii* ATCC 17978 strain, 11 deaths were observed in the group of unvaccinated mice during the first 24 hours, which means a mortality rate of 92% in this group (n=12). In contrast, all vaccinated mice (n=12) survived to the challenge, overcoming the infection, which means a 100% survival (see FIG. 16) rate in this group. Differences in survival between the two groups were highly statistically significant (P<0.0001, according to the Mantel-Cox log-rank test).

Furthermore, it was determined whether the response produced by immunization with the Δ0380/Δ3398 strain was sufficient to provide protection from lethal infection with other *A. baumannii* strains, including highly virulent and pathogenic strains. In the case of challenge with the AbH12O-A2 strain, 9 deaths were observed in the group of unvaccinated mice during the first 19 hours, which means a mortality rate of 100% (n=9). On the other hand, all vaccinated mice survived (n=9; 100% survival rate) (see FIG. 17). Differences in survival between the two groups were highly statistically significant (P<0.0001, according to the Mantel-Cox log-rank test).

In the case of challenge with the Ab307-0294 capsulated strain, we recorded a 100% mortality rate in the group of unvaccinated mice within the first 24 hours and a 83% survival rate in the group of mice previously immunized with the Δ0380/Δ3398 strain (see FIG. 18). This confirms that vaccination with the mutant strain confers protection against a systemic infection caused by an *A. baumannii* strain with marked virulence. Differences in survival between the two groups were highly significant (P<0.0022, according to the Mantel-Cox log-rank test).

All these results suggest that vaccination with the Δ0380/Δ3398 strain can provide protective immunity against infection with a diverse group of *A. baumannii* strains.

Example 11: Environmental Safety Assessment of the Δ0380/Δ3398 Strain—Evaluation of Water Osmolisis The live attenuated bacterial strain constituting the active ingredient of a vaccine candidate should be incapable of replicating and persisting in the general environment once it leaves the vaccinated individual. To compare the ability of *A. baumannii* ATCC 17978 wild type and the mutant strain Δ0380/Δ3398 to be long-time traced in the general environment, we evaluated survival of these strains in water without any contribution of nutrients or salts, at 37° C. and under agitation (180 rpm) conditions for the time necessary to observe the loss of viability by cellular osmolisis. Daily samples of the culture were taken for 2 days and finally two times per week, for the determination of CFU counts in LB agar (wild type strain) and LB agar supplemented with 10 mM D-glutamate (mutant strain). All cultures were performed in triplicate.

Figure 19:
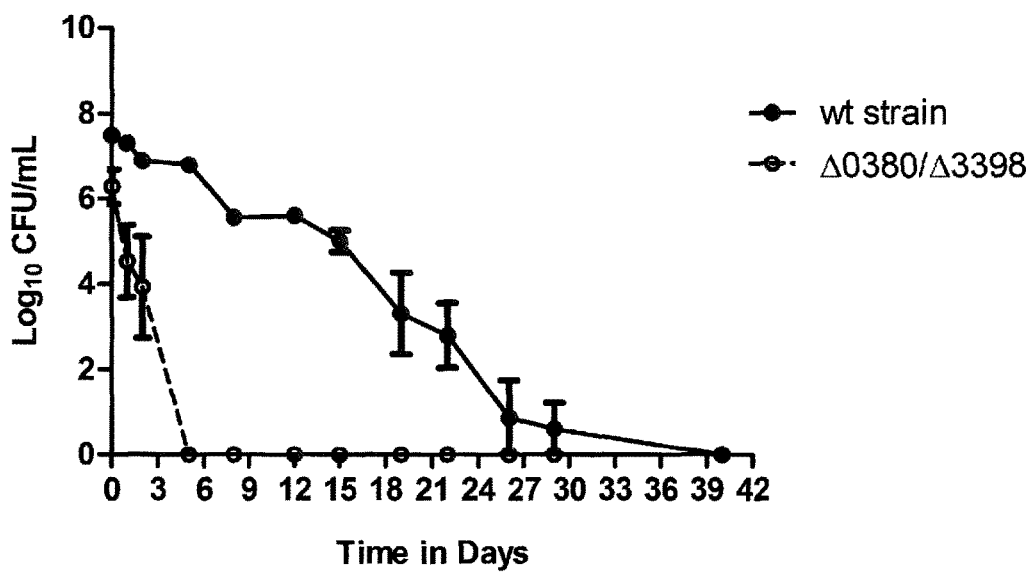
FIG. 19 is the $Log_{10}$ CFU/mL of recovered *A. baumannii* ATCC 17978 wild type and Δ0380/Δ3398 strains when grown in distilled water at 37° C. with agitation (180 rpm) during 40 days. CFU's were determined by counting colonies plated onto LB (wild type strain) and LB supplemented with 10 mM D-glutamate (mutant strain). All cultures were performed in triplicate.

A significant decrease in the viability of the mutant strain Δ0380/Δ3398 was observed, as no viable bacteria were recovered within and after 5 days of culture. In contrast, its wild counterpart, the wild type strain, remained viable until the $29^{th}$ day of culture, being totally irrecoverable at day 40 (see FIG. 19). Differences in survival between the two strain were highly significant (P=0.0061, according to Student's t test).

Example 12: Evaluation of the Stability of the Auxotrophic Phenotype in the Δ0380/Δ3398 Strain To test the irreversibility of the nutritional auxotrophy of *A. baumannii* Δ0380/Δ3398 for the compound D-glutamate, Δ0380/Δ3398 strain was grown in 100 mL of LB supplemented with 10 mM D-glutamate in optimal conditions for 8 days at 37° C. under agitation conditions (180 rpm). Samples from this culture were taken at the beginning of the incubation period and at days 1, 2, 7 and 8 for the determination of CFU in LB agar and LB agar supplemented with 10 mM D-glutamate. All cultures were performed in triplicate. In the hypothetical case of a phenotype reversion, similar bacterial counts should be recovered in agar plates over time, independently of the presence or absence of the compound in the medium. In contrast, we observed significant differences between the bacterial counts obtained when the culture was plated on agar medium with and without D-glutamate.

Figure 20:
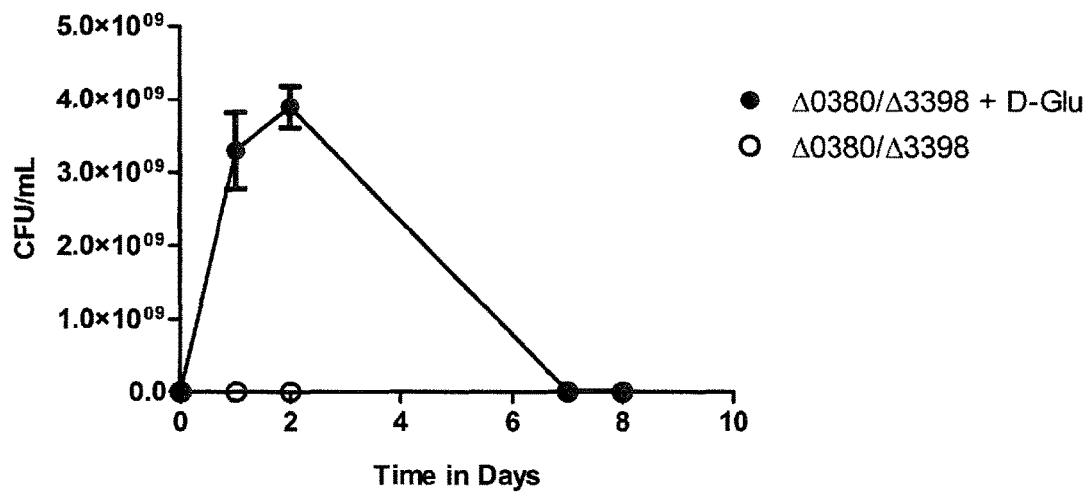
FIG. 20 is the number of *A. baumannii* Δ0380/Δ3398 colonies (CFU/mL) recovered from LB (○) and LB supplemented with 10 mM D-glutamate (●) when this strain was cultivated onto LB supplemented with 10 mM D-glutamate at 37° C. with agitation (180 rpm) during 8 days.

Resulting bacterial counts were significantly higher in the first case (agar plates supplemented with D-glutamate), at the initial stage of incubation (0 days) and on days 1, 2, 7 and 8 (see FIG. 20) (P=0.0006, according to Student's t test). The recovery of a significantly lower number of colonies in the agar plates without D-glutamate can be due to a residual growth derived from the accumulation of this compound in the cytoplasm of bacterial cells during growth in supplemented media. This difference indicates that Δ0380/Δ3398 strain remains auxotrophic for D-glutamate over time, without the possibility of reversion to the wild type phenotype.

Example 13: In Vivo Clearance of *A. baumannii* Δ0380/Δ3398 Strain After Intraperitoneal Administration in Mice In order to evaluate the safety of *A. baumannii* Δ0380/Δ3398 as a vaccine, bacterial counts were performed from the blood of BALB/c mice inoculated intraperitoneally (100 µL) with a 1× dose of the wild type and Δ0380/Δ3398 mutant strains prepared in saline medium independently of each other. After 45 minutes and after 2, 4, 6, 12 and 18 hours of the administration, mice were euthanized and blood was obtained directly from the heart and plated on LB agar with and without 10 mM D-glutamate, with D-glutamate for the auxotrophic strain and without for the wild type.

Figure 21:
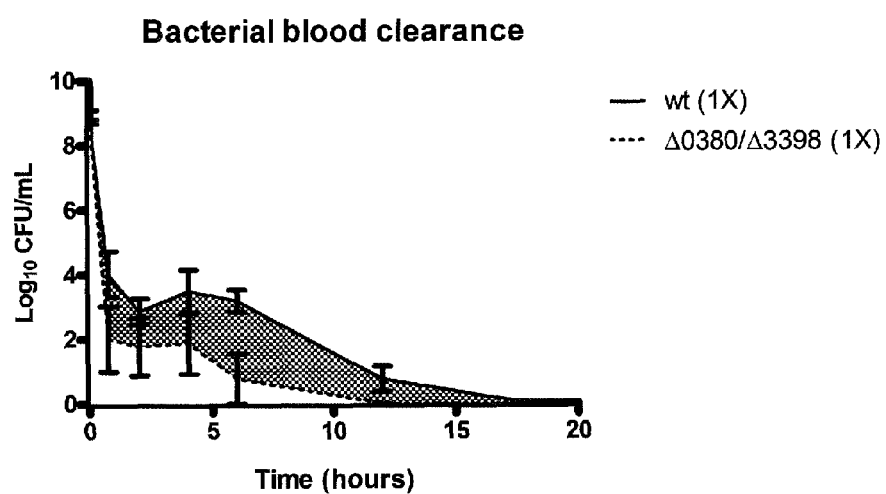
FIG. 21 shows the number of *A. baumannii* colonies ($Log_{10}$) CFU/mL) recovered from the blood of mice inoculated with 100 μL *A. baumannii* ATCC 17978 wild type and Δ0380/Δ3398 strains (1× dose) along the time.

We observed significant differences between the bacterial counts obtained with wild type and Δ0380/Δ3398 strains after 45 minutes post administration (see FIG. 21). In the case of the Δ0380/Δ3398 mutant strain, no colonies were recovered beyond 6 hours. These results suggest an acceptable threshold of security for the administration of this strain as a vaccine candidate, as this live attenuated bacterium is eliminated from the body within hours from its administration.

Example 14. Identification of Genes in *P. aeruginosa* PAO1 that Encode Glutamate Racemases Analysis of the genome sequence of *P. aeruginosa* strain PAO1 using the Protein Knowledgebase (UniProtKB) and the *Pseudomonas* Genome Database revealed a single putative glutamate racemase gene: PA4662, which encodes a 265 amino acid protein. FIG. 4 compares and aligns the predicted amino acid sequences for this putative glutamate racemase from *P. aeruginosa* PAO1 with the two reported glutamate racemases from *A. baumannii* ATCC 17978 and the single reported glutamate racemase from *E. coli* K12. The MurI protein encoded by PA4662 of *P. aeruginosa* PAO1 has 37.5% amino acid sequence similarity with the MurI protein encoded by the *E. coli* K12 (MURI_ECOLI), 35.9% amino acid sequence similarity with the MurI protein encoded by the A1S_0380 locus of *A. baumannii* (A3M1P5_ACIBT, SEQ ID NO: 1) and 37.5% similarity with the MurI protein encoded by the A1S_3398 locus (A3MA43_ACIBT, SEQ ID NO: 2) of *A. baumannii*.

Example 15: Construction and Characterization of a *P. aeruginosa* Glutamate Racemase Deficient Mutant We used in vitro methods to construct a mutant allele, designated ΔPA4662, with an in-frame deletion corresponding to the coding region of PA4662. This mutant allele was substituted for the corresponding wild type allele in the chromosome of *P. aeruginosa* strain PAO1 by using the pEX18Gm allelic exchange system.

The plasmid pEX18Gm was used to generate an unmarked deletion in the *P. aeruginosa* PA4662 gene, LPA4662, by allelic exchange in PAO1 strain. The pEX18GmUP/DOWNPA4662 plasmid was constructed by cloning two PCR fragments, approximately 1 kb in length, spanning the upstream and downstream regions of the PA4662 of *P. aeruginosa* PAO1. The upstream fragment was amplified using primers UPPA4662(HindIII)F_II and UPPA4662(NotI)R and the resulting PCR product was digested with HindIII and NotI. The downstream fragment was amplified using DOWNPA4662(NotI)F and DOWN0380(XbaI)R and the resulting PCR product was digested with NotI and XbaI. Digested upstream and downstream fragments were ligated into vector pEX18Gm linearized with HindIII and XbaI to generate pEX18GmUP/DOWNPA4662.

The pEX18GmUP/DOWNPA4662 plasmid was first introduced into *E. coli* S17-1 by transformation. Briefly, electrocompetent *E. coli* S17-1 cells were cultivated with 15 µg/ml gentamicin overnight at 37° C. after applying the electric pulse. Following incubation, resulting colonies were analyzed by PCR using the primers UPPA4662(HindIII)F_II and DOWNPA4662(XbaI)R to confirm the desired presence of the pEX18GmUP/DOWNPA4662 plasmid.

The pEX18GmUP/DOWNPA4662 plasmid was introduced in *P. aeruginosa* PAO1 strain by electroporation as described above and cells were cultivated in LB with 30 µg/ml gentamicin for 3 days at 37° C. Independently isolated co-integrant colonies were inoculated into 1 mL of LB broth supplemented with 10 mM D-glutamate and 15% sucrose and grown at 37° C. overnight while shaking. Cultures were then serially diluted using NaCl 0.9% and dilutions were plated onto LB agar containing 15% sucrose and 10 mM D-glutamate. Individual colonies of resolved co-integrants were picked from LB agar plates containing 15% sucrose and 10 mM D-glutamate and inoculated in patches at comparable locations on LB agar plates with and without 10 mM D-glutamate. Resolvants with the ΔPA4662 genotype grew only on the LB agar with D-glutamate, and resolvants with the wild type genotype grew on LB agar with or without D-glutamate.

Figure 22:
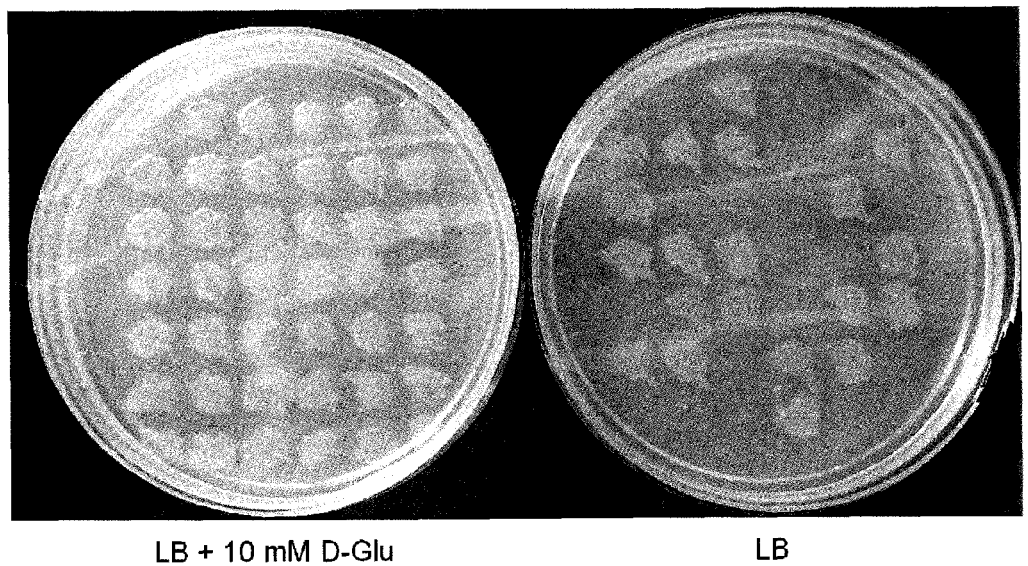
FIG. 22 shows the screening of resolved co-integrants during construction of the ΔPA4662 mutant of P. aeruginosa.

In this *P. aeruginosa* strain, the resulting ΔPA4662 single mutant required exogenous D-glutamate for growth. FIG. 22 illustrates the patch tests that were used to distinguish individual resolved co-integrants with the ΔPA4662 mutant genotype that grow only on LB agar containing D-glutamate from individual resolved co-integrants with the wild type genotype that do not require D-glutamate for growth.

Figure 23:
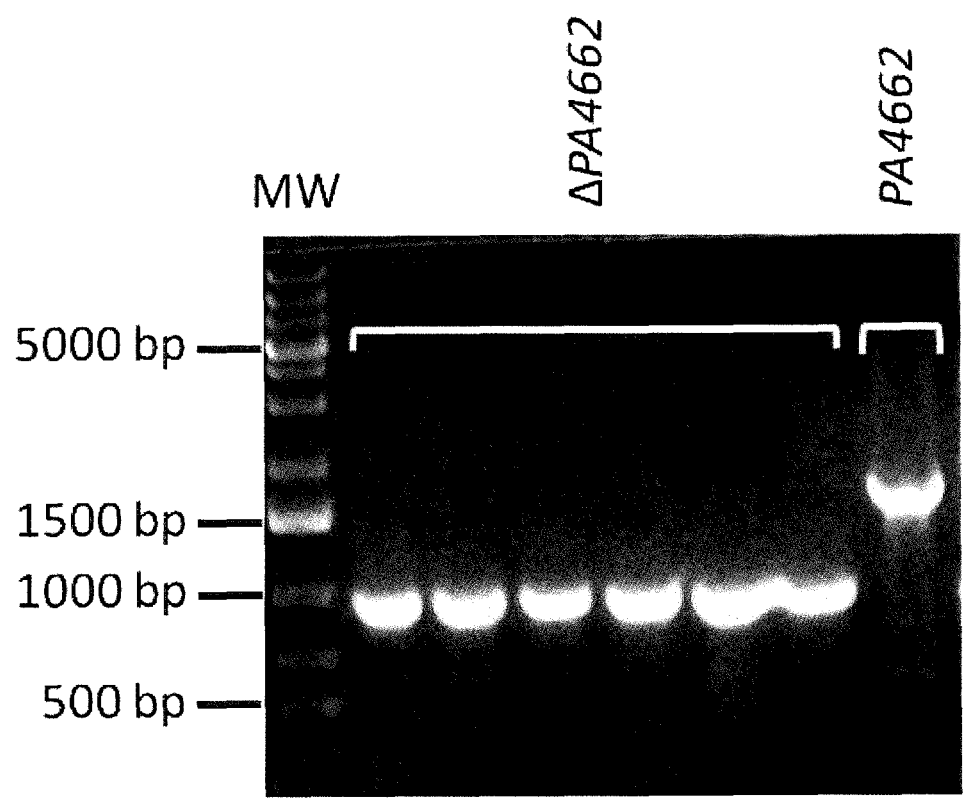
FIG. 23 illustrates the PCR confirmation of deletions in ΔPA4662 mutant of P. aeruginosa. Primers EXTFWPA4662 and EXTRVPA4662 were used to generate a 1741 by fragment from strains carrying the wild type PA4662 allele or a 943 bp fragment from strains carrying the ΔPA4662 allele. Lane labels and samples analyzed are as follows: MW: DNA ladder; ΔPA4662: amplicon from strain carrying the ΔPA4662 mutant allele; and PA4662: amplicon from strain carrying the wild type PA4662 allele.

The presence of the appropriate wild type or in-frame deletion variant of PA4662 in the newly constructed mutants was confirmed by PCR using primers UPPA4662(HindIII) F_II/DOWNPA4662(XbaI)R; INTFWPA4662/IN-TRVPA4662 and EXTFWPA4662/EXTRVPA4662 (screening using the last combination of primers is illustrated in FIG. 23).

Our results showed that a single in-frame deletion at the PA4662 locus of *P. aeruginosa* PAO1 strain introduced by allelic exchange using the highly homologous pEX18GmUP/DOWNPA4662 plasmid, conferred a stringent growth requirement for exogenous D-glutamate. This finding indicates that PA4662 is the only gene in *P. aeruginosa* PAO1 that directs production of functional glutamate racemase.

Example 16: Determination of the Lethal Doses (LD) of *P. aeruginosa* Wild Type and ΔPA4662 Glutamate Racemase Deficient Strain in a Mice Model of Acute Infection Evaluation of Antibody Immune Response (IgG) by Indirect ELISA BALB/c mice (n=4 mice/group) were administered different doses of *P. aeruginosa* PAO1 wild type and ΔPA4662 with the purpose of determining the lethal doses of these strains during an acute sepsis infection.

For preparation of the administered inoculums, bacteria were grown in LB (wild type strain) and LB supplemented with 10 mM D-glutamate (ΔPA4662 mutant) at 37° C. with shaking until an $OD_{600\ nm}$=0.7 (1× dose). Cultures were then centrifuged and the bacterial pellet was washed 2 times with LB. After cell washing, bacterial suspensions were adjusted with NaCl 0.9% at different doses (0.1×; 0.4×; 1×; 4×; 10×y 40×), according to the previous $OD_{600\ nm}$ value, and inoculated (100 µL) in BALB/c mice by intraperitoneal injection (1× meaning as bacterial inoculums with $OD_{600\ nm}$=0.7, 0.1× the bacterial inoculums diluted 1:10, 2× the bacterial inoculums 2:1 concentrated, and so on . . . ).

Mice were monitored for 7 days after infection and survival rates were determined for different doses of injected bacteria. Lethal doses (LD) titer of each bacterial strain were determined considering the observed survival of mice in both cases, meaning $LD_{100}$ the minimal dose for which 100% of susceptible mice will die.

In FIG. 24A we can see different degrees of survival in animals infected with increasing doses of *P. aeruginosa* PAO1 wild type strain. For this strain, the $LD_{100}$ is =0.4×. In FIG. 24B we can see different degrees of survival in animals infected with increasing doses of the ΔPA4662 mutant. For this strain, the $LD_{100}$ is >40×, a very high dose of bacterial inoculum, which can lead to death of the mice from septic shock (and not due to replication of the bacteria). This indicates that this strain has a much reduced virulence (a dose 100 times higher than the wild strain $LD_{100}$ only decreases by 50% survival of mice).

In addition, we evaluated the antibody immune response (IgG) by indirect ELISA. To that end, groups of 4 mice were immunized once with one of the following doses: 0.1×, 0.4×, 1×, 4×, 10× and 40×. As shown in FIG. 44, one vaccine dose of 0.1× of ΔPA4662 mutant strain (1×=5×10$^8$ CFU/mL) is sufficient to trigger IgG production significantly (P<0.001), even when detected at day 40 after the vaccine administration. Nonetheless, vaccine doses equal or greater than 0.4× elicit higher levels of IgG production.

As shown in FIG. 45, IgG levels are significantly incremented at day 7 after administering the first vaccine dose (0.4×). However, antibody production is significantly higher when the 2$^{nd}$ vaccine dose is administered (0.4×).

Lastly, ELISA was performed with respect to different strains of *P. aeruginosa* with sera obtained on day 34 from mice vaccinated with 3 dosis (0.4×) of the ΔPA4662 strain (administered on days 0, 14 and 28) and mice administrated saline (on the same days) to measure the capacity of ΔPA4662 vaccine to generate a broad immune response. Results similar to those observed with respect to *P. aeruginosa* strain PAO1 were obtained with strain PA28562 whereas high levels of cross-reactivity were also seen with respect to rest of *P. aeruginosa* strains tested (PA51430664, PA26132, PAST175, PA29475 and PA12142) (FIG. 46). This demonstrates that immunization with strain ΔPA4662 not only generates antibodies against the isogenic wild type strain, but also generates IgG antibodies that react against multiple *P. aeruginosa* strains.

Example 17: Morphological Analysis of *P. aeruginosa* PAO1 Wild Type and ΔPA4662 Mutant Strains by Electron Microscopy For obtaining electron micrographs by transmission electron microscopy (TEM), the ΔPA4662 mutant strain was first grown in LB agar supplemented with 10 mM D-glutamate for 18 h at 37° C. and finally plated onto MH agar, LB and LB supplemented with $MgCl_2$ (30 mg/L) and $CaCl_2$ (75 mg/L) and incubated for 18 h at 37° C. After incubation, 2-3 colonies were dissolved in PBS buffer, the suspension was centrifuged, and the resulting pellet was first washed with cacodilate buffer and immediately cells were fixed in 2.5% ice cold gluteraldehyde prepared in sodium cacodilate buffer (0.2 M, pH 7.4) for 4 hours at room temperature. The pellets were then washed with cacodilate buffer, dehydrated in acetone and embedded in Spurr (Spurr's Epoxy Embedding Medium). Ultrathin sections (70 nm) of the samples were stained with uranyl acetate and plumb citrate for observation in a JEOL JEM 1010 (80 kV) transmission electron microscope.

Figure 25:
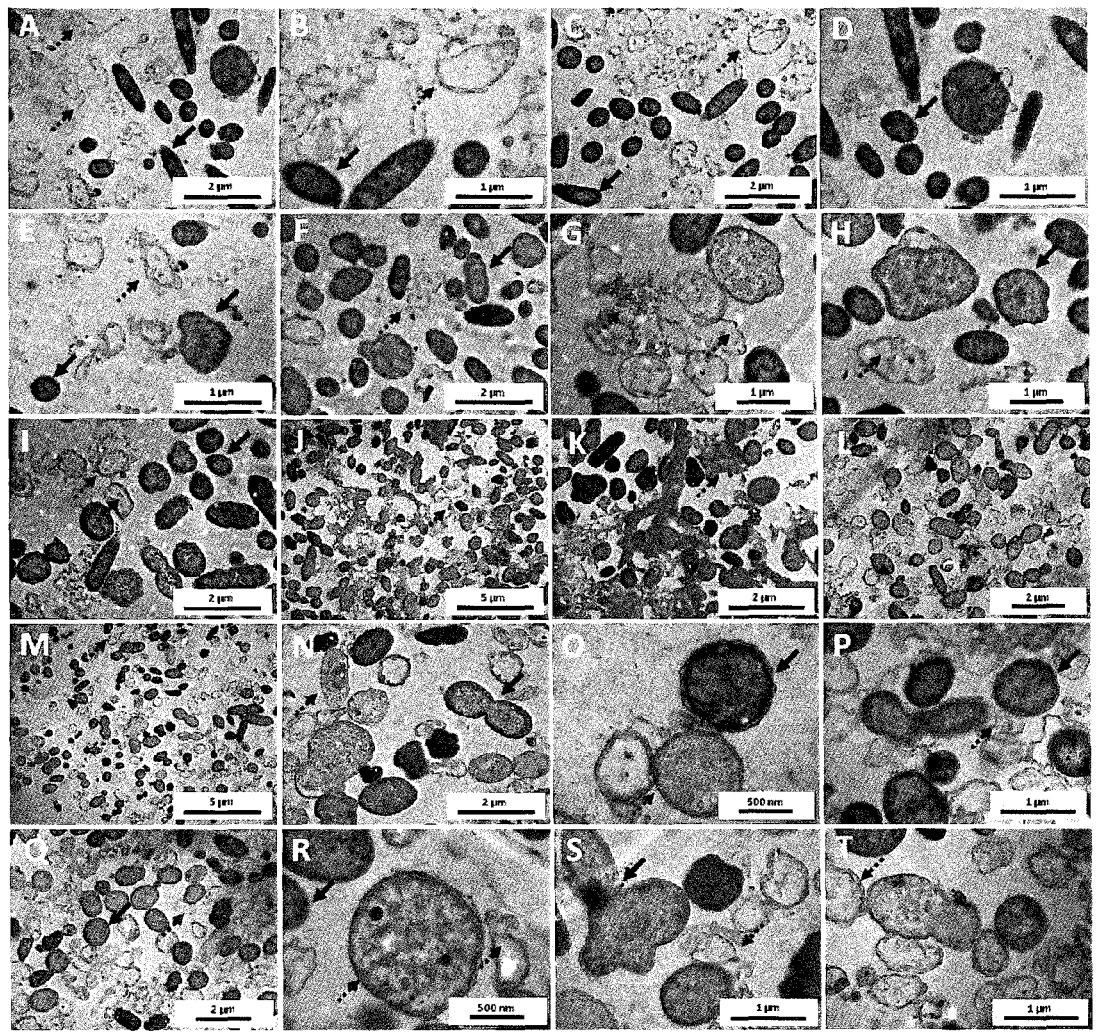
FIG. 25 shows the atypical morphology and the progressive degeneration of the cell wall and lysis of the P. aeruginosa mutant strain ΔPA4662 when maintained in the absence of D-glutamate. A-E: MH media; F-I: LB media; J-T: LB+$MgCl_2$ (30 mg/L)+$CaCl_2$ (75 mg/L). Micrographs were taken with a transmission electron microscope at different scales. Black arrows indicate intact bacterial cells with normal morphology or atypical cell division; dashed arrows indicate fragmented cells without bacterial cell wall, lysed cells or disorganized internal content, dispersed genetic material, aggregation of membranes and/or liposomes.

FIG. 25 shows the different stages of the cell wall degeneration of the ΔPA4662 mutant strain: from cells with altered conformation that lose their rigid structure to cells that present several ruptures and displacement of the outer membrane, lysis and extrusion of the intracellular content (especially genetic material). The mechanism of bacterial destruction can be followed with this order: 1) the absence of the cell wall leaves the bacterial protoplasm surrounded only by the inner cell membrane (protoplast), which makes this cell body totally exposed to variations in the tonicity of the medium; 2) protoplasts burst and leave traces of the cytoplasmatic membranes—called "ghosts" that can aggregate, also individual membranes and liposomes can be visible.

Example 18: Protection of BALB/c Mice Against Challenge with *P. aeruginosa* PAO1 Strain by Immunization with the ΔPA4662 Mutant To evaluate the efficacy of the ΔPA4662 strain as a vaccine, BALB/c mice (n=8) were administered 100 µL of the ΔPA4662 strain (0.4× dose in saline) on days 0 and 14. Control mice were administered only saline identically at days 0 and 14. Twenty five days after the second injection, mice were challenged with *P. aeruginosa* PAO1 wild type strain (0.4× dose in saline) in order to establish a lethal systemic infection in both cases (100 µL of intraperitoneal injection). After the challenge, mice were monitored for 7 days to determine the survival rate of vaccinated mice compared to control mice (unvaccinated).

When infected with a 0.4× dose of the *P. aeruginosa* PAO1 wild type strain, 8 deaths were observed in the group of unvaccinated mice during the first 15 hours, which means a mortality rate of 100% in this group (n=8). In contrast, all vaccinated mice (n=8) survived to the challenge, overcoming the infection, which means a 100% survival (see FIG. 26A) rate in this group. Differences in survival between the two groups were extremely statistical significant (P<0.0001, according to the Mantel-Cox log-rank test).

These results suggest that vaccination with the APA4662 strain can provide protective immunity against infection with *P. aeruginosa*.

Figure 47:
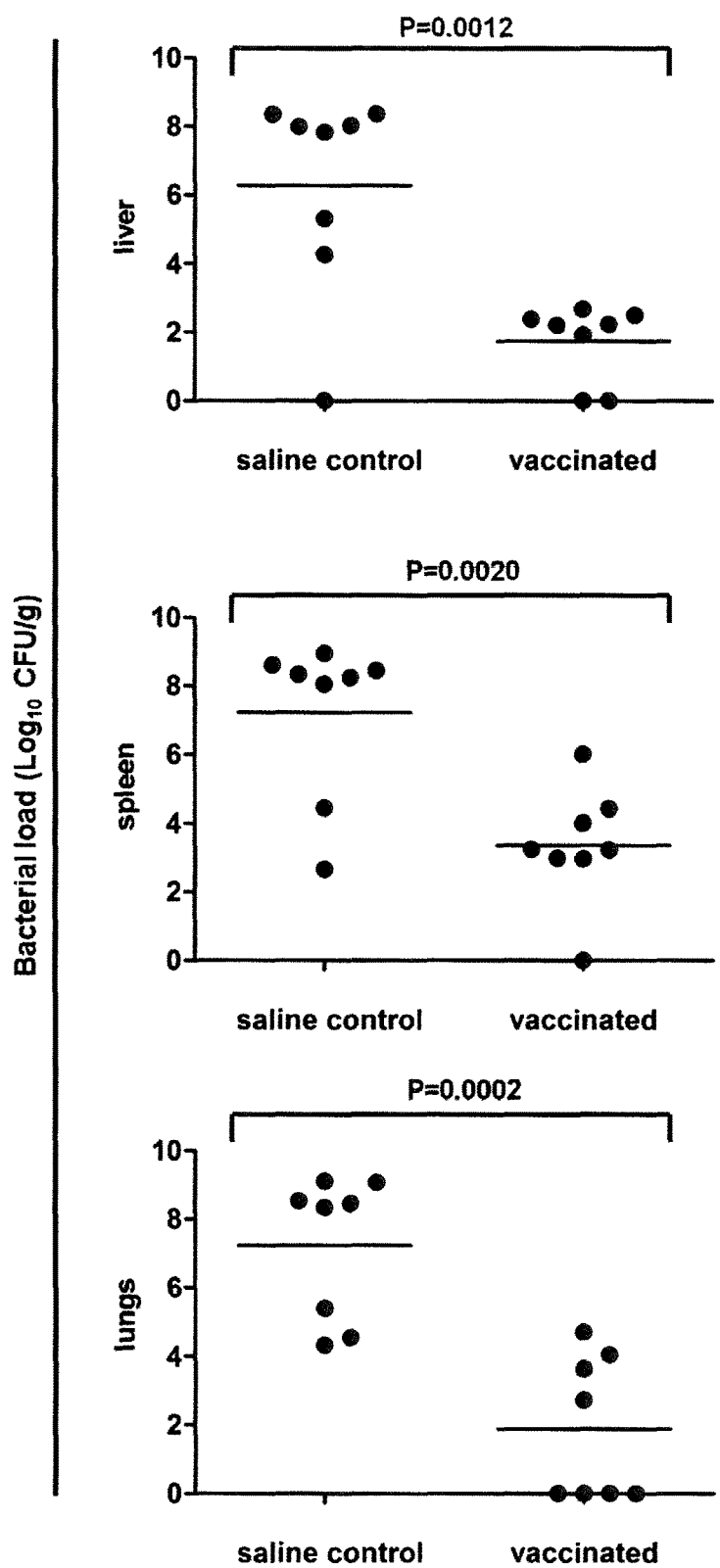
FIG. 47 shows the bacterial load in the liver, spleen and lungs of BALB/c mice (n=8) 10 hours post-infection with a 0.4× dose of the *P. aeruginosa* wild type strain PAO1 administered on day 22, after the mice were pre-immunized on days 0 and 15 with strain ΔPA4662, or non-immunized (saline control). P-value according to the unpaired t test. Each dot represents the individual bacterial load of the organ of a mouse. The average value of each group is represented by a horizontal line.

These results are further confirmed as follows. First, FIG. 26B shows the percent survival (87.5% vaccine efficacy) of BALB/c mice (n=8) following intraperitoneal infection with a 0.4× dose of *P. aeruginosa* PAO1 wild type strain. Vaccinated mice were immunized on days 0 and 14 with *P. aeruginosa* ΔPA4662 strain (0.04× dose) and infected with the wild type strain at day 25. Non-vaccinated mice were administered saline on days 0 and 14 and infected with the wild type strain at the same day. *P<0.0001 survival of vaccinated group compared to unvaccinated group. P-value, according to the Mantel-Cox test (log-rank test). Secondly, FIG. 47 shows that vaccinated mice had a significant decrease in CFUs of *P. aeruginosa* in liver, spleen and lungs after 10 hours of acute sepsis infection.

Figure 49:
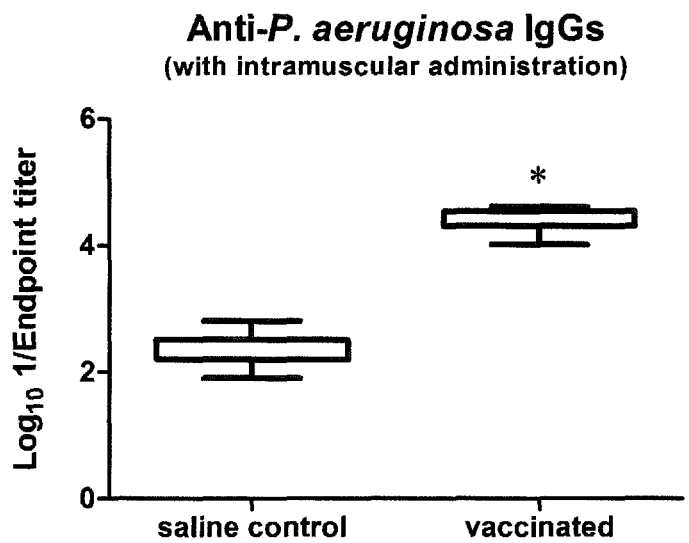
FIG. 49 shows the $Log_{10}$ 1/endpoint titer of IgG antibodies produced against the *P. aeruginosa* strain PAO1 in BALB/c mice (n=8) on post-vaccination day 34 and in non-vaccinated control mice (with intramuscular administration). The antibody titers were determined by indirect ELISA. *P<0.0001 compared with the group of control mice; P-value according to unpaired t test. The boxes represent the first and third quartiles; the horizontal line represents the median; the whiskers represent the range.

To evaluate the protective efficacy of the ΔPA4662 strain as a vaccine using one of the preferred route for administration in humans, BALB/c mice (n=8/per group) were inyected with 100 µL of the ΔPA4662 strain (0.4× dose in saline) on days 0, 14 and 28 using the intramuscular route. Control mice were administered only saline identically at days 0, 14 and 28. At day 34, blood were collected from the submandibular vein from all mice without euthanasia, the sera was separated and IgG quantification was performed as above. Significant differences between IgG antibody production were observed between the group of mice immunized compared to control group (P<0.0001, according to unpaired t test) (FIG. 49).

At day 35, mice were challenged with *P. aeruginosa* PAO1 wild type strain (0.4× dose in saline) in order to establish a lethal systemic infection in both cases (100 μL of intraperitoneal injection). After the challenge, mice were monitored for 7 days to determine the survival rate of vaccinated mice compared to control mice (unvaccinated). After the challenge, 8 deaths were observed in the group of unvaccinated mice which means a mortality rate of 100% in this group. In contrast, all vaccinated mice survived to this challenge, overcoming the infection. This means a 100% survival rate in this group (see FIG. 50). Differences in survival between vaccinated and control mice were extremely statistical significant (P<0.0001, according to the Mantel-Cox log-rank test). This result suggests that vaccination using the intramuscular route of administration is as effective as the intraperitoneal route.

Example 19: Passive Immunization with ΔPA4662 Vaccine Antisera

In situations in which the completion of a vaccination schedule prior to bacterial exposure is not possible, when individuals cannot synthesize antibody, or even after exposure to the pathogen, the use of passive immunization may be beneficial. Those antibodies formed with ΔPA4662 vaccination can be removed from the host and transferred into another recipient where they can provide immediate passive immunity or help fight the infectious disease.

We first determined if vaccine serum from mice immunized with the ΔPA4662 strain could be used to passively immunize mice before the exposure to *P. aeruginosa*. One dosis of vaccine or naïve sera were administered by intraperitoneal injection (200 μL) to BALB/c mice (n=8) 3.5 h prior to infection with 0.4× dose of *P. aeruginosa* PAO1 wild type strain and survival of mice was monitored for 3 days after the challenge. As shown in FIG. 27A, all mice administrated vaccine serum were protected from disease, whereas 50% of the mice receiving naïve serum succumbed to infection (P=0.025; Mantel-Cox test (log-rank test)).

These results demonstrate that passive immunization with serum from mice vaccinated with the ΔPA4662 strain is able to confer a significant level of protection from infection, when administered prior to infection, whereas antibodies alone are sufficient for providing protective immunity against *P. aeruginosa* PAO1 acute sepsis.

Next, we determined if vaccine serum from mice immunized with the ΔPA4662 strain could be given as a medication to nonimmune mice having already received a lethal injection of *P. aeruginosa*, in order to ameliorate the prognostics of the disease. As a treatment, two dosis of vaccine or naïve sera (150-200 μL) were given via intravenous injection to BALB/c mice (n=7) 2 h and 4.5 h after the infection with a 0.4× dosis of *P. aeruginosa* PAO1 wild type strain. Survival of mice was monitored for 2 days. Of note, when the first treatment with sera was administered, all mice presented visible symptoms of an acute sepsis infection. As shown in FIG. 27B, all mice receiving the lethal dosis of *P. aeruginosa* succumbed to infection, however, mice administrated vaccine serum survived significantly longer (P=0.0112; Mantel-Cox test (log-rank test)) than mice receiving naïve serum. Thus, vaccine sera offered mice life maintenance during several hours after the development of the acute lethal disease and helped protect right away. In regards to correlates of protection and treatment with vaccine sera, these results also suggest that the optimal antibodies titres and administration schedule may need to be determined.

Example 20: Environment Safety Assessment of the ΔPA4662 Strain—Evaluation of Water Osmolisis A vaccine candidate should also be construed to mean one bacterium which is incapable of replicate and to persist in the general environment, once it leaves the vaccinated individual. To compare the ability of *P. aeruginosa* PAO1 wild type and ΔPA4662 mutant strain to be long-time traced in the general environment, we evaluated survival of these strains in water without any contribution of nutrients or salts, at 37° C. and agitation (180 rpm) for the time necessary to observe the loss of viability by cellular osmolisis.

Daily samples of culture were taken initially for 3 days, next, samples were taken twice a week until day 62, and finally, at least once every two weeks for the determination of CFU counts in LB agar (wild type strain) and LB agar supplemented with 10 mM D-glutamate (mutant strain). All cultures were performed in triplicate.

Figure 28:
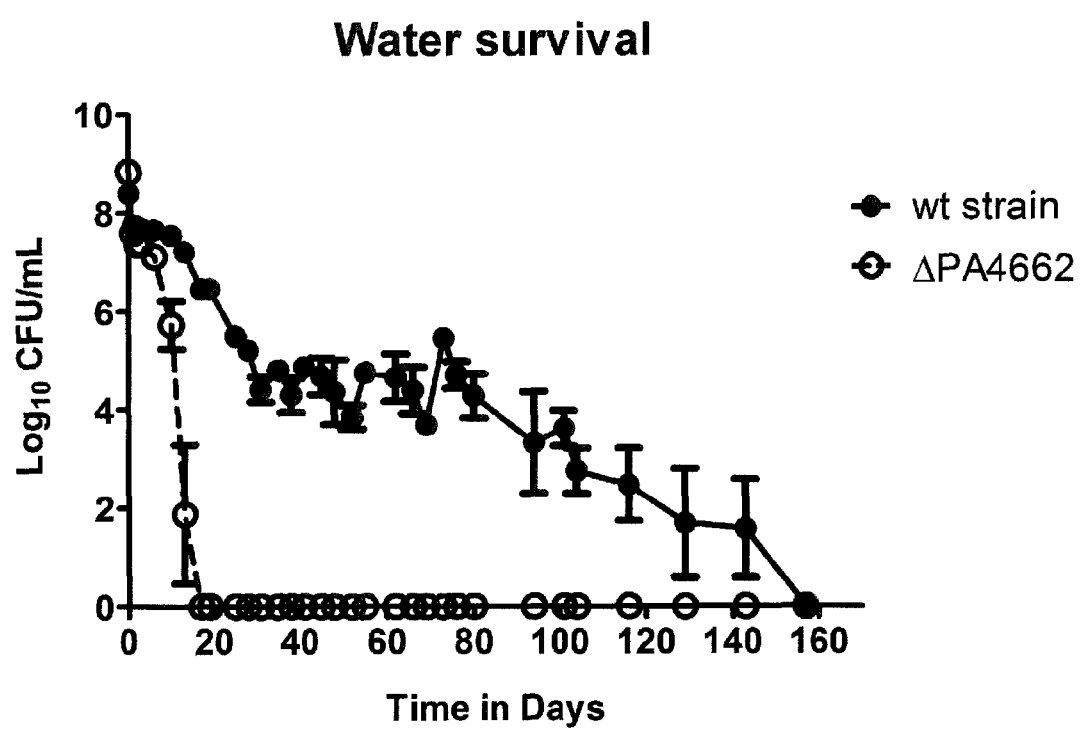
FIG. 28 is the $Log_{10}$ CFU/mL of recovered P. aeruginosa PAO1 wild type and ΔPA4662 strains when grown in distilled water at 37° C. with agitation (180 rpm) during 157 days. CFU's were determined by counting colonies plated onto LB (wild type strain) and LB with 10 mM D-glutamate (mutant strain). All cultures were performed in triplicate.

A significant decrease in the viability of the ΔPA4662 strain was seen, and no viable bacteria were recovered within and after 17 days of culture. In contrast, its wild counterpart, the wild type strain, remained widely recoverable after the 25$^{th}$ day of culture (see FIG. 28) and survived until day 143.

Example 21: Evaluation of the Stability of the Auxotrophic Phenotype in the ΔPA4662 Strain To test the irreversibility of the nutritional auxotrophy of *P. aeruginosa* ΔPA4662 for the compound D-glutamate, ΔPA4662 strain was grown in 100 mL of LB supplemented with 10 mM D-glutamate in optimal conditions for 5 days at 37° C. with agitation (180 rpm). Samples from this culture were taken at the beginning of incubation and at days 3 and 5 for determination of CFU in LB agar and LB agar supplemented with 10 mM D-glutamate. All cultures were performed in triplicate. In the hypothetical case of a phenotype reversion, similar bacterial counts should be recovered in agar plates over time, independently of the presence or absence of the compound in the medium. In contrast, we observed significant differences between the bacterial counts obtained when the culture was plated onto agar medium with and without D-glutamate.

Figure 29:
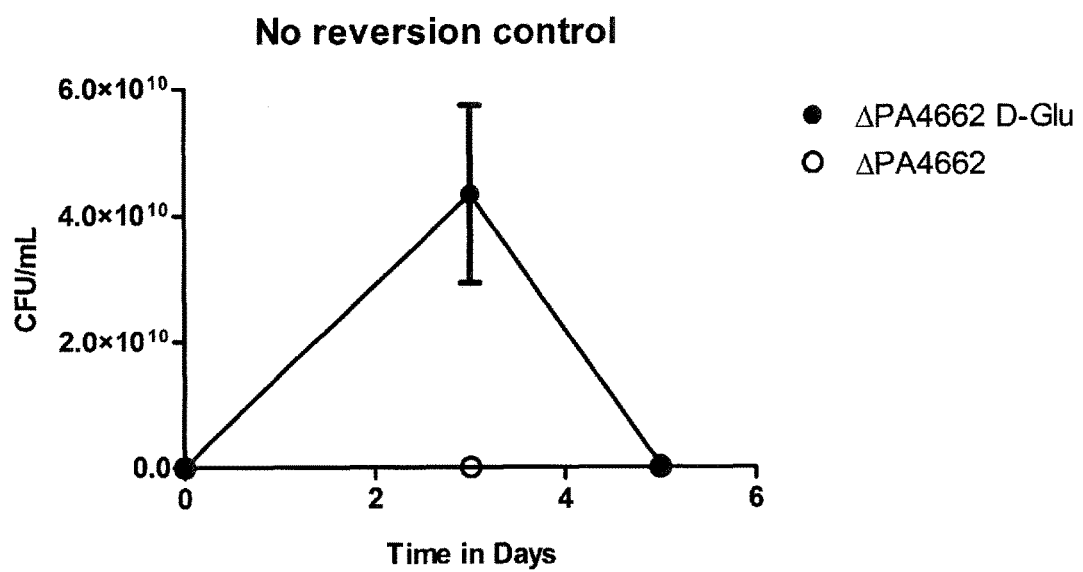
FIG. 29 is the number of P. aeruginosa ΔPA4662 colonies (CFU/mL) recovered from LB (○) and LB supplemented with 10 mM D-glutamate (●) when this strain was cultivated onto LB with 10 mM D-glutamate at 37° C. with agitation (180 rpm) during 5 days.

Resulting bacterial counts were significantly higher in the first case (agar plates supplemented with D-glutamate), at the initial stage of incubation (0 days) and on days 3 and 5 (see FIG. 29) (P=0.0059, according to Student's t test). The recovery of a significantly lower number of colonies in the agar plates without D-glutamate can be due to a residual growth derived from the accumulation of this compound in the cytoplasm of bacterial cells during growth in supplemented media. This difference indicates that ΔPA4662 strain remains auxotrophic for D-glutamate over time, without the possibility of reversion to the wild type phenotype.

Figure 51:
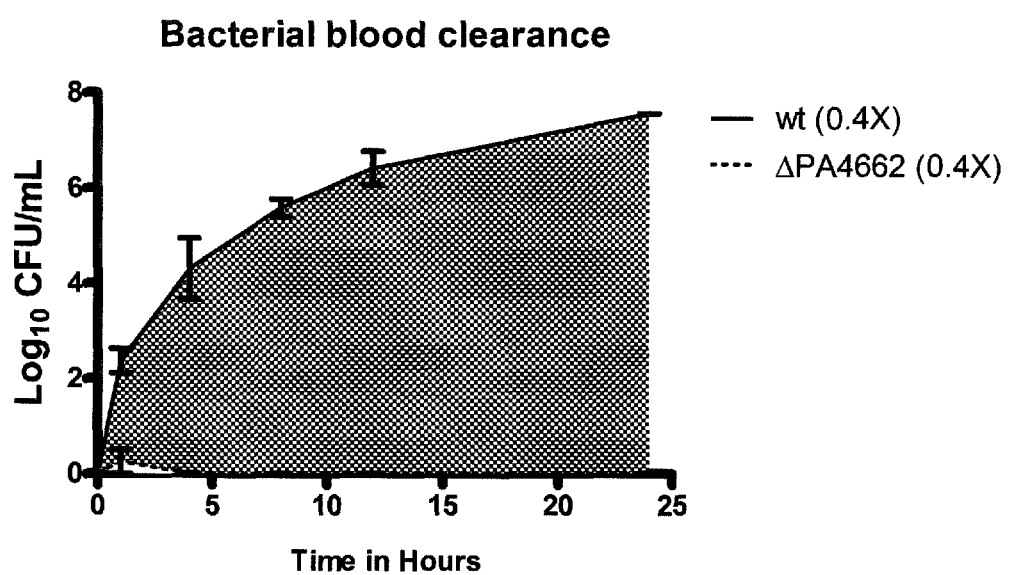
FIG. 51 shows the number of *P. aeruginosa* colonies ($Log_{10}$ CFU/mL) recovered from the blood of mice (n=3/per group) inoculated with 100 μL *P. aeruginosa* PAO1 wild type and ΔPA4662 strains (0.4× doses) along the time.

Moreover, in FIG. 51 we observed significant differences between the bacterial counts obtained with wild type and ΔPA4662 strains after 1 hour after intraperitoneal administration. In the case of the ΔPA4662 mutant strain, no colonies were recovered beyond 1 hour. These results suggest an acceptable threshold of security for the administration of this strain as a vaccine candidate, as this live attenuated bacterium is eliminated from the blood within a few hours from its administration.

Example 22: Construction and Characterization of Single and Double Mutant Strains of S. aureus without Glutamate Racemase and/or D-amino Acid Transaminase Homologous double recombination was carried out using the temperature sensitive replication vector pMAD to construct the mutant strains. First, the unmarked deletion of the annotated glutamate racemase (murI) and D-amino acid transaminase (dat) genes were achieved independently. Each single mutant strain was called ΔmurI and Δdat, respectively.

To achieve the construction of these two mutants, fragments of 1000 bp that correspond to the upstream (left) and downstream (right) DNA that flanked the genes were amplified by PCR and cloned separately into the shuttle plasmid pMAD. The resulting recombinant plasmids were used to remove the chromosomal murI and dat genes located on the chromosome of S. aureus 132 wild type strain.

S. aureus 132 is a clinical MRSA strain used in the present invention as a model organism of the species "Staphylococcus aureus" to generate auxotrophic mutants to D-glutamate. This is a clinical strain resistant to methicillin (MRSA) (Vergara-Irigaray et al, Infection and Immunity, 77 (9): 3978-3991 (2009)).

The upstream fragment of the murI gene was obtained by PCR amplification using the combination of murIUP(MluI)F and murIUP(NotI)R primer pair, and subsequently digested by MluI and NotI restriction enzymes. The downstream fragment of the murI gene was obtained by PCR amplification using the murIDOWN(NotI)F and murIDOWN(BglII)R primers followed by digestion with NotI and BglII enzymes. The digested upstream and downstream fragments of the murI gene were cloned into the pMAD vector previously linearized with MluI and BglII enzymes, yielding the construction named pMAD_UP/DOWN_murI.

The same strategy was completed for the construction of the plasmid pMAD_UP/DOWN_dat. In this case, the upstream and downstream fragments of the dat gene were amplified using the primer pairs datUP(MluI)F/datUP(NotI)R and datDOWN(NotI)F/datDOWN(BglII)R, respectively.

pMAD_UP/DOWN_murI and pMAD_UP/DOWN_dat were introduced into E. coli TG1 by electroporation. Transformant colonies were selected on LB agar supplemented with ampicillin (100 μg/mL) plus X-Gal (150 μg/mL). After incubation at 37° C. for 18 h, ampicillin-resistant blue colonies were PCR checked for the presence of pMAD_UP/DOWN_murI or pMAD_UP/DOWN_dat with the primer combinations murIExtF/murIExtR or datExtF/datExtR, respectively.

The constructions pMAD_UP/DOWN_murI and pMAD_UP/DOWN_dat extracted from E. coli TG1 cells were independently introduced into the intermediate cloning strain S. aureus RN4220 previous electroporation into the targeted strain S. aureus 132. The selection of S. aureus RN4220 colonies that contained recombinant plasmids were performed on TSB agar supplemented with erythromycin (10 μg/mL) plus X-Gal (150 μg/mL) after incubation at 30° C. for 24-48 h.

Each recombinant plasmid was extracted from S. aureus RN4220 and independently introduced into S. aureus 132 wild type strain by electroporation. As well, erythromycin-resistant blue colonies of S. aureus 132 that harboured each construction were grown on TSB agar with erythromycin (10 μg/mL) plus X-Gal (150 μg/mL) at 30° C. for 24-48 h.

To delete the chromosomal murI gene of S. aureus 132 wild type strain, one colony of S. aureus 132 wild type harbouring pMAD_UP/DOWN_murI was transferred to a 5 mL of TSB with 10 μg/mL of erythromycin and grown at 30° C. for 2 h. Afterwards, the culture were incubated at 43.5° C., a non-permissive temperature for pMAD replication, leading the integration of pMAD_UP/DOWN_murI into the bacterial chromosome via a single crossover recombination upstream or downstream region of murI gene. After 6 hours, the TSB culture was serially diluted and spread onto TSA plates supplemented with erythromycin (10 μg/mL) plus X-Gal (150 μg/mL) and incubated at 43.5° C. for 18 h. Several of the resulting colonies were transferred to a 5 mL of TSB without antibiotic and incubated for 18 h at 30° C. in order to induce a second crossover event that lead to pMAD_UP/DOWN_murI excision from the chromosome. The selection of white colonies, which no longer contain pMAD_UP/DOWN_murI, was carried out by plating serial dilutions on TSB plates with X-Gal (150 μg/mL). Each selected colony was transferred onto TSA with X-Gal (150 μg/mL) as well X-Gal (150 μg/mL) plus erythromycin (10 μg/mL). Erythromycin-sensitive white colonies were checked by PCR for the deletion of murI gene (ΔmurI) using murIExtF/murIExtR, murIseqF/murIseqR and murIF/murIR primer pairs.

The deletion of dat gene from the chromosome of S. aureus 132 wild type strain was performed following the protocol previously described for murI but using the pMAD_UP/DOWN_dat plasmid. In this case, colonies suspected to no longer contain the dat gene (Δdat) were confirmed using datExtF/datExtR, datseqF/datseqR and datF/datR primer combinations.

To generate the double mutant ΔmurI/Δdat the pMAD_UP/DOWN_dat plasmid was introduced by electroporation into the mutant ΔmurI strain and the same protocol described before for the single mutants was performed. In this case, the recovering of double mutants required adding exogenous D-glutamate to the medium (20 or 10 mM for TSB or TSB agar respectively) since colonies with double gene deletion require this D-aminoacid for growth. The absence of the murI and dat loci in the genome of S. aureus 132 wild type strain was confirmed by PCR using the following primers: murI ExtF/murI ExtR, murIseqF/murIseqR, murIF/murIR, datExtF/datExtR, datseqF/datseqR and datF/datR.

Figure 30:
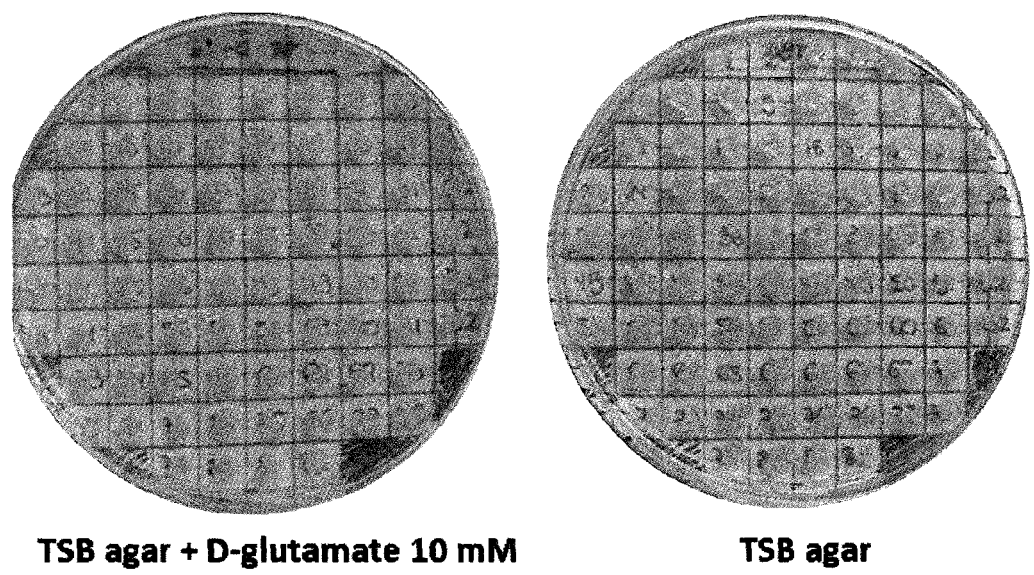
FIG. 30 shows the screening of the colonies resulting from the single mutant ΔmurI after the second crossover event during construction of the S. aureus double mutant ΔmurI/Δdat. The individual erythromycin-sensitive colonies were selected from TSB agar plates supplemented with X-Gal (150 μg/mL) and inoculated in the same position in TSB agar plates with and without 10 mM D-glutamate. Colonies with the ΔmurI/Δdat genotype grow exclusively in plates with D-glutamate; colonies with the ΔmurI genotype (lacking the murI gene but with an intact copy of the dat gene) grew properly with and without D-glutamate.

The culture of the different mutant strains in medium with and without D-glutamate revealed that the single deletion of murI or dat genes does not affect bacterial growth. However, the double mutant requires the presence of D-glutamate in the medium for growth. FIG. 30 represents the colony screening method carried out for the selected erythromycin-sensitive white colonies resulting from the second crossover event of the single mutant ΔmurI.

Figure 31:
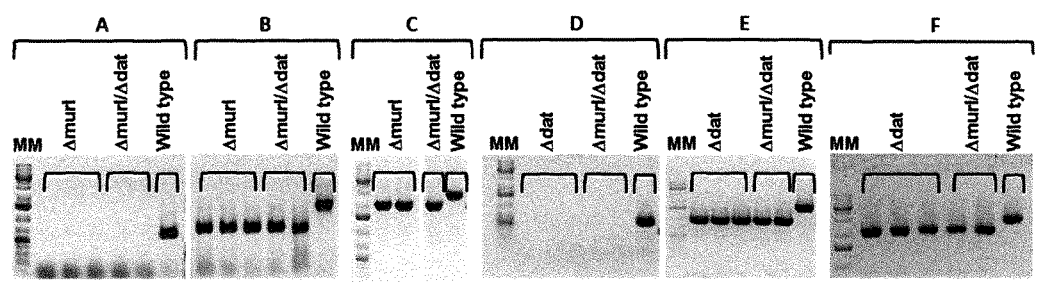
FIG. 31 is the PCR confirmation of the deletions in S. aureus 132 mutants ΔmurI, Δdat and ΔmurI/Δdat. The primers used were A: murIF/murIR; B: murIExtF/murIExtR; C: murIseqF/murIseqR; D: datF/datR; E: datExtF/datExtR; and F: datseqF/datseqR. Lanes: MM, molecular marker GeneRuler 1 kb; ΔmurI, fragments obtained from strains carrying mutant locus ΔmurI; Δdat, fragments obtained from strains carrying mutant locus Δdat; ΔmurI/Δdat, fragments obtained from strains defective in the two loci ΔmurI and Δdat; wild type, fragments obtained from S. aureus 132 wild type strain carrying two loci, murI and dat.

FIG. 31 shows PCR confirmation of the different deletions in the three mutant strains of S. aureus 132 wild type. The results obtained so far demonstrate that the presence of either any of the two wild type loci, murI or/and dat, is sufficient for the normal growth of S. aureus 132 in TSB agar without added D-glutamate, and that the simultaneous deletion of both genes make this strain unable to grow without the presence of D-glutamate. In conclusion, it is demonstrated that the murI and dat genes of S. aureus 132, are the only genes involved in the biosynthesis of D-glutamate in this strain.

It is thus worth noting that the inactivation of both glutamate racemase and D-amino acid transaminase enzymes results in an auxotrophy to D-glutamate and that the method for obtaining auxotrophic mutants pertaining to *Staphylococcus aureus* species is independent of the strain selected.

Example 23: Effect of D-glutamate on the Double Mutant ΔmurI/Δdat Growth and Viability in Liquid Culture Medium To evaluate the growth and viability curve of the *S. aureus* double mutant ΔmurI/Δdat in comparison with the *S. aureus* 132 wild type, both strains were inoculated in exponential growth phase to a final 1/200 dilution into 100 ml of TSB and TSB supplemented with 20 mM D-glutamate, and incubated at 37° C. with constant shaking (180 rpm). At 1, 2, 3, 4, 5 and 18 h, the optical density of the culture and bacterial concentration were determined. The optical density was assessed by measuring aliquots of each flask at $OD_{600\ nm}$ whilst the bacterial concentration (CFU/mL) was calculated by spreading serial 10-fold dilutions onto TSB agar plates. All the cultures were performed in triplicate.

Growth curves for the *S. aureus* wild type strain as well as for double mutant strain ΔmurI/Δdat were performed to evaluate the effect of the absence of D-glutamate in the medium along the time, as well as, the viability of the strains in the presence and absence of this compound.

Figure 32:
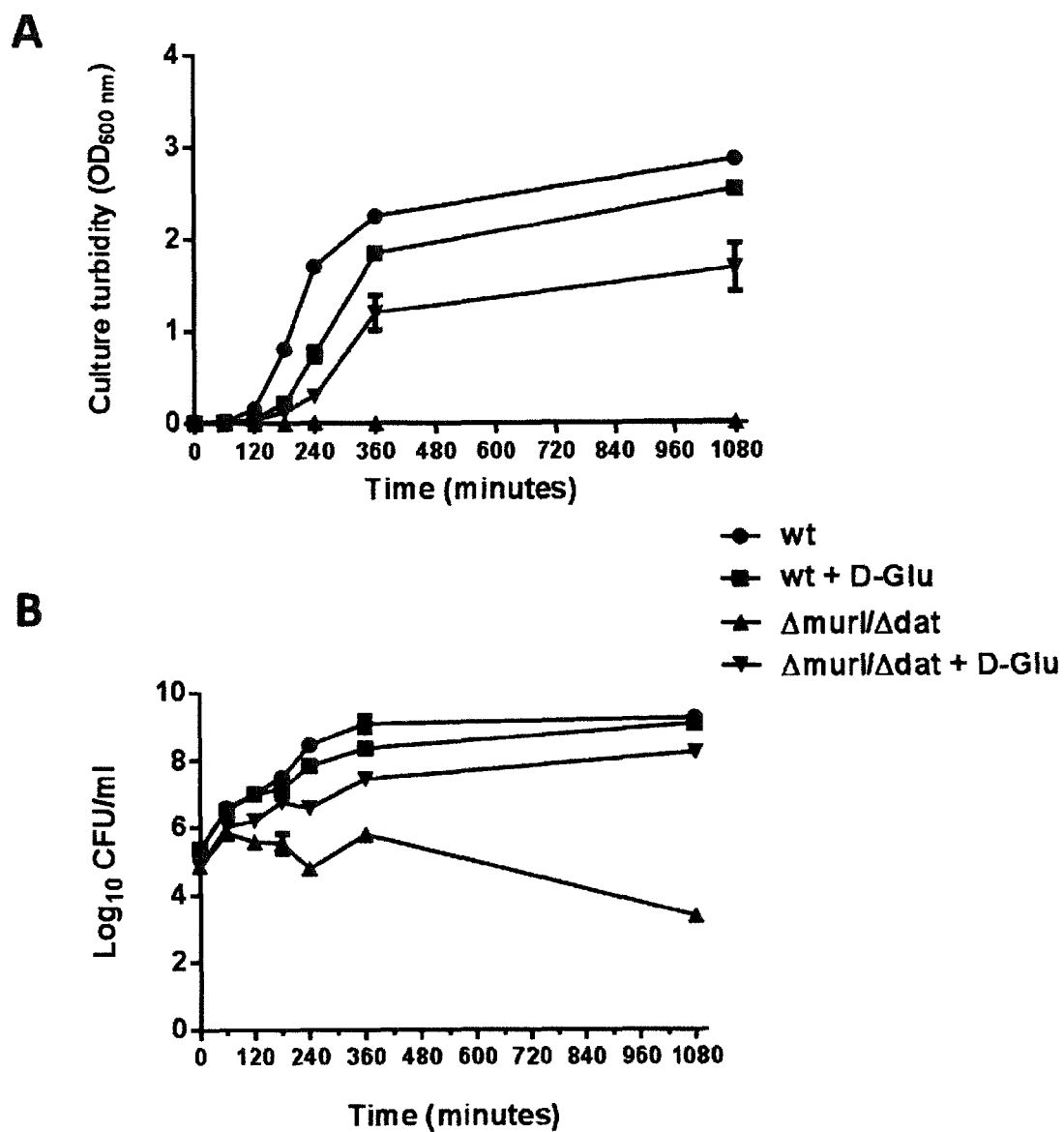
FIG. 32 shows the growth and viability assays of S. aureus 132 wild type and of double mutant strain ΔmurI/Δdat. Strain ΔmurI/Δdat shows normal growth in TSB supplemented with 20 mM of D-glutamate but is incapable to grow without the exogenous supply of this compound. In contrast, the wild type strain grows in TSB with and without the addition of D-glutamate. Each symbol represents one strain as indicated in the legend. A: Culture turbidity; B: Culture viability.

A total absence of growth was observed for the double mutant strain in TSB medium without D-glutamate (FIG. 32A), being almost totally restored when adding D-glutamate to the medium. With regard to bacterial viability (FIG. 32B) it is shown that the viability of the double mutant significantly decreased (2 $Log_{10}$) at 18 h due to the limitation of D-glutamate in the culture medium.

Example 24: Morphological Analysis of *S. aureus* 132 Wild Type and Double Mutant ΔmurI/Δdat Strains by Electron Microscopy To prepare electron microscopy samples pellets recovered from the liquid cultures of *S. aureus* wild type and double mutant ΔmurI/Δdat strains in TSB supplemented with 20 mM of D-glutamate (37° C. for 16 h) were washed twice in saline and re-suspended in 1 mL of TSB. 50 μL of each suspension was transferred to 5 mL of TSB supplemented with increasing concentrations of D-glutamate: 0, 0.1, 1.5 and 20 mM and incubated at 37° C. for 3 hours with constant shaking (180 rpm). The obtained bacterial cultures were centrifuged and pellets were washed twice with PBS. Afterwards, pellets were fixed with paraformaldehyde 4% in PBS 1M pH 7.4 for 30 minutes at room temperature and shaking. The samples were additional washed twice with PBS and dehydrated with a series of increasing alcohol concentrations (50%, 70%, 90%, 100%) for 15 minutes each. Finally, the samples were dried at critical point with $CO_2$ (Bal-Tec CPD 030). One drop of each sample was placed onto a slide cover and fixed onto an aluminium support for gold coating (Bal-Tec SCD 004 sputter coater). Samples were observed and photographed in a transmission electron microscope Jeol JSM-6400.

Figure 33:
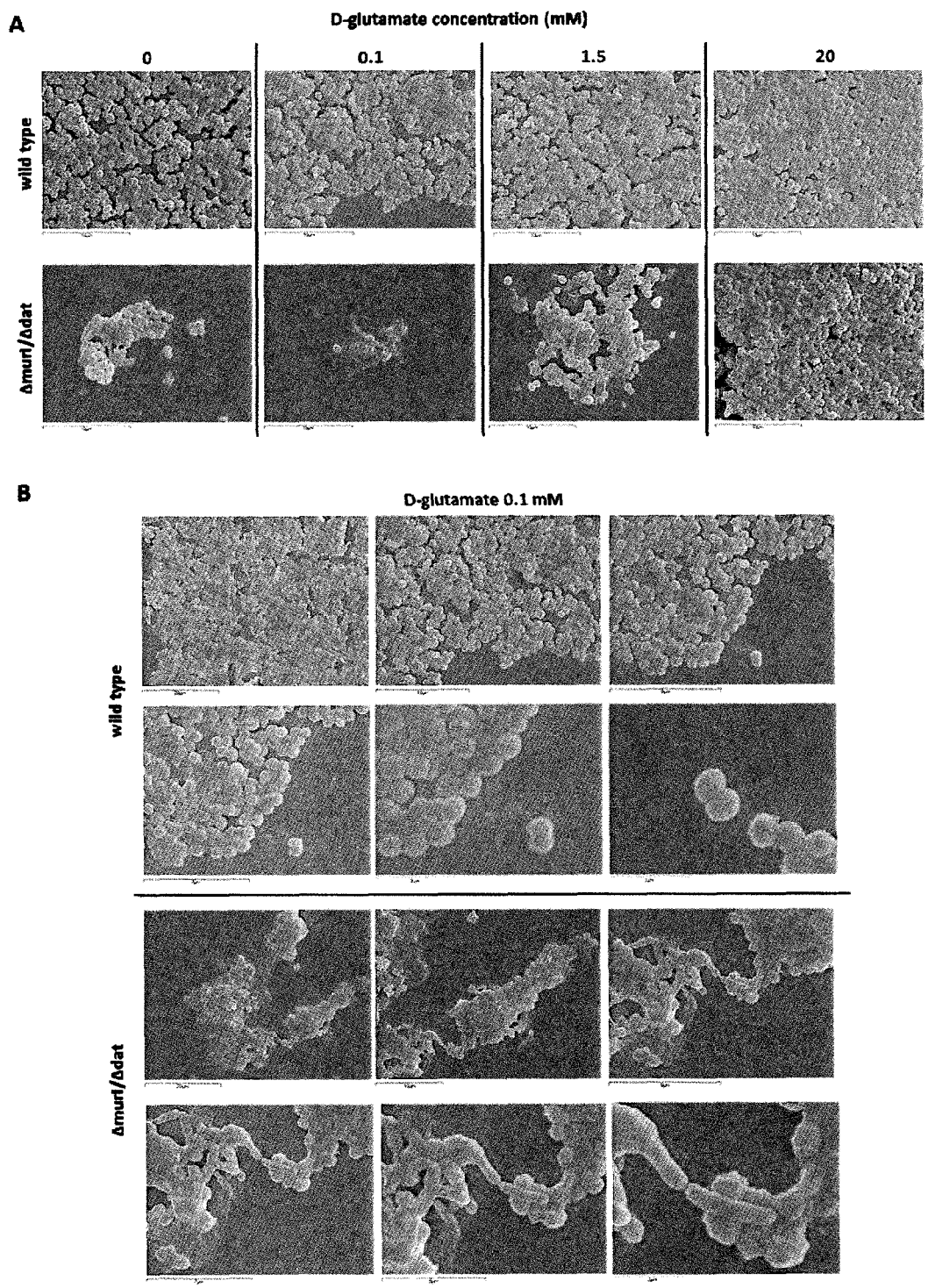
FIG. 33 shows alterations at morphological level in the S. aureus 132 double mutant ΔmurI/Δdat with respect to the S. aureus wild type strain thereof in the presence of different concentrations of D-glutamate. Images were taken with a scanning electron microscope. A: both strains were incubated at increasing concentrations of D-glutamate and the microphotographs were taken on the same scale (horizontal bars indicate a scale of 10 μm); B: both strains were cultured in medium supplemented with 0.1 mM D-glutamate and the images were taken progressively on scales of a decreasing order.

Microscopic observation enabled to detect substantial morphological and structural changes in the double mutant ΔmurI/Δdat strain as D-glutamate in the medium decrease. FIG. 33 shows the scanning electron images comparing wild type and double mutant strains after growing in TSB medium supplemented with different concentrations of D-glutamate.

FIG. 33A shows that the double mutant is unable to divide without external addition of D-glutamate. Accordingly, at 0 mM of D-glutamate the bacterial cells detected mostly correspond to the initial inoculum which was previously grown in the presence of this compound. Some abnormal cellular shapes can be also observed as consequence of incomplete cellular division occurred due to reminiscent intracellular D-glutamate. When the double mutant is incubated in medium supplemented with 0.1 mM of D-glutamate some cellular division occurred but continues being atypical owing to the low concentration of this D-amino acid. Thus, the process of cell wall biosynthesis and division is not complete thus generating deformed cells and protoplasts (bacterial cells lacking peptidoglycan but still harbouring plasmatic membrane). In the presence of D-glutamate at 1.5 mM the bacterial density slightly increased in relation to cultures derived from medium with lower concentrations of this compound, indicating a higher growth rate of the double mutant. Protoplasts and lengthened shapes are still present but typical spherical bacterial cells with the same configuration than the wild type strain can be observed. Finally, when the medium is supplemented with D-glutamate 20 mM the cellular density as well as morphology of the double mutant is comparable with that shown by the wild type strain. No atypical division pattern is observed.

On the other hand, FIG. 33B displays different scanning electron micrographs of the bacterial cultures of the double mutant and wild type strains incubated in medium supplemented with 0.1 mM of D-glutamate. Wild type strain shows the characteristic spherical shape of gram-positive coccus, high cellular density and a typical division pattern. *S. aureus* division is characterized by an incomplete cell wall separation thus appearing bacterial cells in grape-clusters that remain connected by segments of peptidoglycan. Conversely, cells of the double mutant become forming part of large compact aggregates or conglomerates as consequence of the exacerbated incomplete cell division. The lack of enough concentration of D-glutamate in the medium impaired peptidoglycan biosynthesis and correct cell wall division. Indeed, cellular density is lower than that observed in the wild type preparations. Moreover, abundant deformed shapes are visualized including unusual lengthened bacteria. Under this condition, the double mutant also shows rough and irregular surface in comparison with the wild type strain.

Figure 34:
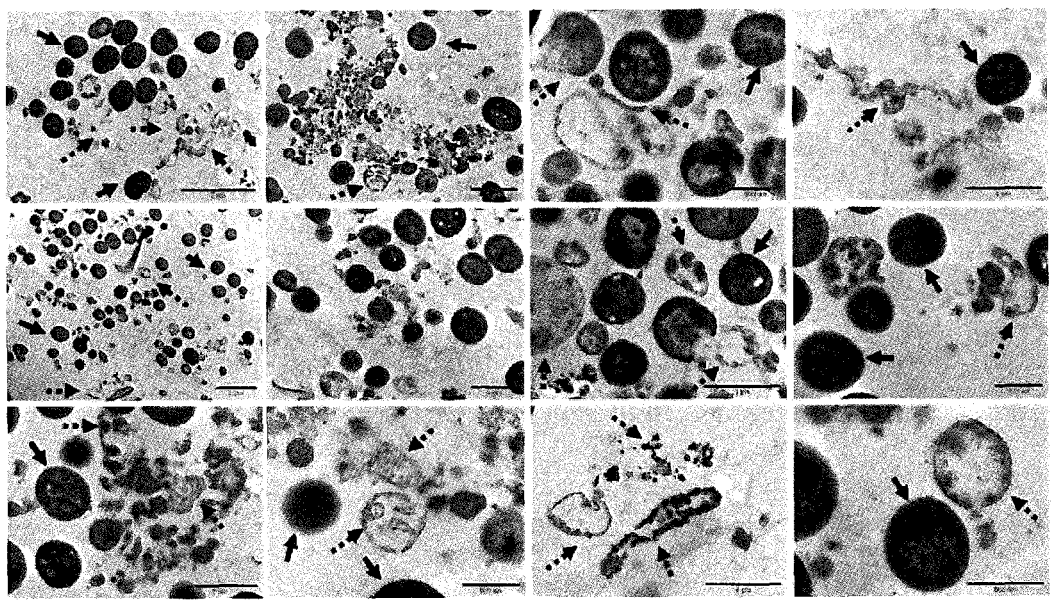
FIG. 34 shows different atypical morphologies, progressive degeneration of the cell wall and lysis of the S. aureus 132 double mutant strain ΔmurI/Δdat when kept in the absence of D-glutamate. Images were taken with a transmission electron microscope on different scales as specified by horizontal bars. Black arrows indicate intact bacterial cells with normal morphology or atypical cell division; dashed arrows indicate fragmented cells without bacterial cell wall, lysed cells or disorganized internal content, dispersed genetic material, aggregation of membranes and/or liposomes.

Furthermore, the progressive disintegration of the cell wall, bacterial degeneration and subsequent bacterial death was detected in the double mutant by transmission electronic microscopy. To this end, sample preparations were obtained by short-term maintenance of the double mutant strain in absence of D-glutamate as described in example 4. As can be seen from FIG. 34, this approach allowed to the observation of different gradual disintegration stages until bacterial death. Initial morphological changes observed included diminishing of murein layer and consequently an increase in cell size (protoplasts), since peptidoglycan constitute the mechanically resistant part of the wall cell. Permeability and disruption of the plasma membrane can be also observed which results in the extrusion of cytoplasmic constituents. Large amount of debris, membrane aggregates, liposomes and genetic material can be seen around these collapsed cells. On the other hand, some bacterial cells still maintain an intact envelope and hence the typical S. aureus bacterial shape and size could be observed.

Example 25: Determining the Lethal Dose (LD) of S. aureus Wild Type 132 and Double Mutant ΔmurI/Δdat Strain in BALB/c Mice in an Acute Infection Model With the aim of producing a systemic infection in BALB/c mice, saline inoculum with 3% of hog mucin of S. aureus wild type and double mutant strains were intraperitoneally administered to mice.

For preparation of the inoculum, bacteria were grown in TSB (wild type) and TSB supplemented with 20 mM D-glutamate (double mutant) at 37° C. with shaking (180 rpm) until reaching $OD_{600\ nm}$ of 0.7. The cultures were centrifuged, washed twice with saline serum, and re-suspended in saline serum with 3% of hog mucin (wild type and double mutant strains for intraperitoneal sepsis model) or in saline serum (double mutant for immunize animals, following examples) to a final concentration of ~$10^8$ CFU/mL. This suspension is called 1× and corresponds to $5 \times 10^7$ CFU/mouse when a volume of 250 μL is administered to mice. Bacterial suspensions were further adjusted at different doses (for instance, a suspension 3× is understood as the bacterial inoculum three-times concentrated and so on). BALB/c (n=3-4) were inoculated intraperitoneally with different doses (250 μL) of bacterial suspension and monitored for 14 days post-infection. $LD_{100}$ is defined as the minimum lethal dose for 100% mice mortality.

In FIG. 35A is shown different degrees of survival in mice when administered increasing doses of S. aureus wild type strain. The minimum dose that reduces survival of the mice to 0% was determined as 3×. In FIG. 35B survival in mice when administered increasing doses of double mutant strain is illustrated. In clear contrast this figure shows that inoculating a dose of the double mutant 10-fold higher than the LD100 of the wild type strain results in a 100% survival rate. Therefore, the lethal dose for the double mutant is greater than 30× $LD_{100}$>30×. This clearly demonstrates that the double mutant of S. aureus is a highly attenuated strain showing lower virulence potential than the wild type counterpart strain.

Example 26: Determining the Bacterial Load in Spleen and Blood of BALB/c Mice Pre-Immunized with the Double Mutant ΔmurI/Δdat Using a Systemic Infection Model To evaluate the effectiveness (protection level) of the S. aureus double mutant ΔmurI/Δdat strain as a vaccine, two independent experiments were performed.

Firstly, BALB/c mice (n=4-6) were intraperitoneally pre-immunized (250 μL) with the double mutant ΔmurI/Δdat strain in saline serum (10× dose) on days 0 and 14. One group of mice were identically administered 250 μL saline at days 0 and 14. At day 21, mice were infected intraperitoneally with a lethal inoculum (5× dosis, 250 μL with 3% of hog mucin) of S. aureus 132 wild type strain. At 20 hours post-infection mice were euthanized with sodium thiopental. The spleen of each mouse was aseptically removed and after being homogenized in saline, the CFUs per gram of organ were determined by plating serial dilutions in TSB agar. The presence of bacteria in blood was evaluated by inoculating 50 μL of blood sample aseptically removed from the mice heart into 5 mL of TSB medium. The bacterial inoculum were prepared and adjusted as described previously.

The protective effect of the vaccination with the double mutant ΔmurI/Δdat was confirmed when it was observed that pre-immunization with this strain causes a significant reduction in bacterial load in spleens of mice infected with a lethal dose of S. aureus 132 wild type strain. Indeed, we observed a severe reduction (2 $Log_{10}$) in the bacterial load of immunized mice compared to non-immunized mice (P=0.0095, Mann-Whitney U-test, FIG. 36A). In addition, the absence of bacteria in the blood of all vaccinated mice (negative blood cultures) further supports the protective effect of vaccination (FIG. 36B).

Figure 37:
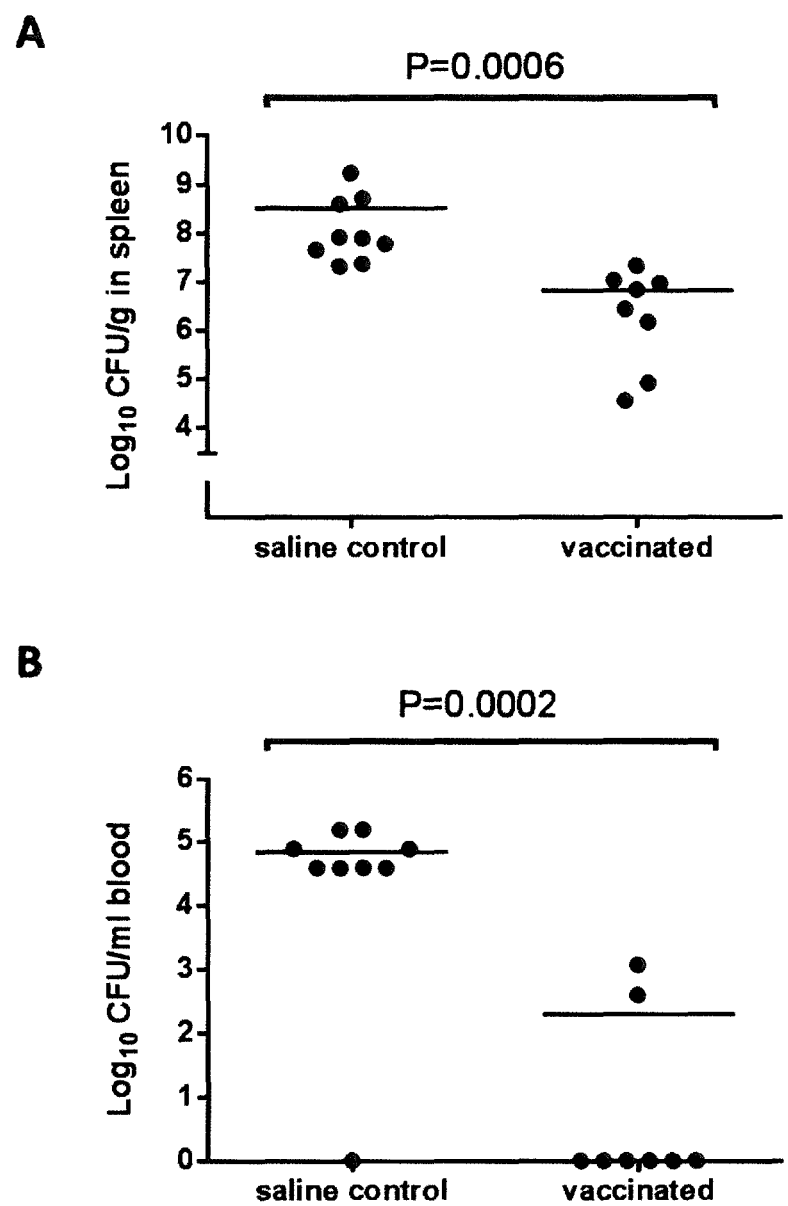
FIG. 37 shows bacterial load in the spleen (A) and blood (B) of BALB/c mice (n=8-9) 22 hours post-infection with a 5× dose of *S. aureus* 132 wild type strain. Mice were immunized on days 0 and 14 with an 8× dose of strain ΔmurI/Δdat, or non-immunized (saline control). Each dot represents the individual bacterial load of spleen or blood of a mouse. The average value of each group is represented by a horizontal line. P=0.0006 and P=0.0002 compared with the group of non-vaccinated mice. P-value according to the Mann-Whitney U test.

These results are further confirmed as follows. First, FIG. 37 shows that in pre-immunized BALB/c mice (n=8-9) with the double mutant ΔmurI/Δdat strain (8× dose in this case) the bacterial counts in spleen (FIG. 37A) and blood (FIG. 37B) were significantly lower compared to the non-immunized group (P=0.0006 and P=0.0002, respectively, according to Mann-Whitney U test) 22 hours after infected with a lethal inoculum of S. aureus 132 wild type strain (5× dose, 250 μL with 3% of hog mucin). Immunization schedule was performed as above.

Example 27: Protection of BALB/c Mice Against Challenge with S. aureus 132 Strain by Immunization with the ΔmurI/Δdat Mutant To evaluate the efficacy of the ΔmurI/Δdat as a vaccine, BALB/c mice (n=10-13) were administered 250 μL of the ΔmurI/Δdat strain (10× dose in saline) on days 0 and 14. Control mice were administered only saline identically at days 0 and 14. Seven days after the second injection, mice were challenged with a lethal dose of S. aureus 132 wild type strain (5× dose in saline with 3% hog mucin) in order to establish a lethal systemic infection in both cases. After the challenge, mice were monitored to determine the survival rate of vaccinated mice compared with control group (non-vaccinated).

When infected with a 5× dose of the S. aureus 132 wild type strain, 9 deaths were observed in the group of non-vaccinated mice, which means a mortality rate of 90% in this group (n=10). In contrast, 8 mice of vaccinated group (n=13) survived to the challenge, overcoming the infection, which means a 61.5% survival rate in this group (see FIG. 38). Differences in survival between the two groups were statistical significant (P<0.031, according to Mann-Whitney U test).

These results show that vaccination with the ΔmurI/Δdat strain can provide protective immunity against subsequent infection with S. aureus.

Example 28: Quantification of IgG Antibodies Against the Isogenic S. aureus 132 Δspa Strain Through Indirect ELISA in BALB/c Mice Subjected to Vaccination the Double Mutant ΔmurI/Δdat Strain To evaluate the immune response to vaccination mediated by antibodies, BALB/c mice (n=10) were immunized by intraperitoneal injection (250 μL) of double mutant ΔmurI/Δdat in saline (10× dose) on days 0 and 14. At day 21, mice were anesthetized with sodium thiopental and blood was collected via retro-orbital plexus puncture. Sera were separated from blood cells by centrifugation and stored at −80° C. until analysis.

IgGs detection was performed using an indirect enzyme linked immunosorbent assay (ELISA). 96-well ELISA plates were coated with whole S. aureus 132 Δspa strain.

This strain is an isogenic strain of S. aureus 132 wild type strain defective for Protein A. Thus, the whole-bacteria was fixed to the bottom of the wells after 18 h of incubation at 4° C. in carbonate-bicarbonate buffer 100 mM, pH 9.6 (1/10 dilution of a culture with $OD_{600}=1$). Five (5) washes were performed with phosphate buffered saline solution (PBS) buffer to remove unfixed bacteria. Blocking residual sites was performed in two steps to reduce non-specific interactions with the mouse sera. Firstly, plates were incubated at room temperature for 1 h with 100 μL per well of blocking solution (5% skim milk in PBS) and secondly, at 37° C. for 1 h with 100 μL of rabbit serum (1/1000). After 5 washing steps with wash buffer (0.005% TWEEN® 20 in PBS), the plates were incubated overnight at 4° C. with 100 μL of serial diluted sera in dilution buffer (DMEM medium with 5 to 10% FCS). The following day, 5 washes were performed with wash buffer to remove unreacted antibodies and 100 μL of secondary antibody was added per well (anti-mouse IgG peroxidase HRP-labeled) diluted 1/5000 in dilution buffer. Incubation was performed over 1 h at room temperature. Plates were washed 5 times with wash buffer. To perform the develop process the plates were incubated for 3 min with 100 μl of TMB (HRP-peroxidase substrate). The reaction was stopped with 50 μL of 1 M HCl per well. Colorimetric measure was performed at 450 nm. A positive (anti-*Staphylococcus aureus* monoclonal antibody), negative (serum from non-vaccinated mice) and reference (dilution buffer) controls were included in all plates. To determine the titers of IgGs for each serum, the endpoint titer was estimated. Titers were defined as the last serum dilution with an absorbance 0.1 point higher than the reference control (dilution buffer).

Thus, the blood samples collected from each mouse were used to determine the titer of antibodies (IgG) against S. aureus 132 Δspa strain by ELISA, hence measuring the ability of the vaccine to generate an immune response. Significant differences between IgG antibody production were observed between the group of mice immunized with a 10× dose of the mutant ΔmurI/Δdat compared with mice in the control group (P<0.0001, according to Mann-Whitney U test) (FIG. 39), demonstrating the efficacy of this strain in triggering IgG responses in mice.

Example 29: Cross-Reactivity of IgG Antibodies Generated with the Double Mutant ΔmurI/Δdat Against Unrelated S. aureus Strains ELISA was performed with the sera indicated in the example 28 with respect to USA300LAC, RF122, ED133 and ED98 strains to evaluate the antibody-mediated immune response in BALB/c mice immunized with the ΔmurI/Δdat strain against unrelated S. aureus strains from different origin and thus, measure the ability of the vaccine to generate a broad immune response. It is well known that S. aureus USA300LAC is an epidemic MRSA strain cause unusually invasive disease in healthy individuals being a predominant cause of community acquired infections in United States, Canada and Europe. On the other hand, RF122 (bovine, ST151 and CC151), ED133 (ovine, ST133 and CC133) and ED98 (poultry, ST5 and CC5) were selected as representative strains of three major clones of animal host-adapted S. aureus strains that cause pathogenesis in livestock.

To that end, plates were processed as described in example 28 but were previously "coated" with each of the above strains, independently.

As shown in FIG. 40, high significant titers of antibodies were detected against the four unrelated S. aureus strains demonstrating that immunization with ΔmurI/Δdat strain not only generates antibodies against the isogenic 132 Δspa strain, but also against the relevant clinical strain USA300LAC, as well as three other strains well-adapted to animal hosts.

Example 30: Environmental Safety Assessment of the ΔmurI/Δdat Strain—Evaluation of Water Osmolisis and Resistance to Desiccation Conditions The live attenuated vaccine candidate should be unable of persisting in the general environment once it leaves the vaccinated individual with the aim of keeping to a minimum the associated risks.

To compare the ability of S. aureus wild type and ΔmurI/Δdat strains to be long-time traced in the general environment, we evaluated survival of these strains in water without any contribution of nutrients or salts, at room temperature and under agitation (180 rpm) conditions for the time necessary to observe the loss of viability by cellular osmolisis. Daily samples of the suspension were taken for the determination of CFU counts in TSB agar (wild type strain) and TSB agar supplemented with 10 mM D-glutamate (mutant strain). All cultures were performed in triplicate.

Figure 41:
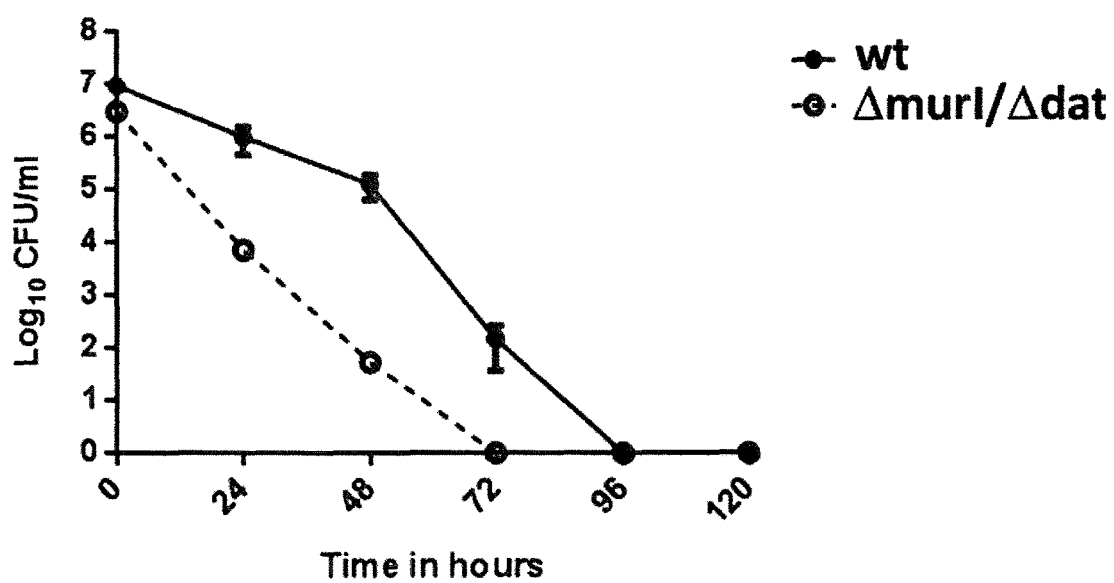
FIG. 41 shows the $Log_{10}$ CFU/mL of recovered *S. aureus* wild type and ΔmurI/Δdat strains when grown in distilled water at room temperature with agitation (180 rpm) during 5 days. CFU were determined by counting colonies plated onto TSB agar (wild type) and TSB supplemented with 10 mM D-glutamate (double mutant strain). All cultures were performed in triplicate.

As shown in FIG. 41 a decrease in the viability of the mutant ΔmurI/Δdat strain was observed along the time being the time elapse for a 2-$\log_{10}$ reduction 24 hours. Moreover, no viable bacteria of ΔmurI/Δdat strain were recovered beyond 72 hours of culture.

Figure 52:
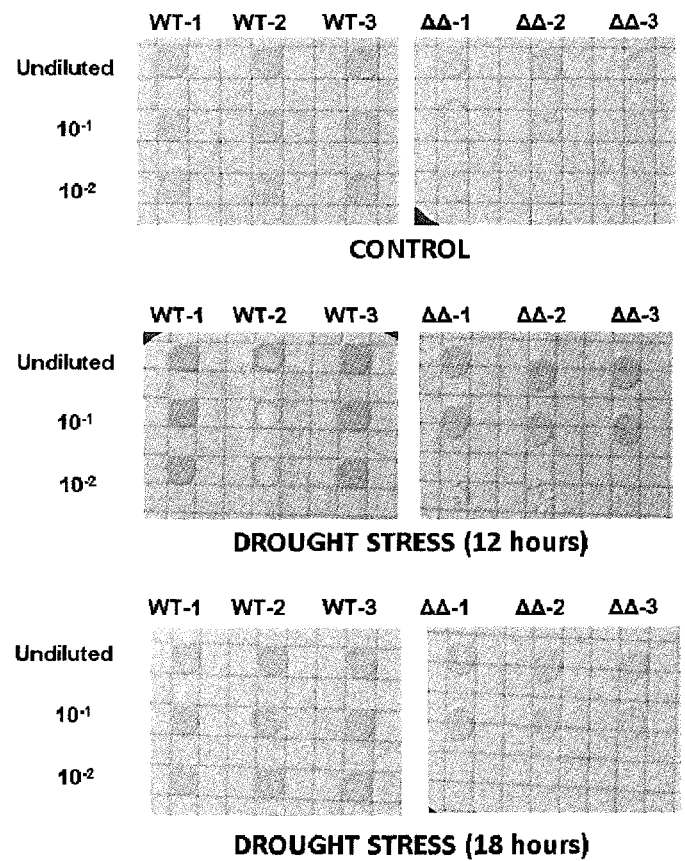
FIG. 52 shows the cell viability of *S. aureus* wild-type (WT) and double mutant ΔmurI/Δdat (ΔΔ) strains on TSB plates supplemented with D-glutamate immediately (growth control) and after 12 and 18 hours of drought stress at 37° C. All cultures and dilution series were performed in triplicate.

In addition, FIG. 52 shows the resistance of double mutant ΔmurI/Δdat strain to dryness compared to the wild type strain. To evaluate drought resistance the cell viability of the wild type and double mutant strains was tested by spotting dilution series of washed cells in the exponentially growth phase into nitrocellulose filters (0.45 μm pore size). The filters were either not dried (growth control) or dried for 12 or 18 hours inside a sterile petri plate at 37° C. (drought stress conditions) before they were placed on TSB plates supplemented with D-glutamate and incubated for 24 hours at 37° C. All cultures and dilution series were performed in triplicate.

As shown in the figure, no difference in the cell viability was observed for the wild type strain after keep under drought conditions compared with growth control (not dried filters). In contrast, the growth of the 2-$\log_{10}$ diluted culture of the ΔmurI/Δdat strain notably decreased after 12 hours of dryness. Complete absence of cell viability (no grown) was observed in the same dilution of the double mutant when keep under desiccation stress for 18 hours. These results indicate that the ΔmurI/Δdat strain is more sensitive to desiccation than the wild type parent strain and further support an appropriate threshold of security for its use as a vaccine.

Example 31: Evaluation of the Stability of the Auxotrophic Phenotype in the S. aureus ΔmurI/Δdat Strain To test the irreversibility of the nutritional auxotrophy of S. aureus ΔmurI/Δdat for the compound D-glutamate, ΔmurI/Δdat strain was grown in 100 mL of TSB supplemented with 20 mM D-glutamate in optimal conditions for 11 days at 37° C. with agitation (180 rpm). Samples from this culture were taken at the beginning of incubation and at days 3, 5 and 11 for determination of CFU in TSB agar and TSB agar supplemented with 10 mM D-glutamate. All cultures were performed in triplicate. In the hypothetical case of a phenotype reversion, similar bacterial counts should be recovered in agar plates over time, independently of the presence or absence of the compound in the medium. In contrast, we observed significant differences between the bacterial counts obtained when the culture was plated onto agar medium with and without D-glutamate.

Figure 42:
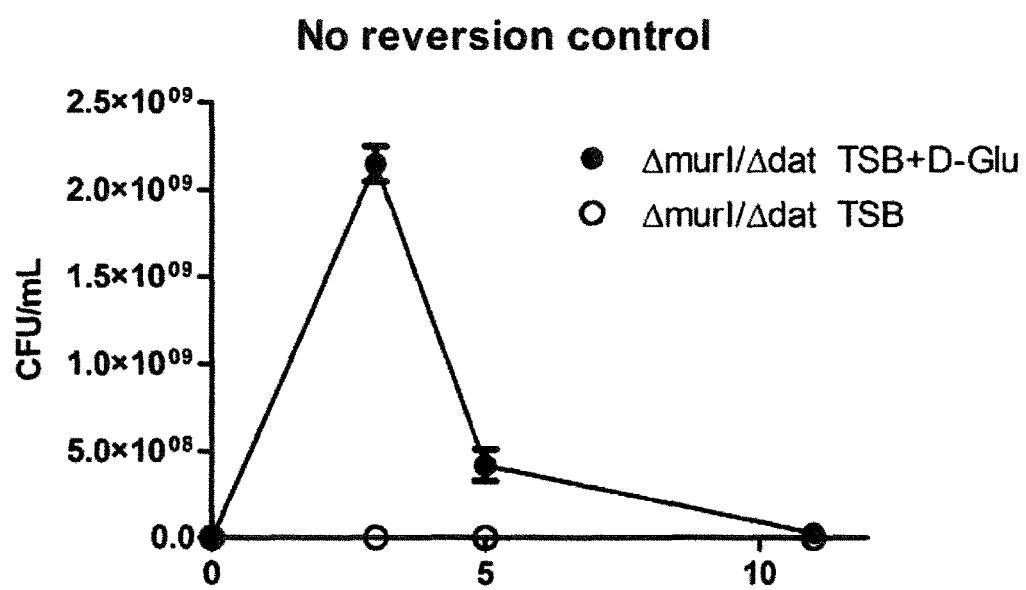
FIG. 42 shows the number of *S. aureus* ΔmurI/Δdat colonies (CFU/mL) recovered from TSB (○) and TSB supplemented with 10 mM D-glutamate (●) when this strain was cultivated onto TSB supplemented with 20 mM D-glutamate at 37° C. with agitation (180 rpm) during 11 days.

Resulting bacterial counts were significantly higher in the first case (agar plates supplemented with D-glutamate), at the initial stage of incubation (0 days) and on days 3, 5 and 11 (see FIG. 42). This difference indicates that ΔmurI/Δdat strain remains auxotrophic for D-glutamate over time, without the possibility of reversion to the wild type phenotype.

Example 32: In Vivo Clearance of *S. aureus* ΔmurI/Δdat Strain After Intraperitoneal Administration in Mice To evaluate the security of the *S. aureus* ΔmurI/Δdat strain when inoculated in the organism to be used as a vaccine, bacterial loads were determined in spleen, kidney and blood of BALB/c mice inoculated with ΔmurI/Δdat strain compared to wild type strain. Mice (n=3/per strain) were intraperitoneally administrated (250 μL) with a sub-lethal 0.7× dose of wild type strain and with 10× (13-times higher dose) of ΔmurI/Δdat strain. Both cultures were prepared in saline with 3% of hog mucin independently of each other as previously described. One mouse per group was euthanized with sodium thiopental at post-infection days 1, 2 and 6 to determine the bacterial load in organs and blood. Thus, spleen and kidney were aseptically processed as described above, and CFU per gram of organ were determined by plating serial dilutions in TSB agar (wild type) and TSB agar supplemented with 10 mM D-glutamate (double mutant). Bacterial load in blood was determined by plating 50 μl of blood aseptically removed from from heart.

In the acute sepsis model, the infection occurs with a rapid spread of the bacteria through the blood producing a peak in mice death between 24 and 48 hours post-infection. Therefore, from the bacteria counts in the organs and blood can be obtained a measure of the invasive and replicative capability of a particular strain.

Figure 43:
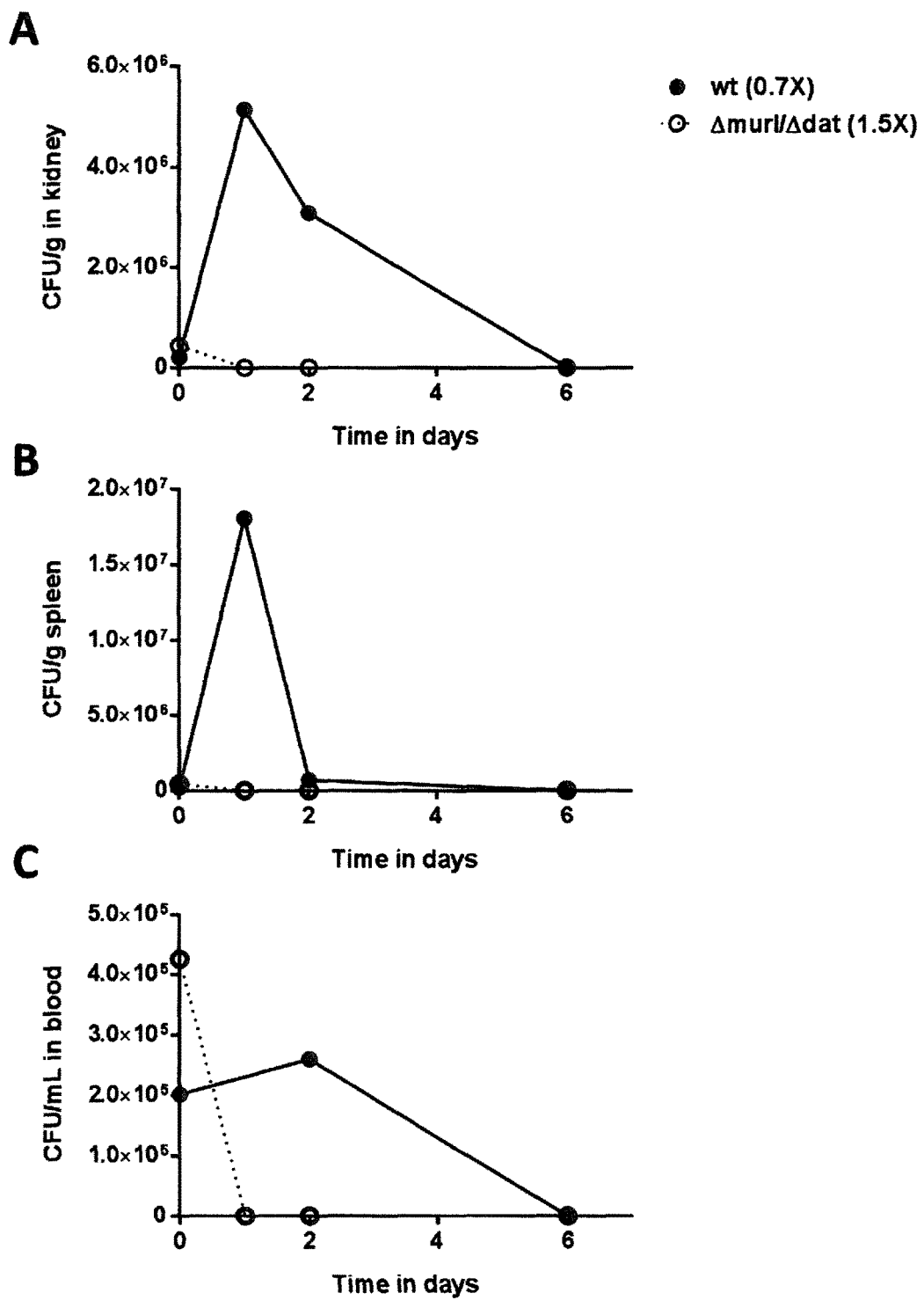
FIG. 43 shows the number of *S. aureus* colonies recovered in kidney (CFU/g) (A), spleen (CFU/g) (B), and blood samples (CFU/ml) (C) of mice (n=3/per group) intraperitoneally inoculated with a sub-lethal 0.7× dose of *S. aureus* 132 wild type strain and a 10× dose of the ΔmurI/Δdat strain, along the time. One mouse (per group/per strain) was euthanized on post-infection days 1, 2 and 6. CFU/mouse inoculated at time zero is indicated in the Y axis for each strain. Colonies were recovered in TSB agar (wild type strain) or TSB agar plus 10 mM D-glutamate (ΔmurI/Δdat strain).

In FIG. 43 we observed a marked difference between the bacterial load in kidneys, spleen and blood from mice administered with ΔmurI/Δdat strain compared to mice infected with wild type strain, over the time. Even when a maximum peak of infection is expected between 24 and 48 hours, no colonies were recovered for the ΔmurI/Δdat strain on post-infection days 1 nor 2. In fact, CFU recovery of virulent wild type strain reached maximum counts on these post-infection even thought an inoculum 1:13 diluted was administered.

Consequently, "in vivo" clearance of ΔmurI/Δdat strain occurs before 24 hours which implies an appropriate security level for its administration as live-attenuated vaccine.

Example 33: Passive Immunization with *S. aureus* 132 ΔmurI/Δdat Vaccine Antisera We next explored the efficacy of vaccine serum from mice immunized with the *S. aureus* 132 ΔmurI/Δdat strain to protect mice against staphylococcal infection.

Vaccine or naïve sera (150 μL) were injected into peritoneal cavity of BALB/c mice (n=5) 3.5 h prior to challenge with a 5× dose of virulent *S. aureus* 132 wild type strain and survival of mice was monitored for 14 days.

Figure 53:
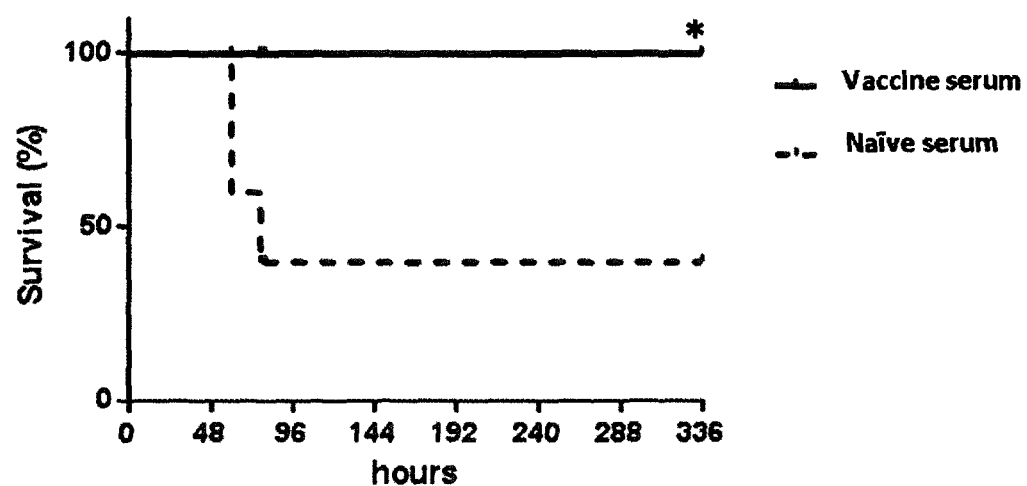
FIG. 53 is the percent survival of BALB/c mice (n=5) following intraperitoneal infection with *S. aureus* 132 wild type strain. Mice were passively immunized with vaccine serum or naïve serum. *P=0.0429 survival of mice administered vaccine serum compared to mice received naïve serum. P-value, according to the Mantel-Cox test (log-rank test).

As shown in FIG. 53, all mice passively immunized with vaccine serum were protected from challenge, whereas 60% of the mice receiving naïve serum succumbed to infection (P=0.0429; Mantel-Cox test (log-rank test)).

These results demonstrate that the transfer of *S. aureus* antiserum, generated with the double mutant ΔmurI/Δdat strain, confers significant level of protection of mice and prevents death when administered 3.5 hours prior to infection with virulent *S. aureus* 132 wild type strain.

Example 34: Exploitation of Different routes for Vaccine Administration

Both, schedule and route of administration could determine the potential immunogenicity of a particular vaccine being key factors in the final success of a vaccination procedure.

Therefore, we evaluated if the antibody immune response (IgG) elicited by using different routes of administration— intraperitoneal, intramuscular, subcutaneous and intranasal could be affected by this variable. Also, the administration schedule was considered, namely the number of doses and vaccine dosage (bacterial inocula content).

All routes have both advantages and disadvantages, such as the absorption, bioavailability and metabolism of the substance. At present, the majority of human vaccines approved are parenteral, using the intramuscular, subcutaneous and intradermic routes for administration. Although intramuscular vaccination is considered till date as the ultimate ways, nasal route offers easy of self administration, induction of mucosal as well as systemic immunity. Also, both liquid and dry power formulations can be given this way. Finally, intranasal administration may be best suited for barrier vaccinations, following the outbreak of highly infections diseases.

Mucosal membranes are intensively exposed to microorganisms and other external agents so they are places of intense immune activity. *A. baumannii*, *P. aeruginosa* and *S. aureus* are common causes of respiratory infections (among many others) therefore the use of intranasal vaccination would be beneficial to prevent colonization and disease caused by these microorganisms.

Figure 48:
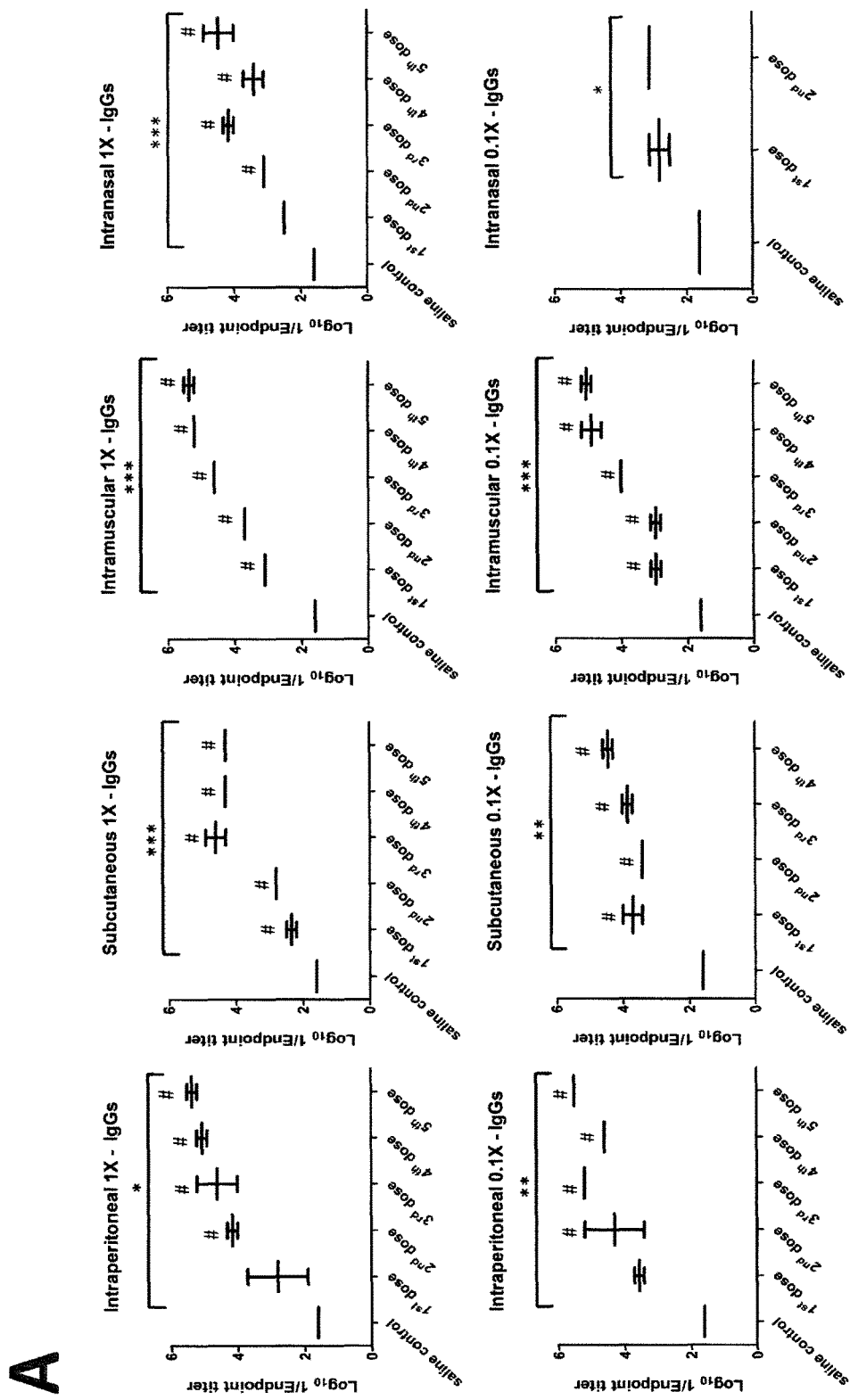
FIG. 48 shows the $Log_{10}$ 1/endpoint titer of IgG antibodies produced against the *A. baumannii* strain ATCC 17978 (A), *P. aeruginosa* strain PAO1 (B) and isogenic *S. aureus* strain 132 Δspa (C) in BALB/c mice (n=2-3/per dosis/per route) on post-vaccination days 7 (after the $1^{st}$ vaccine dosis), 21 (after $2^{nd}$ dosis), 35 (after $3^{rd}$ dosis), 49 (after $4^{th}$ dosis) and 63 (after $5^{th}$ dosis, with exceptions) with Δ0380/Δ3398, ΔPA4662 and ΔmurI/Δdat vaccine strains, respectively, and in non-vaccinated control mice (saline control). Mice were sequentially vaccinated on days 0, 14, 28, 42 and 56 (with exceptions) using different routes of administration—intraperitoneal, subcutaneous, intramuscular, intranasal—and with different vaccine doses (0.1× and 1×, Δ0380/Δ3398–0.4× and 0.04×, ΔPA4662×0.2×, 1×, 3× and 10×, ΔmurI/Δdat). The antibody titers were determined by indirect ELISA. IgG titers produced in vaccinated mice were compared with the group of non-vaccinated mice. Statistical significance was determined using one-way analysis of variance (repeated measures ANOVA) (*P<0.05; P<0.01; *P<0.001) with multiple comparison test (#P<0.05). Each dot represents the individual endpoint titer $Log_{10}$ of IgG of a mouse. The average value of each group is represented by a horizontal line.
Figure 48:
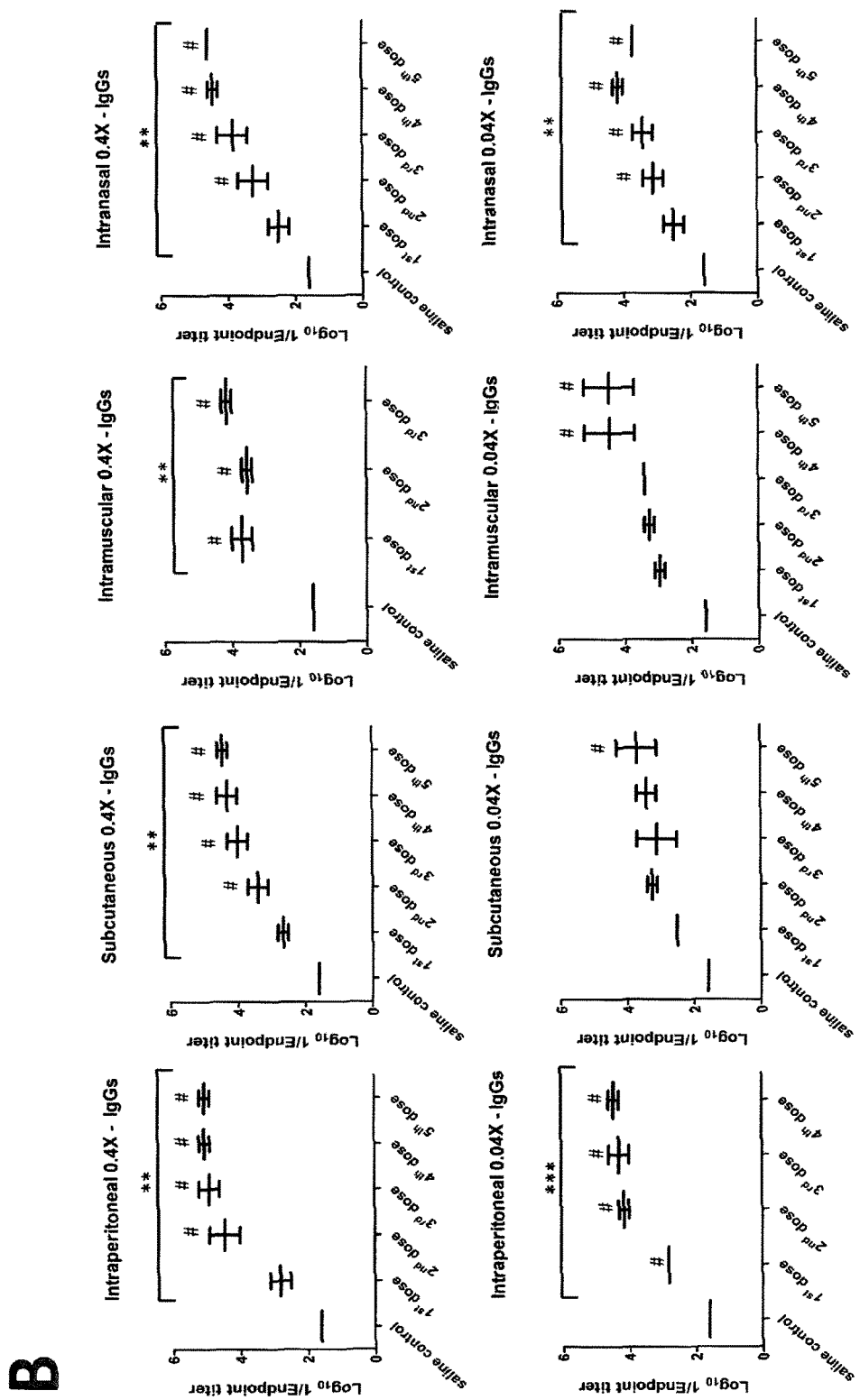
Figure 48:
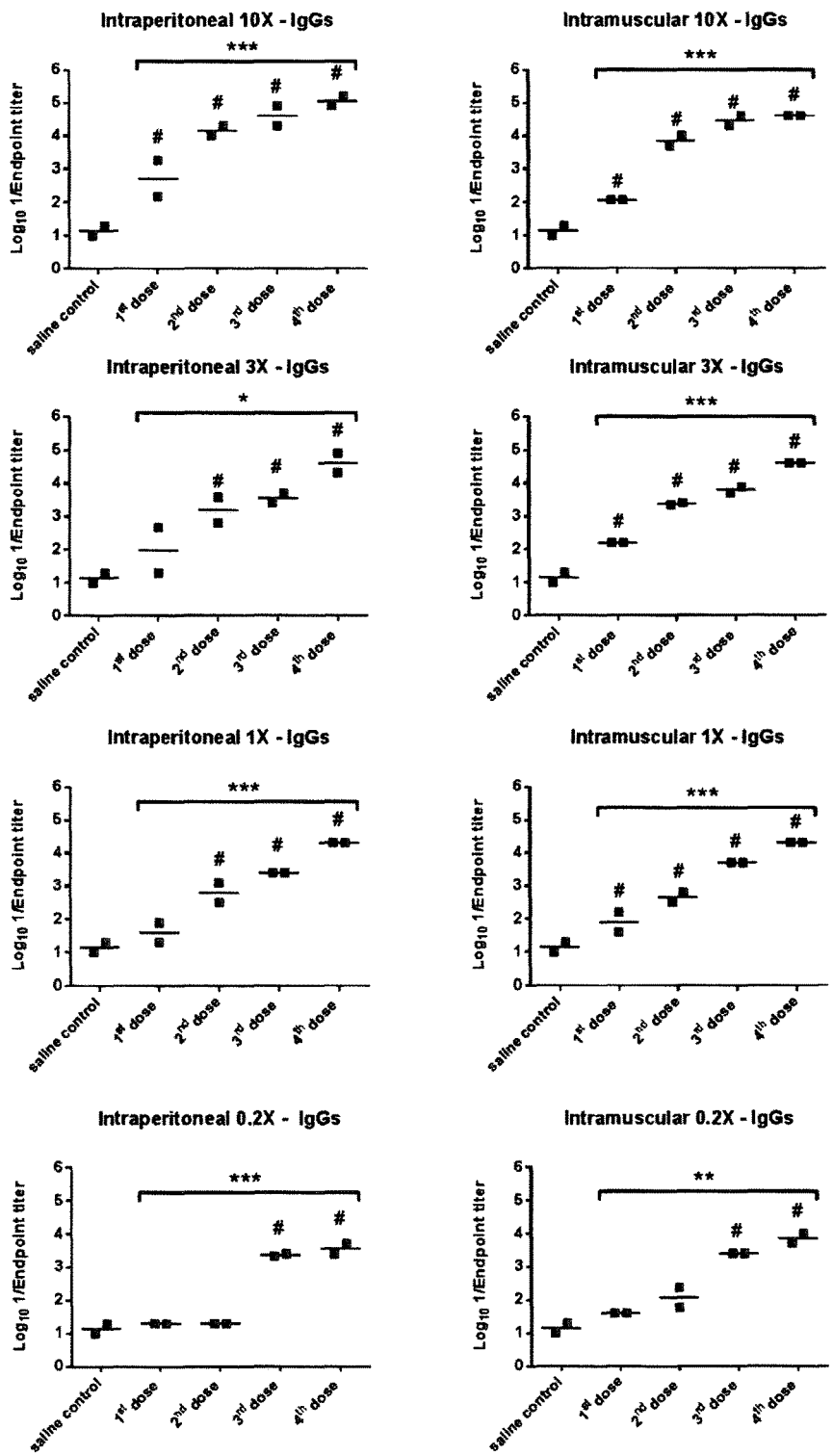
Figure 48:
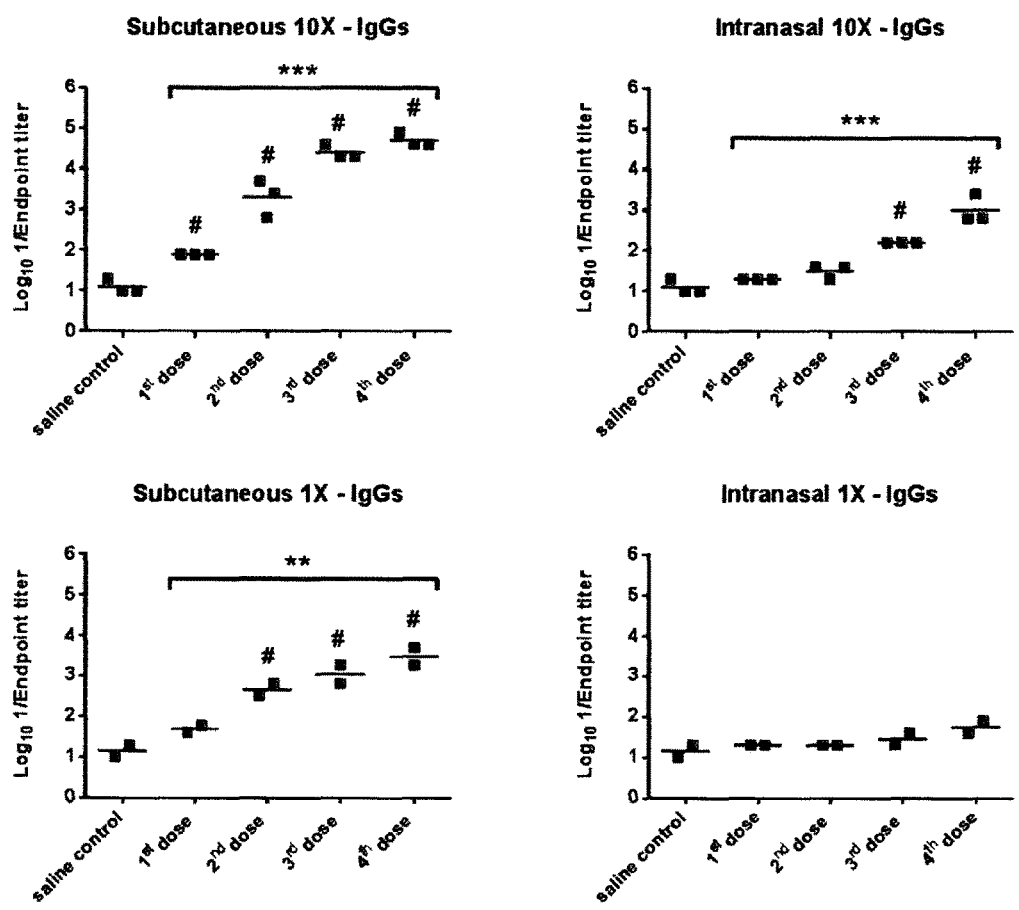

When comparing the three parenteral routes tested we found no differences between intraperitoneal, subcutaneous and intramuscular administration in the generation of antibody mediated immune response. Also, similar high antibody titers were found after intranasal administration of *A. baumanii*- and *P. aeruginosa*-derived vaccines. In contrast, *S. aureus* vaccine elicited IgG production in a lesser extent through mucosal immunization (FIG. 48A-C). In general, repeated immunizations boosted IgG production over the time.

Considering vaccine dosages, different patterns of humoral response were seen depending on the microorganism. Both tested doses of the live-attenuated *A. baumani*- and *P. aeruginosa*-vaccines (1× and 0.1×; 0.4× and 0.04×; respectively), administrated using parenteral routes (also intranasal route for *P. aeruginosa*), triggered the production of antibodies efficiently (FIG. 48A-B). In the case of *S. aureus*-vaccine (FIG. 48C), a marked reduction in IgG titers were observed when the lowest dose (1×) was used to immunize mice by intranasal route. Nevertheless, the use of parental routes for vaccination was effective even using the lowest bacterial dosages (0.2× for intraperitoneal and intramuscular routes; and 1× for subcutaneous).

In order to assess the efficacy of the different routes of vaccine administration for mice protection, once immunization schedules were finished with P. aeruginosa-derived vaccine, mice were challenged with a lethal dose (0.4×) of the wild type PAO1 strain (administered intraperitoneally as described previously) and survival was monitored as above. As expected with the high antibody titers produced after the 5th administration of the vaccine, all mice survived demonstrating a good correlation between IgG and protection. Thus, all the administration routes evaluated can be suitable for preventing acute sepsis caused by this microorganism.

```
SEQUENCE LISTING
SEQ ID No 1: Gutamate racemase MurI of
A. baumannii ATCC 17978 (A3MIP5_ACIBT)
MTAIQPLFTELEPMPKALADAPIGIFDSGIGGMSVAAEIAKYLPNERIVY

YADTAYVPYGPRSDEEIRELTARAVDWLYRQGCKIAVVACNTASAFSLDH

LREHYGEHFPIVGLVPALKPAVLQTRSKVVAVLATPATFRGQLIKDVVEK

FAVPAGVKVMTLTSLELVPCVEAGQQMSPVCLNALREVLQPAVEQGADYL

VLGCTHYPFLNEAIHHLFDNQFTLVDSGLAVARQTARILIKNELLCDQIR

QNVARIECYVSGNNADALQPVLQNMIPQELTWTLHNLS

SEQ ID No 2: Glutamate racemase MurI of
A. baumannii ATCC 17978 (A3MA43_ACIBT)
MNNNNNPIGMIDSGLGGLSLFKYIRQALPNEDIIYFADSKYVPYGDRESD

WIVSRTTHLISNLVTHGKCKAIVIACNTMTAVAVETIRAQINVPLIAIEP

AVKPAVAMTLSKHIAVLATATTVKGKNLKSLIETYAQDIKVSLVPCIGLA

EKIETGKAHTAEVKDYLKNILAPLVEQKVDTIILGCTHYPFVSDTIQEIV

GRDIQIIEPSEAVTAQLIRQLNQYHLSSESPNEGNHIIWTSSDPLEVADV

TFSLLGTRLPVETTDF

SEQ ID No 3: Glutamate racemase MurI of
Escherichia coli (MURI_ECOLI)
MATKLQDGNTPCLAATPSEPRPTVLVFDSGVGGLSVYDEIRHLLPDLHYI

YAFDNVAFPYGEKSEAFIVERVVAIVTAVQERYPLALAVVACNTASTVSL

PALREKFDFPVVGVVPAIKPAARLTANGIVGLLATRGTVKRSYTHELIAR

FANECQIEMLGSAEMVELAEAKLHGEDVSLDALKRILRPWLRMKEPPDTV

VLGCTHFPLLQEELLQVLPEGTRLVDSGAAIARRTAWLLEHEAPDAKSAD

ANIAFCMAMTPGAEQLLPVLQRYGFETLEKLAVLG

SEQ ID No 4: Glutamate racemase MurI of
Pseudomonas aeruginosa (MURI_PSEAE)
MAVESAAVGVFDSGVGGLSVLREIRARLPSESLLYVADNAHVPYGEKSAE

YIRERCERIGDFLLEQGAKALVLACNTATAAAAAELRERYPQVPLVAMEP

AVKPAAAATRNGRVGVLATTGTLKSARFAALLDRFASDVQVFTQPCPGLV

ERIEAGDLYGPQTRALLERLLAPILEQGCDTLILGCTHYPFVKPLLAELI

PAEMAVIDTGAAVARQLERVLSARALLAS

GQAATPRFWTSALPEEMERILPILWGSPESVGKLVV

SEQ ID No 5: Glutamate racemase MurI of
Staphylococcus aureus 132 (MURI)
MNKPIGVIDSGVGGLTVAKEIMRQLPNETIYYLGDIGRCPYGPRPGEQVK

QYTVEIARKLMEFDIKMLVIACNTATAVALEYLQKTLSIPVIGVIEPGAR

TAIMTTRNQNVLVLGTEGTIKSEAYRTHIKRINPHVEVHGVACPGFVPLV

EQMRYSDPTITSIVIHQTLKRWRNSESDTVILGCTHYPLLYKPIYDYFGG

KKTVISSGLETAREVSALLTFSNEHASYTEHPDHRFFATGDPTHITNIIK

EWLNLSVNVERISVND

SEQ ID No 6: D-amino acid transaminase Dat
of Staphylococcus aureus 132 (DAT)
MEKIFLNGEFVSPSEAKVSYNDRGYVFGDGIYEYIRVYNGKLFTVTEHYE

RFLRSANEIGLDLNYSVEELIELSRKLVDMNQIETGAIYIQATRGVAERN

HSFPTPEVEPAIVAYTKSYDRPYDHLENGVNGVTVEDIRWLRCDIKSLNL

LGNVLAKEYAVKYNAVEAIQHRGETVTEGSSSNAYAIKDGVIYTHPINNY

ILNGITRIVIKKIAEDYNIPFKEETFTVDFLKNADEV

IVSSTSAEVTPVIKLDGEPVNDGKVGPITRQLQEGFEKYIESHSI

SEQ ID No 7: UP0380(NotI)F:
CCCGCGGCCGCGGGGTCCTGCACCTACGATGA

SEQ ID No 8: UP0380(BamHI)R:
CCCGGATCCGGGACCTCCAATACCTGAATC

SEQ ID No 9: DOWN0380(BamHI)F:
CCCGGATCCGGGGCTCTGTTGTAGGCATTC

SEQ ID No 10: DOWN0380(SphI)R:
CCCGCATGCGGGCATCCTTGTGATTGCATT

SEQ ID No 11: UP3398(NotI)F_II:
CCCGCGGCCGCGGGTTGGTCAGGTCCTTGTTG

SEQ ID No 12: UP3398(BamHI)R_II:
CCCGGATCCGGGTACAGCCGTCATGGTGTT

SEQ ID No 13: DOWN3398(BamHI)F:
CCCGGATCCGGGACGCGTTTACCTGTAGAA

SEQ ID No 14: DOWN3398(SphI)R:
CCCGCATGCGGGAGCGGTACAACTAATTGG

SEQ ID No 15: EXTFW0380:
GCAATTAGGCACTTGAGG

SEQ ID No 16: EXTRV0380:
ATACGCTCAGGTTGCATC

SEQ ID No 17: INTFW0380:
AGCCTATGTTCCGTATGG

SEQ ID No 18: INTRV0380:
TCAACCAGTGTGAATTGG

SEQ ID No 19: EXTFW3398:
CCGATTGGAATGATTGAC

SEQ ID No 20: EXTRV3398:
AGAGCATTCTGGTCGAAG

SEQ ID No 21: INTFW3398:
TAGCAATAGAACCAGCGG

SEQ ID No 22: INTRV3398:
TTGTGCCGTTACAGCTTC

SEQ ID No 23: UPPA4662(HindIII)F_II:
CCCAAGCTTGGGGGCAATCCGCCGTATATC

SEQ ID No 24: UPPA4662(NotI)R:
CCCGCGGCCGCGGGGGCGTTGCCCGCAGACGG

SEQ ID No 25: DOWNPA4662(NotI)F:
CCCGCGGCCGCGGGTCGTTCCTGGCAGACGTG

SEQ ID No 26: DOWNPA4662(XbaI)R:
CCCTCTAGAGGGTCCGCTCTCGCAGTCCGA

SEQ ID No 27: EXTFWPA4662:
GTATCGGCAAGGTGGAGT
```

```
SEQ ID No 28: EXTRVPA4662:
GAATGGCTTGATCGAGTC

SEQ ID No 29: INTFWPA4662:
ATCCGAATCGTTGCTCTA

SEQ ID No 30: INTRVPA4662:
ACAATACGCGCTCCAGCT sEQ ID No 31: murIUP(MluI)F:
CCCACGCGTGGGCCGAAACAAAAACAGTA SEQ ID No 32: murIUP(NotI)R:
CCCGCGGCCGCGGGATTCGGTCATCCTTACTT SEQ ID No 33: murIDOWN(NotI)F:
CCCGCGGCCGCGGGGAGGATTTTTAATGAAAG SEQ ID No 34: murIDOWN(BglII)R:
CCCAGATCTGGGTTTCTTCCATTGAACTTC SEQ ID No 35: murIF:
TGTCGGAGGTTTGACAGTAG SEQ ID No 36: murIR:
CTAACTTCACGAGCCGTTTC SEQ ID No 37: murIExtF:
GCTTGCCCTAAAGGTATTCC SEQ ID No 38: murIExtR:
GGGCCACTCATACTTATGAC SEQ ID No 39: murIseqF:
ATGACTGAACAATCAGTGAA SEQ ID No 40: murIseqR:
TGATGGTGCCATGTAAAGTT SEQ ID No 41: datUP(MluI)F:
CCCACGCGTGAAACGTATTCATATGAT SEQ ID No 42: datUP(NotI)R:
CCCGCGGCCGCATATTATTCCTCACGCA SEQ ID No 43: datDOWN(NotI)F:
CCCGCGGCCGCAATTCTTTCATCATATTT SEQ ID No 44: datDOWN(BglII)R:
CCCAGATCTGCGAATCTAAACTCGGTA SEQ ID No 45: datF:
TATTCAAGCAACGCGTGGTG SEQ ID No 46: datR:
AGTTGACGTGTAATTGGGCC SEQ ID No 47: datExtF:
GTCATGGGTGACGTGACAAC SEQ ID No 48: datExtR:
GCACCACCTGCTGAATCAAG SEQ ID No 49: datseqF:
GCCGGTTGTAACAGAAGATG SEQ ID No 50: datseqR:
CAATTGCCGGGTCTGCAATC
```

The invention claimed is:

1. A method of vaccinating a warm blooded animal or a human in need thereof against an infection caused by *Pseudomonas aeruginosa*, said method comprising administering to said warm blooded animal or said human a pharmaceutical composition comprising a pharmaceutically acceptable carrier or a diluent and an immunogenically effective amount of a live attenuated mutant of *Pseudomonas aeruginosa*, wherein said mutant is glutamate racemase deficient and is auxotrophic for D-glutamate, wherein said administering protects said warm blooded animal or said human against said infection.

2. The method of claim 1, wherein said pharmaceutical composition is a vaccine.

3. The method of claim 2, wherein said pharmaceutical composition comprises an adjuvant.

4. The method of claim 1, wherein said pharmaceutically acceptable carrier or diluent is selected from the group consisting of water; culture fluid; a solution comprising a physiological salt and/or a stabilizer; a carbohydrate; a protein; a protein containing agent; and a buffer.

5. The method of claim 4, wherein said carbohydrate is selected from the group consisting of sorbitol, mannitol, starch, sucrose, glucose and dextran.

6. The method of claim 4, wherein said protein is albumin or casein.

7. The method of claim 4, wherein said protein containing agent is bovine serum or skimmed milk.

8. The method of claim 4, wherein said buffer is a phosphate buffer.

9. The method of claim 3, wherein said adjuvant is selected from the group consisting of Freunds Complete and Incomplete adjuvant; vitamin E; a non-ionic block polymer; a muramyldipeptide; an immune stimulating complex (ISCOM); a saponin, mineral oil; vegetable oil; CARBOPOL; *E. coli* heat-labile toxin (LT); Cholera toxin (CT); aluminium hydroxide; aluminium phosphate; aluminium oxide, an oil-emulsion; and vitamin-E solubilisate.

10. The method of claim 1, wherein said immunogenically effective amount comprises between $10^3$ and $10^{10}$ cells of the live attenuated mutant of *Pseudomonas aeruginosa*.

11. The method of claim 1, wherein said pharmaceutical composition has been reconstituted from a freeze-dried form.

12. The method of claim 1, wherein said live attenuated mutant of *Pseudomonas aeruginosa* is *Pseudomonas aeruginosa* DeltaPA4662 that is deposited under the Budapest Treaty with the Spanish Type Culture Collection on Apr. 14, 2014 under strain number 8589.

13. A method of protecting a warm blooded animal or a human in need thereof against an infection caused by *Pseudomonas aeruginosa*, said method comprising administering to said warm blooded animal or said human a pharmaceutical composition comprising a pharmaceutically acceptable carrier or a diluent and an immunogenically effective amount of a live attenuated mutant of *Pseudomonas aeruginosa*, wherein said mutant is glutamate racemase deficient and is auxotrophic for D-glutamate, wherein said administering protects said warm blooded animal or said human against said infection.

* * * * *